United States Patent
Berry et al.

(10) Patent No.: US 8,629,157 B2
(45) Date of Patent: Jan. 14, 2014

(54) PYRROLIDINE COMPOUNDS WHICH MODULATE THE CB2 RECEPTOR

(75) Inventors: Angela Berry, Gaylordsville, CT (US);
Rajashekhar Betageri, Bethel, CT (US); Eugene Richard Hickey, Danbury, CT (US); Someina Khor, Didcot (GB); Doris Riether, Biberach an der Riss (DE); Lifen Wu, New Milford, CT (US); Renee M. Zindell, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/141,105

(22) PCT Filed: Dec. 15, 2009

(86) PCT No.: PCT/US2009/067963
§ 371 (c)(1),
(2), (4) Date: Oct. 3, 2011

(87) PCT Pub. No.: WO2010/077836
PCT Pub. Date: Jul. 8, 2010

(65) Prior Publication Data
US 2012/0142677 A1 Jun. 7, 2012

Related U.S. Application Data

(60) Provisional application No. 61/142,411, filed on Jan. 5, 2009.

(51) Int. Cl.
| | |
|---|---|
| A61K 31/506 | (2006.01) |
| A61K 31/4439 | (2006.01) |
| A61K 31/426 | (2006.01) |
| A61K 31/427 | (2006.01) |
| A61K 31/421 | (2006.01) |
| A61K 31/422 | (2006.01) |
| A61K 31/433 | (2006.01) |
| A61K 31/4245 | (2006.01) |
| C07D 417/12 | (2006.01) |
| C07D 417/14 | (2006.01) |
| C07D 413/12 | (2006.01) |
| C07D 413/14 | (2006.01) |
| C07D 401/04 | (2006.01) |

(52) U.S. Cl.
USPC .......... 514/275; 514/342; 514/343; 514/361; 514/363; 514/371; 514/372; 514/377; 514/380; 544/333; 546/268.7; 546/272.1; 546/278.4; 548/128; 548/139; 548/195; 548/214; 548/233; 548/245; 548/246

(58) Field of Classification Search
None
See application file for complete search history.

(56) References Cited

U.S. PATENT DOCUMENTS

| | | |
|---|---|---|
| 5,371,091 A | 12/1994 | Misra et al. |
| 6,288,091 B1 | 9/2001 | Crute et al. |
| 7,595,397 B2 | 9/2009 | Zindell et al. |
| 7,928,123 B2 | 4/2011 | Berry et al. |
| 7,935,715 B2 | 5/2011 | Berry et al. |
| 8,048,899 B2 | 11/2011 | Bartolozzi et al. |
| 8,178,568 B2 | 5/2012 | Regan et al. |
| 8,329,735 B2 | 12/2012 | Ermann et al. |
| 2007/0191340 A1 | 8/2007 | Zindell et al. |
| 2008/0039464 A1 | 2/2008 | Berry et al. |
| 2008/0081822 A1 | 4/2008 | Berry et al. |
| 2009/0275611 A1 | 11/2009 | Riether et al. |
| 2010/0009964 A1 | 1/2010 | Berry et al. |
| 2010/0029644 A1 | 2/2010 | Riether et al. |
| 2010/0076029 A1 | 3/2010 | Bartolozzi et al. |
| 2010/0081644 A1 | 4/2010 | Bartolozzi et al. |
| 2010/0261708 A1 | 10/2010 | Cirillo et al. |
| 2010/0331304 A1 | 12/2010 | Berry et al. |
| 2011/0071127 A1 | 3/2011 | Berry et al. |
| 2011/0071196 A1 | 3/2011 | Bartolozzi et al. |
| 2011/0124696 A1 | 5/2011 | Regan et al. |
| 2011/0130431 A1 | 6/2011 | Berry et al. |
| 2011/0190256 A1 | 8/2011 | Cirillo et al. |
| 2011/0312932 A1 | 12/2011 | Bartolozzi et al. |

(Continued)

FOREIGN PATENT DOCUMENTS

| | | |
|---|---|---|
| GB | 1237126 A | 6/1971 |
| WO | 9724343 A1 | 7/1997 |

(Continued)

OTHER PUBLICATIONS

Ito et al., Cancer Science 94(1), 3-8 (2003).*

(Continued)

Primary Examiner — Alicia L Otton
(74) Attorney, Agent, or Firm — Michael P. Morris; Anthony P. Bottino

(57) ABSTRACT

Compounds which modulate the CB2 receptor are disclosed. Compounds according to the invention bind to and are agonists of the CB2 receptor, and are useful for treating inflammation. Those compounds which are agonists are additionally useful for treating pain (I).

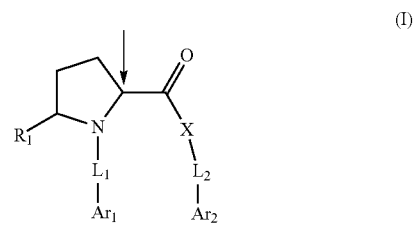

10 Claims, No Drawings

(56) References Cited

U.S. PATENT DOCUMENTS

| | | |
|---|---|---|
| 2011/0312944 A1 | 12/2011 | Bartolozzi et al. |
| 2012/0010184 A1 | 1/2012 | Bartolozzi et al. |
| 2012/0015988 A1 | 1/2012 | Hickey et al. |
| 2012/0071529 A1 | 3/2012 | Ermann et al. |
| 2012/0142666 A1 | 6/2012 | Hickey et al. |
| 2012/0142677 A1 | 6/2012 | Berry et al. |
| 2012/0316173 A1 | 12/2012 | Bartolozzi et al. |

FOREIGN PATENT DOCUMENTS

| | | | |
|---|---|---|---|
| WO | 0033788 A2 | 6/2000 | |
| WO | 2004026301 A1 | 4/2004 | |
| WO | 2006074445 A2 | 7/2006 | |
| WO | 2007070760 A2 | 6/2007 | |
| WO | 2007118041 A1 | 10/2007 | |
| WO | 2007140385 A2 | 12/2007 | |
| WO | 2008003697 A1 | 1/2008 | |
| WO | 2008014199 A2 | 1/2008 | |
| WO | 2008039645 A1 | 4/2008 | |
| WO | 2008048914 A1 | 4/2008 | |
| WO | 2008064054 A2 | 5/2008 | |
| WO | 2008098025 A1 | 8/2008 | |
| WO | 2009055357 A1 | 4/2009 | |
| WO | 2009061652 A1 | 5/2009 | |
| WO | WO 2009/074518 * | 6/2009 | ......... A61K 31/4015 |
| WO | 2009105509 A1 | 8/2009 | |
| WO | 2009140089 A2 | 11/2009 | |
| WO | 2010005782 A1 | 1/2010 | |
| WO | 2010036630 A2 | 4/2010 | |
| WO | 2010036631 A2 | 4/2010 | |
| WO | 2010077836 A2 | 7/2010 | |
| WO | 2010096371 A2 | 8/2010 | |
| WO | 2010147791 A1 | 12/2010 | |
| WO | 2010147792 A2 | 12/2010 | |
| WO | 2011037795 | 3/2011 | |
| WO | 2011088015 A1 | 7/2011 | |
| WO | 2011109324 A1 | 9/2011 | |
| WO | 2012012307 A1 | 1/2012 | |

OTHER PUBLICATIONS

RN 1028062-52-3, Database Registry Chemical Abstracts Service, Columbus, Ohio, Accession No., Entered STN: Jun. 13, 2008.*

International Search Report and Written Opinion for PCT/US2009/067963 mailed Jul. 30, 2010.

Chem Abstract: 2009-N97073. Database WPI Week 200968, Thomson Scientific, London, GB and IN 192822, council Sci & IND. Res India, May 22, 2004.

Chem Abstract: Accession No. 909412-06-2. Online Database Registry Chemical Abstracts Service, May 22, 2004.

Chem Abstract: Accession No. 909411-79-6, Online Database Registry Chemical Abstracts Service, May 22, 2004.

* cited by examiner

PYRROLIDINE COMPOUNDS WHICH MODULATE THE CB2 RECEPTOR

BACKGROUND OF THE INVENTION

1. Technical Field

The present invention relates to novel compounds which modulate the CB2 receptor and their use as medicaments.

2. Background Information

Cannabinoids are a group of about 60 distinct compounds found in *Cannabis sativa* (also know as marijuana) with cannabinol, cannabidiol and $\Delta^9$-tetrahydrocannabinol (THC) being the most representative molecules. The therapeutic usage of *Cannabis* can be dated back to ancient dynasties of China and includes applications for various illnesses ranging from lack of appetite, emesis, cramps, menstrual pain, spasticity to rheumatism. The long history of *Cannabis* use has led to the development of several pharmaceutical drugs. For example, Marinol and Cesamet which are based on THC and its analogous nabilone, respectively, are used as anti-emetic and appetite stimulant. Despite of the clinical benefits, the therapeutic usage of cannabis is limited by its psychoactive effects including hallucination, addiction and dependence. Mechoulam R, ed. *Cannabinoids as Therapeutic Agents*, Boca Raton, Fla.; CRC Press, 1986 provides a review of the medicinal use of cannabis.

The physiological effects of cannabinoids are mediated by at least two G-protein coupled receptors, CB1 and CB2. Autoradiographic studies have demonstrated that CB1 receptors are expressed primarily in the central nervous system, specifically in the cerebral cortex, hippocampus, basal ganglia and cerebellum. They are also found to a lesser degree in the reproductive system and other peripheral tissues including that of the immune system. CB1 receptors regulate the release of neurotransmitters from the pre-synaptic neurons and are believed to mediate most of the euphoric and other central nervous system effects of cannabis, such as THC-induced ring-catalepsy, hypomobility, and hypothermia, which were found to be completely absent in mice with a deletion of the CB1 gene (Zimmer et al., Increased mortality, hypoactivity, and hypoalgesia in cannabinoid CB1 receptor knockout mice. Proc Natl Acad Sci USA. (1999) 96:5780-5785.)

CB2 receptors are almost exclusively found in the immune system, with the greatest density in the spleen. It is estimated that the expression level of CB2 in the immune cells is about 10 to 100 times higher than CB1. Within the immune system, CB2 is found in various cell types, includung B cells, NK cells, monocytes, microglial cells, neutrophils, T cells, dentritic cells and mast cells, suggesting that a wide range of immune functions can be regulated through CB2 modulators (Klein et al., The cannabinoid system and immune system. J Leukoc Biol (2003) 74:486-496). This is supported by the finding that the immunomodulatory effect of THC is absent in CB2 deficient mice (Bicklet et al., Immunomodulation by cannabinoid is absent in mice deficient for the cannabinoid CB2 receptor. Eur J Pharmacol (2000) 396:141-149). CB2 selective ligands have been developed and tested for their effects in various imflammatory settings. For example, in animal models of inflammation, CB2 selective agonists, inverse agonists and antagonists have been shown to be effective in suppressing inflammation (Hanus et al., HU-308: a specific agonist for CB(2), a peripheral cannabinoid receptor. Proc Natl Acad Sci USA. (1999) 96:14228-14233, Ueda et al., Involvement of cannabinoid CB(2) receptor-mediated response and efficacy of cannabinoid CB(2) receptor inverse agonist, JTE-907, in cutaneous inflammation in mice. Eur J Pharmacol. (2005) 520:164-171 and Smith et al., The anti-inflammatory activities of cannabinoid receptor ligands in mouse peritonitis models Eur J Pharmacol. (2001) 432:107-119.). Furthermore, CB2 selective agonists inhibit disease severity and spasticity in animal models for multiple sclerosis (Baker et al., Cannabinoids control spasticity and tremor in a multiple sclerosis model. Nature (2000) 404:84-87. Arevalo-Martin et al., Therapeutic action of cannabinoids in a murine model of multiple sclerosis J Neurosci. (2003) 23:2511-2516.). Taken together, these results support the notion that CB2 receptor modulators can be employed for the treatment of medical conditions having an inflammatory component.

In addition to inflammation, CB2 agonists have been shown to inhibit pain and emesis. For instance, CB2 selective agonists blunt the pain response induced by thermal or other stimuli (Malan et al., CB2 cannabinoid receptor-mediated peripheral antinociception. Pain. (2001) 93:239-45 and Nackley et al., Selective activation of cannabinoid CB(2) receptors suppresses spinal fos protein expression and pain behavior in a rat model of inflammation. Neuroscience (2003) 119:747-57.) CB2 activation has also been demonstrated to inhibit neuropathic pain response (Ibrahim et al., Activation of CB2 cannabinoid receptors by AM1241 inhibits experimental neuropathic pain: pain inhibition by receptors not present in the CNS. Proc Natl Acad Sci USA. (2003) 100: 10529-33.) Finally, in contrast to the earlier data which did not find CB2 in the brain, a recent article demonstrated the expression of CB2 in the brain, at about 1.5% of the level in the spleen. CB2 activation is shown by this article to be responsible for the anti-emetic effect of endocannabinoid (Van Sickle et al., Identification and functional characterization of brainstem cannabinoid CB2 receptors. Science. 2005 310:329-332.) The foregoing results confirm that CB2 agonists can be used for the treatment of inflammatory and neuropathic pain as well as emesis.

BRIEF SUMMARY OF THE INVENTION

The present invention provides novel compounds which bind to and modulate the CB2 receptor. The invention also provides a method and pharmaceutical compositions for treating inflammation by way of the administration of therapeutic amounts of these compounds. Lastly, the invention provides a method and pharmaceutical compositions for treating pain by way of the administration of therapeutic amounts of the new compounds which are CB2 agonists.

DETAILED DESCRIPTION OF THE INVENTION

In one generic aspect of the invention there is provided a compound of the formula (I)

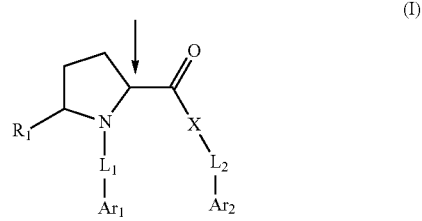

X is NH or N;

$Ar_1$ is chosen from carbocycle, heterocyclyl and heteroaryl each optionally substituted by 1-3 $C_{1-10}$ alkyl, $C_{1-10}$ alkoxy, CN, halogen, $NO_2$, $—S(O)_m—C_{1-10}$ alkyl, $—CO_2—C_{1-10}$ alkyl, $—NH(C_{1-5}$ alkyl)-$CO_2—C_{1-10}$ alkyl, $—C(O)—NH$ (C$_{1-5}$ alkyl), —C(O)—N(C$_{1-5}$ alkyl)$_2$, —NH(C$_{1-5}$ alkyl), —N(C$_{1-5}$ alkyl)-C(O)—C$_{1-10}$ alkyl, —N(C$_{1-5}$ alkyl)-S(O)$_m$—C$_{1-10}$ alkyl and heterocyclyl;

Ar$_2$ is chosen from carbocycle, heterocyclyl and heteroaryl each optionally substituted by 1-3 C$_{1-10}$ alkylcarbocycle, heteroaryl, CN, halogen, C$_{1-10}$ acyl, hydroxyl or oxo (=O), wherein the C$_{1-10}$ alkyl and carbocycle may be optionally substituted by hydroxyl, C$_{1-5}$ alkoxycarbonyl or C$_{1-5}$ alkoxy;

L$_1$ and L$_2$ are each independently chosen from a bond or C$_{1-10}$ alkyl chain wherein each —CH$_2$— of said chain is optionally replaced by —O—, S(O)$_m$ or —NH—;

wherein each L$_1$ and L$_2$ where possible is optionally substituted by halogen or C$_{1-3}$ alkyl;

R$_1$ is chosen from oxo (=O) and OH;

m is 0, 1 or 2;

wherein each Ar$_1$ and Ar$_2$, or the substituents thereof are optionally partially or fully halogenated;

and wherein if X is N it can cyclize to form a 5-7 membered heterocyclic ring;

or a pharmaceutically acceptable salt thereof.

The compound according to the embodiment described immediately above and wherein:

X is NH;

Ar$_1$ is chosen from phenyl, C$_{3-6}$ cycloalkyl, benzoxazolyl, benzothiazolyl, benzimidazolyl, dioxanyl, tetrahydrofuranyl, oxazolyl, isoxazolyl, thiazolyl, pyrazolyl, pyrrolyl, imidazolyl, thienyl, thiadiazolyl, triazolyl, thiomorpholinyl, 1,1-Dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, Dihydro-2H-quinolinyl, isoquinolinyl, quinazolinyl, indazolyl, indolyl, isoindolyl, benzofuranyl, benzopyranyl and benzodioxolyl each optionally substituted by 1-3 C$_{1-6}$ alkyl, C$_{1-6}$ alkoxy, CN, halogen, NO$_2$, —S(O)$_2$—C$_{1-3}$ alkyl, —CO$_2$—C$_{1-4}$ alkyl, —NH(C$_{1-3}$ alkyl)-CO$_2$—C$_{1-4}$ alkyl, —C(O)—NH(C$_{1-3}$ alkyl), —C(O)—N(C$_{1-3}$ alkyl)$_2$, —NH(C$_{1-3}$ alkyl), —N(C$_{1-3}$ alkyl)-C(O)—C$_{1-4}$ alkyl, —N(C$_{1-3}$ alkyl)-S(O)$_2$—C$_{1-3}$ alkyl, morpholinyl or piperazinyl;

Ar$_2$ is chosen from cyclohexyl, cyclohexenyl, phenyl, benzoxazolyl, benzothiazolyl, benzimidazolyl, tetrahydropyranyl, dioxanyl, tetrahydrofuranyl, oxazolyl, isoxazolyl, thiazolyl, pyrazolyl, pyrrolyl, imidazolyl, thienyl, thiadiazolyl, triazolyl, thiomorpholinyl, 1,1-Dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, Dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, [1,2,4]triazolo[1,5-a]pyrimidinyl and furazanyl each optionally substituted by 1-3 C$_{1-6}$ alkyl, cyclopropyl, cyclohexyl, phenyl, CN, halogen, pyrimidinyl, acetyl or oxo (=O);

R$_1$ is oxo (=O);

L$_1$ is a bond;

L$_2$ is chosen from a bond, —CH$_2$— and —CH$_2$—CH$_2$—;

wherein L$_2$ where possible is optionally substituted by halogen or C$_{1-3}$ alkyl.

The compound according to the embodiment described immediately above and wherein:

Ar$_1$ is chosen from phenyl, thienyl, pyridinyl, pyrimidinyl, pyrazine, triazine, and C$_{3-6}$ cycloalkyl each optionally substituted by 1-3 C$_{1-6}$ alkyl, C$_{1-6}$ alkoxy, CN, halogen, NO$_2$, —S(O)$_2$—C$_{1-3}$ alkyl, —CO$_2$—C$_{1-4}$ alkyl, —NH(C$_{1-3}$ alkyl)-CO$_2$—C$_{1-4}$ alkyl, —C(O)—NH(C$_{1-3}$ alkyl), —C(O)—N(C$_{1-3}$ alkyl)$_2$, —NH(C$_{1-3}$ alkyl), —N(C$_{1-3}$ alkyl)-C(O)—C$_{1-4}$ alkyl, —N(C$_{1-3}$ alkyl)-S(O)$_2$—C$_{1-3}$ alkyl, morpholinyl or piperazinyl;

Ar$_2$ is chosen from cyclohexyl, cyclohexenyl, phenyl, oxazolyl, isoxazolyl, thiadiazolyl, pyrazolyl, triazolyl, thiazolyl, tetrahydropyranyl, piperadinyl, piperazinyl, pyridinyl, benzimidazolyl, benzothiazolyl, benzoxazolyl, [1,2,4]triazolo[1,5-a]pyrimidinyl, furazanyl and 1,1-Dioxo-1$\lambda^6$-thiomorpholine each optionally substituted by 1-3 C$_{1-5}$ alkyl, cyclopropyl, cyclohexyl, phenyl, CN, halogen, pyrimidinyl, acetyl or oxo (=O);

L$_2$ is chosen from a bond and —CH$_2$—.

The compound according to the embodiment described immediately above and wherein:

Ar$_1$ is chosen from pyridinyl, phenyl and thienyl each optionally substituted by 1-3 C$_{1-6}$ alkyl, C$_{1-6}$ alkoxy, CN, halogen, NO$_2$, —S(O)$_2$—C$_{1-3}$ alkyl, —CO$_2$—C$_{1-4}$ alkyl, —NH(C$_{1-3}$ alkyl)-CO$_2$—C$_{1-4}$ alkyl, —C(O)—NH(C$_{1-3}$ alkyl), —C(O)—N(C$_{1-3}$ alkyl)$_2$, —NH(C$_{1-3}$ alkyl), —N(C$_{1-3}$ alkyl)-C(O)—C$_{1-4}$ alkyl or —N(C$_{1-3}$ alkyl)-S(O)$_2$—C$_{1-3}$ alkyl;

Ar$_2$ is chosen from isoxazolyl optionally substituted by 1-3 C$_{1-5}$ alkyl and cyclopropyl.

The compound according to the embodiment described immediately above and wherein:

Ar$_2$ is chosen from

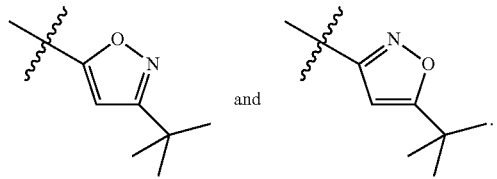

In another embodiment of the invention, for any of the above mentioned embodiments of the formula (I), the stereogenic carbon indicated with an arrow is in the (S) configuration.

In another generic aspect of the invention there is provided a compound of the formula (II)

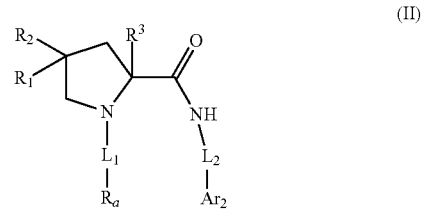

(II)

wherein

R$_a$ is chosen from C$_{1-6}$ alkyl and Ar$_1$, each R$_a$ is optionally substituted by 1-3 C$_{1-10}$ alkyl, C$_{1-10}$ alkoxy, CN, halogen, NO$_2$, —S(O)$_m$—C$_{1-10}$ alkyl, —CO$_2$—C$_{1-10}$ alkyl, —NH(C$_{1-5}$ alkyl)-CO$_2$—C$_{1-10}$ alkyl, —C(O)—NH(C$_{1-5}$ alkyl), —C(O)—N(C$_{1-5}$ alkyl)$_2$, —NH(C$_{1-5}$ alkyl), —N(C$_{1-5}$ alkyl)-C(O)—C$_{1-10}$ alkyl, —N(C$_{1-5}$ alkyl)-S(O)$_m$—C$_{1-10}$ alkyl and heterocyclyl the heterocyclyl being further optionally substituted by C$_{1-5}$ alkyl;

Ar$_1$ is chosen from carbocycle, heterocyclyl and heteroaryl;

Ar$_2$ is chosen from C$_{1-6}$ alkyl, carbocycle, heterocyclyl and heteroaryl each optionally substituted by 1-3 C$_{1-10}$ alkyl, carbocycle, heteroaryl, CN, halogen, C$_{1-10}$ acyl or oxo (=O), wherein the C$_{1-6}$ alkyl and carbocycle may be optionally substituted by hydroxyl, C$_{1-5}$ alkoxycarbonyl or C$_{1-5}$ alkoxy;

$L_1$ and $L_2$ are each independently chosen from a bond or $C_{1-10}$ alkyl chain wherein each —$CH_2$— of said chain is optionally replaced by —O—, C(O), S(O)$_m$ or —NH—;

wherein each $L_1$ and $L_2$ where possible is optionally substituted by halogen or $C_{1-3}$ alkyl;

$R_1$ is chosen from hydrogen and halogen;

$R_2$ is chosen from hydrogen, halogen and OH;

or $R_1$ and $R_2$ combined are oxo (=O);

$R_3$ is hydrogen or $C_{1-3}$ alkyl;

m is 0, 1 or 2;

wherein each $R_a$, $Ar_2$, $L_1$, $L_2$ or $R_3$ or the substituents thereof are optionally partially or fully halogenated;

or a pharmaceutically acceptable salt thereof.

The compound according to the embodiment described immediately above and wherein:

i) $L_1$ is chosen from a bond or —$CH_2$—;

$R_a$ is tetrahydropyranyl;

$Ar_2$ is chosen from $C_{1-5}$ alkyl, cyclohexyl, cyclohexenyl, phenyl, benzoxazolyl, benzothiazolyl, benzimidazolyl, tetrahydropyranyl, dioxanyl, tetrahydrofuranyl, oxazolyl, isoxazolyl, thiazolyl, pyrazolyl, pyrrolyl, imidazolyl, thienyl, thiadiazolyl, triazolyl, thiomorpholinyl, 1,1-Dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, Dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, [1,2,4]triazolo[1,5-a]pyrimidinyl and furazanyl each optionally substituted by 1-3 $C_{1-5}$ alkyl, cyclopropyl, cyclohexyl, phenyl, CN, halogen, pyrimidinyl, acetyl o r oxo (=O) wherein the $Ar_2$ substituents $C_{1-5}$ alkyl, cyclopropyl, cyclohexyl and phenyl, may be optionally substituted by hydroxyl, $C_{1-5}$ alkoxycarbonyl or $C_{1-5}$ alkoxy;

or ii) $L_2$ is a bond;

$Ar_2$ is chosen from isoxazolyl and thiadiazolyl each optionally substituted by 1-3 $C_{1-3}$ alkyl, cyclopropyl, cyclohexyl, phenyl, CN, halogen, pyrimidinyl, acetyl or oxo (=O);

$R_a$ is chosen from $C_{1-5}$ alkyl, phenyl, $C_{3-6}$ cycloalkyl, benzoxazolyl, benzothiazolyl, benzimidazolyl, tetrahydropyranyl, dioxanyl, tetrahydrofuranyl, oxazolyl, isoxazolyl, thiazolyl, pyrazolyl, pyrrolyl, imidazolyl, thienyl, thiadiazolyl, triazolyl, thiomorpholinyl, 1,1-Dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, Dihydro-2H-quinolinyl, isoquinolinyl, quinazolinyl, indazolyl, indolyl, isoindolyl, benzofuranyl, benzopyranyl and benzodioxolyl each optionally substituted by 1-3 $C_{1-6}$ alkyl, $C_{1-6}$ alkoxy, CN, halogen, NO$_2$, —S(O)$_2$—$C_{1-3}$ alkyl, —CO$_2$—$C_{1-4}$ alkyl, —NH($C_{1-3}$ alkyl), -, morpholinyl or piperazinyl each being further optionally substituted by $C_{1-3}$ alkyl.

The compound according to the embodiment described immediately above and wherein:

i) $Ar_2$ is chosen from $C_{1-5}$ alkyl, cyclohexyl, cyclohexenyl, phenyl, oxazolyl, isoxazolyl, thiadiazolyl, pyrazolyl, triazolyl, thiazolyl, tetrahydropyranyl, piperadinyl, piperazinyl, pyridinyl, benzimidazolyl, benzothiazolyl, benzoxazolyl, [1,2,4]triazolo[1,5-a]pyrimidinyl, furazanyl and each optionally substituted by 1-3 $C_{1-5}$ alkyl, cyclopropyl, cyclohexyl, phenyl, CN, halogen, pyrimidinyl, acetyl or oxo (=O), wherein the $Ar_2$ substituents $C_{1-5}$ alkyl, cyclopropyl, cyclohexyl and phenyl, may be optionally substituted by hydroxyl, $C_{1-5}$ alkoxycarbonyl or $C_{1-5}$ alkoxy;

ii) $R_a$ is chosen from $C_1$ alkyl, phenyl, tetrahydropyranyl, tetrahydrofuranyl, thienyl, pyridinyl, pyrimidinyl, 1,1-Dioxo-1$\lambda^6$-thiomorpholine, morpholinyl and $C_{3-6}$ cycloalkyl each optionally substituted by 1-3 $C_{1-6}$ alkyl, $C_{1-6}$ alkoxy, CN, halogen, —S(O)$_2$—$C_{1-3}$ alkyl, —CO$_2$—$C_{1-4}$ alkyl, —NH($C_{1-3}$ alkyl), morpholinyl or piperazinyl each being further optionally substituted by $C_{1-2}$ alkyl.

In another embodiment of the invention, for any of the above mentioned embodiments of the formula (II), the stereogenic carbon indicated with an arrow is in the (S) configuration.

In another embodiment of the invention, for any of the above mentioned embodiments of the formula (II), the stereogenic carbon indicated with an arrow is in the (R) configuration.

In another generic aspect of the invention there is provided a compound of the formula (III)

(III)

wherein 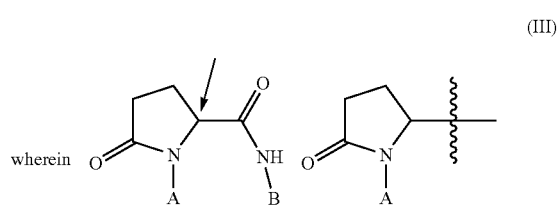

of the formula (III) is chosen from A1-A56 of Table I, and

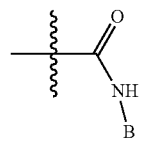

of the formula (III) is chosen from B1-B37 of Table I,

TABLE I

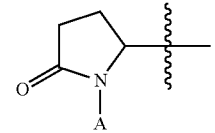

| | |
|---|---|
| A1 | 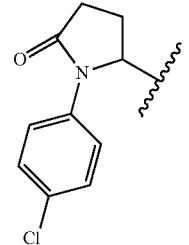 [SMILES: *C1CCC(=O)N1c1ccc(Cl)cc1] |
| A2 | 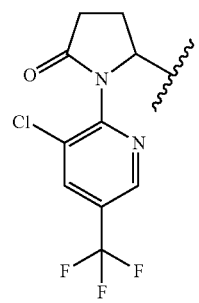 [SMILES: *C1CCC(=O)N1c1ncc(C(F)(F)F)cc1Cl] |

TABLE I-continued
| | |
|---|---|
| A3 | 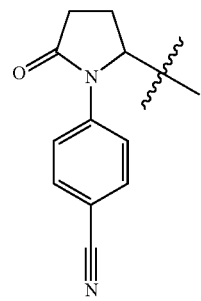 [SMILES: *C1CCC(=O)N1c1ccc(C#N)cc1] |
| A4 | 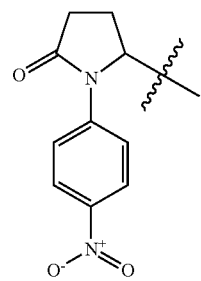 [SMILES: *C1CCC(=O)N1c1ccc([N+](=O)[O-])cc1] |
| A5 | 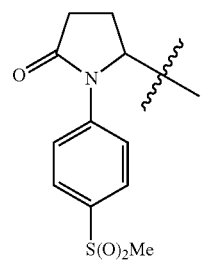 |
| A6 | 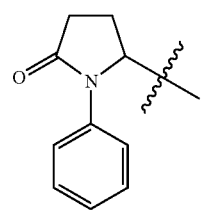 [SMILES: *C1CCC(=O)N1c1ccccc1] |
| A7 | 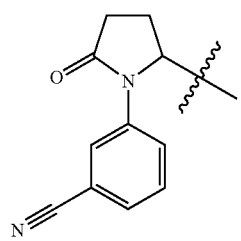 [SMILES: *C1CCC(=O)N1c1cccc(C#N)c1] |
| A8 | 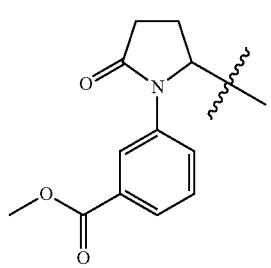 [SMILES: *C1CCC(=O)N1c1cccc(C(=O)OC)c1] |
| A9 | 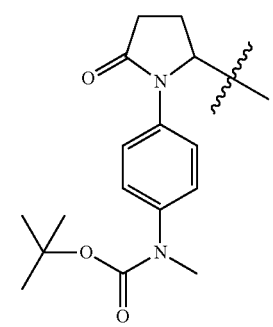 [SMILES: *C1CCC(=O)N1c1ccc(N(C)C(=O)OC(C)(C)C)cc1] |
| A10 | 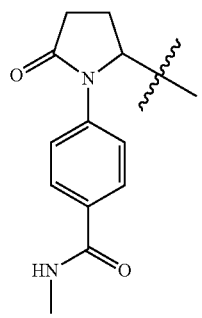 [SMILES: *C1CCC(=O)N1c1ccc(C(=O)NC)cc1] |
| A11 | 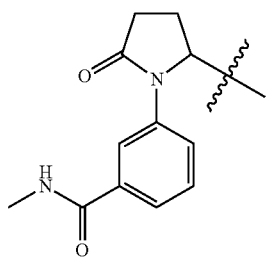 [SMILES: *C1CCC(=O)N1c1cccc(C(=O)NC)c1] |
| A12 | 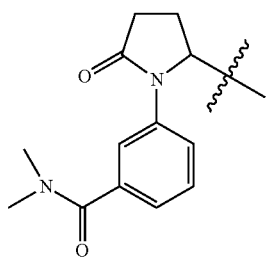 [SMILES: *C1CCC(=O)N1c1cccc(C(=O)N(C)C)c1] |
| A13 | 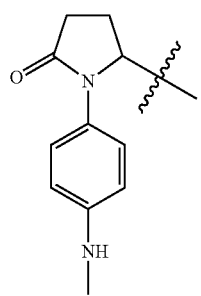 [SMILES: *C1CCC(=O)N1c1ccc(NC)cc1] |

TABLE I-continued
A14 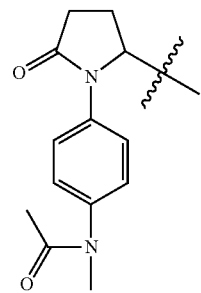 [SMILES: *C1CCC(=O)N1c1ccc(N(C)C(C)=O)cc1]
A15 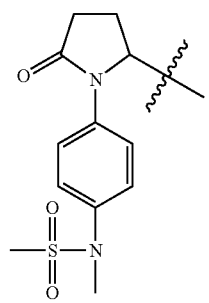 [SMILES: *C1CCC(=O)N1c1ccc(N(C)S(C)(=O)=O)cc1]
A16 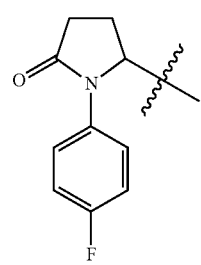 [SMILES: *C1CCC(=O)N1c1ccc(F)cc1]
A17 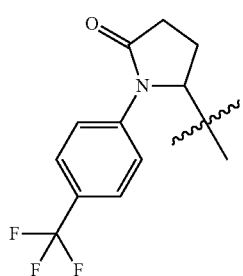 [SMILES: *C1CCC(=O)N1c1ccc(C(F)(F)F)cc1]
A18 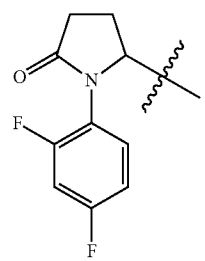 [SMILES: *C1CCC(=O)N1c1ccc(F)cc1F]
A19 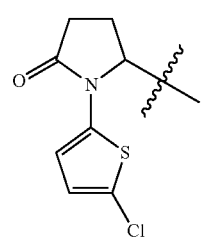 [SMILES: *C1CCC(=O)N1c1ccc(Cl)s1]
A20 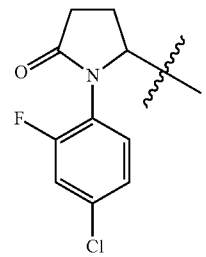
A21 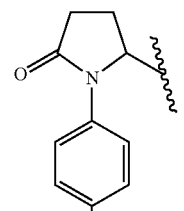
A22 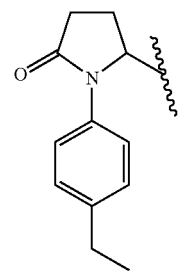 [SMILES: *C1CCC(=O)N1c1ccc(CC)cc1]
A23 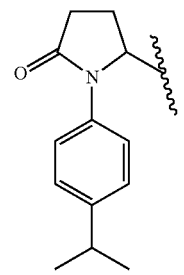 [SMILES: *C1CCC(=O)N1c1ccc(C(C)C)cc1]
A24 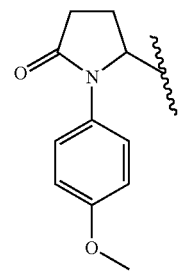 [SMILES: *C1CCC(=O)N1c1ccc(OC)cc1]
A25 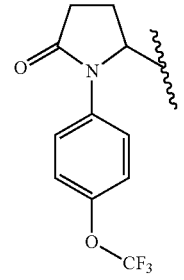 [SMILES: *C1CCC(=O)N1c1ccc(OC(F)(F)F)cc1]

TABLE I-continued
| | | | | |
|---|---|---|---|---|
| A26 | 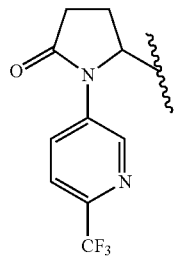 [SMILES: *C1CCC(=O)N1c1ccc(C(F)(F)F)nc1] | | A32 | 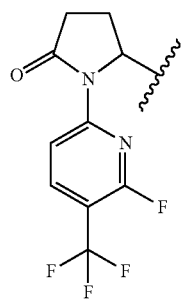 |
| A27 | 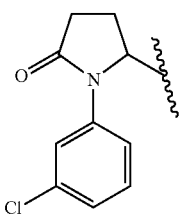 [SMILES: *C1CCC(=O)N1c1cccc(Cl)c1] | | A33 | 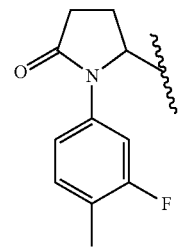 |
| A28 | 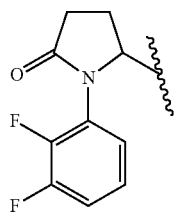 [SMILES: *C1CCC(=O)N1c1cccc(F)c1F] | | A34 | 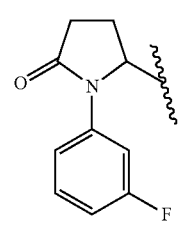 |
| A29 | 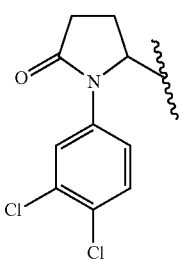 [SMILES: *C1CCC(=O)N1c1ccc(Cl)c(Cl)c1] | | A35 | 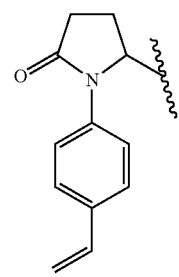 |
| A30 | 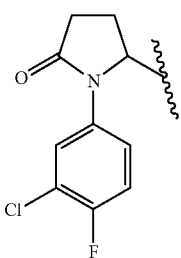 [SMILES: *C1CCC(=O)N1c1ccc(F)c(Cl)c1] | | A36 | 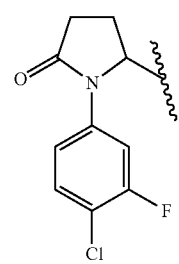 [SMILES: *C1CCC(=O)N1c1ccc(Cl)c(F)c1] |
| A31 | 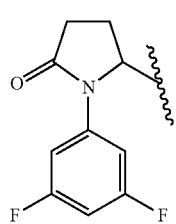 | | A37 | 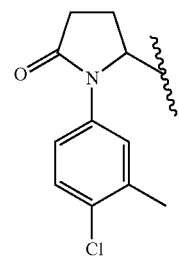 [SMILES: *C1CCC(=O)N1c1ccc(Cl)c(C)c1] |

TABLE I-continued
| | | |
|---|---|---|
| A38 | 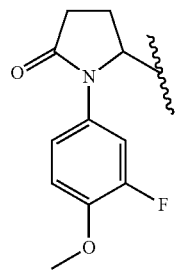 [SMILES: *C1CCC(=O)N1c1ccc(OC)c(F)c1] | |
| A39 | 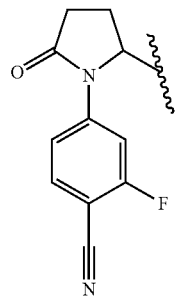 [SMILES: *C1CCC(=O)N1c1ccc(C#N)c(F)c1] | |
| A40 | 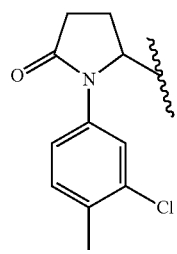 | |
| A41 | 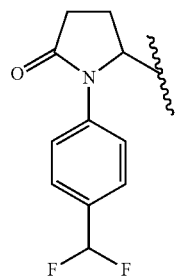 [SMILES: *C1CCC(=O)N1c1ccc(C(F)F)cc1] | |
| A42 | 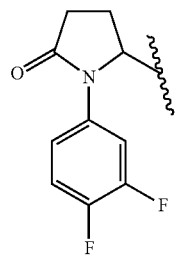 [SMILES: *C1CCC(=O)N1c1ccc(F)c(F)c1] | |
| A43 | 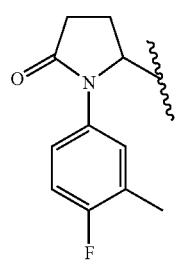 | |
| A44 | 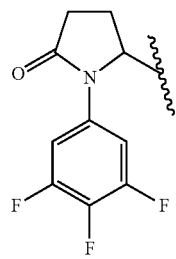 | |
| A45 | 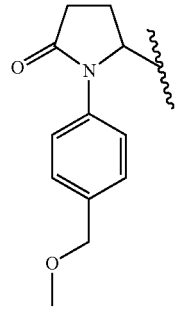 [SMILES: *C1CCC(=O)N1c1ccc(COC)cc1] | |
| A46 | 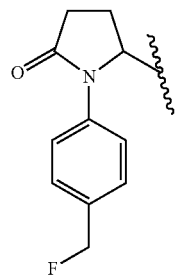 [SMILES: *C1CCC(=O)N1c1ccc(CF)cc1] | |
| A47 | 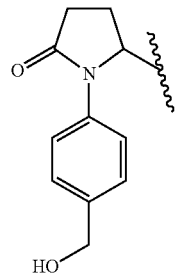 [SMILES: *C1CCC(=O)N1c1ccc(CO)cc1] | |
| A48 | 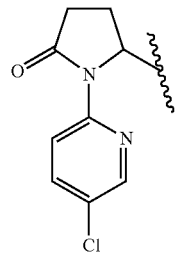 [SMILES: *C1CCC(=O)N1c1ccc(Cl)cn1] | |

TABLE I-continued
| | | | | |
|---|---|---|---|---|
| A49 | 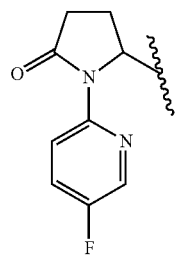 [SMILES: *C1CCC(=O)N1c1ccc(F)cn1] | | A55 | 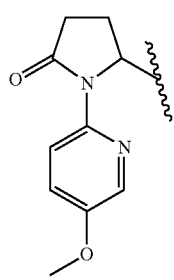 |
| A50 | 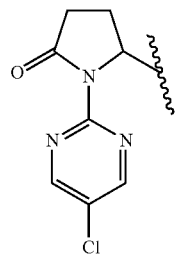 | | A56 | 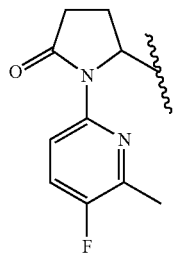 |
| A51 | 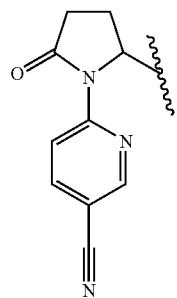 [SMILES: *C1CCC(=O)N1c1ccc(C#N)cn1] | | | 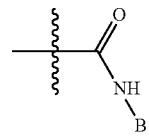 |
| A52 | 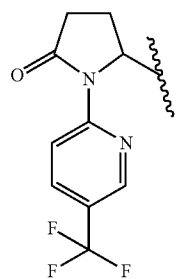 [SMILES: *C1CCC(=O)N1c1ccc(C(F)(F)F)cn1] | | B1 | 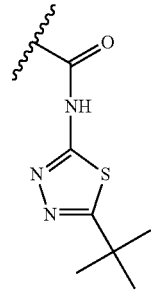 |
| A53 | 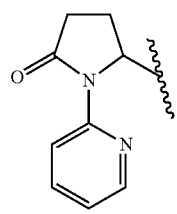 [SMILES: *C1CCC(=O)N1c1ccccn1] | | B2 | 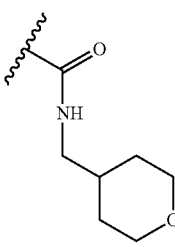 |
| A54 | 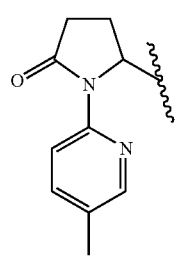 [SMILES: *C1CCC(=O)N1c1ccc(C)cn1] | | B3 | |

TABLE I-continued
| | |
|---|---|
| B4 | 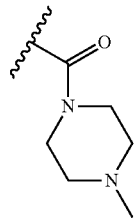 [SMILES: *C(=O)N1CCN(C)CC1] |
| B5 | 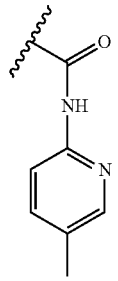 |
| B6 | 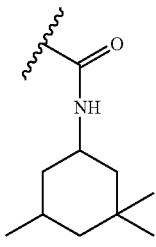 |
| B7 | 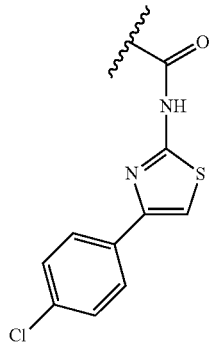 [SMILES: *C(=O)Nc1nc(-c2ccc(Cl)cc2)cs1] |
| B8 | 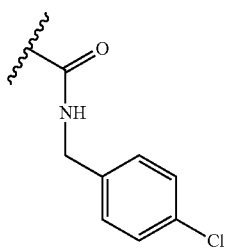 [SMILES: *C(=O)NCc1ccc(Cl)cc1] |
| B9 | 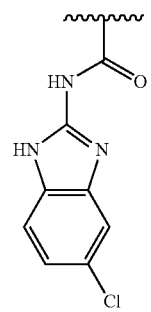 [SMILES: *C(=O)Nc1nc2cc(Cl)ccc2[nH]1] |
| B10 | 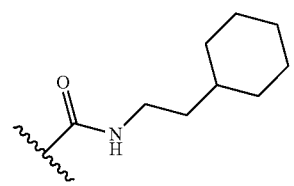 [SMILES: *C(=O)NCCC1CCCCC1] |
| B11 | 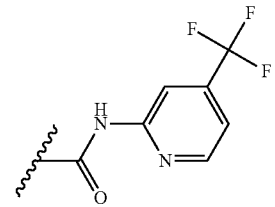 [SMILES: *C(=O)Nc1cc(C(F)(F)F)ccn1] |
| B12 | 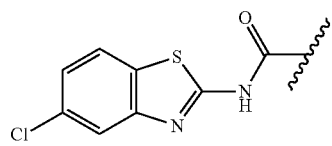 [SMILES: *C(=O)Nc1nc2cc(Cl)ccc2s1] |
| B13 | 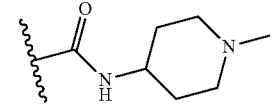 [SMILES: *C(=O)NC1CCN(C)CC1] |
| B14 | 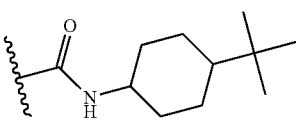 [SMILES: *C(=O)NC1CCC(C(C)(C)C)CC1] |
| B15 | 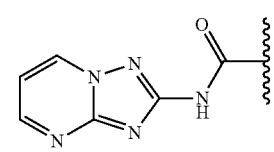 [SMILES: *C(=O)Nc1nc2ncccn2n1] |
| B16 | 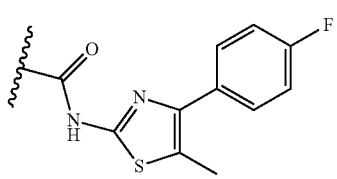 [SMILES: *C(=O)Nc1nc(-c2ccc(F)cc2)c(C)s1] |
| B17 | 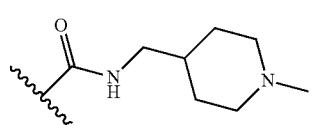 [SMILES: *C(=O)NCC1CCN(C)CC1] |

TABLE I-continued
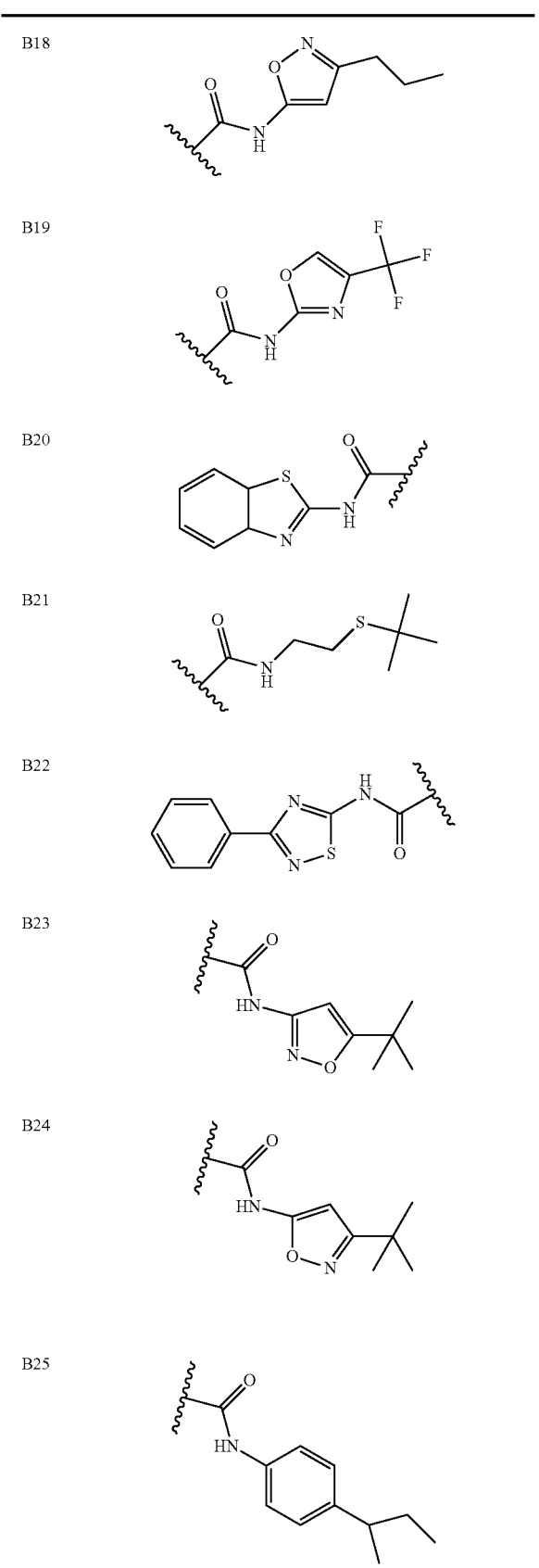
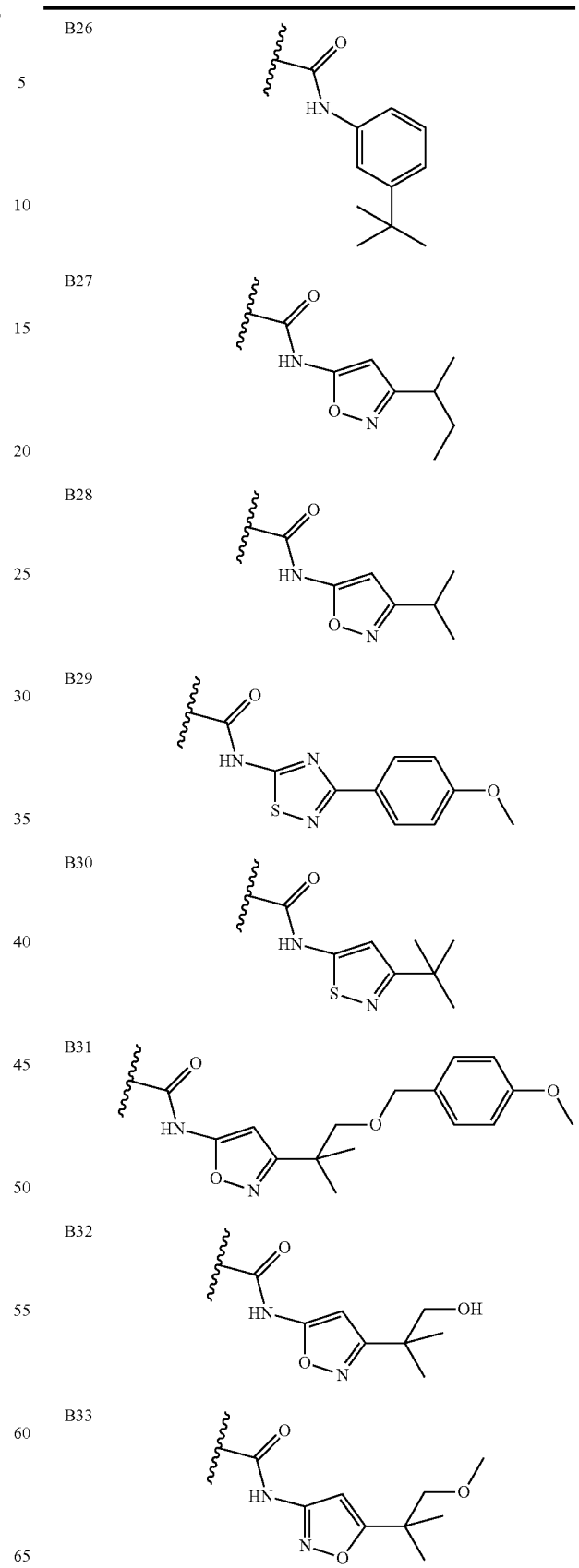

TABLE I-continued

B34 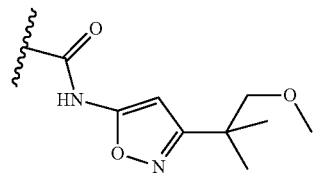 [SMILES: *C(=O)Nc1cc(C(C)(C)COC)no1]

B35 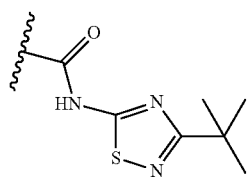 [SMILES: *C(=O)Nc1nc(C(C)(C)C)ns1]

B36 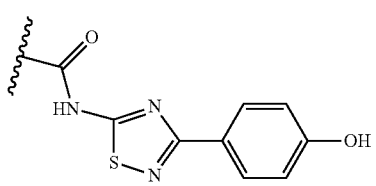 [SMILES: *C(=O)Nc1nc(-c2ccc(O)cc2)ns1]

B37 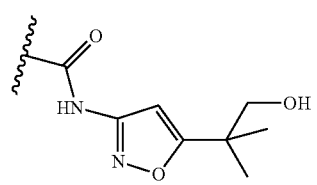 [SMILES: *C(=O)Nc1cc(C(C)(C)CO)on1]

or a pharmaceutically acceptable salt thereof.

In another embodiment of the invention, the stereogenic carbon indicated with an arrow formula (III) is in the (S) configuration.

In another generic aspect of the invention there is provided a compound of the formula (IV)

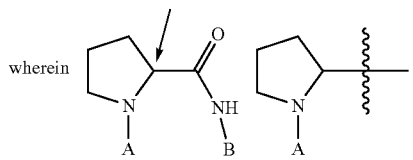 (IV)

wherein of the formula (IV) is chosen from A1-A72 of Table II, and

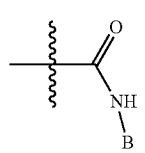

of the formula (IV) is chosen from B1-B55 of Table II,

TABLE II

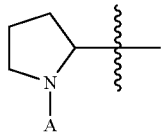

| | |
|---|---|
| A1 | 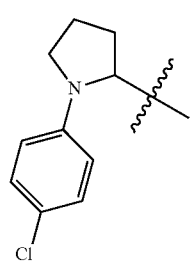 [SMILES: *C1CCCN1c1ccc(Cl)cc1] |
| A2 | 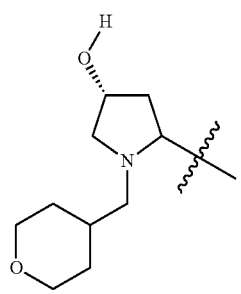 [SMILES: *C1C[C@@H](O)CN1CC1CCOCC1] |
| A3 | 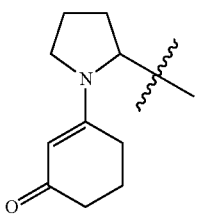 [SMILES: *C1CCCN1C1=CC(=O)CCC1] |
| A4 | 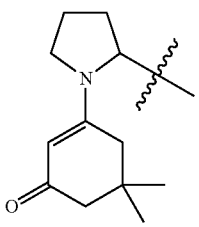 [SMILES: *C1CCCN1C1=CC(=O)CC(C)(C)C1] |
| A5 | 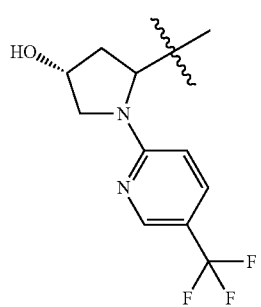 [SMILES: *C1C[C@@H](O)CN1c1ccc(C(F)(F)F)cn1] |

TABLE II-continued
| | |
|---|---|
| A6 | 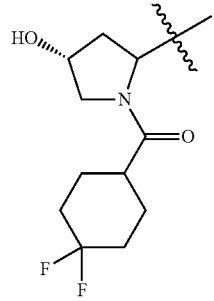 [SMILES: *C1C[C@@H](O)CN1C(=O)C1CCC(F)(F)CC1] |
| A7 | 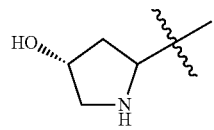 [SMILES: *C1C[C@@H](O)CN1] |
| A8 | 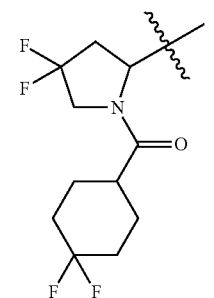 [SMILES: *C1CC(F)(F)CN1C(=O)C1CCC(F)(F)CC1] |
| A9 | 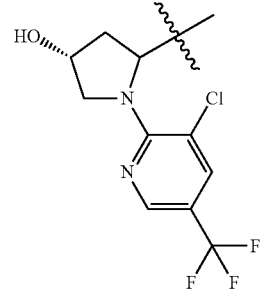 [SMILES: *C1C[C@@H](O)CN1c1ncc(C(F)(F)F)cc1Cl] |
| A10 | 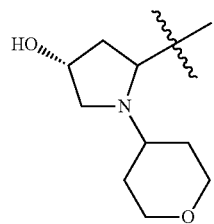 [SMILES: *C1C[C@@H](O)CN1C1CCOCC1] |
| A11 | 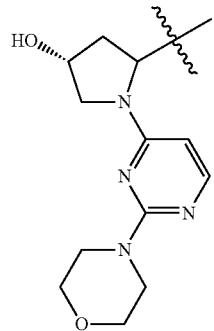 [SMILES: *C1C[C@@H](O)CN1c1ccnc(N2CCOCC2)n1] |
TABLE II-continued
| | |
|---|---|
| A12 | 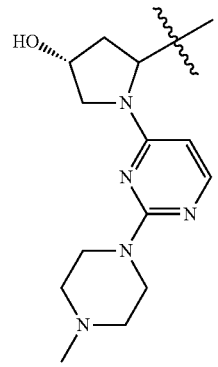 [SMILES: *C1C[C@@H](O)CN1c1ccnc(N2CCN(C)CC2)n1] |
| A13 | 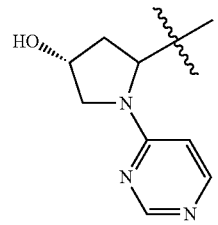 [SMILES: *C1C[C@@H](O)CN1c1ccncn1] |
| A14 | 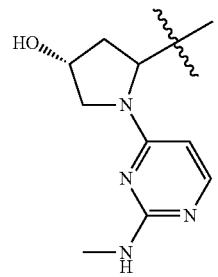 [SMILES: *C1C[C@@H](O)CN1c1ccnc(NC)n1] |
| A15 | 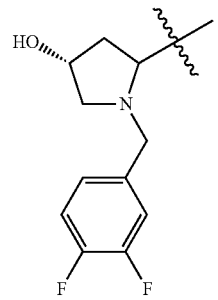 [SMILES: *C1C[C@@H](O)CN1Cc1ccc(F)c(F)c1] |
| A16 | 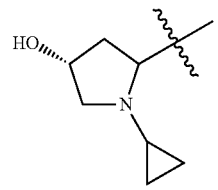 [SMILES: *C1C[C@@H](O)CN1C1CC1] |
| A17 | 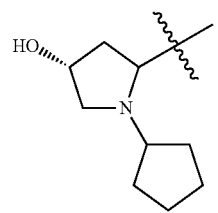 [SMILES: *C1C[C@@H](O)CN1C1CCCC1] |

TABLE II-continued
| A18 | 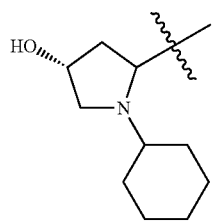 [SMILES: *C1C[C@@H](O)CN1C1CCCCC1] |
| --- | --- |
| A19 | 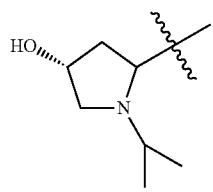 [SMILES: *C1C[C@@H](O)CN1C(C)C] |
| A20 | 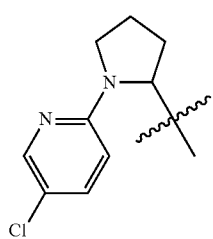 [SMILES: *C1CCCN1c1ccc(Cl)cn1] |
| A21 | 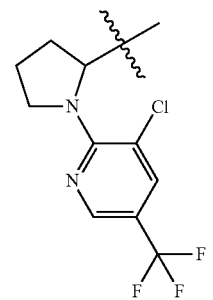 [SMILES: *C1CCCN1c1ncc(C(F)(F)F)cc1Cl] |
| A22 | 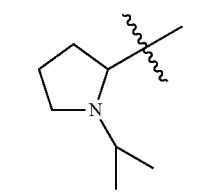 [SMILES: *C1CCCN1C(C)C] |
| A23 | 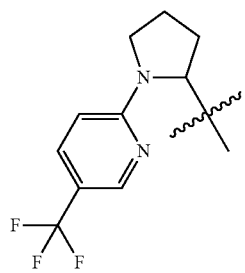 [SMILES: *C1CCCN1c1ccc(C(F)(F)F)cn1] |
| A24 | 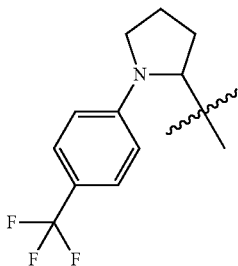 [SMILES: *C1CCCN1c1ccc(C(F)(F)F)cc1] |
| A25 | 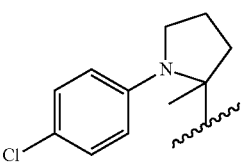 [SMILES: *C1(C)CCCN1c1ccc(Cl)cc1] |
| A26 | 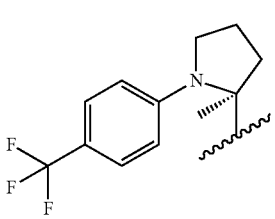 [SMILES: *[C@]1(C)CCCN1c1ccc(C(F)(F)F)cc1] |
| A27 | 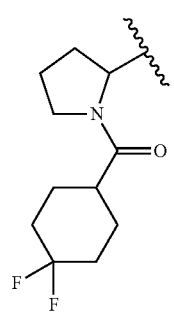 [SMILES: *C1CCCN1C(=O)C1CCC(F)(F)CC1] |
| A28 | 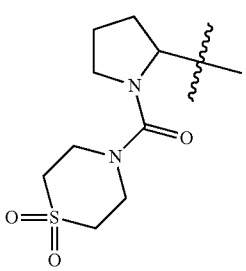 [SMILES: *C1CCCN1C(=O)N1CCS(=O)(=O)CC1] |
| A29 | 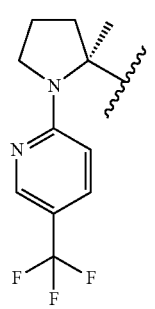 [SMILES: *[C@]1(C)CCCN1c1ccc(C(F)(F)F)cn1] |

TABLE II-continued
| | |
|---|---|
| A30 | 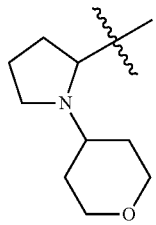 [SMILES: *C1CCCN1C1CCOCC1] |
| A31 | 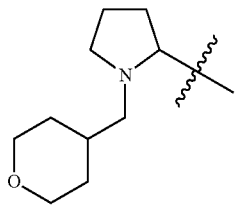 [SMILES: *C1CCCN1CC1CCOCC1] |
| A32 | 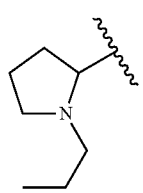 [SMILES: *C1CCCN1CCC] |
| A33 | 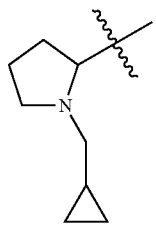 [SMILES: *C1CCCN1CC1CC1] |
| A34 | 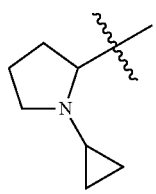 [SMILES: *C1CCCN1C1CC1] |
| A35 | 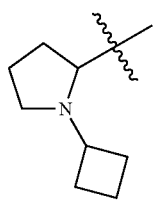 [SMILES: *C1CCCN1C1CCC1] |
| A36 | 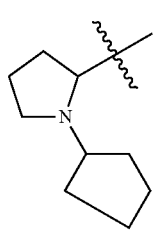 [SMILES: *C1CCCN1C1CCCC1] |
| A37 | 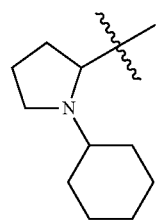 [SMILES: *C1CCCN1C1CCCCC1] |
| A38 | 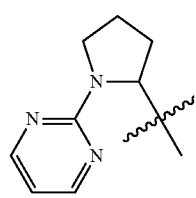 [SMILES: *C1CCCN1c1ncccn1] |
| A39 | 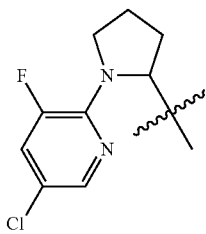 [SMILES: *C1CCCN1c1ncc(Cl)cc1F] |
| A40 | 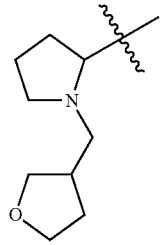 [SMILES: *C1CCCN1CC1CCOC1] |
| A41 | 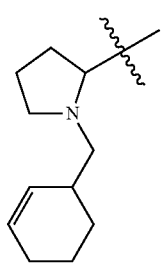 [SMILES: *C1CCCN1CC1C=CCCC1] |
| A42 | 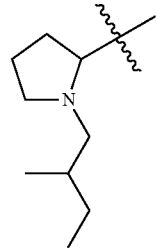 [SMILES: *C1CCCN1CC(C)CC] |

TABLE II-continued
A43 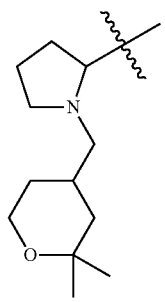 [SMILES: *C1CCCN1CC1CCOC(C)(C)C1]
A44 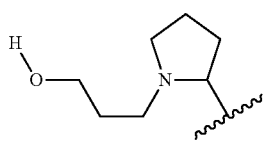
A45 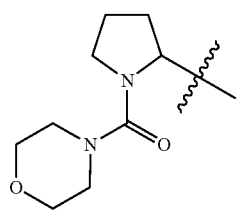 [SMILES: *C1CCCN1C(=O)N1CCOCC1]
A46 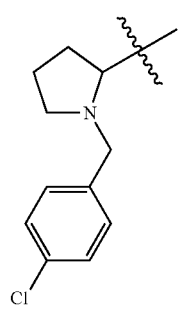 [SMILES: *C1CCCN1Cc1ccc(Cl)cc1]
A47 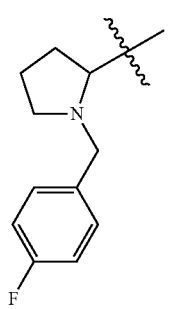 [SMILES: *C1CCCN1Cc1ccc(F)cc1]
A48 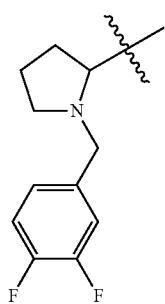 [SMILES: *C1CCCN1Cc1ccc(F)c(F)c1]
A49 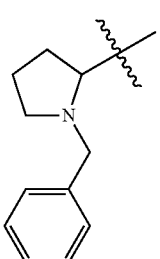
A50 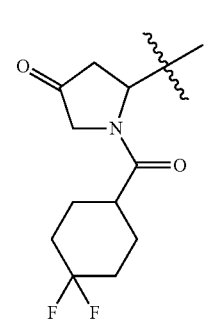 [SMILES: *C1CC(=O)CN1C(=O)C1CCC(F)(F)CC1]
A51 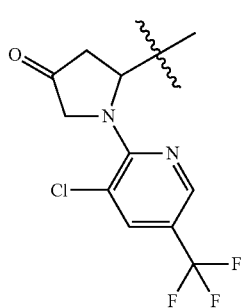 [SMILES: *C1CC(=O)CN1c1ncc(C(F)(F)F)cc1Cl]
A52 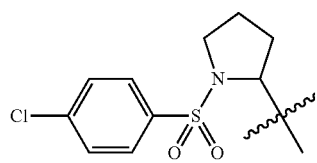 [SMILES: *C1CCCN1S(=O)(=O)c1ccc(Cl)cc1]
A53 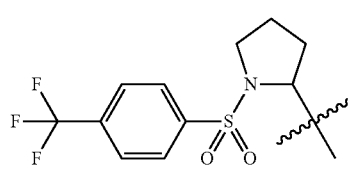 [SMILES: *C1CCCN1S(=O)(=O)c1ccc(C(F)(F)F)cc1]
A54 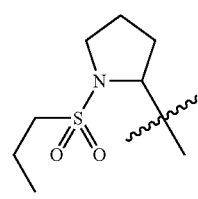 [SMILES: *C1CCCN1S(=O)(=O)CCC]

TABLE II-continued
| | | | | |
|---|---|---|---|---|
| A55 | 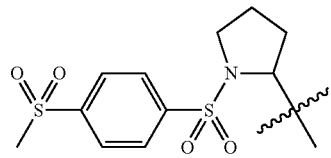 [SMILES: *C1CCCN1S(=O)(=O)c1ccc(S(C)(=O)=O)cc1] | | A63 | 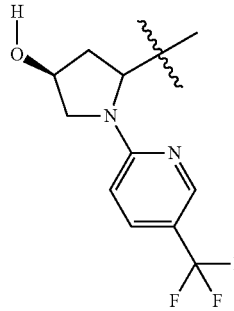 |
| A56 | 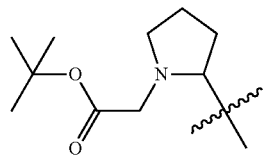 [SMILES: *C1CCCN1CC(=O)OC(C)(C)C] | | | |
| A57 | 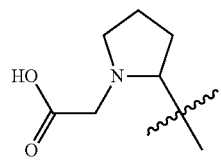 [SMILES: *C1CCCN1CC(=O)O] | | A64 | 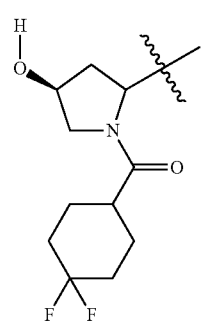 |
| A58 | 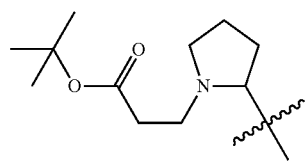 [SMILES: *C1CCCN1CCC(=O)OC(C)(C)C] | | | |
| A59 | 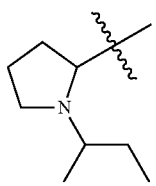 [SMILES: *C1CCCN1C(C)CC] | | A65 | 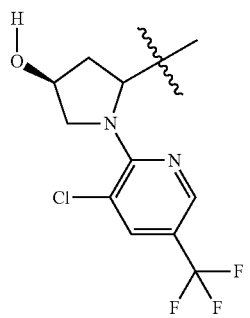 |
| A60 |  | | | |
| A61 | 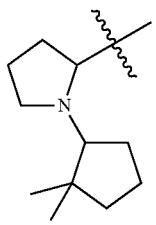 [SMILES: *C1CCCN1C1CCCC1(C)C] | | A66 | 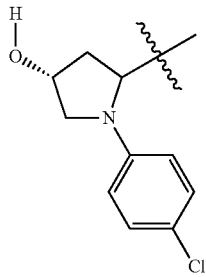 [SMILES: *C1C[C@@H](O)CN1c1ccc(Cl)cc1] |
| A62 | 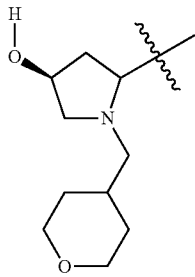 | | A67 | 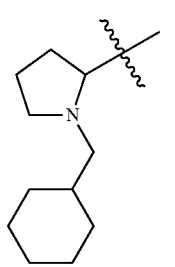 [SMILES: *C1CCCN1CC1CCCCC1] |

TABLE II-continued
| | |
|---|---|
| A68 | 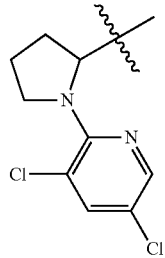 [SMILES: *C1CCCN1c1ncc(Cl)cc1Cl] |
| A69 | 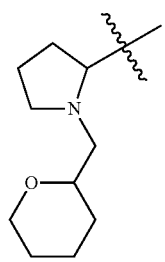 [SMILES: *C1CCCN1CC1CCCCO1] |
| A70 | 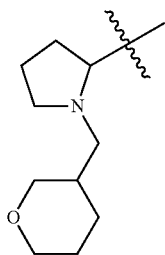 [SMILES: *C1CCCN1CC1CCCOC1] |
| A71 | 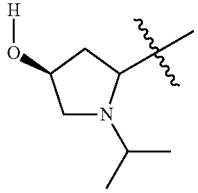 [SMILES: *C1C[C@H](O)CN1C(C)C] |
| A72 | 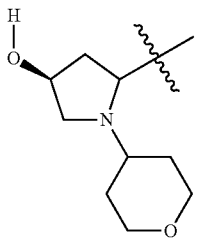 [SMILES: *C1C[C@H](O)CN1C1CCOCC1] |
TABLE II-continued
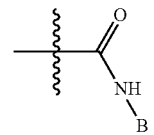
| | |
|---|---|
| B1 | 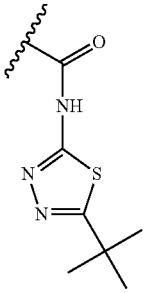 [SMILES: *C(=O)Nc1nnc(C(C)(C)C)s1] |
| B2 | 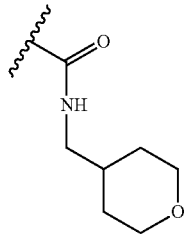 [SMILES: *C(=O)NCC1CCOCC1] |
| B3 | 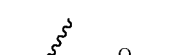 |
| B4 | 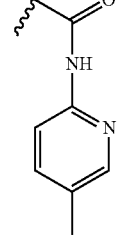 |
| B5 | |

TABLE II-continued
| | |
|---|---|
| B6 | 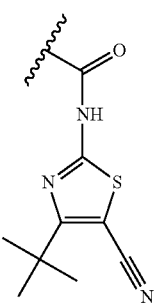 [SMILES: *C(=O)Nc1nc(C(C)(C)C)c(C#N)s1] |
| B7 | 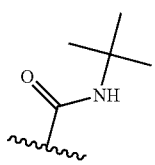 [SMILES: *C(=O)NC(C)(C)C] |
| B8 | 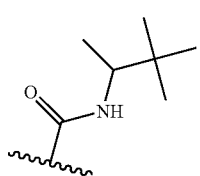 [SMILES: *C(=O)NC(C)C(C)(C)C] |
| B9 | 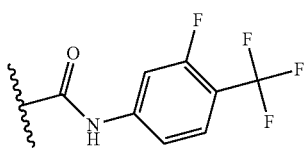 [SMILES: *C(=O)Nc1ccc(C(F)(F)F)c(F)c1] |
| B10 | 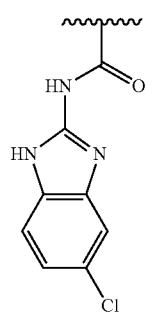 |
| B11 | 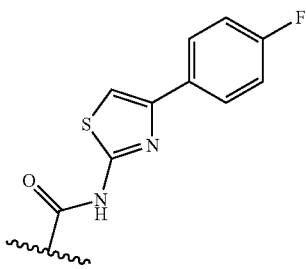 [SMILES: *C(=O)Nc1nc(-c2ccc(F)cc2)cs1] |
| B12 | 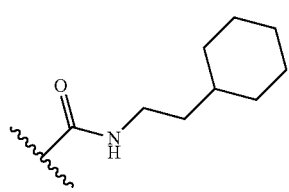 [SMILES: *C(=O)NCCC1CCCCC1] |
| B13 | 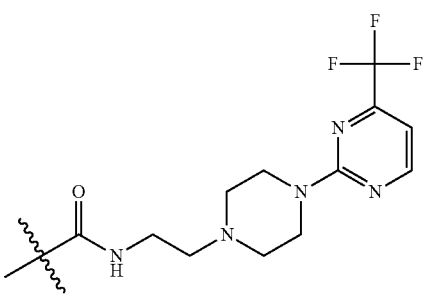 [SMILES: *C(=O)NCCN1CCN(c2nccc(C(F)(F)F)n2)CC1] |
| B14 | 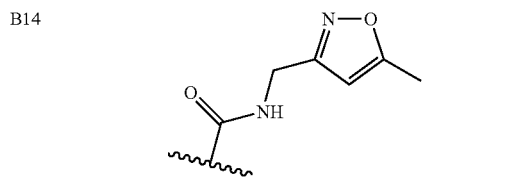 |
| B15 | 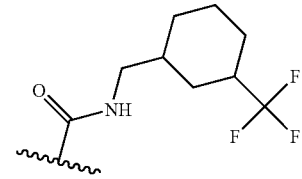 [SMILES: *C(=O)NCC1CCCC(C(F)(F)F)C1] |
| B16 | 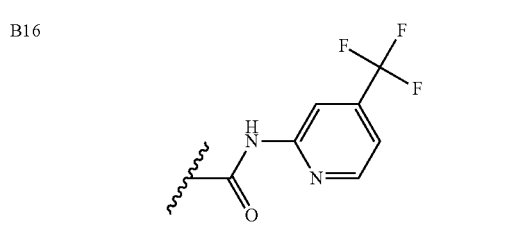 |
| B17 | 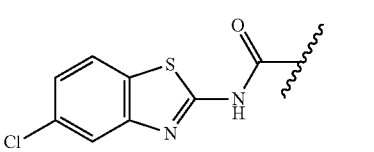 [SMILES: *C(=O)Nc1nc2cc(Cl)ccc2s1] |
| B18 | 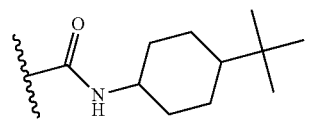 [SMILES: *C(=O)NC1CCC(C(C)(C)C)CC1] |
| B19 | 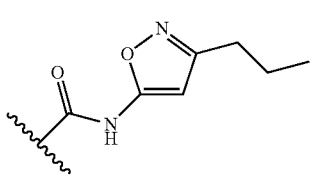 [SMILES: *C(=O)Nc1cc(CCC)no1] |
| B20 | 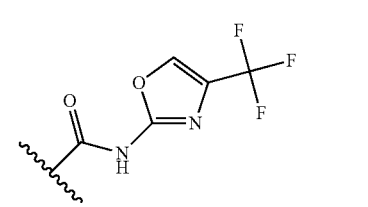 [SMILES: *C(=O)Nc1nc(C(F)(F)F)co1] |

TABLE II-continued
B21 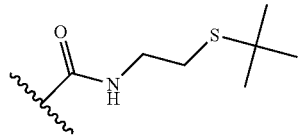 [SMILES: *C(=O)NCCSC(C)(C)C]
B22 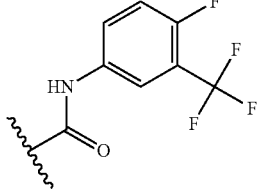
B23 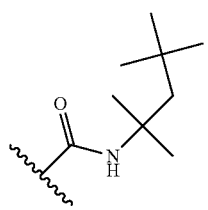 [SMILES: *C(=O)NC(C)(C)CC(C)(C)C]
B24 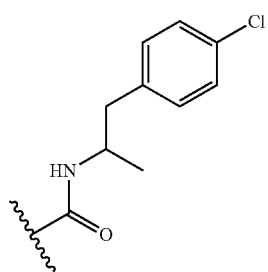 [SMILES: *C(=O)NC(C)Cc1ccc(Cl)cc1]
B25 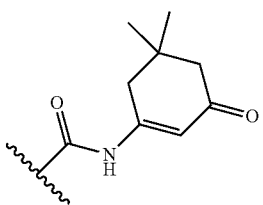 [SMILES: *C(=O)NC1=CC(=O)CC(C)(C)C1]
B26 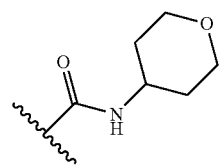 [SMILES: *C(=O)NC1CCOCC1]
B27 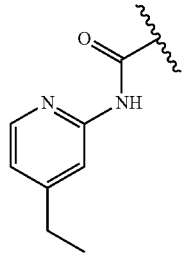 [SMILES: *C(=O)Nc1cc(CC)ccn1]
TABLE II-continued
B28 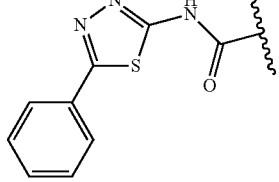
B29 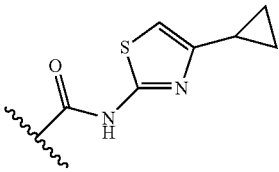 [SMILES: *C(=O)Nc1nc(C2CC2)cs1]
B30 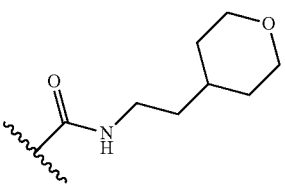 [SMILES: *C(=O)NCCC1CCOCC1]
B31 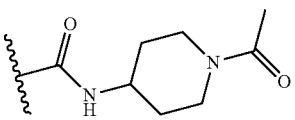 [SMILES: *C(=O)NC1CCN(C(C)=O)CC1]
B32 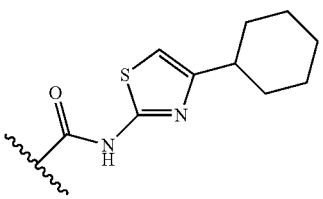 [SMILES: *C(=O)Nc1nc(C2CCCCC2)cs1]
B33 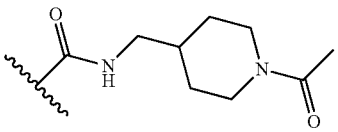 [SMILES: *C(=O)NCC1CCN(C(C)=O)CC1]
B34 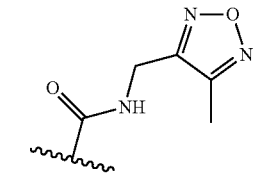 [SMILES: *C(=O)NCc1nonc1C]
B35 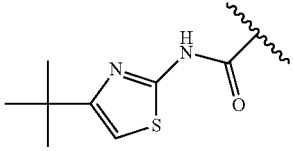 [SMILES: *C(=O)Nc1nc(C(C)(C)C)cs1]
B36 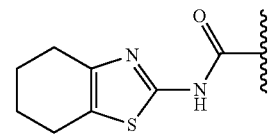 [SMILES: *C(=O)Nc1nc2c(s1)CCCC2]

TABLE II-continued
B37 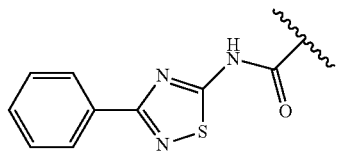 [SMILES: *C(=O)Nc1nc(-c2ccccc2)ns1]
B38 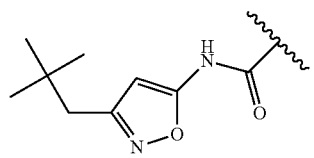 [SMILES: *C(=O)Nc1cc(CC(C)(C)C)no1]
B39 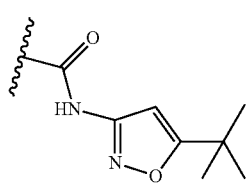 [SMILES: *C(=O)Nc1cc(C(C)(C)C)on1]
B40 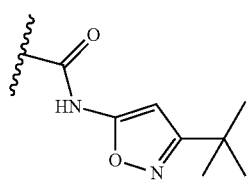 [SMILES: *C(=O)Nc1cc(C(C)(C)C)no1]
B41 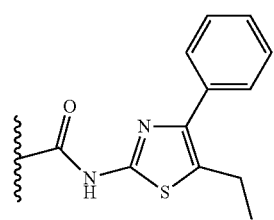 [SMILES: *C(=O)Nc1nc(-c2ccccc2)c(CC)s1]
B42 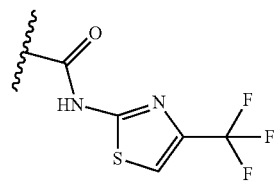 [SMILES: *C(=O)Nc1nc(C(F)(F)F)cs1]
B43 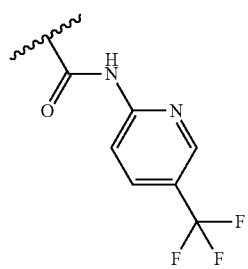 [SMILES: *C(=O)Nc1ccc(C(F)(F)F)cn1]
B44 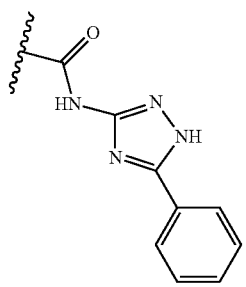 [SMILES: *C(=O)Nc1n[nH]c(-c2ccccc2)n1]
B45 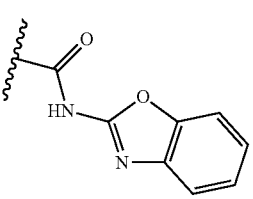 [SMILES: *C(=O)Nc1nc2ccccc2o1]
B46 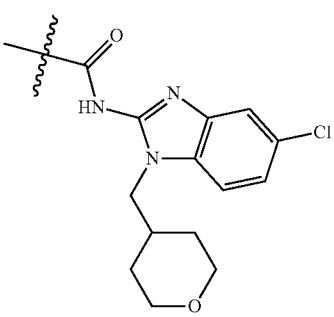 [SMILES: *C(=O)Nc1nc2cc(Cl)ccc2n1CC1CCOCC1]
B47 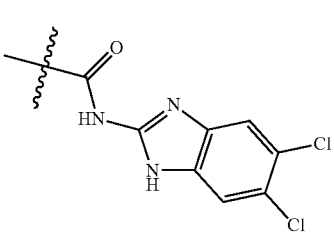 [SMILES: *C(=O)Nc1nc2cc(Cl)c(Cl)cc2[nH]1]
B48 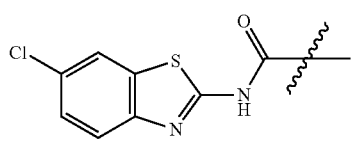 [SMILES: *C(=O)Nc1nc2ccc(Cl)cc2s1]
B49 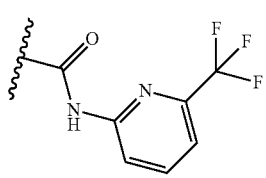 [SMILES: *C(=O)Nc1cccc(C(F)(F)F)n1]
B50 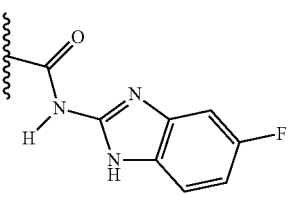 [SMILES: *C(=O)Nc1nc2cc(F)ccc2[nH]1]

TABLE II-continued

B51 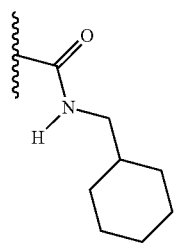 [SMILES: *C(=O)NCC1CCCCC1]

B52 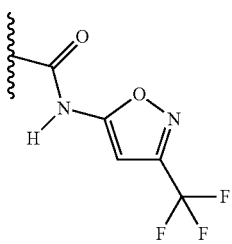 [SMILES: *C(=O)Nc1cc(C(F)(F)F)no1]

B53 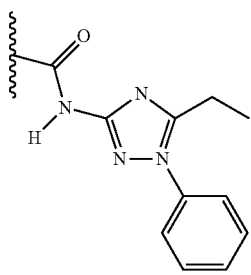

B54 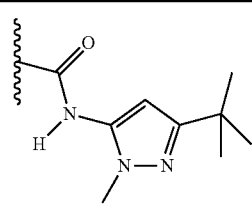

B55 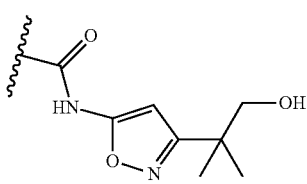 [SMILES: *C(=O)Nc1cc(C(C)(C)CO)no1]

or a pharmaceutically acceptable salt thereof.

In another embodiment of the invention, the compounds in Table II, the stereogenic carbon indicated with an arrow in formula (IV) is in the (S) configuration.

In another embodiment of the invention, the compounds in Table II, the stereogenic carbon in formula (IV) indicated with an arrow is in the (R) configuration.

In another embodiment of the invention, there is provided compounds in Table III, which can be made by the methods and examples shown herein and methods known in the art.

TABLE III

| Example | Structure | Name | ESI m/z (+) | Patent Method |
|---|---|---|---|---|
| 1 | 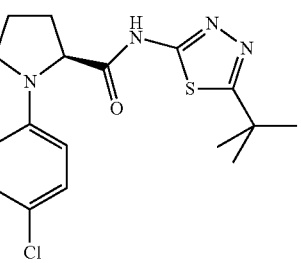 | (S)-1-(4-Chloro-phenyl)-pyrrolidine-2-carboxylic acid (5-tert-butyl-1,3,4-thiadiazol-2-yl)-amide | 365 | 8 |
| 2 | 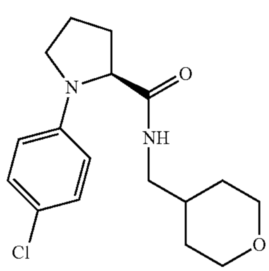 [SMILES: O=C(NCC1CCOCC1)[C@@H]1CCCN1c1ccc(Cl)cc1] | (S)-1-(4-Chloro-phenyl)-pyrrolidine-2-carboxylic acid (tetrahydro-pyran-4-ylmethyl)-amide | 323 | 8 |

TABLE III-continued

| Example | Structure | Name | ESI m/z (+) | Patent Method |
|---|---|---|---|---|
| 3 | 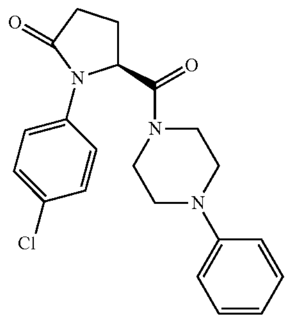 [SMILES: O=C([C@@H]1CCC(=O)N1c1ccc(Cl)cc1)N1CCN(c2ccccc2)CC1] | (S)-1-(4-Chloro-phenyl)-5-(4-phenyl-piperazine-1-carbonyl)-pyrrolidin-2-one | 384 | 17 |
| 4 | 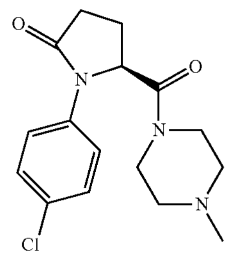 [SMILES: CN1CCN(C(=O)[C@@H]2CCC(=O)N2c2ccc(Cl)cc2)CC1] | (S)-1-(4-Chloro-phenyl)-5-(4-methyl-piperazine-1-carbonyl)-pyrrolidin-2-one | 322 | 17 |
| 5 | 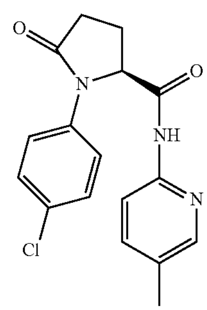 [SMILES: Cc1ccc(NC(=O)[C@@H]2CCC(=O)N2c2ccc(Cl)cc2)nc1] | (S)-1-(4-Chloro-phenyl)-5-oxo-pyrrolidine-2-carboxylic acid (5-methyl-pyridin-2-yl)-amide | 330 | 17 |
| 6 | 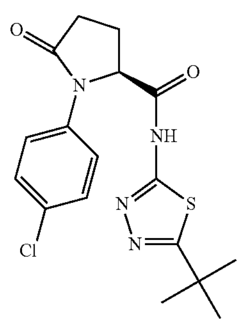 [SMILES: CC(C)(C)c1nnc(NC(=O)[C@@H]2CCC(=O)N2c2ccc(Cl)cc2)s1] | (S)-1-(4-Chloro-phenyl)-5-oxo-pyrrolidine-2-carboxylic acid (5-tert-butyl-1,3,4-thiadiazol-2-yl)-amide | 379 | 17 |
| 7 | 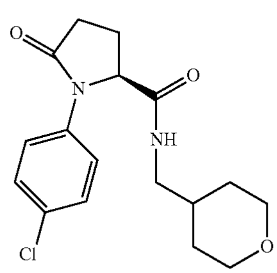 [SMILES: O=C(NCC1CCOCC1)[C@@H]1CCC(=O)N1c1ccc(Cl)cc1] | (S)-1-(4-Chloro-phenyl)-5-oxo-pyrrolidine-2-carboxylic acid (tetrahydro-pyran-4-ylmethyl)-amide | 337 | 17 |

TABLE III-continued

| Example | Name | ESI m/z (+) | Patent Method |
|---|---|---|---|
| 8 | (S)-1-(4-Chloro-phenyl)-pyrrolidine-2-carboxylic acid (3,3,5-trimethyl-cyclohexyl)-amide | 349 | 8 |
| 9 | (S)-1-(4-Chloro-phenyl)-pyrrolidine-2-carboxylic acid [4-(4-chloro-phenyl)-thiazol-2-yl]-amide | 418/420 | 8 |
| 10 | (S)-1-(4-Chloro-phenyl)-pyrrolidine-2-carboxylic acid (4-tert-butyl-5-cyano-thiazol-2-yl)-amide | 389 | 8 |
| 11 | (S)-1-(4-Chloro-phenyl)-5-oxo-pyrrolidine-2-carboxylic acid 4-chloro-benzylamide | 363/365 | 17 |
| 12 | (S)-1-(4-Chloro-phenyl)-5-oxo-pyrrolidine-2-carboxylic acid (3,3,5-trimethyl-cyclohexyl)-amide | 363 | 17 |

TABLE III-continued

| Example | Structure | Name | ESI m/z (+) | Patent Method |
|---|---|---|---|---|
| 13 | 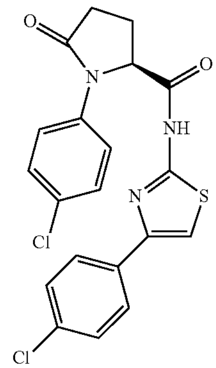 [SMILES: O=C(Nc1nc(-c2ccc(Cl)cc2)cs1)[C@@H]1CCC(=O)N1c1ccc(Cl)cc1] | (S)-1-(4-Chloro-phenyl)-5-oxo-pyrrolidine-2-carboxylic acid [4-(4-chloro-phenyl)-thiazol-2-yl]-amide | 432/434 | 17 |
| 14 | 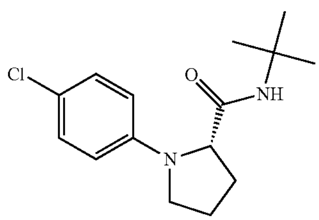 [SMILES: CC(C)(C)NC(=O)[C@@H]1CCCN1c1ccc(Cl)cc1] | (S)-1-(4-Chloro-phenyl)-pyrrolidine-2-carboxylic acid tert-butylamide | 281 | 8 |
| 15 | 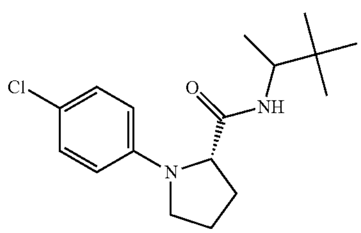 [SMILES: CC(NC(=O)[C@@H]1CCCN1c1ccc(Cl)cc1)C(C)(C)C] | (S)-1-(4-Chloro-phenyl)-pyrrolidine-2-carboxylic acid (1,2,2-trimethyl-propyl)-amide | 309 | 8 |
| 16 | 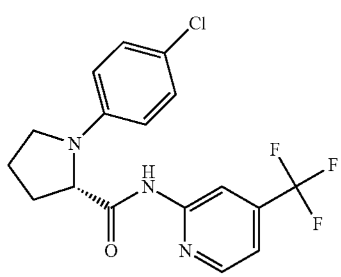 [SMILES: O=C(Nc1cc(C(F)(F)F)ccn1)[C@@H]1CCCN1c1ccc(Cl)cc1] | (S)-1-(4-Chloro-phenyl)-pyrrolidine-2-carboxylic acid (4-trifluoromethyl-pyridin-2-yl)-amide | 370 | 8 |
| 17 | 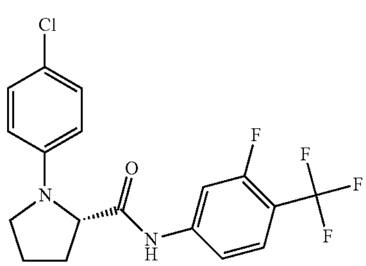 [SMILES: O=C(Nc1ccc(C(F)(F)F)c(F)c1)[C@@H]1CCCN1c1ccc(Cl)cc1] | (S)-1-(4-Chloro-phenyl)-pyrrolidine-2-carboxylic acid (3-fluoro-4-trifluoromethyl-phenyl)-amide | 387 | 8 |

TABLE III-continued

| Example | Name | ESI m/z (+) | Patent Method |
|---|---|---|---|
| 18 | (S)-1-(4-Chloro-phenyl)-pyrrolidine-2-carboxylic acid (5-chloro-1H-benzimidazol-2-yl)-amide | 375/377 | 8 |
| 19 | (S)-1-(4-Chloro-phenyl)-pyrrolidine-2-carboxylic acid [4-(4-fluoro-phenyl)-thiazol-2-yl]-amide | 402 | 8 |
| 20 | (S)-1-(4-Chloro-phenyl)-pyrrolidine-2-carboxylic acid (2-cyclohexyl-ethyl)-amide | 335 | 8 |
| 21 | (S)-1-(4-Chloro-phenyl)-pyrrolidine-2-carboxylic acid {2-[4-(4-trifluoromethyl pyrimidin-2-yl)-piperazin-1-yl]-ethyl}-amide | 483 | 8 |
| 22 | (S)-1-(4-Chloro-phenyl)-pyrrolidine-2-carboxylic acid (5-methyl-isoxazol-3-ylmethyl)-amide | 320 | 8 |

TABLE III-continued

| Example | Structure | Name | ESI m/z (+) | Patent Method |
|---|---|---|---|---|
| 23 | 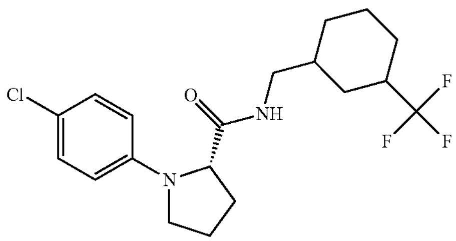 [SMILES: O=C(NCC1CCCC(C(F)(F)F)C1)[C@@H]1CCCN1c1ccc(Cl)cc1] | (S)-1-(4-Chloro-phenyl)-pyrrolidine-2-carboxylic acid (3-trifluoromethyl-cyclohexylmethyl)-amide | 389 | 8 |
| 24 | 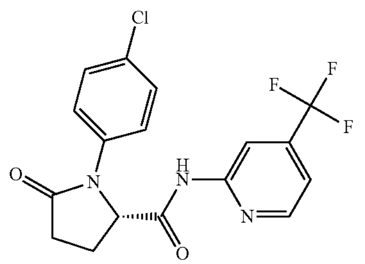 [SMILES: O=C(Nc1cc(C(F)(F)F)ccn1)[C@@H]1CCC(=O)N1c1ccc(Cl)cc1] | (S)-1-(4-Chloro-phenyl)-5-oxo-pyrrolidine-2-carboxylic acid (4-trifluoromethyl-pyridin-2-yl)-amide | 384 | 17 |
| 25 | 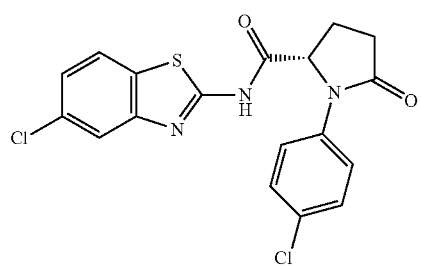 [SMILES: O=C(Nc1nc2cc(Cl)ccc2s1)[C@@H]1CCC(=O)N1c1ccc(Cl)cc1] | (S)-1-(4-Chloro-phenyl)-5-oxo-pyrrolidine-2-carboxylic acid (5-chloro-benzothiazol-2-yl)-amide | 406/408 | 17 |
| 26 | 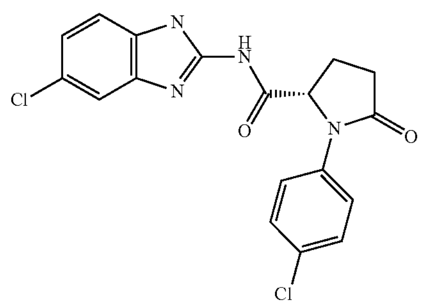 [SMILES: O=C(Nc1nc2cc(Cl)ccc2[nH]1)[C@@H]1CCC(=O)N1c1ccc(Cl)cc1] | (S)-1-(4-Chloro-phenyl)-5-oxo-pyrrolidine-2-carboxylic acid (5-chloro-1H-benzimidazol-2-yl)-amide | 389/391 | 17 |
| 27 | 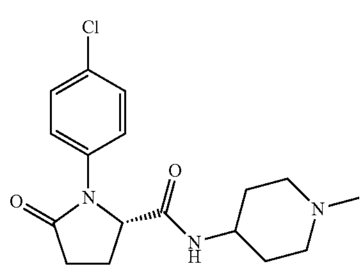 [SMILES: CN1CCC(NC(=O)[C@@H]2CCC(=O)N2c2ccc(Cl)cc2)CC1] | (S)-1-(4-Chloro-phenyl)-5-oxo-pyrrolidine-2-carboxylic acid (1-methyl-piperidin-4-yl)-amide | 336 | 17 |

TABLE III-continued

| Example | Structure | Name | ESI m/z (+) | Patent Method |
|---|---|---|---|---|
| 28 | 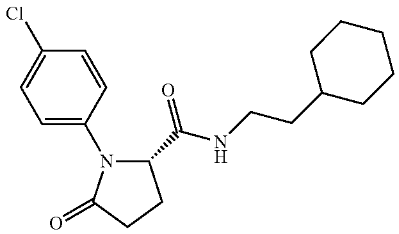 [SMILES: O=C(NCCC1CCCCC1)[C@@H]1CCC(=O)N1c1ccc(Cl)cc1] | (S)-1-(4-Chloro-phenyl)-5-oxo-pyrrolidine-2-carboxylic acid (2-cyclohexyl-ethyl)-amide | 349 | 17 |
| 29 | 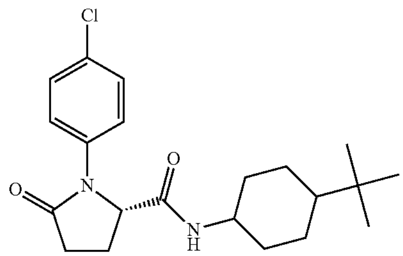 [SMILES: CC(C)(C)C1CCC(NC(=O)[C@@H]2CCC(=O)N2c2ccc(Cl)cc2)CC1] | (S)-1-(4-Chloro-phenyl)-5-oxo-pyrrolidine-2-carboxylic acid (4-tert-butyl-cyclohexyl)-amide | 377 | 17 |
| 30 | 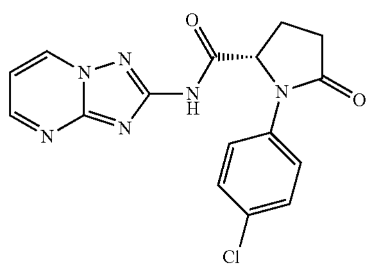 [SMILES: O=C(Nc1nc2ncccn2n1)[C@@H]1CCC(=O)N1c1ccc(Cl)cc1] | (S)-1-(4-Chloro-phenyl)-5-oxo-pyrrolidine-2-carboxylic acid [1,2,4]triazolo[1,5-a]pyrimidin-2-ylamide | 357 | 17 |
| 31 | 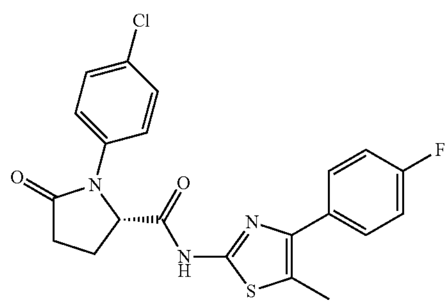 [SMILES: Cc1sc(NC(=O)[C@@H]2CCC(=O)N2c2ccc(Cl)cc2)nc1-c1ccc(F)cc1] | (S)-1-(4-Chloro-phenyl)-5-oxo-pyrrolidine-2-carboxylic acid [4-(4-fluoro-phenyl)-5-methyl-thiazol-2-yl]-amide | 430 | 17 |
| 32 | 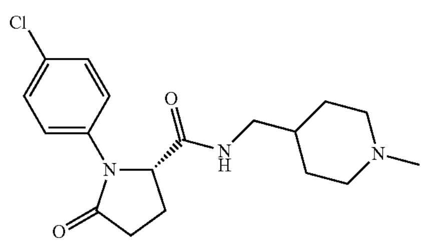 [SMILES: CN1CCC(CNC(=O)[C@@H]2CCC(=O)N2c2ccc(Cl)cc2)CC1] | (S)-1-(4-Chloro-phenyl)-5-oxo-pyrrolidine-2-carboxylic acid (1-methyl-piperidin-4-ylmethyl)-amide | 350 | 17 |
| 33 | 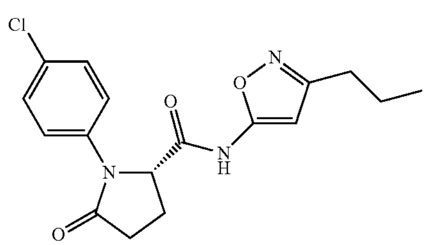 [SMILES: CCCc1cc(NC(=O)[C@@H]2CCC(=O)N2c2ccc(Cl)cc2)on1] | (S)-1-(4-Chloro-phenyl)-5-oxo-pyrrolidine-2-carboxylic acid (3-propyl-isoxazol-5-yl)-amide | 348 | 17 |

TABLE III-continued

| Example | Structure | Name | ESI m/z (+) | Patent Method |
|---|---|---|---|---|
| 34 | 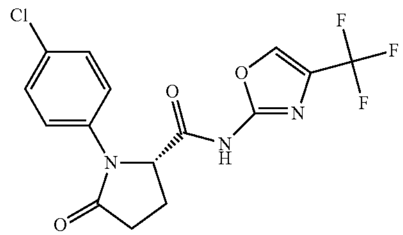 [SMILES: O=C(Nc1nc(C(F)(F)F)co1)[C@@H]1CCC(=O)N1c1ccc(Cl)cc1] | (S)-1-(4-Chloro-phenyl)-5-oxo-pyrrolidine-2-carboxylic acid (4-trifluoromethyl-oxazol-2-yl)-amide | 374 | 17 |
| 35 | 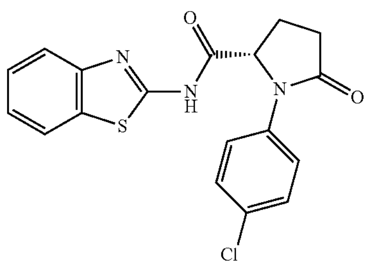 [SMILES: O=C(Nc1nc2ccccc2s1)[C@@H]1CCC(=O)N1c1ccc(Cl)cc1] | (S)-1-(4-Chloro-phenyl)-5-oxo-pyrrolidine-2-carboxylic acid benzothiazol-2-ylamide | 372 | 17 |
| 36 | 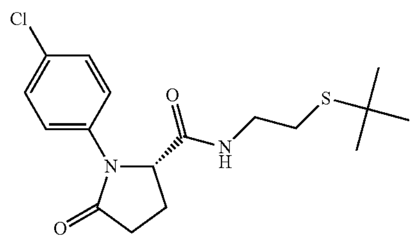 [SMILES: CC(C)(C)SCCNC(=O)[C@@H]1CCC(=O)N1c1ccc(Cl)cc1] | (S)-1-(4-Chloro-phenyl)-5-oxo-pyrrolidine-2-carboxylic acid (2-tert-butylsulfanyl-ethyl)-amide | 355 | 17 |
| 37 | 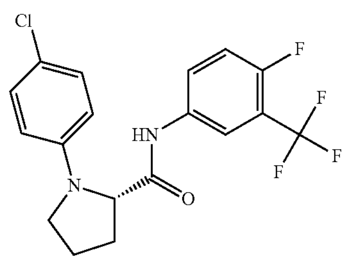 [SMILES: O=C(Nc1ccc(F)c(C(F)(F)F)c1)[C@@H]1CCCN1c1ccc(Cl)cc1] | (S)-1-(4-Chloro-phenyl)-pyrrolidine-2-carboxylic acid (4-fluoro-3-trifluoromethyl-phenyl)-amide | 387 | 8 |
| 38 | 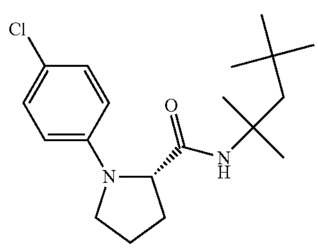 [SMILES: CC(C)(C)CC(C)(C)NC(=O)[C@@H]1CCCN1c1ccc(Cl)cc1] | (S)-1-(4-Chloro-phenyl)-pyrrolidine-2-carboxylic acid (1,1,3,3-tetramethyl-butyl)-amide | 337 | 8 |
| 39 | 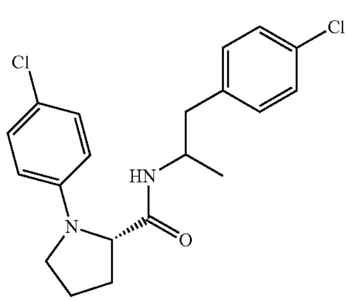 [SMILES: CC(Cc1ccc(Cl)cc1)NC(=O)[C@@H]1CCCN1c1ccc(Cl)cc1] | (S)-1-(4-Chloro-phenyl)-pyrrolidine-2-carboxylic acid [2-(4-chloro-phenyl)-1-methyl-ethyl]-amide | 377/379 | 8 |

TABLE III-continued

| Example | Name | ESI m/z (+) | Patent Method |
|---|---|---|---|
| 40 | (S)-1-(4-Chloro-phenyl)-pyrrolidine-2-carboxylic acid (4-tert-butyl-cyclohexyl)-amide | 363 | 8 |
| 41 | (S)-1-(4-Chloro-phenyl)-pyrrolidine-2-carboxylic acid (5,5-dimethyl-3-oxo-cyclohex-1-enyl)-amide | 347 | 8 |
| 42 | (S)-1-(4-Chloro-phenyl)-pyrrolidine-2-carboxylic acid (tetrahydro-pyran-4-yl)-amide | 309 | 8 |
| 43 | (S)-1-(4-Chloro-phenyl)-pyrrolidine-2-carboxylic acid (4-ethyl-pyridin-2-yl)-amide | 330 | 8 |
| 44 | (S)-1-(4-Chloro-phenyl)-pyrrolidine-2-carboxylic acid (5-phenyl-1,3,4-thiadiazol-2-yl)-amide | 385 | 8 |
| 45 | (S)-1-(4-Chloro-phenyl)-pyrrolidine-2-carboxylic acid (4-cyclopropyl-thiazol-2-yl)-amide | 348 | 8 |

TABLE III-continued

| Example | Structure | Name | ESI m/z (+) | Patent Method |
|---|---|---|---|---|
| 46 | 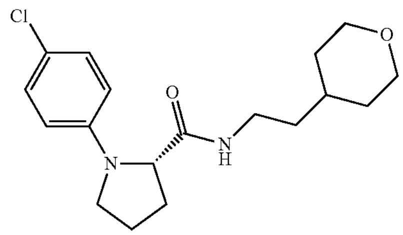 [SMILES: O=C(NCCC1CCOCC1)[C@@H]1CCCN1c1ccc(Cl)cc1] | (S)-1-(4-Chloro-phenyl)-pyrrolidine-2-carboxylic acid [2-(tetrahydro-pyran-4-yl)-ethyl]-amide | 337 | 8 |
| 47 | 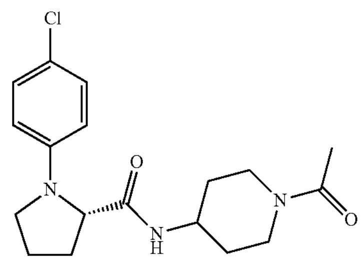 [SMILES: CC(=O)N1CCC(NC(=O)[C@@H]2CCCN2c2ccc(Cl)cc2)CC1] | (S)-1-(4-Chloro-phenyl)-pyrrolidine-2-carboxylic acid (1-acetyl-piperidin-4-yl)-amide | 350 | 8 |
| 48 | 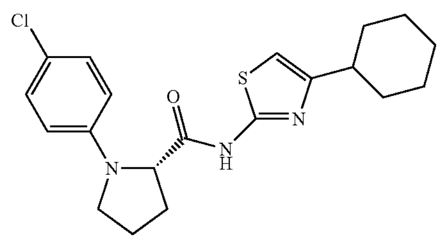 [SMILES: O=C(Nc1nc(C2CCCCC2)cs1)[C@@H]1CCCN1c1ccc(Cl)cc1] | (S)-1-(4-Chloro-phenyl)-pyrrolidine-2-carboxylic acid (4-cyclohexyl-thiazol-2-yl)-amide | 390 | 8 |
| 49 | 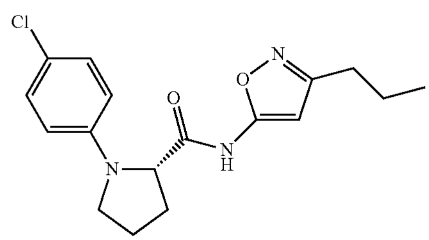 [SMILES: CCCc1cc(NC(=O)[C@@H]2CCCN2c2ccc(Cl)cc2)on1] | (S)-1-(4-Chloro-phenyl)-pyrrolidine-2-carboxylic acid (3-propyl-isoxazol-5-yl)-amide | 334 | 8 |
| 50 | 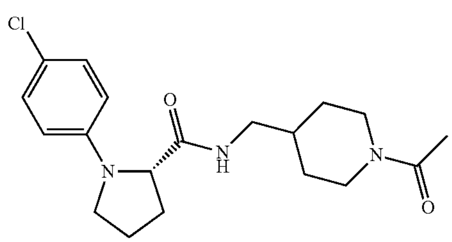 [SMILES: CC(=O)N1CCC(CNC(=O)[C@@H]2CCCN2c2ccc(Cl)cc2)CC1] | (S)-1-(4-Chloro-phenyl)-pyrrolidine-2-carboxylic acid (1-acetyl-piperidin-4-ylmethyl)-amide | 364 | 8 |
| 51 | 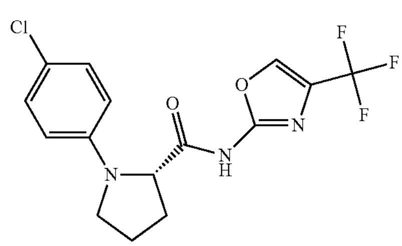 [SMILES: O=C(Nc1nc(C(F)(F)F)co1)[C@@H]1CCCN1c1ccc(Cl)cc1] | (S)-1-(4-Chloro-phenyl)-pyrrolidine-2-carboxylic acid (4-trifluoromethyl-oxazol-2-yl)-amide | 360 | 8 |

TABLE III-continued

| Example | Structure | Name | ESI m/z (+) | Patent Method |
|---|---|---|---|---|
| 52 | 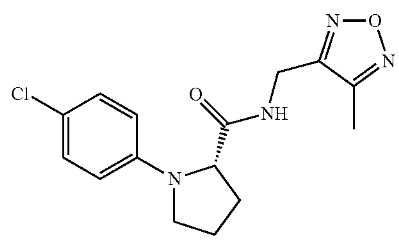 [SMILES: Cc1nonc1CNC(=O)[C@@H]1CCCN1c1ccc(Cl)cc1] | (S)-1-(4-Chloro-phenyl)-pyrrolidine-2-carboxylic acid (4-methyl-furazan-3-ylmethyl)-amide | 321 | 8 |
| 53 | 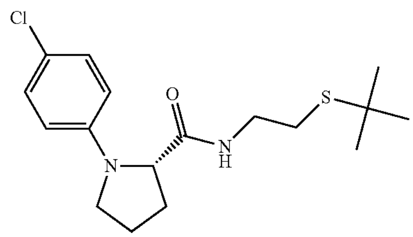 [SMILES: CC(C)(C)SCCNC(=O)[C@@H]1CCCN1c1ccc(Cl)cc1] | (S)-1-(4-Chloro-phenyl)-pyrrolidine-2-carboxylic acid (2-tert-butylsulfanyl-ethyl)-amide | 341 | 8 |
| 54 | 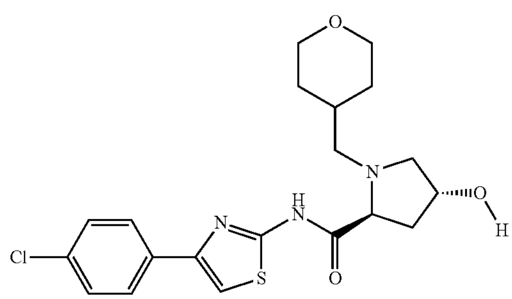 [SMILES: O=C(Nc1nc(-c2ccc(Cl)cc2)cs1)[C@@H]1C[C@@H](O)CN1CC1CCOCC1] | (2S,4R)-4-Hydroxy-1-(tetrahydro-pyran-4-ylmethyl)-pyrrolidine-2-carboxylic acid [4-(4-chloro-phenyl)-thiazol-2-yl]-amide | 422 | 23 |
| 55 | 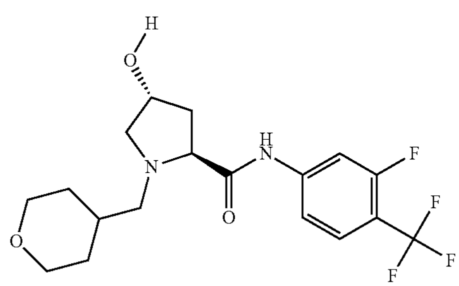 [SMILES: O=C(Nc1ccc(C(F)(F)F)c(F)c1)[C@@H]1C[C@@H](O)CN1CC1CCOCC1] | (2S,4R)-4-Hydroxy-1-(tetrahydro-pyran-4-ylmethyl)-pyrrolidine-2-carboxylic acid (3-fluoro-4-trifluoromethyl-phenyl)-amide | 392 | 23 |
| 56 | 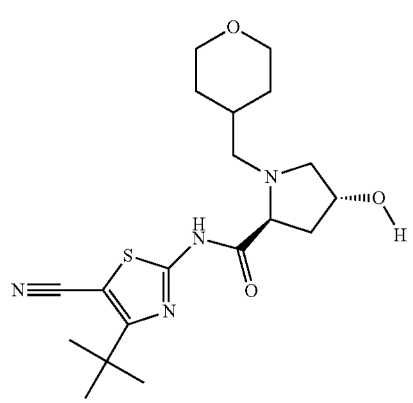 [SMILES: CC(C)(C)c1nc(NC(=O)[C@@H]2C[C@@H](O)CN2CC2CCOCC2)sc1C#N] | (2S,4R)-4-Hydroxy-1-(tetrahydro-pyran-4-ylmethyl)-pyrrolidine-2-carboxylic acid (4-tert-butyl-5-cyano-thiazol-2-yl)-amide | 394 | 23 |

TABLE III-continued

| Example | Structure | Name | ESI m/z (+) | Patent Method |
|---|---|---|---|---|
| 57 | 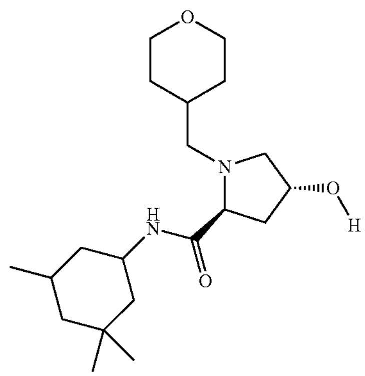 [SMILES: CC1CC(NC(=O)[C@@H]2C[C@@H](O)CN2CC2CCOCC2)CC(C)(C)C1] | (2S,4R)-4-Hydroxy-1-(tetrahydro-pyran-4-ylmethyl)-pyrrolidine-2-carboxylic acid (3,3,5-trimethyl-cyclohexyl)-amide | 353 | 23 |
| 58 | 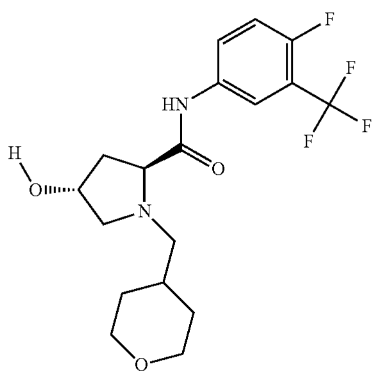 [SMILES: O=C(Nc1ccc(F)c(C(F)(F)F)c1)[C@@H]1C[C@@H](O)CN1CC1CCOCC1] | (2S,4R)-4-Hydroxy-1-(tetrahydro-pyran-4-ylmethyl)-pyrrolidine-2-carboxylic acid (4-fluoro-3-trifluoromethyl-phenyl)-amide | 391 | 23 |
| 59 | 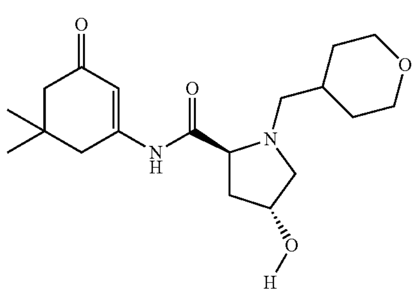 [SMILES: CC1(C)CC(=O)C=C(NC(=O)[C@@H]2C[C@@H](O)CN2CC2CCOCC2)C1] | (2S,4R)-4-Hydroxy-1-(tetrahydro-pyran-4-ylmethyl)-pyrrolidine-2-carboxylic acid (5,5-dimethyl-3-oxo-cyclohex-1-enyl)-amide | 351 | 23 |
| 60 | 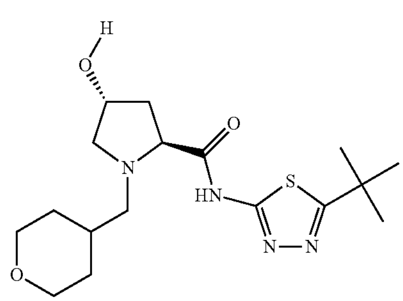 [SMILES: CC(C)(C)c1nnc(NC(=O)[C@@H]2C[C@@H](O)CN2CC2CCOCC2)s1] | (2S,4R)-4-Hydroxy-1-(tetrahydro-pyran-4-ylmethyl)-pyrrolidine-2-carboxylic acid (5-tert-butyl-1,3,4-thiadiazol-2-yl)-amide | 369 | 23 |

TABLE III-continued

| Example | Name | ESI m/z (+) | Patent Method |
|---|---|---|---|
| 61 | (2S,4R)-4-Hydroxy-1-(tetrahydro-pyran-4-ylmethyl)-pyrrolidine-2-carboxylic acid (4-tert-butyl-thiazol-2-yl)-amide | 368 | 23 |
| 62 | (2S,4R)-4-Hydroxy-1-(tetrahydro-pyran-4-ylmethyl)-pyrrolidine-2-carboxylic acid (4-ethyl-pyridin-2-yl)-amide | 334 | 23 |
| 63 | (2S,4R)-4-Hydroxy-1-(tetrahydro-pyran-4-ylmethyl)-pyrrolidine-2-carboxylic acid (4-cyclohexyl-thiazol-2-yl)-amide | 395 | 23 |
| 64 | (2S,4R)-4-Hydroxy-1-(tetrahydro-pyran-4-ylmethyl)-pyrrolidine-2-carboxylic acid [2-(tetrahydro-pyran-4-yl)-ethyl]-amide | 341 | 23 |
| 65 | (2S,4R)-4-Hydroxy-1-(tetrahydro-pyran-4-ylmethyl)-pyrrolidine-2-carboxylic acid (2-cyclohexyl-ethyl)-amide | 339 | 23 |

TABLE III-continued

| Example | Structure | Name | ESI m/z (+) | Patent Method |
|---|---|---|---|---|
| 66 | 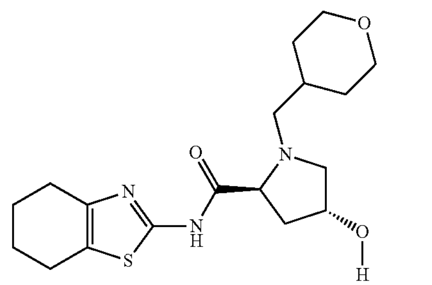 [SMILES: O=C(Nc1nc2c(s1)CCCC2)[C@@H]1C[C@@H](O)CN1CC1CCOCC1] | (2S,4R)-4-Hydroxy-1-(tetrahydro-pyran-4-ylmethyl)-pyrrolidine-2-carboxylic acid (4,5,6,7-tetrahydro-benzothiazol-2-yl)-amide | 366 | 23 |
| 67 | 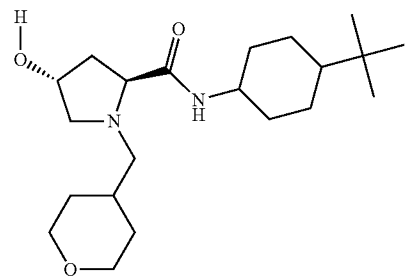 [SMILES: CC(C)(C)C1CCC(NC(=O)[C@@H]2C[C@@H](O)CN2CC2CCOCC2)CC1] | (2S,4R)-4-Hydroxy-1-(tetrahydro-pyran-4-ylmethyl)-pyrrolidine-2-carboxylic acid (4-tert-butyl-cyclohexyl)-amide | 367 | 23 |
| 68 | 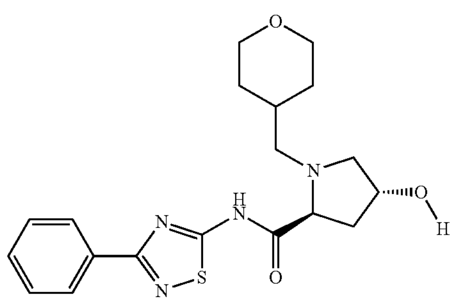 [SMILES: O=C(Nc1nc(-c2ccccc2)ns1)[C@@H]1C[C@@H](O)CN1CC1CCOCC1] | (2S,4R)-4-Hydroxy-1-(tetrahydro-pyran-4-ylmethyl)-pyrrolidine-2-carboxylic acid (3-phenyl-1,2,4-thiadiazol-5-yl)-amide | 389 | 23 |
| 69 | 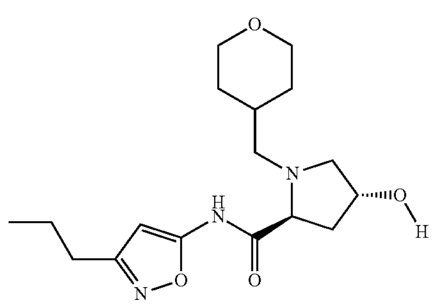 [SMILES: CCCc1cc(NC(=O)[C@@H]2C[C@@H](O)CN2CC2CCOCC2)on1] | (2S,4R)-4-Hydroxy-1-(tetrahydro-pyran-4-ylmethyl)-pyrrolidine-2-carboxylic acid (3-propyl-isoxazol-5-yl)-amide | 338 | 23 |
| 70 | 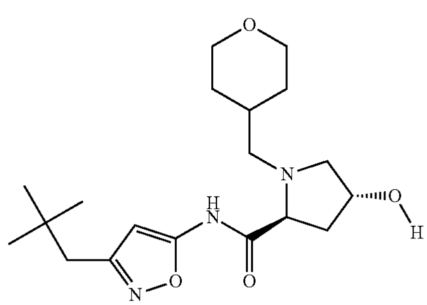 [SMILES: CC(C)(C)Cc1cc(NC(=O)[C@@H]2C[C@@H](O)CN2CC2CCOCC2)on1] | (2S,4R)-4-Hydroxy-1-(tetrahydro-pyran-4-ylmethyl)-pyrrolidine-2-carboxylic acid [3-(2,2-dimethyl-propyl)-isoxazol-5-yl]-amide | 366 | 23 |

TABLE III-continued

| Example | Name | ESI m/z (+) | Patent Method |
|---|---|---|---|
| 71 | (2S,4R)-4-Hydroxy-1-(tetrahydro-pyran-4-ylmethyl)-pyrrolidine-2-carboxylic acid (5-trifluoromethyl-pyridin-2-yl)-amide | 374 | 23 |
| 72 | (2S,4R)-4-Hydroxy-1-(tetrahydro-pyran-4-ylmethyl)-pyrrolidine-2-carboxylic acid (4-trifluoromethyl-pyridin-2-yl)-amide | 374 | 23 |
| 73 | (2S,4S)-4-Hydroxy-1-(tetrahydro-pyran-4-ylmethyl)-pyrrolidine-2-carboxylic acid (3-fluoro-4-trifluoromethyl-phenyl)-amide | 391 | 24 |
| 74 | (2S,4S)-4-Hydroxy-1-(tetrahydro-pyran-4-ylmethyl)-pyrrolidine-2-carboxylic acid (4-tert-butyl-5-cyano-thiazol-2-yl)-amide | 393 | 24 |
| 75 | (2S,4S)-4-Hydroxy-1-(tetrahydro-pyran-4-ylmethyl)-pyrrolidine-2-carboxylic acid (3,3,5-trimethyl-cyclohexyl)-amide | 353 | 24 |

TABLE III-continued

| Example | Structure | Name | ESI m/z (+) | Patent Method |
|---|---|---|---|---|
| 76 | 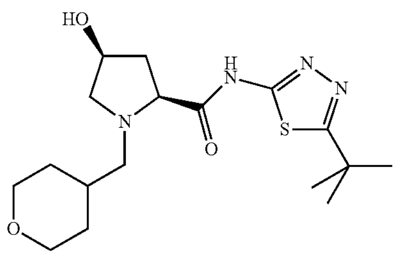 [SMILES: CC(C)(C)c1nnc(NC(=O)[C@@H]2C[C@H](O)CN2CC2CCOCC2)s1] | (2S,4S)-4-Hydroxy-1-(tetrahydro-pyran-4-ylmethyl)-pyrrolidine-2-carboxylic acid (5-tert-butyl-1,3,4-thiadiazol-2-yl)-amide | 369 | 24 |
| 77 | 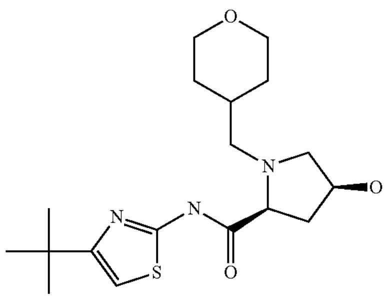 [SMILES: CC(C)(C)c1csc(NC(=O)[C@@H]2C[C@H](O)CN2CC2CCOCC2)n1] | (2S,4S)-4-Hydroxy-1-(tetrahydro-pyran-4-ylmethyl)-pyrrolidine-2-carboxylic acid (4-tert-butyl-thiazol-2-yl)-amide | 368 | 24 |
| 78 | 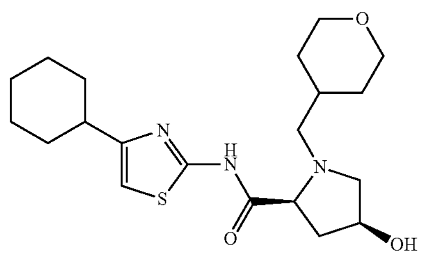 [SMILES: O=C(Nc1nc(C2CCCCC2)cs1)[C@@H]1C[C@H](O)CN1CC1CCOCC1] | (2S,4S)-4-Hydroxy-1-(tetrahydro-pyran-4-ylmethyl)-pyrrolidine-2-carboxylic acid (4-cyclohexyl-thiazol-2-yl)-amide | 394 | 24 |
| 79 | 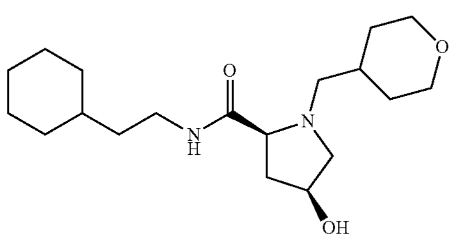 [SMILES: O=C(NCCC1CCCCC1)[C@@H]1C[C@H](O)CN1CC1CCOCC1] | (2S,4S)-4-Hydroxy-1-(tetrahydro-pyran-4-ylmethyl)-pyrrolidine-2-carboxylic acid (2-cyclohexyl-ethyl)-amide | 340 | 24 |
| 80 | 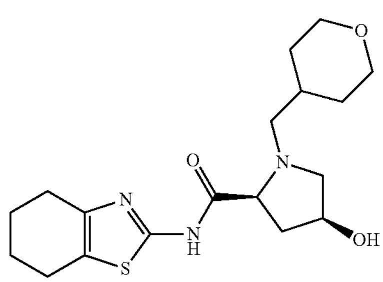 [SMILES: O=C(Nc1nc2c(s1)CCCC2)[C@@H]1C[C@H](O)CN1CC1CCOCC1] | (2S,4S)-4-Hydroxy-1-(tetrahydro-pyran-4-ylmethyl)-pyrrolidine-2-carboxylic acid (4,5,6,7-tetrahydro-benzothiazol-2-yl)-amide | 366 | 24 |

TABLE III-continued

| Example | Name | ESI m/z (+) | Patent Method |
|---|---|---|---|
| 81 | (2S,4S)-4-Hydroxy-1-(tetrahydro-pyran-4-ylmethyl)-pyrrolidine-2-carboxylic acid (4-tert-butyl-cyclohexyl)-amide | 367 | 24 |
| 82 | (S)-1-(4-chloro-phenyl)-5-oxo-pyrrolidine-2-carboxylic acid (5-tert-butyl-isoxazol-3-yl)-amide | 362 | 6 |
| 83 | (S)-1-(4-chloro-phenyl)-5-oxo-pyrrolidine-2-carboxylic acid (3-tert-butyl-isoxazol-5-yl)-amide | 362 | 6 |
| 84 | (S)-1-(4-chloro-5-trifluoromethyl-pyridin-2-yl)-5-oxo-pyrrolidine-2-carboxylic acid (4-sec-butyl-phenyl)-amide | 440 | 21 |
| 85 | (S)-1-(4-chloro-phenyl)-5-oxo-pyrrolidine-2-carboxylic acid (3-phenyl-1,2,4-thiadiazol-5-yl)-amide | 399 | 6 |

TABLE III-continued

| Example | Structure | Name | ESI m/z (+) | Patent Method |
|---|---|---|---|---|
| 86 | 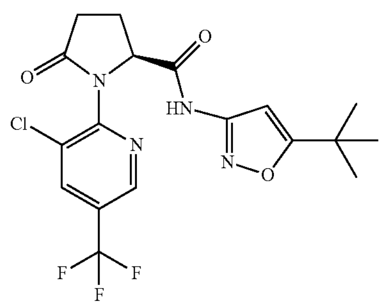 [SMILES: CC(C)(C)c1cc(NC(=O)[C@@H]2CCC(=O)N2c2ncc(C(F)(F)F)cc2Cl)no1] | (S)-1-(3-chloro-5-trifluoromethyl-pyridin-2-yl)-5-oxo-pyrrolidine-2-carboxylic acid (5-tert-butyl-isoxazol-3-yl)-amide | 431 | 21 |
| 87 | 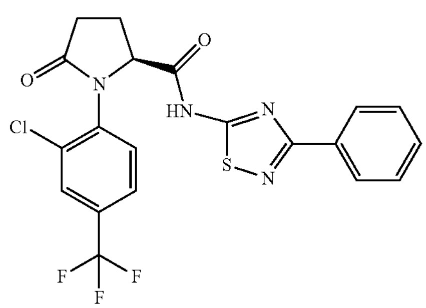 [SMILES: O=C(Nc1nc(-c2ccccc2)ns1)[C@@H]1CCC(=O)N1c1ccc(C(F)(F)F)cc1Cl] | (S)-1-(3-chloro-5-trifluoromethyl-pyridin-2-yl)-5-oxo-pyrrolidine-2-carboxylic acid (3-phenyl-1,2,4-thiadiazol-5-yl)-amide | 468 | 21 |
| 88 | 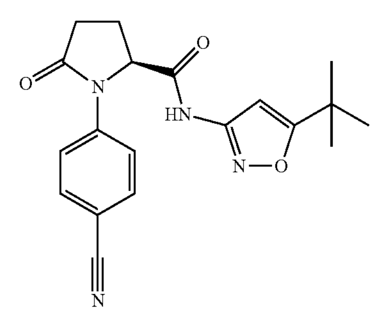 [SMILES: CC(C)(C)c1cc(NC(=O)[C@@H]2CCC(=O)N2c2ccc(C#N)cc2)no1] | (S)-1-(4-cyano-phenyl)-5-oxo-pyrrolidine-2-carboxylic acid (5-tert-butyl-isoxazol-3-yl)-amide | 353 | 6 |
| 89 | 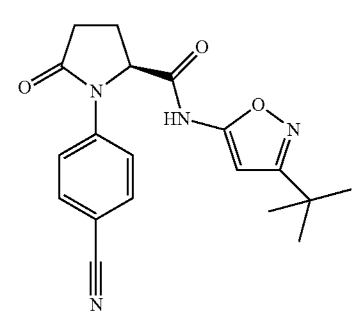 [SMILES: CC(C)(C)c1cc(NC(=O)[C@@H]2CCC(=O)N2c2ccc(C#N)cc2)on1] | (S)-1-(4-cyano-phenyl)-5-oxo-pyrrolidine-2-carboxylic acid (3-tert-butyl-isoxazol-5-yl)-amide | 353 | 6 |
| 90 | 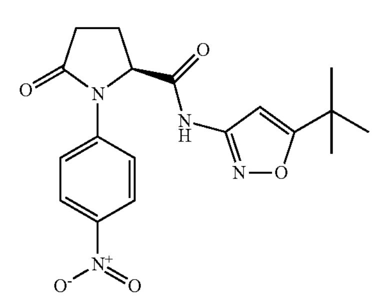 [SMILES: CC(C)(C)c1cc(NC(=O)[C@@H]2CCC(=O)N2c2ccc([N+](=O)[O-])cc2)no1] | (S)-1-(4-cyano-phenyl)-5-oxo-pyrrolidine-2-carboxylic acid (5-tert-butyl-isoxazol-3-yl)-amide | 373 | 18 |

TABLE III-continued

| Example | Structure | Name | ESI m/z (+) | Patent Method |
|---|---|---|---|---|
| 91 | 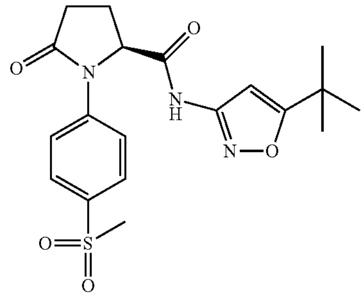 [SMILES: CC(C)(C)c1cc(NC(=O)[C@@H]2CCC(=O)N2c2ccc(S(C)(=O)=O)cc2)no1] | (S)-1-(4-methanesulfonyl-phenyl)-5-oxo-pyrrolidin-2-carboxylic acid (5-tert-butyl-isoxazol-3-yl)-amide | 406 | 6 |
| 92 | 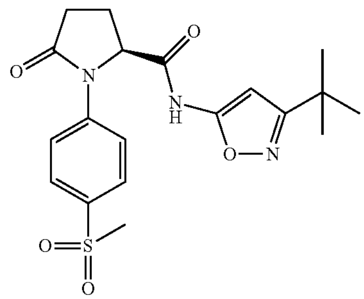 [SMILES: CC(C)(C)c1cc(NC(=O)[C@@H]2CCC(=O)N2c2ccc(S(C)(=O)=O)cc2)on1] | (S)-1-(4-methanesulfonyl-phenyl)-5-oxo-pyrrolidin-2-carboxylic acid (3-tert-butyl-isoxazol-5-yl)-amide | 406 | 6 |
| 93 | 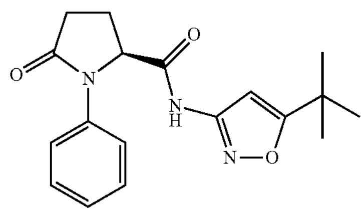 [SMILES: CC(C)(C)c1cc(NC(=O)[C@@H]2CCC(=O)N2c2ccccc2)no1] | (S)-5-oxo-1-phenyl-pyrrolidine-2-carboxylic acid (5-tert-butyl-isoxazol-3-yl)-amide | 328 | 6 |
| 94 | 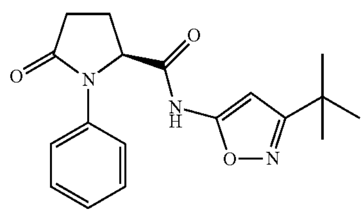 [SMILES: CC(C)(C)c1cc(NC(=O)[C@@H]2CCC(=O)N2c2ccccc2)on1] | (S)-5-oxo-1-phenyl-pyrrolidine-2-carboxylic acid (3-tert-butyl-isoxazol-5-yl)-amide | 328 | 6 |
| 95 | 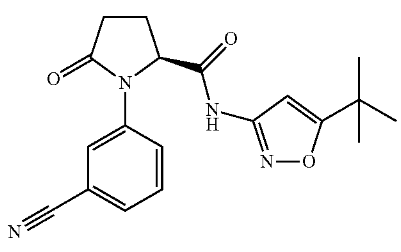 [SMILES: CC(C)(C)c1cc(NC(=O)[C@@H]2CCC(=O)N2c2cccc(C#N)c2)no1] | (S)-1-(3-cyano-phenyl)-5-oxo-pyrrolidine-2-carboxylic acid (5-tert-butyl-isoxazol-3-yl)-amide | 353 | 6 |
| 96 | 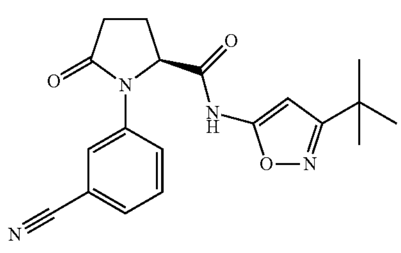 [SMILES: CC(C)(C)c1cc(NC(=O)[C@@H]2CCC(=O)N2c2cccc(C#N)c2)on1] | (S)-1-(3-cyano-phenyl)-5-oxo-pyrrolidine-2-carboxylic acid (3-tert-butyl-isoxazol-5-yl)-amide | 353 | 6 |

TABLE III-continued

| Example | Structure | Name | ESI m/z (+) | Patent Method |
|---|---|---|---|---|
| 97 | 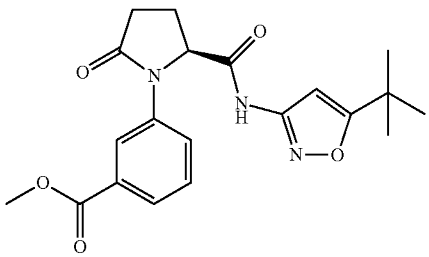 [SMILES: COC(=O)c1cccc(N2C(=O)CC[C@H]2C(=O)Nc2cc(C(C)(C)C)on2)c1] | 3-[(S)-2-(5-tert-butyl-isoxazol-3-ylcarbamoyl)-5-oxo-pyrrolidin-1-yl]-benzoic acid methyl ester | 386 | 6 |
| 98 | 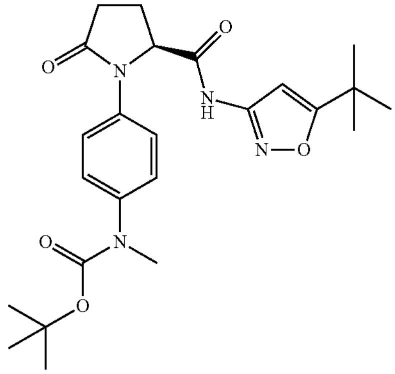 [SMILES: CN(C(=O)OC(C)(C)C)c1ccc(N2C(=O)CC[C@H]2C(=O)Nc2cc(C(C)(C)C)on2)cc1] | {4-[(S)-2-(5-tert-butyl-isoxazol-3-ylcarbamoyl)-5-oxo-pyrrolidin-1-yl]-phenyl}-methyl-carbamic-acid tert-butyl ester | 457 | 6 |
| 99 | 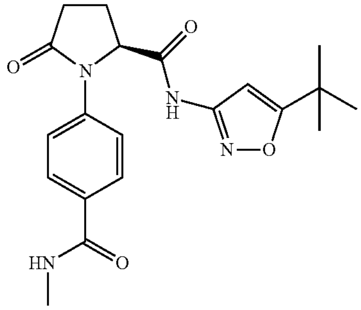 [SMILES: CNC(=O)c1ccc(N2C(=O)CC[C@H]2C(=O)Nc2cc(C(C)(C)C)on2)cc1] | (S)-1-(4-methylcarbamoyl-phenyl)-5-oxo-pyrrolidine-2-carboxylic acid (5-tert-butyl-isoxazol-3-yl)-amide | 385 | 19 |
| 100 | 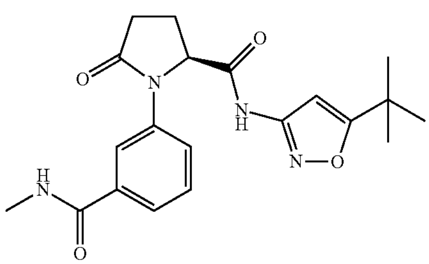 [SMILES: CNC(=O)c1cccc(N2C(=O)CC[C@H]2C(=O)Nc2cc(C(C)(C)C)on2)c1] | (S)-1-(3-methylcarbamoyl-phenyl)-5-oxo-pyrrolidine-2-carboxylic acid (5-tert-butyl-isoxazol-3-yl)-amide | 385 | 19 |
| 101 | 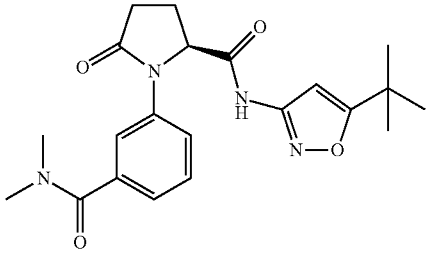 [SMILES: CN(C)C(=O)c1cccc(N2C(=O)CC[C@H]2C(=O)Nc2cc(C(C)(C)C)on2)c1] | (S)-1-(3-dimethylcarbamoyl-phenyl)-5-oxo-pyrrolidine-2-carboxylic acid (5-tert-butyl-isoxazol-3-yl)-amide | 399 | 19 |

TABLE III-continued

| Example | Structure | Name | ESI m/z (+) | Patent Method |
|---|---|---|---|---|
| 102 | 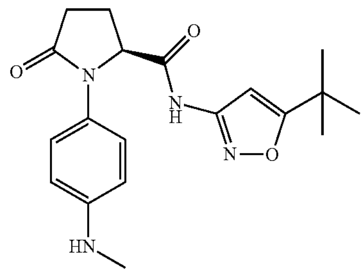 [SMILES: CNc1ccc(N2C(=O)CC[C@H]2C(=O)Nc2cc(C(C)(C)C)on2)cc1] | (S)-1-(4-methylamino-phenyl)-5-oxo-pyrrolidine-2-carboxylic acid (5-tert-butyl-isoxazol-3-yl)-amide | 357 | 20 |
| 103 | 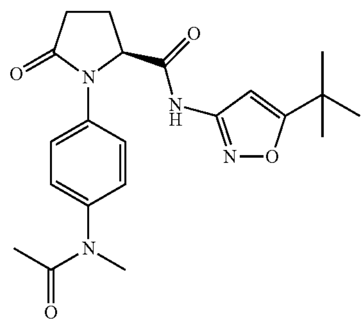 [SMILES: CC(=O)N(C)c1ccc(N2C(=O)CC[C@H]2C(=O)Nc2cc(C(C)(C)C)on2)cc1] | (S)-1-[4-(acetyl-methyl-amino)-phenyl]-5-oxo-pyrrolidine-2-carboxylic acid (5-tert-butyl-isoxazol-3-yl)-amide | 399 | 20 |
| 104 | 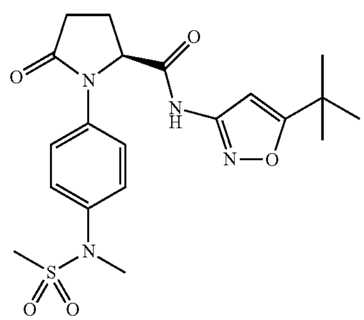 [SMILES: CN(c1ccc(N2C(=O)CC[C@H]2C(=O)Nc2cc(C(C)(C)C)on2)cc1)S(C)(=O)=O] | (S)-1-[4-(methanesulfonyl-methyl-amino)-phenyl]-5-oxo-pyrrolidine-2-carboxylic acid (5-tert-butyl-isoxazol-3-yl)-amide | 435 | 20 |
| 105 | 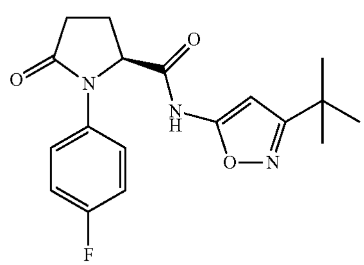 [SMILES: CC(C)(C)c1cc(NC(=O)[C@@H]2CCC(=O)N2c2ccc(F)cc2)on1] | (S)-1-(4-fluoro-phenyl)-5-oxo-pyrrolidine-2-carboxylic acid (3-tert-butyl-isoxazol-5-yl)-amide | 346 | 6 |
| 106 | 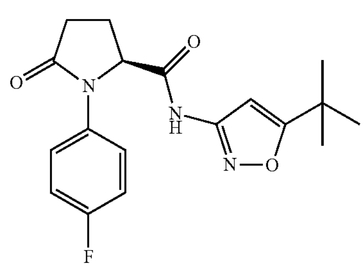 [SMILES: CC(C)(C)c1cc(NC(=O)[C@@H]2CCC(=O)N2c2ccc(F)cc2)no1] | (S)-1-(4-fluoro-phenyl)-5-oxo-pyrrolidine-2-carboxylic acid (5-tert-butyl-isoxazol-3-yl)-amide | 346 | 6 |

TABLE III-continued

| Example | Structure | Name | ESI m/z (+) | Patent Method |
|---|---|---|---|---|
| 107 | 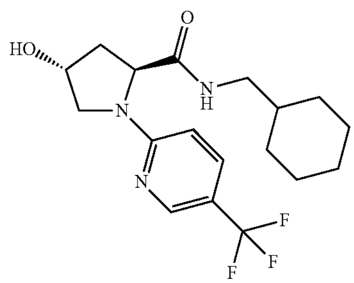 [SMILES: O=C(NCC1CCCCC1)[C@@H]1C[C@@H](O)CN1c1ccc(C(F)(F)F)cn1] | (2S,4R)-4-Hydroxy-1-(5-trifluoromethyl-pyridin-2-yl)-pyrrolidine-2-carboxylic acid cyclohexylmethyl-amide | 372 | 25 |
| 108 | 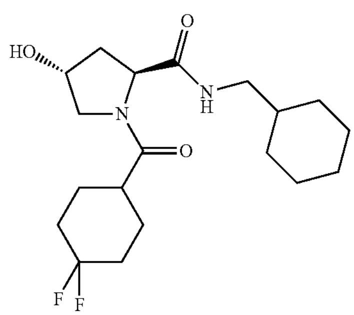 [SMILES: O=C(NCC1CCCCC1)[C@@H]1C[C@@H](O)CN1C(=O)C1CCC(F)(F)CC1] | (2S,4R)-1-(4,4-Difluoro-cyclohexanecarbonyl)-4-hydroxy-pyrrolidine-2-carboxylic acid cyclohexylmethyl-amide | 373 | 26 |
| 109 | 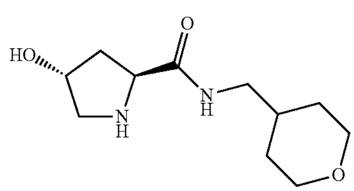 [SMILES: O=C(NCC1CCOCC1)[C@@H]1C[C@@H](O)CN1] | (2S,4R)-4-Hydroxy-pyrrolidine-2-carboxylic acid (tetrahydro-pyran-4-ylmethyl)-amide | 229 | Table 2 |
| 110 | 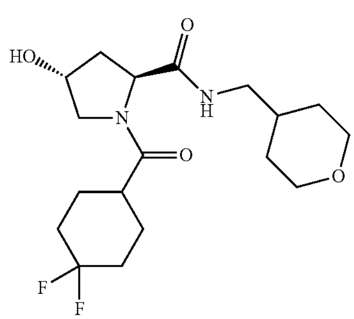 [SMILES: O=C(NCC1CCOCC1)[C@@H]1C[C@@H](O)CN1C(=O)C1CCC(F)(F)CC1] | (2S,4R)-1-(4,4-Difluoro-cyclohexanecarbonyl)-4-hydroxy-pyrrolidine-2-carboxylic acid (tetrahydro-pyran-4-ylmethyl)-amide | 375 | 26 |
| 111 | 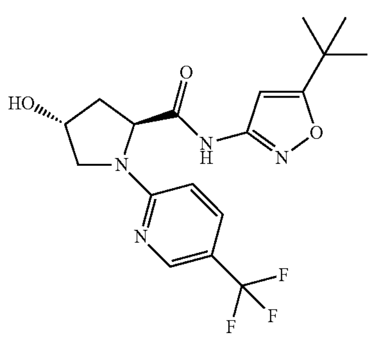 [SMILES: CC(C)(C)c1cc(NC(=O)[C@@H]2C[C@@H](O)CN2c2ccc(C(F)(F)F)cn2)no1] | (2S,4R)-4-Hydroxy-1-(5-trifluoromethyl-pyridin-2-yl)-pyrrolidine-2-carboxylic acid (5-tert-butyl-isoxazol-3-yl)-amide | 399 | 10 |

TABLE III-continued

| Example | Name | ESI m/z (+) | Patent Method |
|---|---|---|---|
| 112 | (2R,4R)-4-Hydroxy-1-(5-trifluoromethyl-pyridin-2-yl)-pyrrolidine-2-carboxylic acid (5-trifluoromethyl-pyridin-2-yl)-amide | 421 | 33 |
| 113 | (S)-1-(4,4-Difluoro-cyclohexanecarbonyl)-4,4-difluoro-pyrrolidine-2-carboxylic acid (5-tert-butyl-isoxazol-3-yl)-amide | 420 | 28 |
| 114 | (2S,4R)-1-(3-Chloro-5-trifluoromethyl-pyridin-2-yl)-4-hydroxy-pyrrolidine-2-carboxylic acid (5-tert-butyl-isoxazol-3-yl)-amide | 433 | 10 |
| 115 | (2S,4R)-1-(4,4-Difluoro-cyclohexanecarbonyl)-4-hydroxy-pyrrolidine-2-carboxylic acid (5-trifluoromethyl-pyridin-2-yl)-amide | 422 | 26 |

TABLE III-continued

| Example | Name | ESI m/z (+) | Patent Method |
|---|---|---|---|
| 116 | (2S,4R)-1-(4,4-Difluoro-cyclohexanecarbonyl)-4-hydroxy-pyrrolidine-2-carboxylic acid (3-phenyl-1,2,4-thiadiazol-5-yl)-amide | 437 | 26 |
| 117 | (S)-1-(4,4-Difluoro-cyclohexanecarbonyl)-4-oxo-pyrrolidine-2-carboxylic acid (5-tert-butyl-isoxazol-3-yl)-amide | 400 | 26 |
| 118 | (2S,4R)-4-Hydroxy-1-(5-trifluoromethyl-pyridin-2-yl)-pyrrolidine-2-carboxylic acid (3-phenyl-1,2,4-thiadiazol-5-yl)-amide | 436 | 10 |
| 119 | (2S,4S)-1-(3-Chloro-5-trifluoromethyl-pyridin-2-yl)-4-hydroxy-pyrrolidine-2-carboxylic acid (5-tert-butyl-isoxazol-3-yl)-amide | 433 | 25 |

TABLE III-continued

| Example | Name | ESI m/z (+) | Patent Method |
|---|---|---|---|
| 120 | (2S,4S)-4-Hydroxy-1-(5-trifluoromethyl-pyridin-2-yl)-pyrrolidine-2-carboxylic acid (5-tert-butyl-isoxazol-3-yl)-amide | 399 | 10 |
| 121 | (2S,4S)-1-(4,4-Difluoro-cyclohexanecarbonyl)-4-hydroxy-pyrrolidine-2-carboxylic acid (5-tert-butyl-isoxazol-3-yl)-amide | 400 | 26 |
| 122 | (S)-1-(3-Chloro-5-trifluoromethyl-pyridin-2-yl)-4-oxo-pyrrolidine-2-carboxylic acid (5-tert-butyl-isoxazol-3-yl)-amide | 431 | 29 |
| 123 | (2S,4S)-1-(3-Chloro-5-trifluoromethyl-pyridin-2-yl)-4-hydroxy-pyrrolidine-2-carboxylic acid (3-phenyl-1,2,4-thiadiazol-5-yl)-amide | 470 | 10 |

TABLE III-continued

| Example | Name | ESI m/z (+) | Patent Method |
|---|---|---|---|
| 124 | (2S,4S)-1-(4,4-Difluoro-cyclohexanecarbonyl)-4-hydroxy-pyrrolidine-2-carboxylic acid (3-phenyl-1,2,4-thiadiazol-5-yl)-amide | 437 | 26 |
| 125 | (2S,4S)-4-Hydroxy-1-(5-trifluoromethyl-pyridin-2-yl)-pyrrolidine-2-carboxylic acid (3-phenyl-1,2,4-thiadiazol-5-yl)-amide | 436 | 10 |
| 126 | (2S,4R)-4-Hydroxy-1-(5-trifluoromethyl-pyridin-2-yl)-pyrrolidine-2-carboxylic acid (3-tert-butyl-isoxazol-5-yl)-amide | 399 | 10 |
| 127 | (2S,4R)-1-(4-Chloro-phenyl)-4-hydroxy-pyrrolidine-2-carboxylic acid (5-tert-butyl-isoxazol-3-yl)-amide | 364 | 30 |

TABLE III-continued

| Example | Structure | Name | ESI m/z (+) | Patent Method |
|---|---|---|---|---|
| 128 | 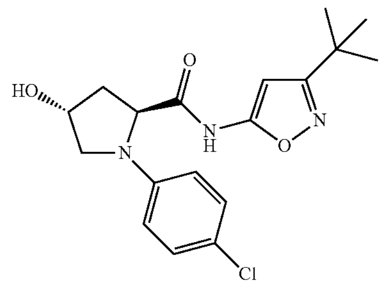 [SMILES: CC(C)(C)c1cc(NC(=O)[C@@H]2C[C@@H](O)CN2c2ccc(Cl)cc2)on1] | (2S,4R)-1-(4-Chloro-phenyl)-4-hydroxy-pyrrolidine-2-carboxylic acid (3-tert-butyl-isoxazol-5-yl)-amide | 364 | 30 |
| 129 | 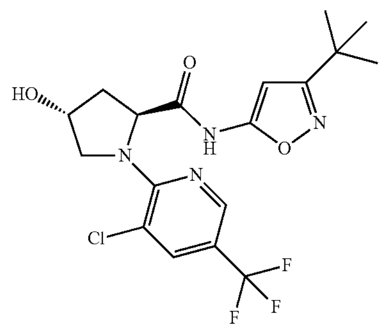 [SMILES: CC(C)(C)c1cc(NC(=O)[C@@H]2C[C@@H](O)CN2c2ncc(C(F)(F)F)cc2Cl)on1] | (2S,4R)-1-(3-Chloro-5-trifluoromethyl-pyridin-2-yl)-4-hydroxy-pyrrolidine-2-carboxylic acid (3-tert-butyl-isoxazol-5-yl)-amide | 433 | 10 |
| 130 | 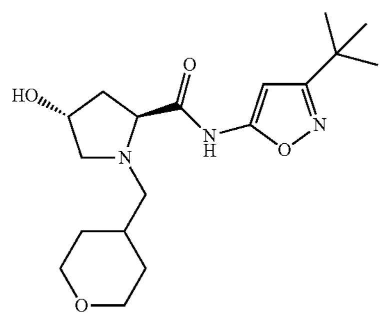 [SMILES: CC(C)(C)c1cc(NC(=O)[C@@H]2C[C@@H](O)CN2CC2CCOCC2)on1] | (2S,4R)-4-Hydroxy-1-(tetrahydro-pyran-4-ylmethyl)-pyrrolidine-2-carboxylic acid (3-tert-butyl-isoxazol-5-yl)-amide | 352 | 27 |
| 131 | 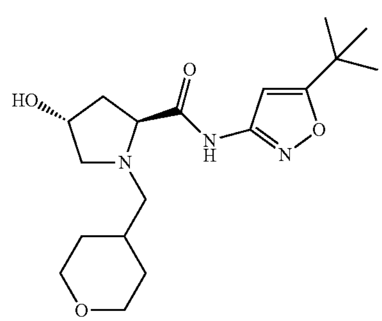 [SMILES: CC(C)(C)c1cc(NC(=O)[C@@H]2C[C@@H](O)CN2CC2CCOCC2)no1] | (2S,4R)-4-Hydroxy-1-(tetrahydro-pyran-4-ylmethyl)-pyrrolidine-2-carboxylic acid (5-tert-butyl-isoxazol-3-yl)-amide | 352 | 27 |
| 132 | 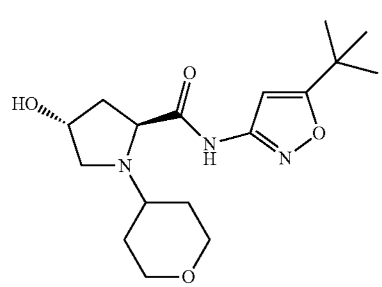 [SMILES: CC(C)(C)c1cc(NC(=O)[C@@H]2C[C@@H](O)CN2C2CCOCC2)no1] | (2S,4R)-4-Hydroxy-1-(tetrahydro-pyran-4-yl)-pyrrolidine-2-carboxylic acid (5-tert-butyl-isoxazol-3-yl)-amide | 338 | 27 |

TABLE III-continued

| Example | Structure | Name | ESI m/z (+) | Patent Method |
|---|---|---|---|---|
| 133 | 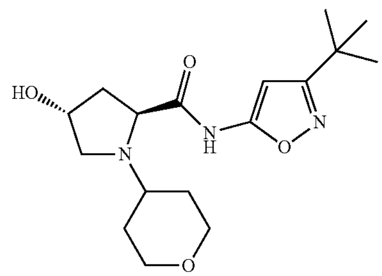 [SMILES: CC(C)(C)c1cc(NC(=O)[C@@H]2C[C@@H](O)CN2C2CCOCC2)on1] | (2S,4R)-4-Hydroxy-1-(tetrahydro-pyran-4-yl)-pyrrolidine-2-carboxylic acid (3-tert-butyl-isoxazol-5-yl)-amide | 338 | 27 |
| 134 | 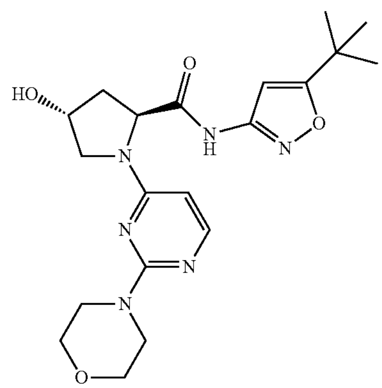 [SMILES: CC(C)(C)c1cc(NC(=O)[C@@H]2C[C@@H](O)CN2c2ccnc(N3CCOCC3)n2)no1] | (2S,4R)-4-Hydroxy-1-(2-morpholin-4-yl-pyrimidin-4-yl)-pyrrolidine-2-carboxylic-acid (5-tert-butyl-isoxazol-3-yl)-amide | 417 | 31 |
| 135 | 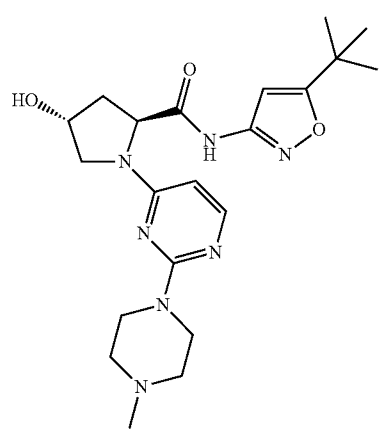 [SMILES: CN1CCN(c2nccc(N3C[C@H](O)C[C@H]3C(=O)Nc3cc(C(C)(C)C)on3)n2)CC1] | (2S,4R)-4-Hydroxy-1-[2-(4-methyl-piperizin-1-yl)-pyrimidin-4-yl]-pyrrolidine-2-carboxylic acid (5-tert-butyl-isoxazol-3-yl)-amide | 430 | 31 |
| 136 | 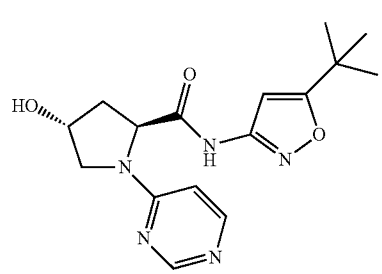 [SMILES: CC(C)(C)c1cc(NC(=O)[C@@H]2C[C@@H](O)CN2c2ccncn2)no1] | (2S,4R)-4-Hydroxy-1-pyrimidin-4-yl-pyrrolidine-2-carboxylic acid (5-tert-butyl-isoxazol-3-yl)-amide | 332 | 32 |

TABLE III-continued

| Example | Name | ESI m/z (+) | Patent Method |
|---|---|---|---|
| 137 | (2S,4R)-4-Hydroxy-1-(2-methylamino-pyrimidin-4-yl)-pyrrolidine-2-carboxylic acid (5-tert-butyl-isoxazol-3-yl)-amide | 361 | 31 |
| 138 | (2S,4R)-1-(3,4-Difluoro-benzyl)-4-hydroxy-pyrrolidine-2-carboxylic acid (5-tert-butyl-isoxazol-3-yl)-amide | 380 | 27 |
| 139 | (2S,4R)-1-(4-Chloro-phenyl)-4-hydroxy-pyrrolidine-2-carboxylic acid (5-ethyl-4-phenyl-thiazol-2-yl)-amide | 428 | 30 |
| 140 | (2S,4R)-4-Hydroxy-1-(tetrahydro-pyran-4-yl)-pyrrolidine-2-carboxylic acid (5-ethyl-4-phenyl-thiazol-2-yl)-amide | 402 | 27 |

TABLE III-continued

| Example | Name | ESI m/z (+) | Patent Method |
|---|---|---|---|
| 141 | (2S,4R)-4-Hydroxy-1-(tetrahydro-pyran-4-ylmethyl)-pyrrolidine-2-carboxylic acid (5-ethyl-4-phenyl-thiazol-2-yl)-amide | 416 | 27 |
| 142 | (2S,4R)-1-Cyclopropyl-4-hydroxy-pyrrolidine-2-carboxylic acid (5-tert-butyl-isoxazol-3-yl)-amide | 294 | 27 |
| 143 | (2S,4R)-1-Cyclopentyl-4-hydroxy-pyrrolidine-2-carboxylic acid (5-tert-butyl-isoxazol-3-yl)-amide | 322 | 27 |
| 144 | (2S,4R)-1-Cyclohexyl-4-hydroxy-pyrrolidine-2-carboxylic acid (5-tert-butyl-isoxazol-3-yl)-amide | 336 | 27 |
| 145 | (2S,4R)-1-(3,4-Difluoro-benzyl)-4-hydroxy-pyrrolidine-2-carboxylic acid (3-tert-butyl-isoxazol-5-yl)-amide | 380 | 27 |

TABLE III-continued

| Example | Structure | Name | ESI m/z (+) | Patent Method |
|---|---|---|---|---|
| 146 | 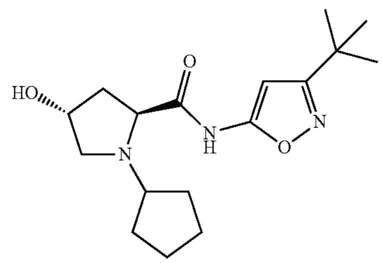 [SMILES: CC(C)(C)c1cc(NC(=O)[C@@H]2C[C@@H](O)CN2C2CCCC2)on1] | (2S,4R)-1-Cyclopentyl-4-hydroxy-pyrrolidine-2-carboxylic acid (3-tert-butyl-isoxazol-5-yl)-amide | 322 | 27 |
| 147 | 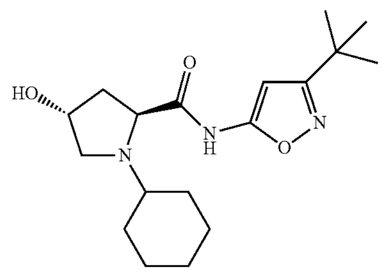 [SMILES: CC(C)(C)c1cc(NC(=O)[C@@H]2C[C@@H](O)CN2C2CCCCC2)on1] | (2S,4R)-1-Cyclohexyl-4-hydroxy-pyrrolidine-2-carboxylic acid (3-tert-butyl-isoxazol-5-yl)-amide | 336 | 27 |
| 148 | 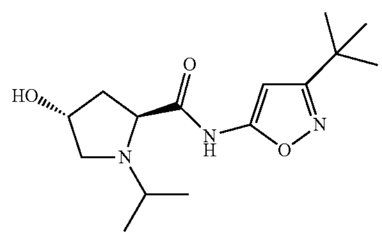 [SMILES: CC(C)N1C[C@H](O)C[C@H]1C(=O)Nc1cc(C(C)(C)C)no1] | (2S,4R)-4-Hydroxy-1-isopropyl-pyrrolidine-2-carboxylic acid (3-tert-butyl-isoxazol-5-yl)-amide | 332 | 27 |
| 149 | 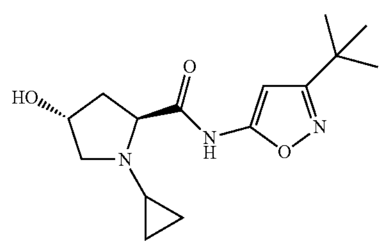 [SMILES: CC(C)(C)c1cc(NC(=O)[C@@H]2C[C@@H](O)CN2C2CC2)on1] | (2S,4R)-1-Cyclopropyl-4-hydroxy-pyrrolidine-2-carboxylic acid (3-tert-butyl-isoxazol-5-yl)-amide | 294 | 27 |
| 150 | 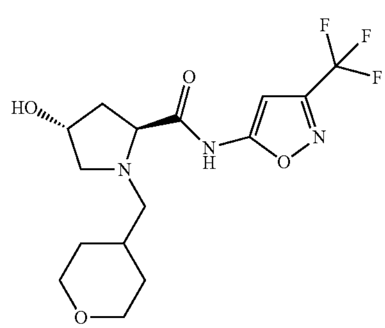 [SMILES: O=C(Nc1cc(C(F)(F)F)no1)[C@@H]1C[C@@H](O)CN1CC1CCOCC1] | (2S,4R)-4-Hydroxy-1-(tetrahydro-pyran-4-ylmethyl)-pyrrolidine-2-carboxylic acid (3-trifluoromethyl-isoxazol-5-yl)-amide | 364 | 30 |

TABLE III-continued

| Example | Name | ESI m/z (+) | Patent Method |
|---|---|---|---|
| 151 | (2S,4R)-4-Hydroxy-1-(tetrahydro-pyran-4-ylmethyl)-pyrrolidine-2-carboxylic acid (5-ethyl-1-phenyl-1H-1,2,4-triazol-3-yl)-amide | 400 | 27 |
| 152 | (2S,4R)-4-Hydroxy-1-(tetrahydro-pyran-4-yl)-pyrrolidine-2-carboxylic acid (5-tert-butyl-1,3,4-thiadiazol-2-yl)-amide | 355 | 27 |
| 153 | 1-(5-Chloro-pyridin-2-yl)-pyrrolidine-2-carboxylic acid (5-tert-butyl-isoxazol-3-yl)-amide | 349 | 1 |
| 154 | 1-(3-Chloro-5-trifluoromethyl-pyridin-2-yl)-pyrrolidine-2-carboxylic acid (5-trifluoromethyl-pyridin-2-yl)-amide | 439 | 1 |
| 155 | 1-(3-Chloro-5-trifluoromethyl-pyridin-2-yl)-pyrrolidine-2-carboxylic acid (5-tert-butyl-2-methyl-2H-pyrazol-3-yl)-amide | 430 | 1 |

TABLE III-continued

| Example | Name | ESI m/z (+) | Patent Method |
|---|---|---|---|
| 156 | (S)-1-(4-Chloro-phenyl)-pyrrolidine-2-carboxylic acid (5-tert-butyl-isoxazol-3-yl)-amide | 349 | 5 |
| 157 | 1-Isopropyl-pyrrolidine-2-carboxylic acid (5-tert-butyl-isoxazol-3-yl)-amide | 280 | 2 |
| 158 | 1-(5-Trifluoromethyl-pyridin-2-yl)-pyrrolidine-2-carboxylic acid (5-tert-butyl-isoxazol-3-yl)-amide | 383 | 1 |
| 159 | (S)-1-(5-Trifluoromethyl-pyridin-2-yl)-pyrrolidine-2-carboxylic acid (5-tert-butyl-isoxazol-3-yl)-amide | 383 | 1 |
| 160 | (R)-1-(5-Trifluoromethyl-pyridin-2-yl)-pyrrolidine-2-carboxylic acid (5-tert-butyl-isoxazol-3-yl)-amide | 383 | 1 |

TABLE III-continued

| Example | Structure | Name | ESI m/z (+) | Patent Method |
|---|---|---|---|---|
| 161 | 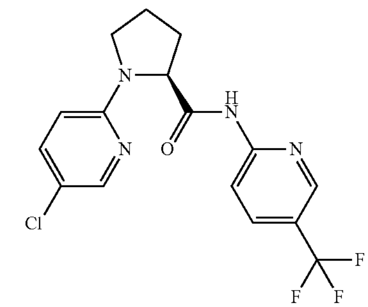 [SMILES: O=C(Nc1ccc(C(F)(F)F)cn1)[C@@H]1CCCN1c1ccc(Cl)cn1] | (S)-1-(4-Chloro-phenyl)-pyrrolidine-2-carboxylic acid (5-trifluoromethyl-pyridin-2-yl)-amide | 370 | 3 |
| 162 | 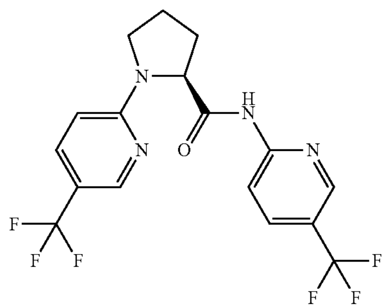 [SMILES: O=C(Nc1ccc(C(F)(F)F)cn1)[C@@H]1CCCN1c1ccc(C(F)(F)F)cn1] | (S)-1-(4-Trifluoromethyl-phenyl)-pyrrolidine-2-carboxylic acid (5-trifluoromethyl-pyridin-2-yl)-amide | 404 | 3 |
| 163 | 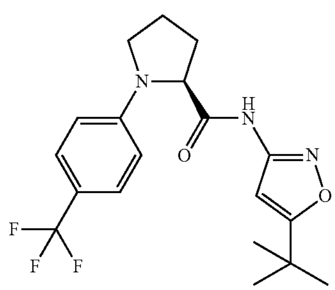 [SMILES: CC(C)(C)c1cc(NC(=O)[C@@H]2CCCN2c2ccc(C(F)(F)F)cc2)no1] | (S)-1-(4-Trifluoromethyl-phenyl)-pyrrolidine-2-carboxylic acid (5-tert-butyl-isoxazol-3-yl)-amide | 383 | 5 |
| 164 | 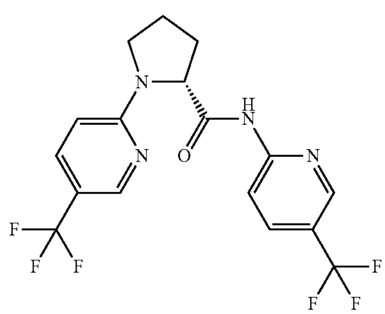 [SMILES: O=C(Nc1ccc(C(F)(F)F)cn1)[C@H]1CCCN1c1ccc(C(F)(F)F)cn1] | (R)-1-(4-Trifluoromethyl-phenyl)-pyrrolidine-2-carboxylic acid (5-trifluoromethyl-pyridin-2-yl)-amide | 404 | 3 |
| 165 | 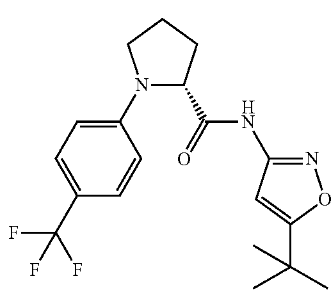 [SMILES: CC(C)(C)c1cc(NC(=O)[C@H]2CCCN2c2ccc(C(F)(F)F)cc2)no1] | (R)-1-(4-Trifluoromethyl-phenyl)-pyrrolidine-2-carboxylic acid (5-tert-butyl-isoxazol-3-yl)-amide | 382 | 3 |

TABLE III-continued

| Example | Name | ESI m/z (+) | Patent Method |
|---|---|---|---|
| 166 | (S)-1-(4-Chloro-phenyl)-2-methyl-pyrrolidine-2-carboxylic acid (5-tert-butyl-isoxazol-3-yl)-amide | 362 | 4 |
| 167 | (S)-2-Methyl-1-(4-trifluoromethyl-phenyl)-pyrrolidine-2-carboxylic acid (5-tert-butyl-isoxazol-3-yl)-amide | 396 | 4 |
| 168 | (S)-1-(4-Chloro-phenyl)-2-methyl-pyrrolidine-2-carboxylic acid (5-trifluoromethyl-pyridin-2-yl)-amide | 384 | 4 |
| 169 | (S)-1-(4-Chloro-phenyl)-pyrrolidine-2-carboxylic acid (6-trifluoromethyl-pyridin-2-yl)-amide | 370 | 5 |
| 170 | (S)-1-(4-Chloro-phenyl)-pyrrolidine-2-carboxylic acid (4-trifluoromethyl-thiazol-2-yl)-amide | 376 | 5 |

TABLE III-continued

| Example | Name | ESI m/z (+) | Patent Method |
|---|---|---|---|
| 171 | (S)-1-(4-Chloro-phenyl)-pyrrolidine-2-carboxylic acid (4,5,6,7-tetrahydro-benzothiazol-2-yl)-amide | 362 | 5 |
| 172 | (S)-1-(4,4-Difluoro-cyclohexanecarbonyl)-pyrrolidine-2-carboxylic acid (5-tert-butyl-isoxazol-3-yl)-amide | 384 | 11 |
| 173 | 1-(5-Trifluoromethyl-pyridin-2-yl)-pyrrolidine-2-carboxylic acid (5-trifluoromethyl-pyridin-2-yl)-amide | 405 | 3 |
| 174 | (R)-1-(4-Chloro-phenyl)-pyrrolidine-2-carboxylic acid (5-tert-butyl-isoxazol-3-yl)-amide | 348 | 3 |
| 175 | (S)-1-(1,1-Dioxo-1l6-thiomorpholine-4-carbonyl)-pyrrolidine-2-carboxylic acid (5-tert-butyl-isoxazol-3-yl)-amide | 399 | 12 |
| 176 | 1-(3-Chloro-5-trifluoromethyl-pyridin-2-yl)-pyrrolidine-2-carboxylic acid (5-tert-butyl-isoxazol-3-yl)-amide | 417 | 1 |

TABLE III-continued

| Example | Name | ESI m/z (+) | Patent Method |
|---|---|---|---|
| 177 | (S)-2-Methyl-1-(5-trifluoromethyl-pyridin-2-yl)-pyrrolidine-2-carboxylic acid (5-tert-butyl-isoxazol-3-yl)-amide | 398 | 5 |
| 178 | (S)-2-Methyl-1-(5-trifluoromethyl-pyridin-2-yl)-pyrrolidine-2-carboxylic acid (3-phenyl-1,2,4-thiadiazol-5-yl)-amide | 434 | 5 |
| 179 | (S)-2-Methyl-1-(5-trifluoromethyl-pyridin-2-yl)-pyrrolidine-2-carboxylic acid (5-trifluoromethyl-pyridin-2-yl)-amide | 419 | 5 |
| 180 | (S)-1-(4-Chloro-phenyl)-pyrrolidine-2-carboxylic acid (5-methyl-pyridin-2-yl)-amide | 316 | 5 |
| 181 | (S)-1-(Tetrahydro-pyran-4-yl)-pyrrolidine-2-carboxylic acid (5-tert-butyl-isoxazol-3-yl)-amide | 322 | 9 |

TABLE III-continued

| Example | Structure | Name | ESI m/z (+) | Patent Method |
|---|---|---|---|---|
| 182 | 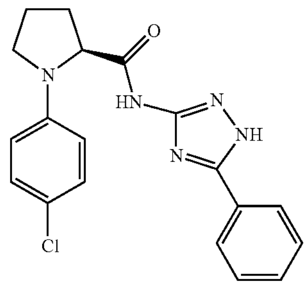 [SMILES: O=C(Nc1n[nH]c(-c2ccccc2)n1)[C@@H]1CCCN1c1ccc(Cl)cc1] | (S)-1-(4-Chloro-phenyl)-pyrrolidine-2-carboxylic acid (5-phenyl-1H-1,2,4-triazol-3-yl)-amide | 368 | 5 |
| 183 | 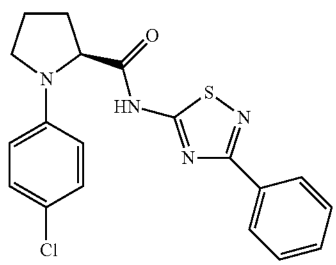 [SMILES: O=C(Nc1nc(-c2ccccc2)ns1)[C@@H]1CCCN1c1ccc(Cl)cc1] | (S)-1-(4-Chloro-phenyl)-pyrrolidine-2-carboxylic acid (3-phenyl-1,2,4-thiadiazol-5-yl)-amide | 385 | 5 |
| 184 | 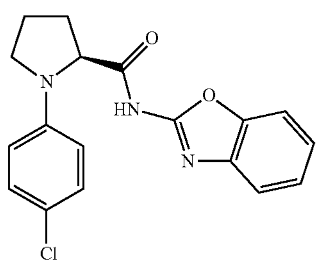 [SMILES: O=C(Nc1nc2ccccc2o1)[C@@H]1CCCN1c1ccc(Cl)cc1] | (S)-1-(4-Chloro-phenyl)-pyrrolidine-2-carboxylic acid benzoxazol-2-ylamide | 342 | 5 |
| 185 | 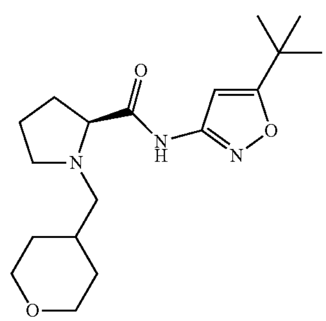 [SMILES: CC(C)(C)c1cc(NC(=O)[C@@H]2CCCN2CC2CCOCC2)no1] | (S)-1-(Tetrahydro-pyran-4-ylmethyl)-pyrrolidine-2-carboxylic acid (5-tert-butyl-isoxazol-3-yl)-amide | 336 | 9 |
| 186 | 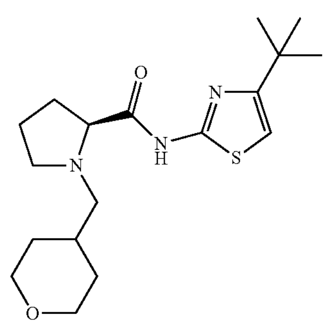 [SMILES: CC(C)(C)c1csc(NC(=O)[C@@H]2CCCN2CC2CCOCC2)n1] | (S)-1-(Tetrahydro-pyran-4-ylmethyl)-pyrrolidine-2-carboxylic acid (4-tert-butyl-thiazol-2-yl)-amide | 352 | 9 |

TABLE III-continued

| Example | Structure | Name | ESI m/z (+) | Patent Method |
|---|---|---|---|---|
| 187 | 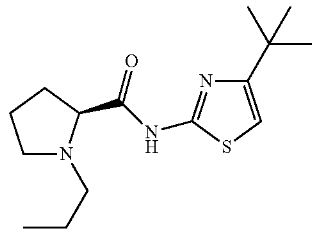 [SMILES: CCCN1CCC[C@H]1C(=O)Nc1nc(C(C)(C)C)cs1] | (S)-1-Propyl-pyrrolidine-2-carboxylic acid (4-tert-butyl-thiazol-2-yl)-amide | 296 | 9 |
| 188 | 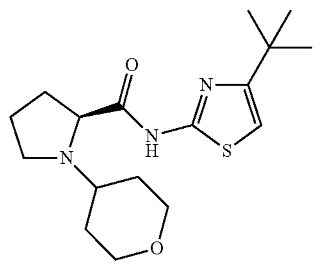 [SMILES: CC(C)(C)c1csc(NC(=O)[C@@H]2CCCN2C2CCOCC2)n1] | (S)-1-(Tetrahydro-pyran-4-yl)-pyrrolidine-2-carboxylic acid (4-tert-butyl-thiazol-2-yl)-amide | 338 | 9 |
| 189 | 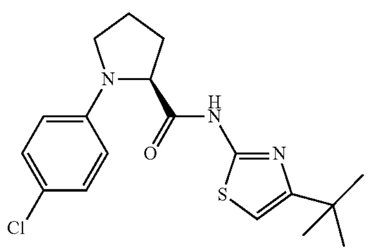 [SMILES: CC(C)(C)c1csc(NC(=O)[C@@H]2CCCN2c2ccc(Cl)cc2)n1] | (S)-1-(4-Chloro-phenyl)-pyrrolidine-2-carboxylic acid (4-tert-butyl-thiazol-2-yl)-amide | 364 | 5 |
| 190 | 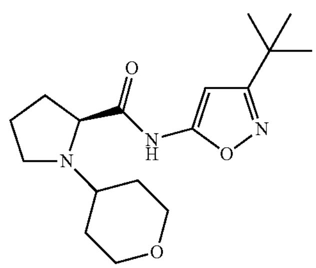 | (S)-1-(Tetrahydro-pyran-4-yl)-pyrrolidine-2-carboxylic acid (3-tert-butyl-isoxazol-5-yl)-amide | 321 | 9 |
| 191 | 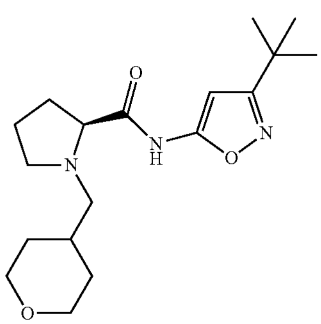 [SMILES: CC(C)(C)c1cc(NC(=O)[C@@H]2CCCN2CC2CCOCC2)on1] | (S)-1-(Tetrahydro-pyran-4-ylmethyl)-pyrrolidine-2-carboxylic acid (3-tert-butyl-isoxazol-5-yl)-amide | 336 | 9 |

TABLE III-continued

| Example | Structure | Name | ESI m/z (+) | Patent Method |
|---|---|---|---|---|
| 192 | 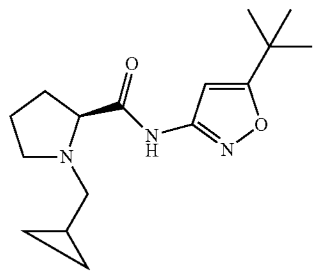 [SMILES: CC(C)(C)c1cc(NC(=O)[C@@H]2CCCN2CC2CC2)no1] | (S)-1-Cyclopropylmethyl-pyrrolidine-2-carboxylic acid (5-tert-butyl-isoxazol-3-yl)-amide | 292 | 9 |
| 193 | 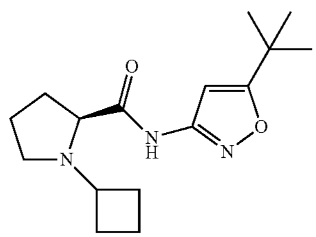 [SMILES: CC(C)(C)c1cc(NC(=O)[C@@H]2CCCN2C2CCC2)no1] | (S)-1-Cyclobutyl-pyrrolidine-2-carboxylic acid (5-tert-butyl-isoxazol-3-yl)-amide | 292 | 9 |
| 194 | 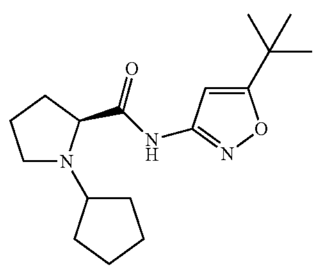 [SMILES: CC(C)(C)c1cc(NC(=O)[C@@H]2CCCN2C2CCCC2)no1] | (S)-1-Cyclopentyl-pyrrolidine-2-carboxylic acid (5-tert-butyl-isoxazol-3-yl)-amide | 306 | 9 |
| 195 | 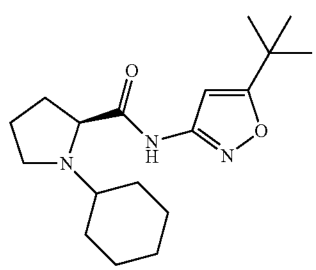 [SMILES: CC(C)(C)c1cc(NC(=O)[C@@H]2CCCN2C2CCCCC2)no1] | (S)-1-Cyclohexyl-pyrrolidine-2-carboxylic acid (5-tert-butyl-isoxazol-3-yl)-amide | 320 | 9 |
| 196 | 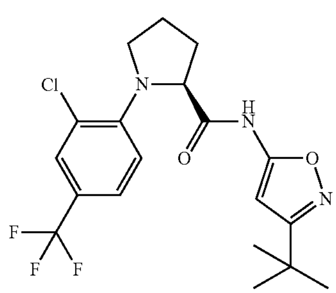 [SMILES: CC(C)(C)c1cc(NC(=O)[C@@H]2CCCN2c2ccc(C(F)(F)F)cc2Cl)on1] | (S)-1-(3-Chloro-5-trifluoromethyl-pyridin-2-yl)-pyrrolidine-2-carboxylic acid (3-tert-butyl-isoxazol-5-yl)-amide | 417 | 10 |

TABLE III-continued

| Example | Name | ESI m/z (+) | Patent Method |
|---|---|---|---|
| 197 | (S)-1-(3-Chloro-5-trifluoromethyl-pyridin-2-yl)-pyrrolidine-2-carboxylic acid (4-tert-butyl-thiazol-2-yl)-amide | 433 | 10 |
| 198 | (S)-1-(3-Chloro-5-trifluoromethyl-pyridin-2-yl)-pyrrolidine-2-carboxylic acid (5-tert-butyl-isoxazol-3-yl)-amide | 417 | 10 |
| 199 | (S)-1-Cyclopropylmethyl-pyrrolidine-2-carboxylic acid (3-tert-butyl-isoxazol-5-yl)-amide | 292 | 9 |
| 200 | (S)-1-Cyclopropylmethyl-pyrrolidine-2-carboxylic acid [3-(2,2-dimethyl-propyl)-isoxazol-5-yl]-amide | 306 | 9 |
| 201 | (S)-1-Cyclopentyl-pyrrolidine-2-carboxylic acid [3-(2,2-dimethyl-propyl)-isoxazol-5-yl]-amide | 320 | 9 |

TABLE III-continued

| Example | Name | ESI m/z (+) | Patent Method |
|---|---|---|---|
| 202 | (S)-1-Cyclohexylmethyl-pyrrolidine-2-carboxylic acid (3-tert-butyl-isoxazol-5-yl)-amide | 334 | 13 |
| 203 | (S)-1-Cyclobutyl-pyrrolidine-2-carboxylic acid (3-tert-butyl-isoxazol-5-yl)-amide | 292 | 9 |
| 204 | (S)-1-Cyclopentyl-pyrrolidine-2-carboxylic acid (3-tert-butyl-isoxazol-5-yl)-amide | 306 | 9 |
| 205 | (S)-1-Cyclohexyl-pyrrolidine-2-carboxylic acid (3-tert-butyl-isoxazol-5-yl)-amide | 320 | 9 |
| 206 | (S)-1-(5-Trifluoromethyl-pyridin-2-yl)-pyrrolidine-2-carboxylic acid (3-tert-butyl-isoxazol-5-yl)-amide | 383 | 10 |

TABLE III-continued

| Example | Structure | Name | ESI m/z (+) | Patent Method |
|---|---|---|---|---|
| 207 | 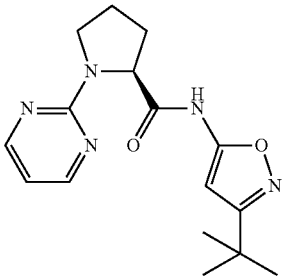 [SMILES: CC(C)(C)c1cc(NC(=O)[C@@H]2CCCN2c2ncccn2)on1] | (S)-1-Pyrimidin-2-yl-pyrrolidine-2-carboxylic acid (3-tert-butyl-isoxazol-5-yl)-amide | 316 | 10 |
| 208 | 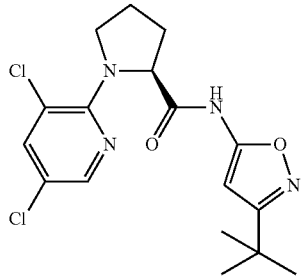 | (S)-1-(3,5-Dichloro-pyridin-2-yl)-pyrrolidine-2-carboxylic acid (3-tert-butyl-isoxazol-5-yl)-amide | 384 | 10 |
| 209 | 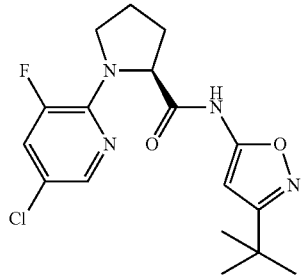 [SMILES: CC(C)(C)c1cc(NC(=O)[C@@H]2CCCN2c2ncc(Cl)cc2F)on1] | (S)-1-(5-Chloro-3-fluoro-pyridin-2-yl)-pyrrolidine-2-carboxylic acid (3-tert-butyl-isoxazol-5-yl)-amide | 367 | 10 |
| 210 | 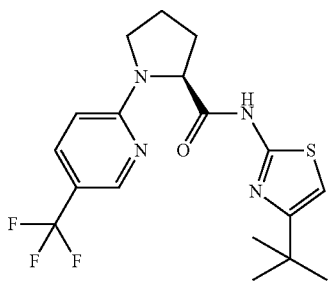 [SMILES: CC(C)(C)c1csc(NC(=O)[C@@H]2CCCN2c2ccc(C(F)(F)F)cn2)n1] | (S)-1-(5-Trifluoromethyl-pyridin-2-yl)-pyrrolidine-2-carboxylic acid (4-tert-butyl-thiazol-2-yl)-amide | 399 | 10 |
| 211 | 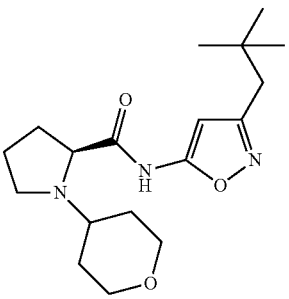 [SMILES: CC(C)(C)Cc1cc(NC(=O)[C@@H]2CCCN2C2CCOCC2)on1] | (S)-1-(Tetrahydro-pyran-4-yl)-pyrrolidine-2-carboxylic acid [3-(2,2-dimethyl-propyl)-isoxazol-5-yl]-amide | 336 | 9 |

TABLE III-continued

| Example | Structure | Name | ESI m/z (+) | Patent Method |
|---|---|---|---|---|
| 212 | 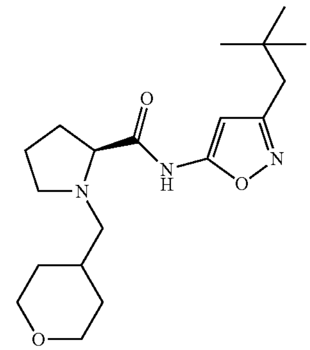 [SMILES: CC(C)(C)Cc1cc(NC(=O)[C@@H]2CCCN2CC2CCOCC2)on1] | (S)-1-(Tetrahydro-pyran-4-ylmethyl)-pyrrolidine-2-carboxylic acid [3-(2,2-dimethyl-propyl)-isoxazol-5-yl]-amide | 350 | 9 |
| 213 | 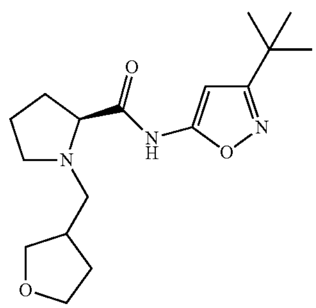 [SMILES: CC(C)(C)c1cc(NC(=O)[C@@H]2CCCN2CC2CCOC2)on1] | (S)-1-(Tetrahydro-furan-3-ylmethyl)-pyrrolidine-2-carboxylic acid (3-tert-butyl-isoxazol-5-yl)-amide | 322 | 9 |
| 214 | 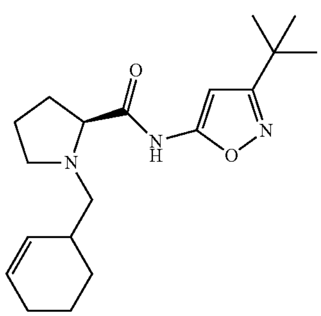 [SMILES: CC(C)(C)c1cc(NC(=O)[C@@H]2CCCN2CC2C=CCCC2)on1] | (S)-1-Cyclohex-2-enylmethyl-pyrrolidine-2-carboxylic acid (3-tert-butyl-isoxazol-5-yl)-amide | 332 | 9 |
| 215 | 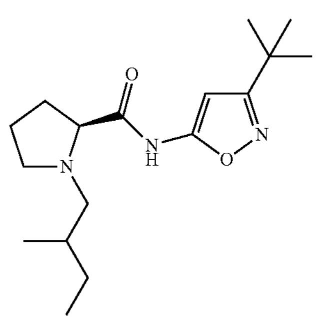 [SMILES: CCC(C)CN1CCC[C@H]1C(=O)Nc1cc(C(C)(C)C)no1] | (S)-1-(2-Methyl-butyl)-pyrrolidine-2-carboxylic acid (3-tert-butyl-isoxazol-5-yl)-amide | 308 | 9 |

TABLE III-continued

| Example | Name | ESI m/z (+) | Patent Method |
|---|---|---|---|
| 216 | (S)-1-(Tetrahydro-pyran-3-ylmethyl)-pyrrolidine-2-carboxylic acid (3-tert-butyl-isoxazol-5-yl)-amide | 336 | 9 |
| 217 | (S)-1-Cyclopropyl-pyrrolidine-2-carboxylic acid (3-tert-butyl-isoxazol-5-yl)-amide | 278 | 14 |
| 218 | 1-(2,2-Dimethyl-tetrahydro-pyran-4-ylmethyl)-pyrrolidine-2-carboxylic acid (3-tert-butyl-isoxazol-5-yl)-amide | 365 | 9 |
| 219 | 1-(Tetrahydro-pyran-2-ylmethyl)-pyrrolidine-2-carboxylic acid (3-tert-butyl-isoxazol-5-yl)-amide | 351 | 15 |
| 220 | (S)-1-(3-Hydroxy-propyl)-pyrrolidine-2-carboxylic acid (3-tert-butyl-isoxazol-5-yl)-amide | 296 | 13 |

TABLE III-continued

| Example | Structure | Name | ESI m/z (+) | Patent Method |
|---|---|---|---|---|
| 221 | 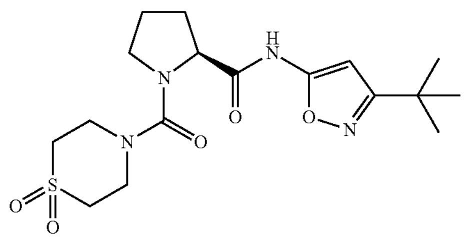 [SMILES: CC(C)(C)c1cc(NC(=O)[C@@H]2CCCN2C(=O)N2CCS(=O)(=O)CC2)on1] | (S)-1-(1,1-Dioxo-1l6-thiomorpholine-4-carbonyl)-pyrrolidine-2-carboxylic acid (3-tert-butyl-isoxazol-5-yl)-amide | 399 | 12 |
| 222 | 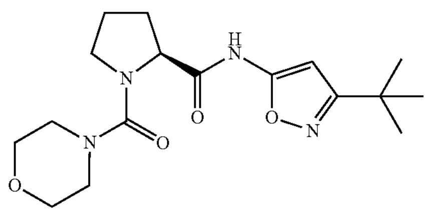 [SMILES: CC(C)(C)c1cc(NC(=O)[C@@H]2CCCN2C(=O)N2CCOCC2)on1] | (S)-1-(Morpholine-4-carbonyl)-pyrrolidine-2-carboxylic acid (3-tert-butyl-isoxazol-5-yl)-amide | 351 | 15 |
| 223 | 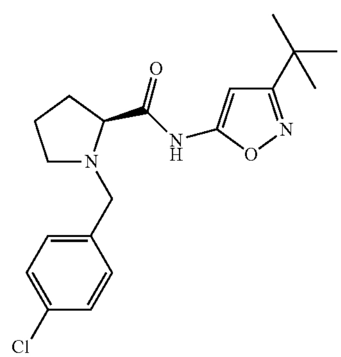 [SMILES: CC(C)(C)c1cc(NC(=O)[C@@H]2CCCN2Cc2ccc(Cl)cc2)on1] | (S)-1-(4-Chloro-benzyl)-pyrrolidine-2-carboxylic acid (3-tert-butyl-isoxazol-5-yl)-amide | 362 | 9 |
| 224 | 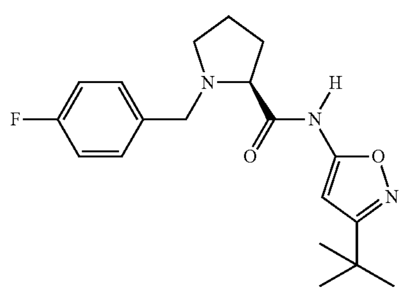 [SMILES: CC(C)(C)c1cc(NC(=O)[C@@H]2CCCN2Cc2ccc(F)cc2)on1] | (S)-1-(4-Fluoro-benzyl)-pyrrolidine-2-carboxylic acid (3-tert-butyl-isoxazol-5-yl)-amide | 346 | 9 |
| 225 | 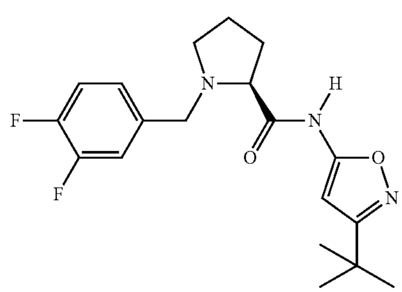 [SMILES: CC(C)(C)c1cc(NC(=O)[C@@H]2CCCN2Cc2ccc(F)c(F)c2)on1] | (S)-1-(3,4-Difluoro-benzyl)-pyrrolidine-2-carboxylic acid (3-tert-butyl-isoxazol-5-yl)-amide | 364 | 9 |

TABLE III-continued

| Example | Structure | Name | ESI m/z (+) | Patent Method |
|---|---|---|---|---|
| 226 | 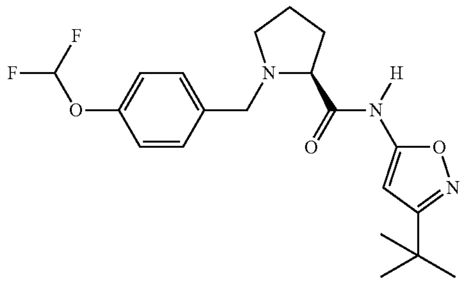 [SMILES: CC(C)(C)c1cc(NC(=O)[C@@H]2CCCN2Cc2ccc(OC(F)F)cc2)on1] | (S)-1-(4-Difluoromethoxy-benzyl)-pyrrolidine-2-carboxylic acid (3-tert-butyl-isoxazol-5-yl)-amide | 394 | 9 |
| 227 | 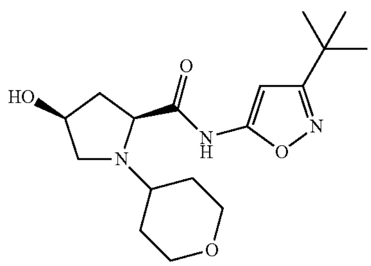 [SMILES: CC(C)(C)c1cc(NC(=O)[C@@H]2C[C@H](O)CN2C2CCOCC2)on1] | (2S,4S)-4-Hydroxy-1-(tetrahydro-pyran-4-yl)-pyrrolidine-2-carboxylic acid (3-tert-butyl-isoxazol-5-yl)-amide | 338 | 2 |
| 228 | 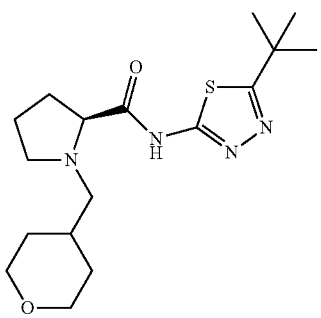 [SMILES: CC(C)(C)c1nnc(NC(=O)[C@@H]2CCCN2CC2CCOCC2)s1] | (S)-1-(Tetrahydro-pyran-4-ylmethyl)-pyrrolidine-2-carboxylic acid (5-tert-butyl-1,3,4-thiadiazol-2-yl)-amide | 353 | 9 |
| 229 | 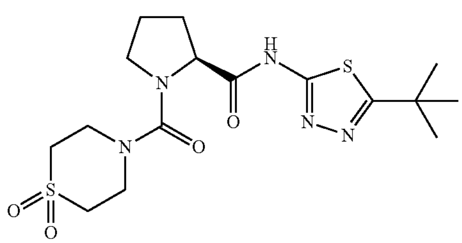 [SMILES: CC(C)(C)c1nnc(NC(=O)[C@@H]2CCCN2C(=O)N2CCS(=O)(=O)CC2)s1] | (S)-1-(1,1-Dioxo-1l6-thiomorpholine-4-carbonyl)-pyrrolidine-2-carboxylic acid (5-tert-butyl-1,3,4-thiadiazol-2-yl)-amide | 416 | 12 |
| 230 | 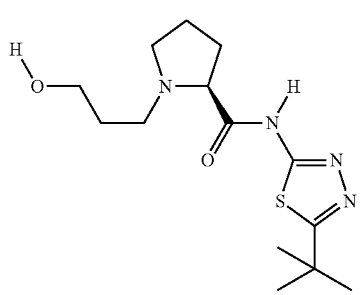 [SMILES: CC(C)(C)c1nnc(NC(=O)[C@@H]2CCCN2CCCO)s1] | (S)-1-(3-Hydroxy-propyl)-pyrrolidine-2-carboxylic acid (5-tert-butyl-1,3,4-thiadiazol-2-yl)-amide | 313 | 13 |

TABLE III-continued

| Example | Structure | Name | ESI m/z (+) | Patent Method |
|---|---|---|---|---|
| 231 | 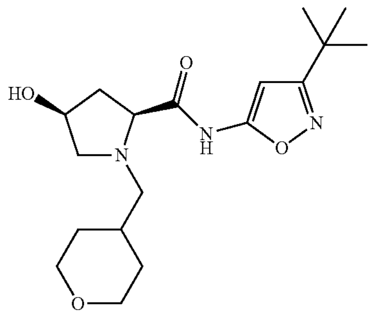 [SMILES: CC(C)(C)c1cc(NC(=O)[C@@H]2C[C@H](O)CN2CC2CCOCC2)on1] | (2S,4S)-4-Hydroxy-1-(tetrahydro-pyran-4-ylmethyl)-pyrrolidine-2-carboxylic acid (3-tert-butyl-isoxazol-5-yl)-amide | 352 | 9 |
| 232 | 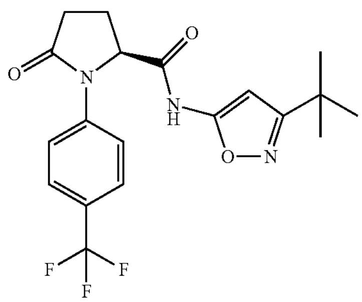 [SMILES: CC(C)(C)c1cc(NC(=O)[C@@H]2CCC(=O)N2c2ccc(C(F)(F)F)cc2)on1] | (S)-5-Oxo-1-(4-trifluoromethyl-phenyl)-pyrrolidine-2-carboxylic acid (3-tert-butyl-isoxazol-5-yl)-amide | 396 | 7 |
| 233 | 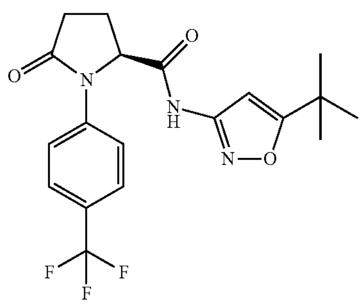 [SMILES: CC(C)(C)c1cc(NC(=O)[C@@H]2CCC(=O)N2c2ccc(C(F)(F)F)cc2)no1] | (S)-5-Oxo-1-(4-trifluoromethyl-phenyl)-pyrrolidine-2-carboxylic acid (5-tert-butyl-isoxazol-3-yl)-amide | 396 | 6 |
| 234 | 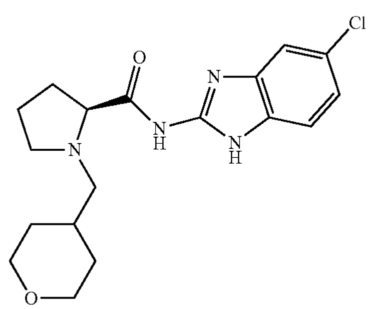 [SMILES: O=C(Nc1nc2cc(Cl)ccc2[nH]1)[C@@H]1CCCN1CC1CCOCC1] | (S)-1-(Tetrahydro-pyran-4-ylmethyl)-pyrrolidine-2-carboxylic acid (5-chloro-1H-benzimidazol-2-yl)-amide | 363 | 9 |
| 235 | 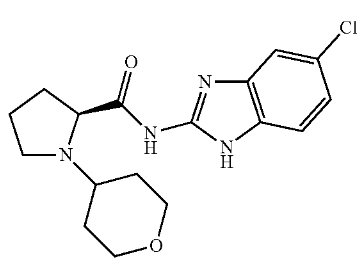 [SMILES: O=C(Nc1nc2cc(Cl)ccc2[nH]1)[C@@H]1CCCN1C1CCOCC1] | (S)-1-(Tetrahydro-pyran-4-yl)-pyrrolidine-2-carboxylic acid (5-chloro-1H-benzimidazol-2-yl)-amide | 349 | 9 |

TABLE III-continued

| Example | Structure | Name | ESI m/z (+) | Patent Method |
|---|---|---|---|---|
| 236 | 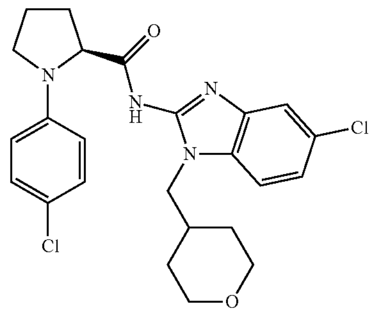 [SMILES: O=C(Nc1nc2cc(Cl)ccc2n1CC1CCOCC1)[C@@H]1CCCN1c1ccc(Cl)cc1] | (S)-1-(4-Chloro-phenyl)-pyrrolidine-2-carboxylic acid [5-chloro-1-(tetrahydro-pyran-4-ylmethyl)-1H-benzimidazol-2-yl]-amide | 473 | 5 |
| 237 | 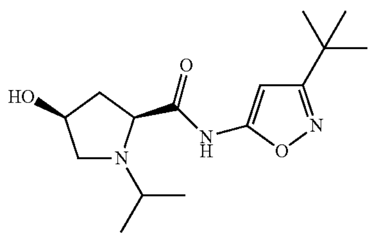 [SMILES: CC(C)N1C[C@@H](O)C[C@H]1C(=O)Nc1cc(C(C)(C)C)no1] | (2S,4S)-4-Hydroxy-1-isopropyl-pyrrolidine-2-carboxylic acid (3-tert-butyl-isoxazol-5-yl)-amide | 296 | 9 |
| 238 | 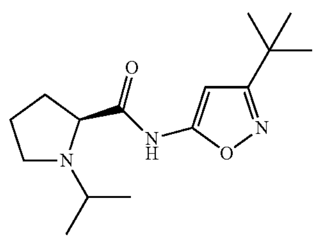 [SMILES: CC(C)N1CCC[C@H]1C(=O)Nc1cc(C(C)(C)C)no1] | (S)-1-Isopropyl-pyrrolidine-2-carboxylic acid (3-tert-butyl-isoxazol-5-yl)-amide | 280 | 9 |
| 239 | 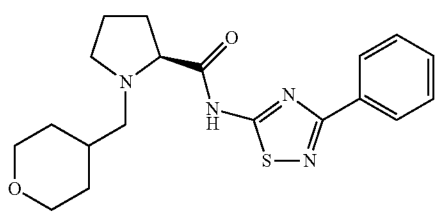 [SMILES: O=C(Nc1nc(-c2ccccc2)ns1)[C@@H]1CCCN1CC1CCOCC1] | (S)-1-(Tetrahydro-pyran-4-ylmethyl)-pyrrolidine-2-carboxylic acid (3-phenyl-1,2,4-thiadiazol-5-yl)-amide | 373 | 6 |
| 240 | 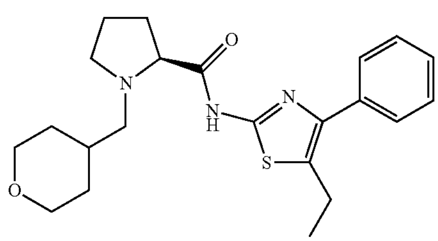 [SMILES: CCc1sc(NC(=O)[C@@H]2CCCN2CC2CCOCC2)nc1-c1ccccc1] | (S)-1-(Tetrahydro-pyran-4-ylmethyl)-pyrrolidine-2-carboxylic acid (5-ethyl-4-phenyl-thiazol-2-yl)-amide | 400 | 6 |
| 241 | 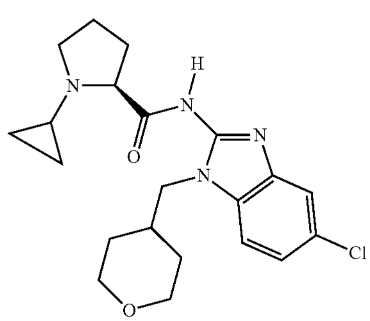 [SMILES: O=C(Nc1nc2cc(Cl)ccc2n1CC1CCOCC1)[C@@H]1CCCN1C1CC1] | (S)-1-Cyclopropyl-pyrrolidine-2-carboxylic acid [5-chloro-1-(tetrahydro-pyran-4-ylmethyl)-1H-benzimidazol-2-yl]-amide | 403 | 14 |

TABLE III-continued

| Example | Name | ESI m/z (+) | Patent Method |
|---|---|---|---|
| 242 | (S)-1-(Tetrahydro-pyran-4-ylmethyl)-pyrrolidine-2-carboxylic acid (5,6-dichloro-1H-benzimidazol-2-yl)-amide | 397/400 | 5 |
| 243 | (S)-1-(Tetrahydro-pyran-4-ylmethyl)-pyrrolidine-2-carboxylic acid (5-chloro-benzimidazol-2-yl)-amide | 380 | 5 |
| 244 | (S)-1-(Tetrahydro-pyran-4-ylmethyl)-pyrrolidine-2-carboxylic acid (6-chloro-benzimidazol-2-yl)-amide | 380 | 5 |
| 245 | (S)-1-(Tetrahydro-pyran-4-ylmethyl)-pyrrolidine-2-carboxylic acid (4-trifluoromethyl-pyridin-2-yl)-amide | 358 | 5 |
| 246 | (S)-1-(Tetrahydro-pyran-4-ylmethyl)-pyrrolidine-2-carboxylic acid (6-trifluoromethyl-pyridin-2-yl)-amide | 358 | 5 |
| 247 | (S)-1-(Tetrahydro-pyran-4-yl)-pyrrolidine-2-carboxylic acid (5-chloro-benzothiazol-2-yl)-amide | 366 | 5 |

TABLE III-continued

| Example | Name | ESI m/z (+) | Patent Method |
|---|---|---|---|
| 248 | (S)-1-(Tetrahydro-pyran-4-yl)-pyrrolidine-2-carboxylic acid (6-chloro-benzothiazol-2-yl)-amide | 366 | 5 |
| 249 | (S)-1-(Tetrahydro-pyran-4-yl)-pyrrolidine-2-carboxylic acid (5,6-dichloro-1H-benzimidazol-2-yl)-amide | 383 | 5 |
| 250 | (S)-1-(Tetrahydro-pyran-4-yl)-pyrrolidine-2-carboxylic acid (5-fluoro-1H-benzimidazol-2-yl)-amide | 333 | 5 |
| 251 | (S)-1-(Tetrahydro-pyran-4-yl)-pyrrolidine-2-carboxylic acid (5-trifluoromethyl-pyridin-2-yl)-amide | 344 | 5 |
| 252 | (S)-1-(Tetrahydro-pyran-4-yl)-pyrrolidine-2-carboxylic acid (4-trifluoromethyl-pyridin-2-yl)-amide | 344 | 5 |
| 253 | (S)-1-(4-Chloro-benzenesulfonyl)-pyrrolidine-2-carboxylic acid (5-tert-butyl-isoxazol-3-yl)-amide | 412 [M = 16]H+ | 22 |

TABLE III-continued

| Example | Structure | Name | ESI m/z (+) | Patent Method |
|---|---|---|---|---|
| 254 | 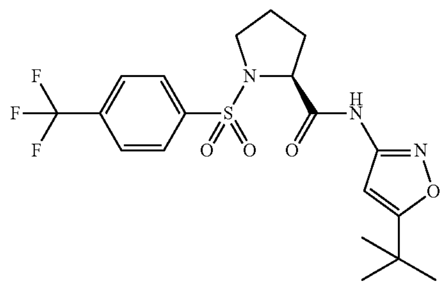 [SMILES: CC(C)(C)c1cc(NC(=O)[C@@H]2CCCN2S(=O)(=O)c2ccc(C(F)(F)F)cc2)no1] | (S)-1-(4-Trifluoromethyl-benzenesufonyl)-pyrrolidine-2-carboxylic acid (5-tert-butyl-isoxazol-3-yl)-amide | 444 [M = 16]H+ | 22 |
| 255 | 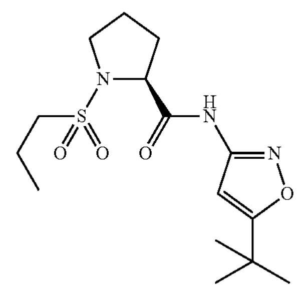 [SMILES: CCCS(=O)(=O)N1CCC[C@H]1C(=O)Nc1cc(C(C)(C)C)on1] | (S)-1-(Propane-1-sulfonyl)-pyrrolidine-2-carboxylic acid (5-tert-butyl-isoxazol-3-yl)-amide | 456 [M = 16]H+ | 22 |
| 256 | 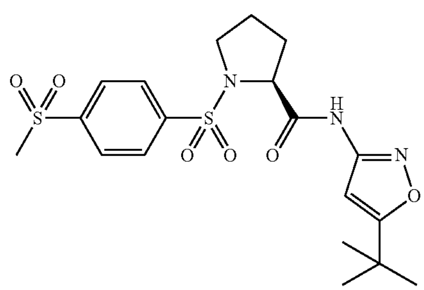 [SMILES: CC(C)(C)c1cc(NC(=O)[C@@H]2CCCN2S(=O)(=O)c2ccc(S(C)(=O)=O)cc2)no1] | (S)-1-(4-Methanesulfonyl-benzenesulfonyl)-pyrrolidine-2-carboxylic acid (5-tert-butyl-isoxazol-3-yl)-amide | 344 [M = 16]H+ | 22 |
| 257 | 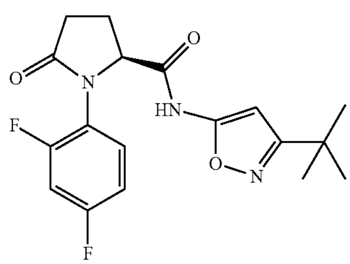 [SMILES: CC(C)(C)c1cc(NC(=O)[C@@H]2CCC(=O)N2c2ccc(F)cc2F)on1] | (S)-1-(2,4-Difluoro-phenyl)-5-oxo-pyrrolidine-2-carboxylic acid (3-tert-butyl-isoxazol-5-yl)-amide | 364 | 7 |
| 258 | 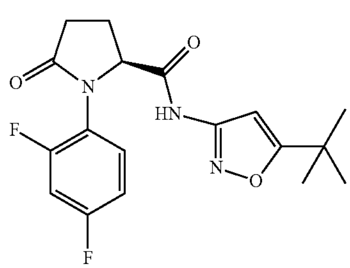 [SMILES: CC(C)(C)c1cc(NC(=O)[C@@H]2CCC(=O)N2c2ccc(F)cc2F)no1] | (S)-1-(2,4-Difluoro-phenyl)-5-oxo-pyrrolidine-2-carboxylic acid (5-tert-butyl-isoxazol-3-yl)-amide | 364 | 7 |

TABLE III-continued

| Example | Name | ESI m/z (+) | Patent Method |
|---|---|---|---|
| 259 | [(S)-2-(3-tert-Butyl-isoxazol-5-ylcarbamoyl)-pyrrolidin-1-yl]-acetic acid tert-butyl ester | 352 | 13 |
| 260 | [(S)-2-(3-tert-Butyl-isoxazol-5-ylcarbamoyl)-pyrrolidin-1-yl]-acetic acid | 296 | 16 |
| 261 | (S)-1-(5-Chloro-thiophen-2-yl)-5-oxo-pyrrolidine-2-carboxylic acid (3-tert-butyl-isoxazol-5-yl)-amide | 368 | 7 |
| 262 | (S)-1-(5-Chloro-2-fluoro-phenyl)-5-oxo-pyrrolidine-2-carboxylic acid (3-tert-butyl-isoxazol-5-yl)-amide | 368 | 7 |
| 263 | (S)-1-(4-Chloro-2-fluoro-phenyl)-5-oxo-pyrrolidine-2-carboxylic acid (3-tert-butyl-isoxazol-5-yl)-amide | 380 | 7 |
| 264 | (S)-1-(4-Chloro-2-fluoro-phenyl)-5-oxo-pyrrolidine-2-carboxylic acid (5-tert-butyl-isoxazol-3-yl)-amide | 380 | 7 |

TABLE III-continued

| Example | Name | ESI m/z (+) | Patent Method |
|---|---|---|---|
| 265 | (S)-1-(Tetrahydro-pyran-4-ylmethyl)-pyrrolidine-2-carboxylic acid (5-trifluoromethyl-pyridin-2-yl)-amide | 358 | 9 |
| 266 | 3-[(S)-2-(3-tert-Butyl-isoxazol-5-ylcarbamoyl)-pyrrolidin-1-yl]-propionic acid tert-butyl ester | 366 | 13 |
| 267 | (S)-1-(Tetrahydro-pyran-4-yl)-pyrrolidine-2-carboxylic acid (5-tert-butyl-1,3,4-thiadiazol-2-yl)-amide | 339 | 9 |
| 268 | (S)-1-Cyclobutyl-pyrrolidine-2-carboxylic acid (5-tert-butyl-1,3,4-thiadiazol-2-yl)-amide | 309 | 9 |
| 269 | (S)-1-Cyclopropylmethyl-pyrrolidine-2-carboxylic acid (5-tert-butyl-1,3,4-thiadiazol-2-yl)-amide | 309 | 9 |

TABLE III-continued

| Example | Structure | Name | ESI m/z (+) | Patent Method |
|---|---|---|---|---|
| 270 | 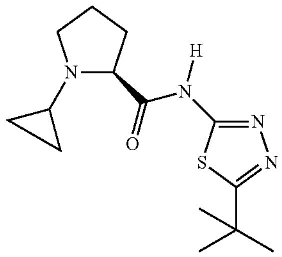 [SMILES: CC(C)(C)c1nnc(NC(=O)[C@@H]2CCCN2C2CC2)s1] | (S)-1-Cyclopropyl-pyrrolidine-2-carboxylic acid (5-tert-butyl-1,3,4-thiadiazol-2-yl)-amide | 295 | 14 |
| 271 | 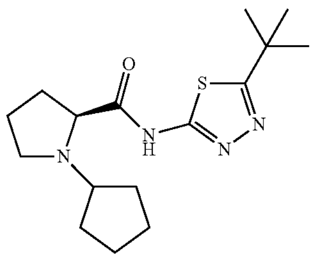 [SMILES: CC(C)(C)c1nnc(NC(=O)[C@@H]2CCCN2C2CCCC2)s1] | (S)-1-Cyclopentyl-pyrrolidine-2-carboxylic acid (5-tert-butyl-1,3,4-thiadiazol-2-yl)-amide | 323 | 9 |
| 272 | 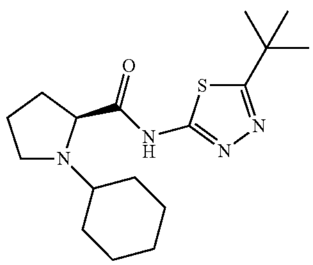 [SMILES: CC(C)(C)c1nnc(NC(=O)[C@@H]2CCCN2C2CCCCC2)s1] | (S)-1-Cyclohexyl-pyrrolidine-2-carboxylic acid (5-tert-butyl-1,3,4-thiadiazol-2-yl)-amide | 337 | 9 |
| 273 | 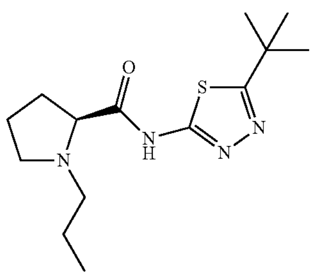 [SMILES: CCCN1CCC[C@H]1C(=O)Nc1nnc(C(C)(C)C)s1] | (S)-1-Propyl-pyrrolidine-2-carboxylic acid (5-tert-butyl-1,3,4-thiadiazol-2-yl)-amide | 297 | 9 |
| 274 | 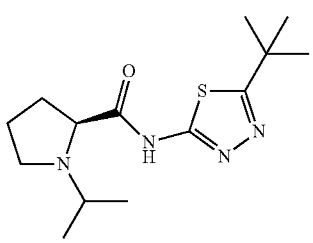 [SMILES: CC(C)N1CCC[C@H]1C(=O)Nc1nnc(C(C)(C)C)s1] | (S)-1-Isopropyl-pyrrolidine-2-carboxylic acid (5-tert-butyl-1,3,4-thiadiazol-2-yl)-amide | 297 | 9 |
| 275 | 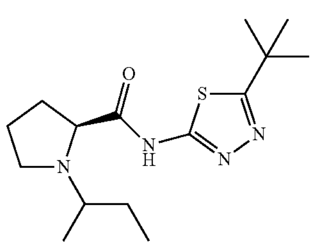 [SMILES: CCC(C)N1CCC[C@H]1C(=O)Nc1nnc(C(C)(C)C)s1] | 1-sec-Butyl-pyrrolidine-2-carboxylic acid (5-tert-butyl-1,3,4-thiadiazol-2-yl)-amide | 311 | 9 |

TABLE III-continued

| Example | Name | ESI m/z (+) | Patent Method |
|---|---|---|---|
| 276 | 1-(2-Methyl-cyclohexyl)-pyrrolidine-2-carboxylic acid (5-tert-butyl-1,3,4-thiadiazol-2-yl)-amide | 351 | 9 |
| 277 | 1-(2,2-Dimethyl-cyclopentyl)-pyrrolidine-2-carboxylic acid (5-tert-butyl-1,3,4-thiadiazol-2-yl)-amide | 351 | 9 |
| 278 | (S)-5-Oxo-1-p-tolyl-pyrrolidine-2-carboxylic acid (3-tert-butyl-isoxazol-5-yl)-amide | 342 | 7 |
| 279 | (S)-5-Oxo-1-p-tolyl-pyrrolidine-2-carboxylic acid (5-tert-butyl-isoxazol-3-yl)-amide | 342 | 7 |
| 280 | (S)-1-(4-Ethyl-phenyl)-5-oxo-pyrrolidine-2-carboxylic acid (3-tert-butyl-isoxazol-5-yl)-amide | 356 | 7 |

TABLE III-continued

| Example | Structure | Name | ESI m/z (+) | Patent Method |
|---|---|---|---|---|
| 281 | 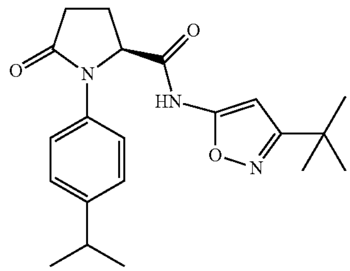 [SMILES: CC(C)c1ccc(N2C(=O)CC[C@H]2C(=O)Nc2cc(C(C)(C)C)no2)cc1] | (S)-1-(4-Isopropyl-phenyl)-5-oxo-pyrrolidine-2-carboxylic acid (3-tert-butyl-isoxazol-5-yl)-amide | 370 | 7 |
| 282 | 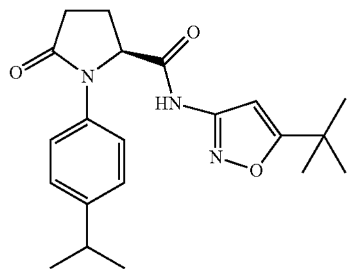 [SMILES: CC(C)c1ccc(N2C(=O)CC[C@H]2C(=O)Nc2cc(C(C)(C)C)on2)cc1] | (S)-1-(4-Isopropyl-phenyl)-5-oxo-pyrrolidine-2-carboxylic acid (5-tert-butyl-isoxazol-3-yl)-amide | 370 | 7 |
| 283 | 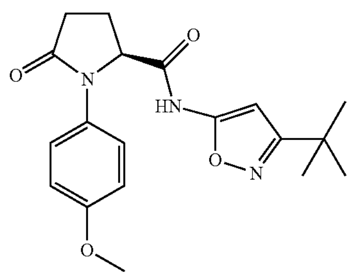 [SMILES: COc1ccc(N2C(=O)CC[C@H]2C(=O)Nc2cc(C(C)(C)C)no2)cc1] | (S)-1-(4-Methoxy-phenyl)-5-oxo-pyrrolidine-2-carboxylic acid (3-tert-butyl-isoxazol-5-yl)-amide | 358 | 7 |
| 284 | 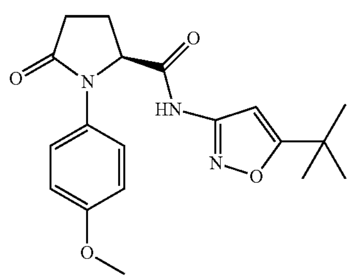 [SMILES: COc1ccc(N2C(=O)CC[C@H]2C(=O)Nc2cc(C(C)(C)C)on2)cc1] | (S)-1-(4-Methoxy-phenyl)-5-oxo-pyrrolidine-2-carboxylic acid (5-tert-butyl-isoxazol-3-yl)-amide | 358 | 7 |
| 285 | 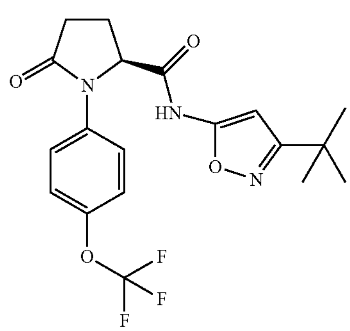 [SMILES: CC(C)(C)c1cc(NC(=O)[C@@H]2CCC(=O)N2c2ccc(OC(F)(F)F)cc2)on1] | (S)-5-Oxo-1-(4-trifluoromethoxy-phenyl)-pyrrolidine-2-carboxylic acid (3-tert-butyl-isoxazol-5-yl)-amide | 412 | 7 |

TABLE III-continued

| Example | Name | ESI m/z (+) | Patent Method |
|---|---|---|---|
| 286 | (S)-5-Oxo-1-(4-trifluoromethoxy-phenyl)-pyrrolidine-2-carboxylic acid (5-tert-butyl-isoxazol-3-yl)-amide | 412 | 7 |
| 287 | (S)-1-(4-Chloro-phenyl)-5-oxo-pyrrolidine-2-carboxylic acid (3-tert-butyl-isoxazol-5-yl)-amide | 371 | 17 |
| 288 | (S)-1-(4-Chloro-phenyl)-5-oxo-pyrrolidine-2-carboxylic acid (3-sec-butyl-isoxazol-5-yl)-amide | 362 | 17 |
| 289 | (S)-1-(4-Chloro-phenyl)-5-oxo-pyrrolidine-2-carboxylic acid (3-isopropyl-isoxazol-5-yl)-amide | 348 | 17 |
| 290 | (S)-1-(4-Chloro-phenyl)-5-oxo-pyrrolidine-2-carboxylic acid [3-(4-methoxy-phenyl)-1,2,4-thiadiazol-5-yl]-amide | 429 | 17 |

TABLE III-continued

| Example | Name | ESI m/z (+) | Patent Method |
|---|---|---|---|
| 291 | (S)-1-(4-Chloro-phenyl)-5-oxo-pyrrolidine-2-carboxylic acid (3-tert-butyl-isothiazol-5-yl)-amide | 378 | 17 |
| 292 | (S)-1-(4-Chloro-phenyl)-5-oxo-pyrrolidine-2-carboxylic acid {3-[2-(4-methoxy-benzyloxy)-1,1-dimethyl-ethyl]-isoxazol-5-yl}-amide | 498 | 17 |
| 293 | (S)-1-(4-Chloro-phenyl)-5-oxo-pyrrolidine-2-carboxylic acid [3-(2-hydroxy-1,1-dimethyl-ethyl)-isoxazol-5-yl]-amide | 478 | 17 |
| 294 | (S)-1-(4-Chloro-phenyl)-5-oxo-pyrrolidine-2-carboxylic acid [5-(2-methoxy-1,1-dimethyl-ethyl)-isoxazol-3-yl]-amide | 392 | 17 |
| 295 | (S)-1-(4-Chloro-phenyl)-5-oxo-pyrrolidine-2-carboxylic acid [3-(2-methoxy-1,1-dimethyl-ethyl)-isoxazol-5-yl]-amide | 392 | 17 |
| 296 | (S)-1-(Tetrahydro-pyran-4-yl)-pyrrolidine-2-carboxylic acid (3-tert-butyl-1,2,4-thiadiazol-5-yl)-amide | 339 | 6 |

TABLE III-continued

| Example | Name | ESI m/z (+) | Patent Method |
|---|---|---|---|
| 297 | 5-Oxo-1-(6-trifluoromethyl-pyridin-3-yl)-pyrrolidine-2-carboxylic acid (3-tert-butyl-isoxazol-5-yl)-amide | 331 | 36 |
| 298 | (S)-5-Oxo-1-(6-trifluoromethyl-pyridin-3-yl)-pyrrolidine-2-carboxylic acid (5-tert-butyl-isoxazol-3-yl)-amide | 397 | 36 |
| 299 | (S)-1-(4-Chloro-phenyl)-pyrrolidine-2-carboxylic acid [3-(2-hydroxy-1,1-dimethyl-ethyl)-isoxazol-5-yl]-amide | 364 | 41 |
| 300 | (S)-1-(3-Chloro-phenyl)-5-oxo-pyrrolidine-2-carboxylic acid (3-tert-butyl-isoxazol-5-yl)-amide | 362 | 7 |
| 301 | (S)-1-(3-Chloro-phenyl)-5-oxo-pyrrolidine-2-carboxylic acid (5-tert-butyl-isoxazol-3-yl)-amide | 362 | 7 |
| 302 | (S)-1-(2,3-Difluoro-phenyl)-5-oxo-pyrrolidine-2-carboxylic acid (3-tert-butyl-isoxazol-5-yl)-amide | 364 | 7 |

TABLE III-continued

| Example | Structure | Name | ESI m/z (+) | Patent Method |
|---|---|---|---|---|
| 303 | 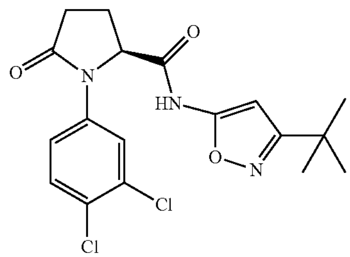 | (S)-1-(3,4-Dichloro-phenyl)-5-oxo-pyrrolidine-2-carboxylic acid (3-tert-butyl-isoxazol-5-yl)-amide | 396 | 7 |
| 304 | 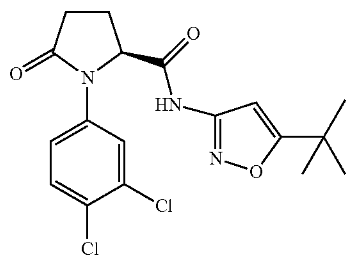 [SMILES: CC(C)(C)c1cc(NC(=O)[C@@H]2CCC(=O)N2c2ccc(Cl)c(Cl)c2)no1] | (S)-1-(3,4-Dichloro-phenyl)-5-oxo-pyrrolidine-2-carboxylic acid (5-tert-butyl-isoxazol-3-yl)-amide | 396 | 7 |
| 305 | 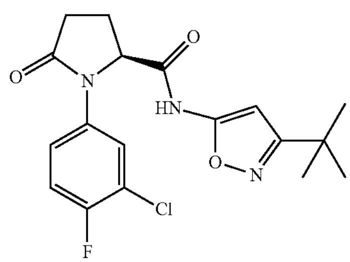 [SMILES: CC(C)(C)c1cc(NC(=O)[C@@H]2CCC(=O)N2c2ccc(F)c(Cl)c2)on1] | (S)-1-(3-Chloro-4-fluoro-phenyl)-5-oxo-pyrrolidine-2-carboxylic acid (3-tert-butyl-isoxazol-5-yl)-amide | 380 | 7 |
| 306 | 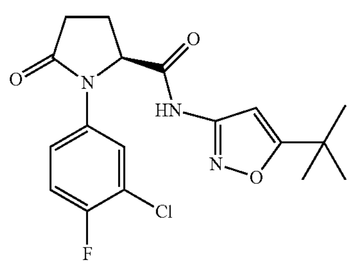 [SMILES: CC(C)(C)c1cc(NC(=O)[C@@H]2CCC(=O)N2c2ccc(F)c(Cl)c2)no1] | (S)-1-(3-Chloro-4-fluoro-phenyl)-5-oxo-pyrrolidine-2-carboxylic acid (5-tert-butyl-isoxazol-3-yl)-amide | 380 | 7 |
| 307 | 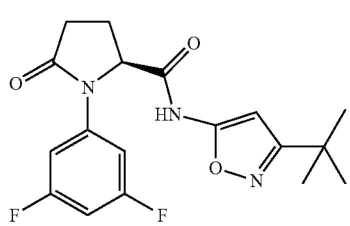 | (S)-1-(3,5-Dichloro-phenyl)-5-oxo-pyrrolidine-2-carboxylic acid (3-tert-butyl-isoxazol-5-yl)-amide | 364 | 7 |
| 308 | 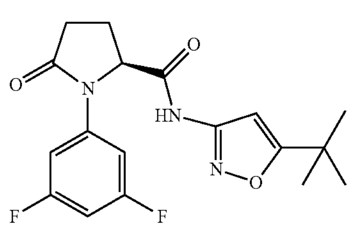 | (S)-1-(3,5-Dichloro-phenyl)-5-oxo-pyrrolidine-2-carboxylic acid (5-tert-butyl-isoxazol-3-yl)-amide | 364 | 7 |

TABLE III-continued

| Example | Structure | Name | ESI m/z (+) | Patent Method |
|---|---|---|---|---|
| 309 | 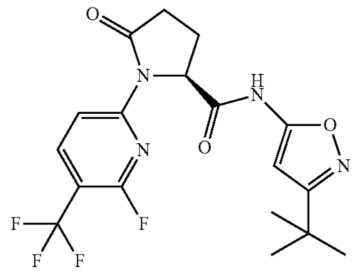 [SMILES: CC(C)(C)c1cc(NC(=O)[C@@H]2CCC(=O)N2c2ccc(C(F)(F)F)c(F)n2)on1] | (S)-1-(6-Fluoro-5-trifluoromethyl-pyridin-2-yl)-oxo-pyrrolidine-2-carboxylic acid (3-tert-butyl-isoxazol-5-yl)-amide | 415 | 37 |
| 310 | 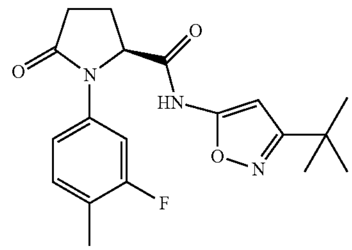 [SMILES: Cc1ccc(N2C(=O)CC[C@H]2C(=O)Nc2cc(C(C)(C)C)no2)cc1F] | (S)-1-(3-Fluoro-4-methyl-phenyl)-5-oxo-pyrrolidine-2-carboxylic acid (3-tert-butyl-isoxazol-5-yl)-amide | 360 | 7 |
| 311 | 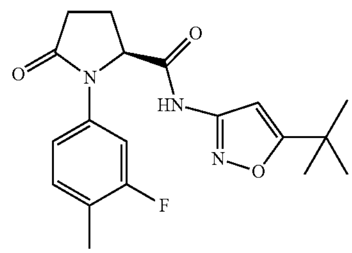 [SMILES: Cc1ccc(N2C(=O)CC[C@H]2C(=O)Nc2cc(C(C)(C)C)on2)cc1F] | (S)-1-(3-Fluoro-4-methyl-phenyl)-5-oxo-pyrrolidine-2-carboxylic acid (5-tert-butyl-isoxazol-3-yl)-amide | 360 | 7 |
| 312 | 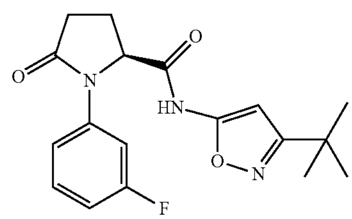 [SMILES: CC(C)(C)c1cc(NC(=O)[C@@H]2CCC(=O)N2c2cccc(F)c2)on1] | (S)-1-(3-Fluoro-phenyl)-5-oxo-pyrrolidine-2-carboxylic acid (3-tert-butyl-isoxazol-5-yl)-amide | 346 | 7 |
| 313 | 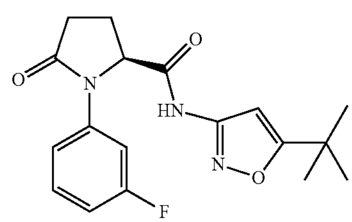 [SMILES: CC(C)(C)c1cc(NC(=O)[C@@H]2CCC(=O)N2c2cccc(F)c2)no1] | (S)-1-(3-Fluoro-phenyl)-5-oxo-pyrrolidine-2-carboxylic acid (5-tert-butyl-isoxazol-3-yl)-amide | 346 | 7 |
| 314 | 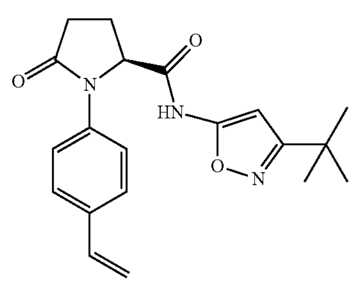 [SMILES: C=Cc1ccc(N2C(=O)CC[C@H]2C(=O)Nc2cc(C(C)(C)C)no2)cc1] | (S)-5-Oxo-1-(4-vinyl-phenyl)-pyrrolidine-2-carboxylic acid (3-tert-butyl-isoxazol-5-yl)-amide | 354 | 7 |

TABLE III-continued

| Example | Structure | Name | ESI m/z (+) | Patent Method |
|---|---|---|---|---|
| 315 | 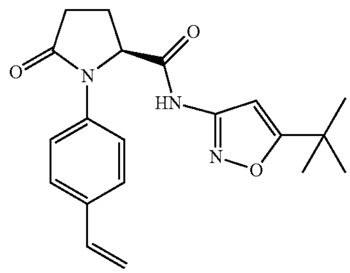 [SMILES: C=Cc1ccc(N2C(=O)CC[C@H]2C(=O)Nc2cc(C(C)(C)C)on2)cc1] | (S)-5-Oxo-1-(4-vinyl-phenyl)-pyrrolidine-2-carboxylic acid (5-tert-butyl-isoxazol-3-yl)-amide | 354 | 7 |
| 316 | 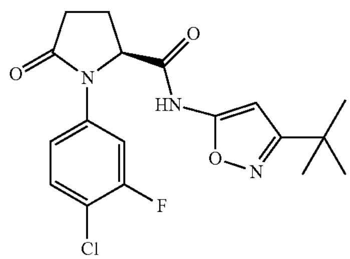 [SMILES: CC(C)(C)c1cc(NC(=O)[C@@H]2CCC(=O)N2c2ccc(Cl)c(F)c2)on1] | (S)-1-(4-Chloro-3-fluoro-phenyl)-5-oxo-pyrrolidine-2-carboxylic acid (5-tert-butyl-isoxazol-3-yl)-amide | 380 | 7 |
| 317 | 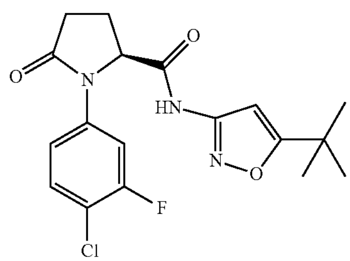 [SMILES: CC(C)(C)c1cc(NC(=O)[C@@H]2CCC(=O)N2c2ccc(Cl)c(F)c2)no1] | (S)-1-(4-Chloro-3-fluoro-phenyl)-5-oxo-pyrrolidine-2-carboxylic acid (3-tert-butyl-isoxazol-5-yl)-amide | 380 | 7 |
| 318 | 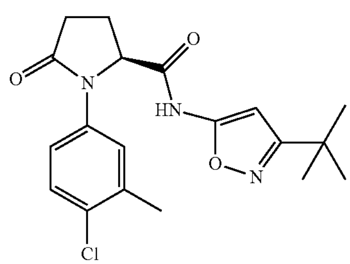 [SMILES: Cc1cc(N2C(=O)CC[C@H]2C(=O)Nc2cc(C(C)(C)C)no2)ccc1Cl] | (S)-1-(4-Chloro-3-methyl-phenyl)-5-oxo-pyrrolidine-2-carboxylic acid (3-tert-butyl-isoxazol-5-yl)-amide | 376 | 7 |
| 319 | 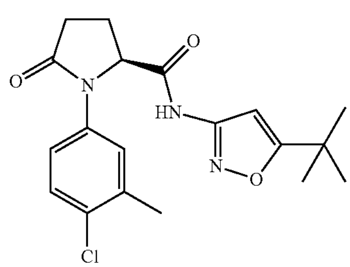 [SMILES: Cc1cc(N2C(=O)CC[C@H]2C(=O)Nc2cc(C(C)(C)C)on2)ccc1Cl] | (S)-1-(4-Chloro-3-methyl-phenyl)-5-oxo-pyrrolidine-2-carboxylic acid (5-tert-butyl-isoxazol-3-yl)-amide | 376 | 7 |

TABLE III-continued

| Example | Structure | Name | ESI m/z (+) | Patent Method |
|---|---|---|---|---|
| 320 | 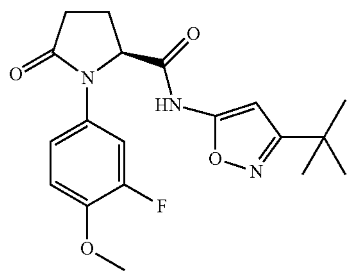 [SMILES: COc1ccc(N2C(=O)CC[C@H]2C(=O)Nc2cc(C(C)(C)C)no2)cc1F] | (S)-1-(3-Fluoro-4-fluoro-phenyl)-5-oxo-pyrrolidine-2-carboxylic acid (3-tert-butyl-isoxazol-5-yl)-amide | 376 | 7 |
| 321 | 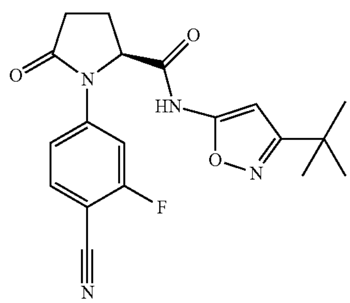 [SMILES: CC(C)(C)c1cc(NC(=O)[C@@H]2CCC(=O)N2c2ccc(C#N)c(F)c2)on1] | (S)-1-(4-Cyano-3-fluoro-phenyl)-5-oxo-pyrrolidine-2-carboxylic acid (5-tert-butyl-isoxazol-3-yl)-amide | 371 | 7 |
| 322 | 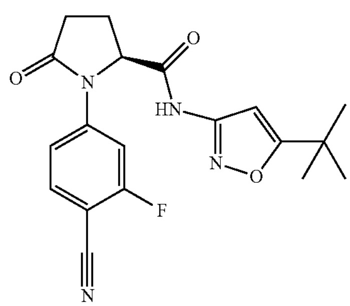 [SMILES: CC(C)(C)c1cc(NC(=O)[C@@H]2CCC(=O)N2c2ccc(C#N)c(F)c2)no1] | (S)-1-(4-Cyano-3-fluoro-phenyl)-5-oxo-pyrrolidine-2-carboxylic acid (5-tert-butyl-isoxazol-3-yl)-amide | 371 | 7 |
| 323 | 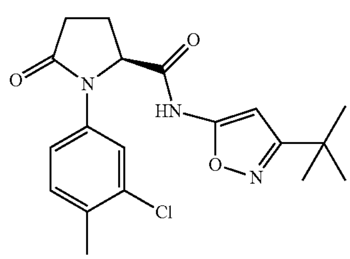 [SMILES: Cc1ccc(N2C(=O)CC[C@H]2C(=O)Nc2cc(C(C)(C)C)no2)cc1Cl] | (S)-1-(3-Chloro-4-methyl-phenyl)-5-oxo-pyrrolidine-2-carboxylic acid (3-tert-butyl-isoxazol-5-yl)-amide | 376 | 7 |
| 324 | 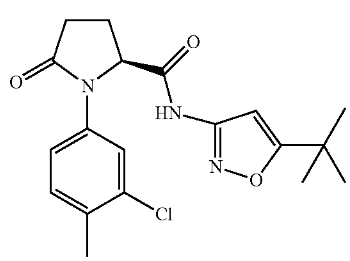 [SMILES: Cc1ccc(N2C(=O)CC[C@H]2C(=O)Nc2cc(C(C)(C)C)on2)cc1Cl] | (S)-1-(3-Chloro-4-methyl-phenyl)-5-oxo-pyrrolidine-2-carboxylic acid (5-tert-butyl-isoxazol-3-yl)-amide | 376 | 7 |

TABLE III-continued

| Example | Structure | Name | ESI m/z (+) | Patent Method |
|---|---|---|---|---|
| 325 | 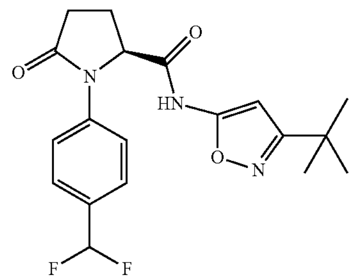 [SMILES: CC(C)(C)c1cc(NC(=O)[C@@H]2CCC(=O)N2c2ccc(C(F)F)cc2)on1] | (S)-1-(4-Difluoromethyl-phenyl)-5-oxo-pyrrolidine-2-carboxylic acid (3-tert-butyl-isoxazol-5-yl)-amide | 378 | 7 |
| 326 | 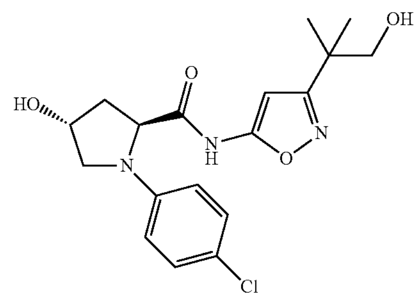 [SMILES: CC(C)(CO)c1cc(NC(=O)[C@@H]2C[C@@H](O)CN2c2ccc(Cl)cc2)on1] | (2S,4R)-1-(4-Chloro-phenyl)-4-hydroxy-pyrrolidine-2-carboxylic acid [3-(2-hydroxy-1,1-dimethyl-ethyl)-isoxazol-5-yl]-amide | 380 | 30 |
| 327 | 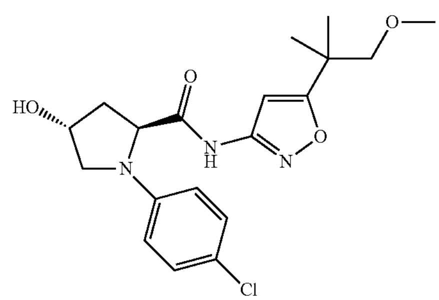 [SMILES: COCC(C)(C)c1cc(NC(=O)[C@@H]2C[C@@H](O)CN2c2ccc(Cl)cc2)no1] | (2S,4R)-1-(4-Chloro-phenyl)-4-hydroxy-pyrrolidine-2-carboxylic acid [5-(2-methoxy-1,1-dimethyl-ethyl)-isoxazol-3-yl]-amide | 394 | 30 |
| 328 | 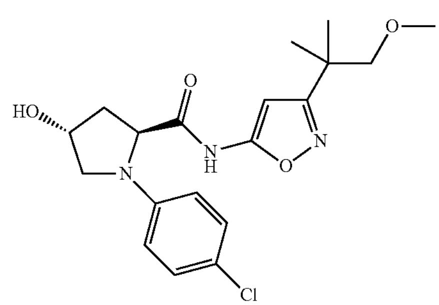 [SMILES: COCC(C)(C)c1cc(NC(=O)[C@@H]2C[C@@H](O)CN2c2ccc(Cl)cc2)on1] | (2S,4R)-1-(4-Chloro-phenyl)-4-hydroxy-pyrrolidine-2-carboxylic acid [3-(2-methoxy-1,1-dimethyl-ethyl)-isoxazol-5-yl]-amide | 394 | 30 |
| 329 | 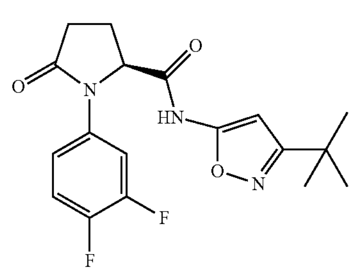 [SMILES: CC(C)(C)c1cc(NC(=O)[C@@H]2CCC(=O)N2c2ccc(F)c(F)c2)on1] | (S)-1-(3,4-Difluoro-phenyl)-5-oxo-pyrrolidine-2-carboxylic acid (3-tert-butyl-isoxazol-5-yl)-amide | 364 | 7 |

TABLE III-continued

| Example | Structure | Name | ESI m/z (+) | Patent Method |
|---|---|---|---|---|
| 330 | 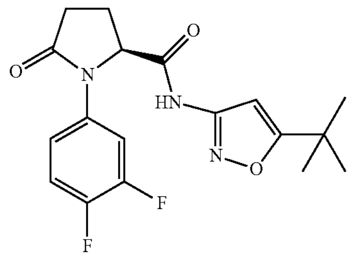 [SMILES: CC(C)(C)c1cc(NC(=O)[C@@H]2CCC(=O)N2c2ccc(F)c(F)c2)no1] | (S)-1-(3,4-Difluoro-phenyl)-5-oxo-pyrrolidine-2-carboxylic acid (5-tert-butyl-isoxazol-3-yl)-amide | 364 | 7 |
| 331 | 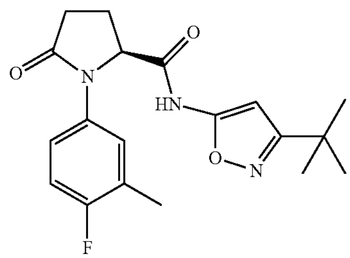 | (S)-1-(4-Fluoro-3-methyl-phenyl)-5-oxo-pyrrolidine-2-carboxylic acid (3-tert-butyl-isoxazol-5-yl)-amide | 360 | 7 |
| 332 | 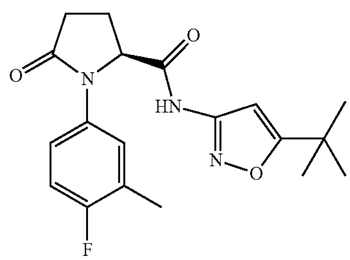 [SMILES: Cc1cc(N2C(=O)CC[C@H]2C(=O)Nc2cc(C(C)(C)C)on2)ccc1F] | (S)-1-(4-Fluoro-3-methyl-phenyl)-5-oxo-pyrrolidine-2-carboxylic acid (5-tert-butyl-isoxazol-3-yl)-amide | 360 | 7 |
| 333 | 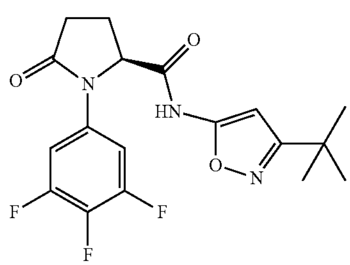 [SMILES: CC(C)(C)c1cc(NC(=O)[C@@H]2CCC(=O)N2c2cc(F)c(F)c(F)c2)on1] | (S)-5-Oxo-1-(3,4,5-trifluoro-phenyl)-pyrrolidine-2-carboxylic acid (5-tert-butyl-isoxazol-3-yl)-amide | 382 | 7 |
| 334 | 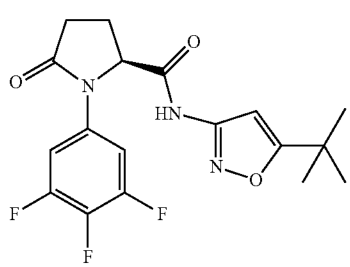 [SMILES: CC(C)(C)c1cc(NC(=O)[C@@H]2CCC(=O)N2c2cc(F)c(F)c(F)c2)no1] | (S)-5-Oxo-1-(3,4,5-trifluoro-phenyl)-pyrrolidine-2-carboxylic acid (3-tert-butyl-isoxazol-5-yl)-amide | 382 | 7 |

TABLE III-continued

| Example | Structure | Name | ESI m/z (+) | Patent Method |
|---|---|---|---|---|
| 335 | 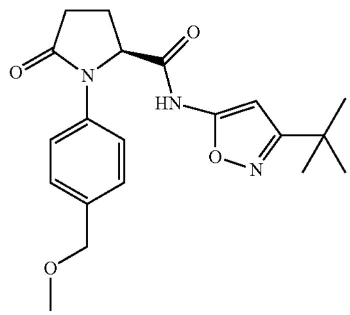 [SMILES: COCc1ccc(N2C(=O)CC[C@H]2C(=O)Nc2cc(C(C)(C)C)no2)cc1] | (S)-1-(4-Methoxymethyl-phenyl)-5-oxo-pyrrolidine-2-carboxylic acid (3-tert-butyl-isoxazol-5-yl)-amide | 372 | 7 |
| 336 | 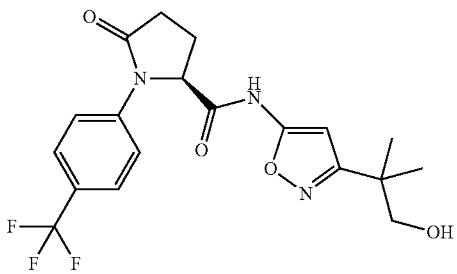 [SMILES: CC(C)(CO)c1cc(NC(=O)[C@@H]2CCC(=O)N2c2ccc(C(F)(F)F)cc2)on1] | (S)-5-Oxo-1-(4-trifluoromethyl-phenyl)-pyrrolidine-2-carboxylic acid [3-(2-hydroxy-1,1-dimethyl-ethyl)-isoxazol-5-yl]-amide | 412 | 38 |
| 337 | 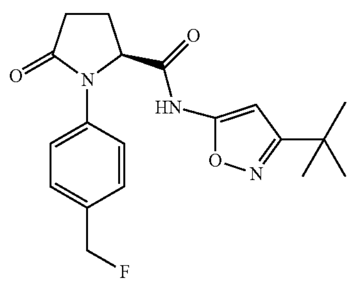 [SMILES: CC(C)(C)c1cc(NC(=O)[C@@H]2CCC(=O)N2c2ccc(CF)cc2)on1] | (S)-1-(4-Fluoromethyl-phenyl)-5-oxo-pyrrolidine-2-carboxylic acid (3-tert-butyl-isoxazol-5-yl)-amide | 360 | 7 |
| 338 | 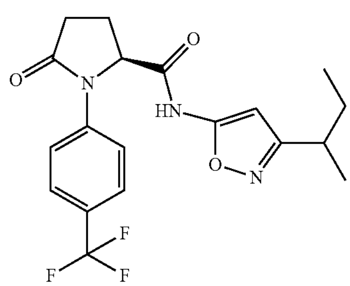 [SMILES: CCC(C)c1cc(NC(=O)[C@@H]2CCC(=O)N2c2ccc(C(F)(F)F)cc2)on1] | (S)-5-Oxo-1-(4-trifluoromethyl-phenyl)-pyrrolidine-2-carboxylic acid (3-sec-butyl-isoxazol-5-yl)-amide | 396 | 7 |
| 339 | 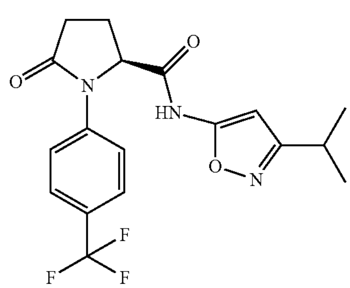 [SMILES: CC(C)c1cc(NC(=O)[C@@H]2CCC(=O)N2c2ccc(C(F)(F)F)cc2)on1] | (S)-5-Oxo-1-(4-trifluoromethyl-phenyl)-pyrrolidine-2-carboxylic acid (3-isopropyl-isoxazol-5-yl)-amide | 382 | 7 |

TABLE III-continued

| Example | Structure | Name | ESI m/z (+) | Patent Method |
|---|---|---|---|---|
| 340 | 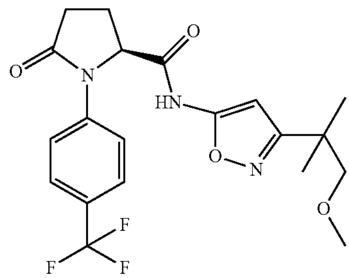 [SMILES: COCC(C)(C)c1cc(NC(=O)[C@@H]2CCC(=O)N2c2ccc(C(F)(F)F)cc2)on1] | (S)-5-Oxo-1-(4-trifluoromethyl-phenyl)-pyrrolidine-2-carboxylic acid [3-(2-hydroxy-1,1-dimethyl-ethyl)-isoxazol-5-yl]-amide | 426 | 7 |
| 341 | 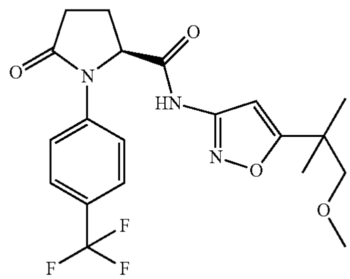 [SMILES: COCC(C)(C)c1cc(NC(=O)[C@@H]2CCC(=O)N2c2ccc(C(F)(F)F)cc2)no1] | (S)-5-Oxo-1-(4-trifluoromethyl-phenyl)-pyrrolidine-2-carboxylic acid [5-(2-hydroxy-1,1-dimethyl-ethyl)-isoxazol-3-yl]-amide | 426 | 7 |
| 342 | 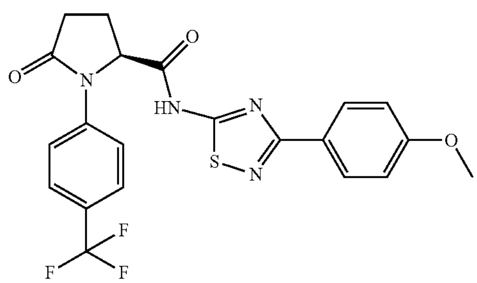 [SMILES: COc1ccc(-c2nsc(NC(=O)[C@@H]3CCC(=O)N3c3ccc(C(F)(F)F)cc3)n2)cc1] | (S)-5-Oxo-1-(4-trifluoromethyl-phenyl)-pyrrolidine-2-carboxylic acid [3-(4-methoxy-phenyl)-1,2,4-thiadiazol-5-yl]-amide | 463 | 7 |
| 343 | 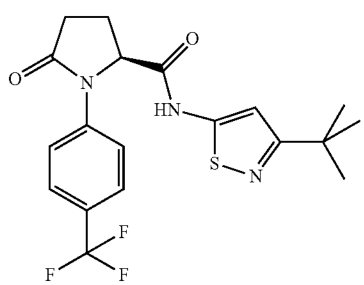 [SMILES: CC(C)(C)c1cc(NC(=O)[C@@H]2CCC(=O)N2c2ccc(C(F)(F)F)cc2)sn1] | (S)-5-Oxo-1-(4-trifluoromethyl-phenyl)-pyrrolidine-2-carboxylic acid (3-tert-butyl-isothiazol-5-yl)-amide | 412 | 7 |
| 344 | 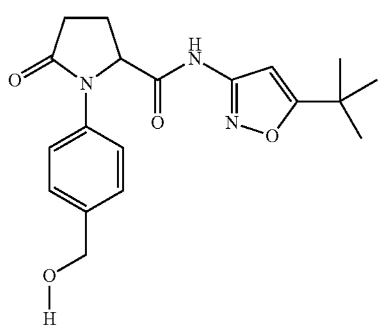 [SMILES: CC(C)(C)c1cc(NC(=O)C2CCC(=O)N2c2ccc(CO)cc2)no1] | 1-(4-Hydroxymethyl-phenyl)-5-oxo-pyrrolidine-2-carboxylic acid (5-tert-butyl-isothiazol-3-yl)-amide | 358 | 39 |

TABLE III-continued

| Example | Name | ESI m/z (+) | Patent Method |
|---|---|---|---|
| 345 | (S)-5-Oxo-1-(4-trifluoromethyl-phenyl)-pyrrolidine-2-carboxylic acid [3-(4-hydroxy-phenyl)-1,2,4-thiadiazol-5-yl]-amide | 402 | 39 |
| 346 | (S)-5-Oxo-1-(4-trifluoromethyl-phenyl)-pyrrolidine-2-carboxylic acid [5-(2-hydroxy-1,1-dimethyl-ethyl)-isoxazol-3-yl]-amide | 412 | 40 |
| 347 | (S)-1-(4-Fluoro-phenyl)-5-oxo-pyrrolidine-2-carboxylic acid [3-(2-hydroxy-1,1-dimethyl-ethyl)-isoxazol-5-yl]-amide | 362 | 38 |
| 348 | (S)-1-(5-Chloro-pyridin-2-yl)-5-oxo-pyrrolidine-2-carboxylic acid (3-tert-butyl-isoxazol-5-yl)-amide | 363 | 37 |
| 349 | (S)-1-(5-Fluoro-pyridin-2-yl)-5-oxo-pyrrolidine-2-carboxylic acid (3-tert-butyl-isoxazol-5-yl)-amide | 347 | 42 |

TABLE III-continued

| Example | Name | ESI m/z (+) | Patent Method |
|---|---|---|---|
| 350 | (S)-1-(5-Chloro-pyrimidin-2-yl)-5-oxo-pyrrolidine-2-carboxylic acid (3-tert-butyl-isoxazol-5-yl)-amide | 364 | 43 |
| 351 | 1-(5-Cyano-pyridin-2-yl)-5-oxo-pyrrolidine-2-carboxylic acid (3-tert-butyl-isoxazol-5-yl)-amide | 354 | 44 |
| 352 | (S)-5-Oxo-1-(5-trifluoromethyl-pyridin-2-yl)-pyrrolidine-2-carboxylic acid (3-tert-butyl-isoxazol-5-yl)-amide | 397 | 44 |
| 353 | (S)-5-Oxo-1-pyridin-2-yl-pyrrolidine-2-carboxylic acid (3-tert-butyl-isoxazol-5-yl)-amide | 329 | 44 |
| 354 | (S)-1-(5-Methyl-pyridin-2-yl)-5-oxo-pyrrolidine-2-carboxylic acid (3-tert-butyl-isoxazol-5-yl)-amide | 343 | 44 |

TABLE III-continued

| Example | Structure | Name | ESI m/z (+) | Patent Method |
|---|---|---|---|---|
| 355 | 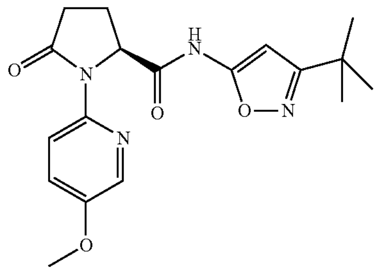 [SMILES: COc1ccc(N2C(=O)CC[C@H]2C(=O)Nc2cc(C(C)(C)C)no2)nc1] | (S)-1-(5-Methoxy-pyridin-2-yl)-5-oxo-pyrrolidine-2-carboxylic acid (3-tert-butyl-isoxazol-5-yl)-amide | 359 | 44 |
| 356 | 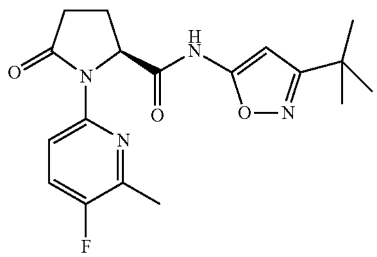 [SMILES: Cc1nc(N2C(=O)CC[C@H]2C(=O)Nc2cc(C(C)(C)C)no2)ccc1F] | (S)-1-(5-Fluoro-6-methyl-pyridin-2-yl)-5-oxo-pyrrolidine-2-carboxylic acid (3-tert-butyl-isoxazol-5-yl)-amide | 361 | 44 |
| 357 | 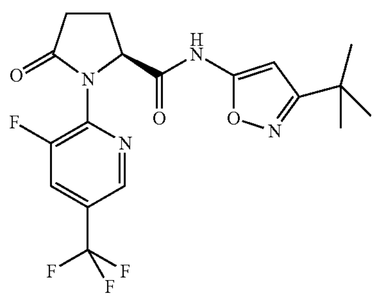 [SMILES: CC(C)(C)c1cc(NC(=O)[C@@H]2CCC(=O)N2c2ncc(C(F)(F)F)cc2F)on1] | (S)-1-(3-Fluoro-5-trifluoromethyl-pyridin-2-yl)-5-oxo-pyrrolidine-2-carboxylic acid (3-tert-butyl-isoxazol-5-yl)-amide | 415 | 44 |
| 358 | | (S)-1-(tetrahydro-pyran-4-yl)-pyrrolidine-2-carboxylic acid [3-(2-hydroxy-1,1-dimethyl-ethyl)-isoxazol-5-yl]-amide | 338 | 45 | or a pharmaceutically acceptable salt thereof.

Of the above compounds, the following are preferred CB2 agonists:

TABLE IV

| Compound | CB2 CAMP @ EC50 nM (mean) |
|---|---|
| (S)-1-(4-Chloro-phenyl)-pyrrolidine-2-carboxylic acid (5-tert-butyl-1,3,4-thiadiazol-2-yl)-amide | .098 |
| (S)-1-(4-Chloro-phenyl)-pyrrolidine-2-carboxylic acid (tetrahydro-pyran-4-ylmethyl)-amide | 414.95 |
| (S)-1-(4-Chloro-phenyl)-5-(4-methyl-piperazine-1-carbonyl)-pyrrolidin-2-one | 355.03 |
| (S)-1-(4-Chloro-phenyl)-5-oxo-pyrrolidine-2-carboxylic acid (5-methyl-pyridin-2-yl)-amide | 485.05 |
| (S)-1-(4-Chloro-phenyl)-pyrrolidine-2-carboxylic acid (3,3,5-trimethyl-cyclohexyl)-amide | 2.16 |

TABLE IV-continued

| Compound | CB2 CAMP @ EC50 nM (mean) |
|---|---|
| (S)-1-(4-Chloro-phenyl)-pyrrolidine-2-carboxylic acid [4-(4-chloro-phenyl)-thiazol-2-yl]-amide | 84.88 |
| (S)-1-(4-Chloro-phenyl)-pyrrolidine-2-carboxylic acid (4-tert-butyl-5-cyano-thiazol-2-yl)-amide | 31.68 |
| (S)-1-(4-Chloro-phenyl)-5-oxo-pyrrolidine-2-carboxylic acid (3,3,5-trimethyl-cyclohexyl)-amide | 212.11 |
| (S)-1-(4-Chloro-phenyl)-pyrrolidine-2-carboxylic acid (4-trifluoromethyl-pyridin-2-yl)-amide | 23.44 |
| (S)-1-(4-Chloro-phenyl)-pyrrolidine-2-carboxylic acid (3-fluoro-4-trifluoromethyl-phenyl)-amide | 30.39 |
| (S)-1-(4-Chloro-phenyl)-pyrrolidine-2-carboxylic acid (5-chloro-1H-benzimidazol-2-yl)-amide | 2.16 |
| (S)-1-(4-Chloro-phenyl)-pyrrolidine-2-carboxylic acid [4-(4-fluoro-phenyl)-thiazol-2-yl]-amide | 115.16 |
| (S)-1-(4-Chloro-phenyl)-pyrrolidine-2-carboxylic acid (2-cyclohexyl-ethyl)-amide | 25.93 |
| (S)-1-(4-Chloro-phenyl)-pyrrolidine-2-carboxylic acid {2-[4-(4-trifluoromethyl-pyrimidin-2-yl)-piperazin-1-yl]-ethyl}-amide | 381 |
| (S)-1-(4-Chloro-phenyl)-5-oxo-pyrrolidine-2-carboxylic acid (5-chloro-1H-benzimidazol-2-yl)-amide | 255.02 |
| (S)-1-(4-Chloro-phenyl)-5-oxo-pyrrolidine-2-carboxylic acid (2-cyclohexyl-ethyl)-amide | 333.88 |
| (S)-1-(4-Chloro-phenyl)-5-oxo-pyrrolidine-2-carboxylic acid (4-tert-butyl-cyclohexyl)-amide | 158.79 |
| (S)-1-(4-Chloro-phenyl)-5-oxo-pyrrolidine-2-carboxylic acid (3-propyl-isoxazol-5-yl)-amide | 262.72 |
| (S)-1-(4-Chloro-phenyl)-pyrrolidine-2-carboxylic acid (4-fluoro-3-trifluoromethyl-phenyl)-amide | 19.12 |
| (S)-1-(4-Chloro-phenyl)-pyrrolidine-2-carboxylic acid (1,1,3,3-tetramethyl-butyl)-amide | 25.14 |
| (S)-1-(4-Chloro-phenyl)-pyrrolidine-2-carboxylic acid [2-(4-chloro-phenyl)-1-methyl-ethyl]-amide | 269.55 |
| (S)-1-(4-Chloro-phenyl)-pyrrolidine-2-carboxylic acid (4-tert-butyl-cyclohexyl)-amide | 7.42 |
| (S)-1-(4-Chloro-phenyl)-pyrrolidine-2-carboxylic acid (5,5-dimethyl-3-oxo-cyclohex-1-enyl)-amide | 17.86 |
| (S)-1-(4-Chloro-phenyl)-pyrrolidine-2-carboxylic acid (tetrahydro-pyran-4-yl)-amide | 253.61 |
| (S)-1-(4-Chloro-phenyl)-pyrrolidine-2-carboxylic acid (4-ethyl-pyridin-2-yl)-amide | 1.2 |
| (S)-1-(4-Chloro-phenyl)-pyrrolidine-2-carboxylic acid (5-phenyl-1,3,4-thiadiazol-2-yl)-amide | 11.17 |
| (S)-1-(4-Chloro-phenyl)-pyrrolidine-2-carboxylic acid (4-cyclopropyl-thiazol-2-yl)-amide | 36.1 |
| (S)-1-(4-Chloro-phenyl)-pyrrolidine-2-carboxylic acid [2-(tetrahydro-pyran-4-yl)-ethyl]-amide | 104.7 |
| (S)-1-(4-Chloro-phenyl)-pyrrolidine-2-carboxylic acid (4-cyclohexyl-thiazol-2-yl)-amide | 35.5 |
| (S)-1-(4-Chloro-phenyl)-pyrrolidine-2-carboxylic acid (3-propyl-isoxazol-5-yl)-amide | 2.41 |
| (S)-1-(4-Chloro-phenyl)-pyrrolidine-2-carboxylic acid (1-acetyl-piperidin-4-ylmethyl)-amide | 0.015 |
| (S)-1-(4-Chloro-phenyl)-pyrrolidine-2-carboxylic acid (4-trifluoromethyl-oxazol-2-yl)-amide | 5.79 |
| (S)-1-(4-Chloro-phenyl)-pyrrolidine-2-carboxylic acid (4-methyl-furazan-3-ylmethyl)-amide | 497.66 |
| (S)-1-(4-Chloro-phenyl)-pyrrolidine-2-carboxylic acid (2-tert-butylsulfanyl-ethyl)-amide | 2.61 |
| (2S,4R)-4-Hydroxy-1-(tetrahydro-pyran-4-ylmethyl)-pyrrolidine-2-carboxylic acid [4-(4-chloro-phenyl)-thiazol-2-yl]-amide | 71.23 |
| (2S,4R)-4-Hydroxy-1-(tetrahydro-pyran-4-ylmethyl)-pyrrolidine-2-carboxylic acid (3,3,5-trimethyl-cyclohexyl)-amide | 219.09 |
| (2S,4R)-4-Hydroxy-1-(tetrahydro-pyran-4-ylmethyl)-pyrrolidine-2-carboxylic acid (5-tert-butyl-1,3,4-thiadiazol-2-yl)-amide | 69.85 |
| (2S,4R)-4-Hydroxy-1-(tetrahydro-pyran-4-ylmethyl)-pyrrolidine-2-carboxylic acid (4-cyclohexyl-thiazol-2-yl)-amide | 149.67 |
| (2S,4R)-4-Hydroxy-1-(tetrahydro-pyran-4-ylmethyl)-pyrrolidine-2-carboxylic acid (3-phenyl-1,2,4-thiadiazol-5-yl)-amide | 303.32 |
| (2S,4R)-4-Hydroxy-1-(tetrahydro-pyran-4-ylmethyl)-pyrrolidine-2-carboxylic acid (3-propyl-isoxazol-5-yl)-amide | 248.19 |

TABLE IV-continued

| Compound | CB2 CAMP @ EC50 nM (mean) |
|---|---|
| (2S,4S)-4-Hydroxy-1-(tetrahydro-pyran-4-ylmethyl)-pyrrolidine-2-carboxylic acid (4-tert-butyl-5-cyano-thiazol-2-yl)-amide | 379.9 |
| (S)-1-(4-chloro-phenyl)-5-oxo-pyrrolidine-2-carboxylic acid (5-tert-butyl-isoxazol-3-yl)-amide | 39.11 |
| (S)-1-(4-chloro-phenyl)-5-oxo-pyrrolidine-2-carboxylic acid (3-tert-butyl-isoxazol-5-yl)-amide | 6.05 |
| (S)-1-(3-chloro-5-trifluoromethyl-pyridin-2-yl)-5-oxo-pyrrolidine-2-carboxylic acid (4-sec-butyl-phenyl)-amide | 28.1 |
| (S)-1-(3-chloro-5-trifluoromethyl-pyridin-2-yl)-5-oxo-pyrrolidine-2-carboxylic acid (5-tert-butyl-isoxazol-3-yl)-amide | 6.5 |
| (S)-1-(3-chloro-5-trifluoromethyl-pyridin-2-yl)-5-oxo-pyrrolidine-2-carboxylic acid (3-phenyl-1,2,4-thiadiazol-5-yl)-amide | 0.549 |
| (S)-1-(4-cyano-phenyl)-5-oxo-pyrrolidine-2-carboxylic acid (5-tert-butyl-isoxazol-3-yl)-amide | 59.91 |
| (S)-1-(4-cyano-phenyl)-5-oxo-pyrrolidine-2-carboxylic acid (3-tert-butyl-isoxazol-5-yl)-amide | 21.58 |
| (S)-1-(4-nitro-phenyl)-5-oxo-pyrrolidine-2-carboxylic acid (5-tert-butyl-isoxazol-3-yl)-amide | 21.09 |
| (S)-1-(4-fluoro-phenyl)-5-oxo-pyrrolidine-2-carboxylic acid (3-tert-butyl-isoxazol-5-yl)-amide | 8.72 |
| (S)-1-(4-fluoro-phenyl)-5-oxo-pyrrolidine-2-carboxylic acid (5-tert-butyl-isoxazol-3-yl)-amide | 35.65 |
| (2S,4R)-1-(4,4-Difluoro-cyclohexanecarbonyl)-4-hydroxy-pyrrolidine-2-carboxylic acid cyclohexylmethyl-amide | 432 |
| (2S,4R)-4-Hydroxy-1-(5-trifluoromethyl-pyridin-2-yl)-pyrrolidine-2-carboxylic acid (5-tert-butyl-isoxazol-3-yl)-amide | 160.94 |
| (S)-1-(4,4-Difluoro-cyclohexanecarbonyl)-4,4-difluoro-pyrrolidine-2-carboxylic acid (5-tert-butyl-isoxazol-3-yl)-amide | 226.36 |
| (2S,4R)-1-(3-Chloro-5-trifluoromethyl-pyridin-2-yl)-4-hydroxy-pyrrolidine-2-carboxylic acid (5-tert-butyl-isoxazol-3-yl)-amide | 5.04 |
| (2S,4R)-4-Hydroxy-1-(5-trifluoromethyl-pyridin-2-yl)-pyrrolidine-2-carboxylic acid (3-phenyl-1,2,4-thiadiazol-5-yl)-amide | 357.21 |
| (2S,4S)-1-(3-Chloro-5-trifluoromethyl-pyridin-2-yl)-4-hydroxy-pyrrolidine-2-carboxylic acid (5-tert-butyl-isoxazol-3-yl)-amide | 1.35 |
| (2S,4S)-4-Hydroxy-1-(5-trifluoromethyl-pyridin-2-yl)-pyrrolidine-2-carboxylic acid (5-tert-butyl-isoxazol-3-yl)-amide | 27.88 |
| (S)-1-(3-Chloro-5-trifluoromethyl-pyridin-2-yl)-4-oxo-pyrrolidine-2-carboxylic acid (5-tert-butyl-isoxazol-3-yl)-amide | 40.22 |
| (2S,4S)-4-Hydroxy-1-(5-trifluoromethyl-pyridin-2-yl)-pyrrolidine-2-carboxylic acid (3-phenyl-1,2,4-thiadiazol-5-yl)-amide | 18.44 |
| (2S,4R)-4-Hydroxy-1-(5-trifluoromethyl-pyridin-2-yl)-pyrrolidine-2-carboxylic acid (3-tert-butyl-isoxazol-5-yl)-amide | 0.433 |
| (2S,4R)-1-(4-Chloro-phenyl)-4-hydroxy-pyrrolidine-2-carboxylic acid (5-tert-butyl-isoxazol-3-yl)-amide | 14.45 |
| (2S,4R)-1-(4-Chloro-phenyl)-4-hydroxy-pyrrolidine-2-carboxylic acid (3-tert-butyl-isoxazol-5-yl)-amide | 6.2 |
| (2S,4R)-1-(3-Chloro-5-trifluoromethyl-pyridin-2-yl)-4-hydroxy-pyrrolidine-2-carboxylic acid (3-tert-butyl-isoxazol-5-yl)-amide | 3.25 |
| (2S,4R)-4-Hydroxy-1-(tetrahydro-pyran-4-ylmethyl)-pyrrolidine-2-carboxylic acid (5-tert-butyl-isoxazol-3-yl)-amide | 3.89 |
| (2S,4R)-4-Hydroxy-1-(tetrahydro-pyran-4-yl)-pyrrolidine-2-carboxylic acid (5-tert-butyl-isoxazol-3-yl)-amide | 363 |
| (2S,4R)-4-Hydroxy-1-(tetrahydro-pyran-4-yl)-pyrrolidine-2-carboxylic acid (3-tert-butyl-isoxazol-5-yl)-amide | 327.73 |
| (2S,4R)-1-(3,4-Difluoro-benzyl)-4-hydroxy-pyrrolidine-2-carboxylic acid (5-tert-butyl-isoxazol-3-yl)-amide | 12.32 |
| (2S,4R)-4-Hydroxy-1-(tetrahydro-pyran-4-yl)-pyrrolidine-2-carboxylic acid (5-ethyl-4-phenyl-thiazol-2-yl)-amide | 58.69 |
| (2S,4R)-4-Hydroxy-1-(tetrahydro-pyran-4-ylmethyl)-pyrrolidine-2-carboxylic acid (5-ethyl-4-phenyl-thiazol-2-yl)-amide | 7.93 |
| (2S,4R)-1-Cyclopentyl-4-hydroxy-pyrrolidine-2-carboxylic acid (5-tert-butyl-isoxazol-3-yl)-amide | 23.24 |
| (2S,4R)-1-Cyclohexyl-4-hydroxy-pyrrolidine-2-carboxylic acid (5-tert-butyl-isoxazol-3-yl)-amide | 4.69 |
| (2S,4R)-1-(3,4-Difluoro-benzyl)-4-hydroxy-pyrrolidine-2-carboxylic acid (3-tert-butyl-isoxazol-5-yl)-amide | 6.88 |
| (2S,4R)-1-Cyclopentyl-4-hydroxy-pyrrolidine-2-carboxylic acid (3-tert-butyl-isoxazol-5-yl)-amide | 61.87 |

TABLE IV-continued

| Compound | CB2 CAMP @ EC50 nM (mean) |
|---|---|
| (2S,4R)-1-Cyclohexyl-4-hydroxy-pyrrolidine-2-carboxylic acid (3-tert-butyl-isoxazol-5-yl)-amide | 11.49 |
| 1-(5-Chloro-pyridin-2-yl)-pyrrolidine-2-carboxylic acid (5-tert-butyl-isoxazol-3-yl)-amide | 0.364 |
| 1-(3-Chloro-5-trifluoromethyl-pyridin-2-yl)-pyrrolidine-2-carboxylic acid (5-trifluoromethyl-pyridin-2-yl)-amide | 23.17 |
| 1-(3-Chloro-5-trifluoromethyl-pyridin-2-yl)-pyrrolidine-2-carboxylic acid (5-tert-butyl-2-methyl-2H-pyrazol-3-yl)-amide | 111.54 |
| (S)-1-(4-Chloro-phenyl)-pyrrolidine-2-carboxylic acid (5-tert-butyl-isoxazol-3-yl)-amide | 0.221 |
| 1-Isopropyl-pyrrolidine-2-carboxylic acid (5-tert-butyl-isoxazol-3-yl)-amide | 30.33 |
| 1-(5-Trifluoromethyl-pyridin-2-yl)-pyrrolidine-2-carboxylic acid (5-tert-butyl-isoxazol-3-yl)-amide | 0.443 |
| (S)-1-(5-Trifluoromethyl-pyridin-2-yl)-pyrrolidine-2-carboxylic acid (5-tert-butyl-isoxazol-3-yl)-amide | 0.067 |
| (R)-1-(5-Trifluoromethyl-pyridin-2-yl)-pyrrolidine-2-carboxylic acid (5-tert-butyl-isoxazol-3-yl)-amide | 172.82 |
| (S)-1-(4-Chloro-phenyl)-pyrrolidine-2-carboxylic acid (5-trifluoromethyl-pyridin-2-yl)-amide | 35.1 |
| (S)-1-(4-Trifluoromethyl-phenyl)-pyrrolidine-2-carboxylic acid (5-trifluoromethyl-pyridin-2-yl)-amide | 15.52 |
| (S)-1-(4-Trifluoromethyl-phenyl)-pyrrolidine-2-carboxylic acid (5-tert-butyl-isoxazol-3-yl)-amide | 0.203 |
| (R)-1-(4-Trifluoromethyl-phenyl)-pyrrolidine-2-carboxylic acid (5-trifluoromethyl-pyridin-2-yl)-amide | 70.69 |
| (R)-1-(4-Trifluoromethyl-phenyl)-pyrrolidine-2-carboxylic acid (5-tert-butyl-isoxazol-3-yl)-amide | 99.14 |
| (S)-1-(4-Chloro-phenyl)-2-methyl-pyrrolidine-2-carboxylic acid (5-tert-butyl-isoxazol-3-yl)-amide | 0.21 |
| (S)-2-Methyl-1-(4-trifluoromethyl-phenyl)-pyrrolidine-2-carboxylic acid (5-tert-butyl-isoxazol-3-yl)-amide | 0.199 |
| (S)-1-(4-Chloro-phenyl)-2-methyl-pyrrolidine-2-carboxylic acid (5-trifluoromethyl-pyridin-2-yl)-amide | 27.17 |
| (S)-1-(4-Chloro-phenyl)-pyrrolidine-2-carboxylic acid (6-trifluoromethyl-pyridin-2-yl)-amide | 48.84 |
| (S)-1-(4-Chloro-phenyl)-pyrrolidine-2-carboxylic acid (4-trifluoromethyl-thiazol-2-yl)-amide | 89.16 |
| (S)-1-(4-Chloro-phenyl)-pyrrolidine-2-carboxylic acid (4,5,6,7-tetrahydro-benzothiazol-2-yl)-amide | 12.7 |
| 1-(5-Trifluoromethyl-pyridin-2-yl)-pyrrolidine-2-carboxylic acid (5-trifluoromethyl-pyridin-2-yl)-amide | 328.33 |
| (R)-1-(4-Chloro-phenyl)-pyrrolidine-2-carboxylic acid (5-tert-butyl-isoxazol-3-yl)-amide | 63.42 |
| (S)-1-(1,1-Dioxo-1$\lambda^6$-thiomorpholine-4-carbonyl)-pyrrolidine-2-carboxylic acid (5-tert-butyl-isoxazol-3-yl)-amide | 390.91 |
| 1-(3-Chloro-5-trifluoromethyl-pyridin-2-yl)-pyrrolidine-2-carboxylic acid (5-tert-butyl-isoxazol-3-yl)-amide | 0.0402 |
| (S)-2-Methyl-1-(5-trifluoromethyl-pyridin-2-yl)-pyrrolidine-2-carboxylic acid (5-tert-butyl-isoxazol-3-yl)-amide | 0.015 |
| (S)-2-Methyl-1-(5-trifluoromethyl-pyridin-2-yl)-pyrrolidine-2-carboxylic acid (3-phenyl-1,2,4-thiadiazol-5-yl)-amide | 0.136 |
| (S)-2-Methyl-1-(5-trifluoromethyl-pyridin-2-yl)-pyrrolidine-2-carboxylic acid (5-trifluoromethyl-pyridin-2-yl)-amide | 0.634 |
| (S)-1-(4-Chloro-phenyl)-pyrrolidine-2-carboxylic acid (5-methyl-pyridin-2-yl)-amide | 119.95 |
| (S)-1-(Tetrahydro-pyran-4-yl)-pyrrolidine-2-carboxylic acid (5-tert-butyl-isoxazol-3-yl)-amide | 1.55 |
| (S)-1-(4-Chloro-phenyl)-pyrrolidine-2-carboxylic acid (3-phenyl-1,2,4-thiadiazol-5-yl)-amide | 4.85 |
| (S)-1-(Tetrahydro-pyran-4-ylmethyl)-pyrrolidine-2-carboxylic acid (5-tert-butyl-isoxazol-3-yl)-amide | 1.07 |
| (S)-1-(Tetrahydro-pyran-4-ylmethyl)-pyrrolidine-2-carboxylic acid (4-tert-butyl-thiazol-2-yl)-amide | 17.62 |
| (S)-1-Propyl-pyrrolidine-2-carboxylic acid (4-tert-butyl-thiazol-2-yl)-amide | 159.42 |
| (S)-1-(Tetrahydro-pyran-4-yl)-pyrrolidine-2-carboxylic acid (4-tert-butyl-thiazol-2-yl)-amide | 279 |
| (S)-1-(4-Chloro-phenyl)-pyrrolidine-2-carboxylic acid (4-tert-butyl-thiazol-2-yl)-amide | 30.11 |
| (S)-1-(Tetrahydro-pyran-4-yl)-pyrrolidine-2-carboxylic acid (3-tert-butyl-isoxazol-5-yl)-amide | 2.8 |
| (S)-1-(Tetrahydro-pyran-4-ylmethyl)-pyrrolidine-2-carboxylic acid (3-tert-butyl-isoxazol-5-yl)-amide | 0.438 |
| (S)-1-Cyclopropylmethyl-pyrrolidine-2-carboxylic acid (5-tert-butyl-isoxazol-3-yl)-amide | 7.72 |

TABLE IV-continued

| Compound | CB2 CAMP @ EC50 nM (mean) |
|---|---|
| (S)-1-Cyclobutyl-pyrrolidine-2-carboxylic acid (5-tert-butyl-isoxazol-3-yl)-amide | 16.92 |
| (S)-1-Cyclopentyl-pyrrolidine-2-carboxylic acid (5-tert-butyl-isoxazol-3-yl)-amide | 3.93 |
| (S)-1-Cyclohexyl-pyrrolidine-2-carboxylic acid (5-tert-butyl-isoxazol-3-yl)-amide | 0.171 |
| (S)-1-(3-Chloro-5-trifluoromethyl-pyridin-2-yl)-pyrrolidine-2-carboxylic acid (3-tert-butyl-isoxazol-5-yl)-amide | 0.055 |
| (S)-1-(3-Chloro-5-trifluoromethyl-pyridin-2-yl)-pyrrolidine-2-carboxylic acid (4-tert-butyl-thiazol-2-yl)-amide | 1.95 |
| (S)-1-(3-Chloro-5-trifluoromethyl-pyridin-2-yl)-pyrrolidine-2-carboxylic acid (5-tert-butyl-isoxazol-3-yl)-amide | 0.08 |
| (S)-1-Cyclopropylmethyl-pyrrolidine-2-carboxylic acid (3-tert-butyl-isoxazol-5-yl)-amide | 11.36 |
| (S)-1-Cyclopropylmethyl-pyrrolidine-2-carboxylic acid [3-(2,2-dimethyl-propyl)-isoxazol-5-yl]-amide | 22.27 |
| (S)-1-Cyclopentyl-pyrrolidine-2-carboxylic acid [3-(2,2-dimethyl-propyl)-isoxazol-5-yl]-amide | 112.89 |
| (S)-1-Cyclohexylmethyl-pyrrolidine-2-carboxylic acid (3-tert-butyl-isoxazol-5-yl)-amide | 0.079 |
| (S)-1-Cyclobutyl-pyrrolidine-2-carboxylic acid (3-tert-butyl-isoxazol-5-yl)-amide | 6.28 |
| (S)-1-Cyclopentyl-pyrrolidine-2-carboxylic acid (3-tert-butyl-isoxazol-5-yl)-amide | 2.39 |
| (S)-1-Cyclohexyl-pyrrolidine-2-carboxylic acid (3-tert-butyl-isoxazol-5-yl)-amide | 0.173 |
| (S)-1-(5-Trifluoromethyl-pyridin-2-yl)-pyrrolidine-2-carboxylic acid (3-tert-butyl-isoxazol-5-yl)-amide | 0.023 |
| (S)-1-Pyrimidin-2-yl-pyrrolidine-2-carboxylic acid (3-tert-butyl-isoxazol-5-yl)-amide | 109.26 |
| (S)-1-(3,5-Dichloro-pyridin-2-yl)-pyrrolidine-2-carboxylic acid (3-tert-butyl-isoxazol-5-yl)-amide | 0.135 |
| (S)-1-(5-Chloro-3-fluoro-pyridin-2-yl)-pyrrolidine-2-carboxylic acid (3-tert-butyl-isoxazol-5-yl)-amide | 0.02 |
| (S)-1-(5-Trifluoromethyl-pyridin-2-yl)-pyrrolidine-2-carboxylic acid (4-tert-butyl-thiazol-2-yl)-amide | 8.56 |
| (S)-1-(Tetrahydro-pyran-4-yl)-pyrrolidine-2-carboxylic acid [3-(2,2-dimethyl-propyl)-isoxazol-5-yl]-amide | 14.9 |
| (S)-1-(Tetrahydro-pyran-4-ylmethyl)-pyrrolidine-2-carboxylic acid [3-(2,2-dimethyl-propyl)-isoxazol-5-yl]-amide | 3.46 |
| (S)-1-(Tetrahydro-furan-3-ylmethyl)-pyrrolidine-2-carboxylic acid (3-tert-butyl-isoxazol-5-yl)-amide | 0.116 |
| (S)-1-Cyclohex-2-enylmethyl-pyrrolidine-2-carboxylic acid (3-tert-butyl-isoxazol-5-yl)-amide | 0.072 |
| (S)-1-(2-Methyl-butyl)-pyrrolidine-2-carboxylic acid (3-tert-butyl-isoxazol-5-yl)-amide | 0.116 |
| (S)-1-(Tetrahydro-pyran-3-ylmethyl)-pyrrolidine-2-carboxylic acid (3-tert-butyl-isoxazol-5-yl)-amide | 0.376 |
| (S)-1-Cyclopropyl-pyrrolidine-2-carboxylic acid (3-tert-butyl-isoxazol-5-yl)-amide | 3.19 |
| 1-(2,2-Dimethyl-tetrahydro-pyran-4-ylmethyl)-pyrrolidine-2-carboxylic acid (3-tert-butyl-isoxazol-5-yl)-amide | 7.1 |
| 1-(Tetrahydro-pyran-2-ylmethyl)-pyrrolidine-2-carboxylic acid (3-tert-butyl-isoxazol-5-yl)-amide | 0.172 |
| (S)-1-(3-Hydroxy-propyl)-pyrrolidine-2-carboxylic acid (3-tert-butyl-isoxazol-5-yl)-amide | 28.62 |
| (S)-1-(1,1-Dioxo-1l$^6$-thiomorpholine-4-carbonyl)-pyrrolidine-2-carboxylic acid (3-tert-butyl-isoxazol-5-yl)-amide | 97.09 |
| (S)-1-(4-Chloro-benzyl)-pyrrolidine-2-carboxylic acid (3-tert-butyl-isoxazol-5-yl)-amide | 2.28 |
| (S)-1-(4-Fluoro-benzyl)-pyrrolidine-2-carboxylic acid (3-tert-butyl-isoxazol-5-yl)-amide | 0.747 |
| (S)-1-(3,4-Difluoro-benzyl)-pyrrolidine-2-carboxylic acid (3-tert-butyl-isoxazol-5-yl)-amide | 0.208 |
| (S)-1-(4-Difluoromethoxy-benzyl)-pyrrolidine-2-carboxylic acid (3-tert-butyl-isoxazol-5-yl)-amide | 8.04 |
| (2S,4S)-4-Hydroxy-1-(tetrahydro-pyran-4-yl)-pyrrolidine-2-carboxylic acid (3-tert-butyl-isoxazol-5-yl)-amide | 59 |
| (S)-1-(Tetrahydro-pyran-4-ylmethyl)-pyrrolidine-2-carboxylic acid (5-tert-butyl-1,3,4-thiadiazol-2-yl)-amide | 16.54 |
| (S)-1-(1,1-Dioxo-1l$^6$-thiomorpholine-4-carbonyl)-pyrrolidine-2-carboxylic acid (5-tert-butyl-1,3,4-thiadiazol-2-yl)-amide | 436 |
| (S)-1-(3-Hydroxy-propyl)-pyrrolidine-2-carboxylic acid (5-tert-butyl-1,3,4-thiadiazol-2-yl)-amide | 320 |

TABLE IV-continued

| Compound | CB2 CAMP @ EC50 nM (mean) |
|---|---|
| (S)-5-Oxo-1-(4-trifluoromethyl-phenyl)-pyrrolidine-2-carboxylic acid (3-tert-butyl-isoxazol-5-yl)-amide | 1.55 |
| (S)-5-Oxo-1-(4-trifluoromethyl-phenyl)-pyrrolidine-2-carboxylic acid (5-tert-butyl-isoxazol-3-yl)-amide | 5.76 |
| (S)-1-(Tetrahydro-pyran-4-ylmethyl)-pyrrolidine-2-carboxylic acid (5-chloro-1H-benzimidazol-2-yl)-amide | 48.64 |
| (S)-1-(Tetrahydro-pyran-4-yl)-pyrrolidine-2-carboxylic acid (5-chloro-1H-benzimidazol-2-yl)-amide | 73.72 |
| (2S,4S)-4-Hydroxy-1-isopropyl-pyrrolidine-2-carboxylic acid (3-tert-butyl-isoxazol-5-yl)-amide | 420.59 |
| (S)-1-Isopropyl-pyrrolidine-2-carboxylic acid (3-tert-butyl-isoxazol-5-yl)-amide | 163.2 |
| (S)-1-(Tetrahydro-pyran-4-ylmethyl)-pyrrolidine-2-carboxylic acid (3-phenyl-1,2,4-thiadiazol-5-yl)-amide | 40 |
| (S)-1-(Tetrahydro-pyran-4-ylmethyl)-pyrrolidine-2-carboxylic acid (5-ethyl-4-phenyl-thiazol-2-yl)-amide | 10.9 |
| (S)-1-(Tetrahydro-pyran-4-ylmethyl)-pyrrolidine-2-carboxylic acid (5,6-dichloro-1H-benzimidazol-2-yl)-amide | 56.21 |
| (S)-1-(Tetrahydro-pyran-4-ylmethyl)-pyrrolidine-2-carboxylic acid (5-chloro-benzothiazol-2-yl)-amide | 3.14 |
| (S)-1-(Tetrahydro-pyran-4-ylmethyl)-pyrrolidine-2-carboxylic acid (6-chloro-benzothiazol-2-yl)-amide | 187.67 |
| (S)-1-(Tetrahydro-pyran-4-yl)-pyrrolidine-2-carboxylic acid (5-chloro-benzothiazol-2-yl)-amide | 4.66 |
| (S)-1-(Tetrahydro-pyran-4-yl)-pyrrolidine-2-carboxylic acid (6-chloro-benzothiazol-2-yl)-amide | 132.82 |
| (S)-1-(Tetrahydro-pyran-4-yl)-pyrrolidine-2-carboxylic acid (5,6-dichloro-1H-benzimidazol-2-yl)-amide | 164.92 |
| (S)-1-(Tetrahydro-pyran-4-yl)-pyrrolidine-2-carboxylic acid (5-fluoro-1H-benzimidazol-2-yl)-amide | 391.15 |
| (S)-1-(4-Chloro-benzenesulfonyl)-pyrrolidine-2-carboxylic acid (5-tert-butyl-isoxazol-3-yl)-amide | 284.41 |
| (S)-1-(4-Trifluoromethyl-benzenesulfonyl)-pyrrolidine-2-carboxylic acid (5-tert-butyl-isoxazol-3-yl)-amide | 222.05 |
| (S)-1-(Propane-1-sulfonyl)-pyrrolidine-2-carboxylic acid (5-tert-butyl-isoxazol-3-yl)-amide | 119.96 |
| (S)-1-(4-Methanesulfonyl-benzenesulfonyl)-pyrrolidine-2-carboxylic acid (5-tert-butyl-isoxazol-3-yl)-amide | 183.23 |
| [(S)-2-(3-tert-Butyl-isoxazol-5-ylcarbamoyl)-pyrrolidin-1-yl]-acetic acid tert-butyl ester | 0.1 |
| (S)-1-(5-Chloro-thiophen-2-yl)-5-oxo-pyrrolidine-2-carboxylic acid (3-tert-butyl-isoxazol-5-yl)-amide | 67.54 |
| (S)-1-(4-Chloro-2-fluoro-phenyl)-5-oxo-pyrrolidine-2-carboxylic acid (3-tert-butyl-isoxazol-5-yl)-amide | 81.98 |
| (S)-1-(Tetrahydro-pyran-4-ylmethyl)-pyrrolidine-2-carboxylic acid (5-trifluoromethyl-pyridin-2-yl)-amide | 212.13 |
| 3-[(S)-2-(3-tert-Butyl-isoxazol-5-ylcarbamoyl)-pyrrolidin-l-yl]-propionic acid tert-butyl ester | 20 |
| (S)-1-(Tetrahydro-pyran-4-yl)-pyrrolidine-2-carboxylic acid (5-tert-butyl-l,3,4-thiadiazol-2-yl)-amide | 40 |
| (S)-1-Cyclobutyl-pyrrolidine-2-carboxylic acid (5-tert-butyl-1,3,4-thiadiazol-2-yl)-amide | 255 |
| (S)-1-Cyclopropylmethyl-pyrrolidine-2-carboxylic acid (5-tert-butyl-1,3,4-thiadiazol-2-yl)-amide | 340 |
| (S)-1-Cyclopropyl-pyrrolidine-2-carboxylic acid (5-tert-butyl-1,3,4-thiadiazol-2-yl)-amide | 109 |
| (S)-1-Cyclopentyl-pyrrolidine-2-carboxylic acid (5-tert-butyl-1,3,4-thiadiazol-2-yl)-amide | 165 |
| (S)-1-Cyclohexyl-pyrrolidine-2-carboxylic acid (5-tert-butyl-1,3,4-thiadiazol-2-yl)-amide | 30 |
| 1-sec-Butyl-pyrrolidine-2-carboxylic acid (5-tert-butyl-1,3,4-thiadiazol-2-yl)-amide | 390 |
| 1-(2-Methyl-cyclohexyl)-pyrrolidine-2-carboxylic acid (5-tert-butyl-1,3,4-thiadiazol-2-yl)-amide | 255 |
| 1-(2,2-Dimethyl-cyclopentyl)-pyrrolidine-2-carboxylic acid (5-tert-butyl-1,3,4-thiadiazol-2-yl)-amide | 445 |
| (S)-5-Oxo-1-p-tolyl-pyrrolidine-2-carboxylic acid (3-tert-butyl-isoxazol-5-yl)-amide | 163.49 |
| (S)-1-(4-Ethyl-phenyl)-5-oxo-pyrrolidine-2-carboxylic acid (3-tert-butyl-isoxazol-5-yl)-amide | 173.02 |
| (S)-1-(4-Isopropyl-phenyl)-5-oxo-pyrrolidine-2-carboxylic acid (3-tert-butyl-isoxazol-5-yl)-amide | 159.4 |
| (S)-1-(4-Methoxy-phenyl)-5-oxo-pyrrolidine-2-carboxylic acid (3-tert-butyl-isoxazol-5-yl)-amide | 163.38 |
| (S)-5-Oxo-1-(4-trifluoromethoxy-phenyl)-pyrrolidine-2-carboxylic acid (3-tert-butyl-isoxazol-5-yl)-amide | 34.47 |

TABLE IV-continued

| Compound | CB2 CAMP @ EC50 nM (mean) |
|---|---|
| (S)-5-Oxo-1-(4-trifluoromethoxy-phenyl)-pyrrolidine-2-carboxylic acid (5-tert-butyl-isoxazol-3-yl)-amide | 132.11 |
| (S)-1-(4-Chloro-phenyl)-5-oxo-pyrrolidine-2-carboxylic acid (3-tert-butyl-phenyl)-amide | 58.65 |
| (S)-1-(4-Chloro-phenyl)-5-oxo-pyrrolidine-2-carboxylic acid (3-sec-butyl-isoxazol-5-yl)-amide | 103.95 |
| (S)-1-(4-Chloro-phenyl)-5-oxo-pyrrolidine-2-carboxylic acid (3-isopropyl-isoxazol-5-yl)-amide | 289.52 |
| (S)-1-(4-Chloro-phenyl)-5-oxo-pyrrolidine-2-carboxylic acid [3-(4-methoxy-phenyl)-1,2,4-thiadiazol-5-yl]-amide | 194.34 |
| (S)-1-(4-Chloro-phenyl)-5-oxo-pyrrolidine-2-carboxylic acid (3-tert-butyl-isothiazol-5-yl)-amide | 135.27 |
| (S)-1-(4-Chloro-phenyl)-5-oxo-pyrrolidine-2-carboxylic acid [3-(2-hydroxy-1,1-dimethyl-ethyl)-isoxazol-5-yl]-amide | 151.83 |
| (S)-l-(4-Chloro-phenyl)-5-oxo-pyrrolidine-2-carboxylic acid [5-(2-methoxy-1,1-dimethyl-ethyl)-isoxazol-3-yl]-amide | 86.13 |
| (S)-l-(4-Chloro-phenyl)-5-oxo-pyrrolidine-2-carboxylic acid [3-(2-methoxy-1,1-dimethyl-ethyl)-isoxazol-5-yl]-amide | 48.73 |
| (S)-1-(Tetrahydro-pyran-4-yl)-pyrrolidine-2-carboxylic acid (3-tert-butyl-1,2,4-thiadiazol-5-yl)-amide | 104.57 |
| (S)-1-(4-Chloro-phenyl)-pyrrolidine-2-carboxylic acid [3-(2-hydroxy-1,1-dimethyl-ethyl)-isoxazol-5-yl]-amide | 0.378 |
| (S)-1-(3-Chloro-phenyl)-5-oxo-pyrrolidine-2-carboxylic acid (3-tert-butyl-isoxazol-5-yl)-amide | 203 |
| (S)-1-(3-Chloro-phenyl)-5-oxo-pyrrolidine-2-carboxylic acid (5-tert-butyl-isoxazol-3-yl)-amide | 296.11 |
| (S)-1-(2,3-Difluoro-phenyl)-5-oxo-pyrrolidine-2-carboxylic acid (3-tert-butyl-isoxazol-5-yl)-amide | 260.94 |
| (S)-1-(3,4-Dichloro-phenyl)-5-oxo-pyrrolidine-2-carboxylic acid (3-tert-butyl-isoxazol-5-yl)-amide | 16.07 |
| (S)-1-(3,4-Dichloro-phenyl)-5-oxo-pyrrolidine-2-carboxylic acid (5-tert-butyl-isoxazol-3-yl)-amide | 49.72 |
| (S)-1-(3-Chloro-4-fluoro-phenyl)-5-oxo-pyrrolidine-2-carboxylic acid (3-tert-butyl-isoxazol-5-yl)-amide | 26.68 |
| (S)-1-(3-Chloro-4-fluoro-phenyl)-5-oxo-pyrrolidine-2-carboxylic acid (5-tert-butyl-isoxazol-3-yl)-amide | 59.32 |
| (S)-1-(6-Fluoro-5-trifluoromethyl-pyridin-2-yl)-5-oxo-pyrrolidine-2-carboxylic acid (3-tert-butyl-isoxazol-5-yl)-amide | 8.05 |
| (S)-1-(3-Fluoro-phenyl)-5-oxo-pyrrolidine-2-carboxylic acid (3-tert-butyl-isoxazol-5-yl)-amide | 356.69 |
| (S)-5-Oxo-1-(4-vinyl-phenyl)-pyrrolidine-2-carboxylic acid (3-tert-butyl-isoxazol-5-yl)-amide | 20.33 |
| (S)-5-Oxo-1-(4-vinyl-phenyl)-pyrrolidine-2-carboxylic acid (5-tert-butyl-isoxazol-3-yl)-amide | 69.98 |
| (S)-1-(4-Chloro-3-fluoro-phenyl)-5-oxo-pyrrolidine-2-carboxylic acid (5-tert-butyl-isoxazol-3-yl)-amide | 12.72 |
| (S)-1-(4-Chloro-3-fluoro-phenyl)-5-oxo-pyrrolidine-2-carboxylic acid (3-tert-butyl-isoxazol-5-yl)-amide | 14.2 |
| (S)-1-(4-Chloro-3-methyl-phenyl)-5-oxo-pyrrolidine-2-carboxylic acid (3-tert-butyl-isoxazol-5-yl)-amide | 23.73 |
| (S)-1-(4-Chloro-3-methyl-phenyl)-5-oxo-pyrrolidine-2-carboxylic acid (5-tert-butyl-isoxazol-3-yl)-amide | 59.37 |
| (S)-1-(3-Fluoro-4-methoxy-phenyl)-5-oxo-pyrrolidine-2-carboxylic acid (3-tert-butyl-isoxazol-5-yl)-amide | 314.2 |
| (S)-1-(4-Cyano-3-fluoro-phenyl)-5-oxo-pyrrolidine-2-carboxylic acid (3-tert-butyl-isoxazol-5-yl)-amide | 285.71 |
| (S)-1-(4-Cyano-3-fluoro-phenyl)-5-oxo-pyrrolidine-2-carboxylic acid (5-tert-butyl-isoxazol-3-yl)-amide | 78.49 |
| (S)-l-(3-Chloro-4-methyl-phenyl)-5-oxo-pyrrolidine-2-carboxylic acid (3-tert-butyl-isoxazol-5-yl)-amide | 77.44 |
| (S)-l-(3-Chloro-4-methyl-phenyl)-5-oxo-pyrrolidine-2-carboxylic acid (5-tert-butyl-isoxazol-3-yl)-amide | 333.17 |
| (S)-1-(4-Difluoromethyl-phenyl)-5-oxo-pyrrolidine-2-carboxylic acid (3-tert-butyl-isoxazol-5-yl)-amide | 15.21 |
| (2S,4R)-1-(4-Chloro-phenyl)-4-hydroxy-pyrrolidine-2-carboxylic acid [3-(2-hydroxy-1,1-dimethyl-ethyl)-isoxazol-5-yl]-amide | 196.19 |
| (2S,4R)-1-(4-Chloro-phenyl)-4-hydroxy-pyrrolidine-2-carboxylic acid [5-(2-methoxy-1,1-dimethyl-ethyl)-isoxazol-3-yl]-amide | 80.92 |
| (2S,4R)-1-(4-Chloro-phenyl)-4-hydroxy-pyrrolidine-2-carboxylic acid [3-(2-methoxy-1,1-dimethyl-ethyl)-isoxazol-5-yl]-amide | 87.03 |
| (S)-1-(3,4-Difluoro-phenyl)-5-oxo-pyrrolidine-2-carboxylic acid (3-tert-butyl-isoxazol-5-yl)-amide | 15.99 |

TABLE IV-continued

| Compound | CB2 CAMP @ EC50 nM (mean) |
|---|---|
| (S)-1-(3,4-Difluoro-phenyl)-5-oxo-pyrrolidine-2-carboxylic acid (5-tert-butyl-isoxazol-3-yl)-amide | 64.18 |
| (S)-1-(4-Fluoro-3-methyl-phenyl)-5-oxo-pyrrolidine-2-carboxylic acid (3-tert-butyl-isoxazol-5-yl)-amide | 91.17 |
| (S)-1-(4-Fluoro-3-methyl-phenyl)-5-oxo-pyrrolidine-2-carboxylic acid (5-tert-butyl-isoxazol-3-yl)-amide | 361.96 |
| (S)-5-Oxo-1-(3,4,5-trifluoro-phenyl)-pyrrolidine-2-carboxylic acid (3-tert-butyl-isoxazol-5-yl)-amide | 80.02 |
| (S)-5-Oxo-1-(3,4,5-trifluoro-phenyl)-pyrrolidine-2-carboxylic acid (5-tert-butyl-isoxazol-3-yl)-amide | 74.74 |
| (S)-5-Oxo-1-(4-trifluoromethyl-phenyl)-pyrrolidine-2-carboxylic acid [3-(2-hydroxy-1,1-dimethyl-ethyl)-isoxazol-5-yl]-amide | 37.68 |
| (S)-1-(4-Fluoromethyl-phenyl)-5-oxo-pyrrolidine-2-carboxylic acid (3-tert-butyl-isoxazol-5-yl)-amide | 55.82 |
| (S)-5-Oxo-1-(4-trifluoromethyl-phenyl)-pyrrolidine-2-carboxylic acid (3-sec-butyl-isoxazol-5-yl)-amide | 40.9 |
| (S)-5-Oxo-1-(4-trifluoromethyl-phenyl)-pyrrolidine-2-carboxylic acid (3-isopropyl-isoxazol-5-yl)-amide | 41.85 |
| (S)-5-Oxo-1-(4-trifluoromethyl-phenyl)-pyrrolidine-2-carboxylic acid [3-(2-methoxy-1,1-dimethyl-ethyl)-isoxazol-5-yl]-amide | 11.92 |
| (S)-5-Oxo-1-(4-trifluoromethyl-phenyl)-pyrrolidine-2-carboxylic acid [5-(2-methoxy-1,1-dimethyl-ethyl)-isoxazol-3-yl]-amide | 15.24 |
| (S)-5-Oxo-1-(4-trifluoromethyl-phenyl)-pyrrolidine-2-carboxylic acid [3-(4-methoxy-phenyl)-1,2,4-thiadiazol-5-yl]-amide | 178.29 |
| (S)-5-Oxo-1-(4-trifluoromethyl-phenyl)-pyrrolidine-2-carboxylic acid (3-tert-butyl-isothiazol-5-yl)-amide | 112.47 |
| (S)-5-Oxo-1-(4-trifluoromethyl-phenyl)-pyrrolidine-2-carboxylic acid [5-(2-hydroxy-1,1-dimethyl-ethyl)-isoxazol-3-yl]-amide | 80.79 |
| (S)-1-(5-Chloro-pyridin-2-yl)-5-oxo-pyrrolidine-2-carboxylic acid (3-tert-butyl-isoxazol-5-yl)-amide | 3.44 |
| (S)-1-(5-Fluoro-pyridin-2-yl)-5-oxo-pyrrolidine-2-carboxylic acid (3-tert-butyl-isoxazol-5-yl)-amide | 8.15 |
| (S)-1-(5-Chloro-pyrimidin-2-yl)-5-oxo-pyrrolidine-2-carboxylic acid (3-tert-butyl-isoxazol-5-yl)-amide | 455.5 |
| 1-(5-Cyano-pyridin-2-yl)-5-oxo-pyrrolidine-2-carboxylic acid (3-tert-butyl-isoxazol-5-yl)-amide | 1.17 |
| (S)-5-Oxo-1-(5-trifluoromethyl-pyridin-2-yl)-pyrrolidine-2-carboxylic acid (3-tert-butyl-isoxazol-5-yl)-amide | 0.105 |
| (S)-5-Oxo-1-pyridin-2-yl-pyrrolidine-2-carboxylic acid (3-tert-butyl-isoxazol-5-yl)-amide | 135.95 |
| (S)-1-(5-Methyl-pyridin-2-yl)-5-oxo-pyrrolidine-2-carboxylic acid (3-tert-butyl-isoxazol-5-yl)-amide | 15.4 |
| (S)-1-(5-Methoxy-pyridin-2-yl)-5-oxo-pyrrolidine-2-carboxylic acid (3-tert-butyl-isoxazol-5-yl)-amide | 22.09 |
| (S)-1-(5-Fluoro-6-methyl-pyridin-2-yl)-5-oxo-pyrrolidine-2-carboxylic acid (3-tert-butyl-isoxazol-5-yl)-amide | 74.37 |
| (S)-1-(3-Fluoro-5-trifluoromethyl-pyridin-2-yl)-5-oxo-pyrrolidine-2-carboxylic acid (3-tert-butyl-isoxazol-5-yl)-amide | 5 |
| (S)-1-(tetrahydro-pyran-4-yl)-pyrrolidine-2-carboxylic acid [3-(2-hydroxy-1,1-dimethyl-ethyl)-isoxazol-5-yl]-amide | 50 |

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocyclic or cycloalkyl groups include hydrocarbon rings containing from three to twelve carbon atoms. These carbocyclic or cycloalkyl groups may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic or spirocyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N, O and S.

Unless otherwise stated, heterocycles and heteroaryl include but are not limited to, for example furanyl, pyranyl, benzoxazolyl, benzothiazolyl, benzimidazolyl, tetrahydropyranyl, dioxanyl, tetrahydrofuranyl, oxazolyl, isoxazolyl, oxadiazolyl, triazolyl, thiazolyl, pyrazolyl, pyrrolyl, imidazolyl, thienyl, thiadiazolyl, thiomorpholinyl, 1,1-dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, Dihydro-2H-quinolinyl, isoquinolinyl, quinazolinyl, indazolyl, thieno[2,3-d]pyrimidinyl, indolyl, isoindolyl, benzofuranyl, benzopyranyl and benzodioxolyl, or 2-aza-spiro[4.5]dec-2-yl, 1-aza-spiro[4.5]dec-1-yl, 1-aza-spiro[4.4]non-1-yl, 2-aza-spiro[4.4]non-2-yl, 2-aza-spiro[5.5]undec-2-yl, 1-aza-spiro[5.5]undec-1-yl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle as defined herein. Each aryl unless otherwise specified includes it's partially or fully hydrogenated derivative. For example, naphthyl may include its hydrogenated derivatives such as tetrahydranaphthyl. Other partially or fully hydrogenated derivatives of the aryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "alkyl" refers to a saturated aliphatic radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups. It should be understood that any combination term using an "alk" or "alkyl" prefix refers to analogs according to the above definition of "alkyl". For example, terms such as "alkoxy", "alkylhio" refer to alkyl groups linked to a second group via an oxygen or sulfur atom. "Alkanoyl" refers to an alkyl group linked to a carbonyl group (C=O).

The term "halogen" as used in the present specification shall be understood to mean bromine, chlorine, fluorine or iodine, preferably fluorine. The definitions "halogenated", "partially or fully halogenated"; partially or fully fluorinated; "substituted by one or more halogen atoms", includes for example, mono, di or tri halo derivatives on one or more carbon atoms. For alkyl, a nonlimiting example would be —CH$_2$CHF$_2$, —CF$_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of the invention. A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C$_1$-C$_4$ alkyl)$_4$$^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention may be made using the general synthetic methods described below, which also constitute part of the invention.

General Synthetic Methods

The invention also provides processes for making compounds of Formula (I), (II), (III) and (IV). In all Schemes, unless specified otherwise, R$_1$, R$_2$, R$_3$, L$_1$, L$_2$, X, Ar$_1$, Ar$_2$, A and B in the Formulas below shall have the meaning of R$_1$, R$_2$, R$_3$, L$_1$, L$_2$, X, Ar$_1$, Ar$_2$, A and B in Formula (I), (II), (III) and (IV) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the Schemes below, are either commercially available or easily prepared from commercially available materials by those skilled in the art.

Compounds of Formula (I and III) may be synthesized by methods outlined in scheme 1.

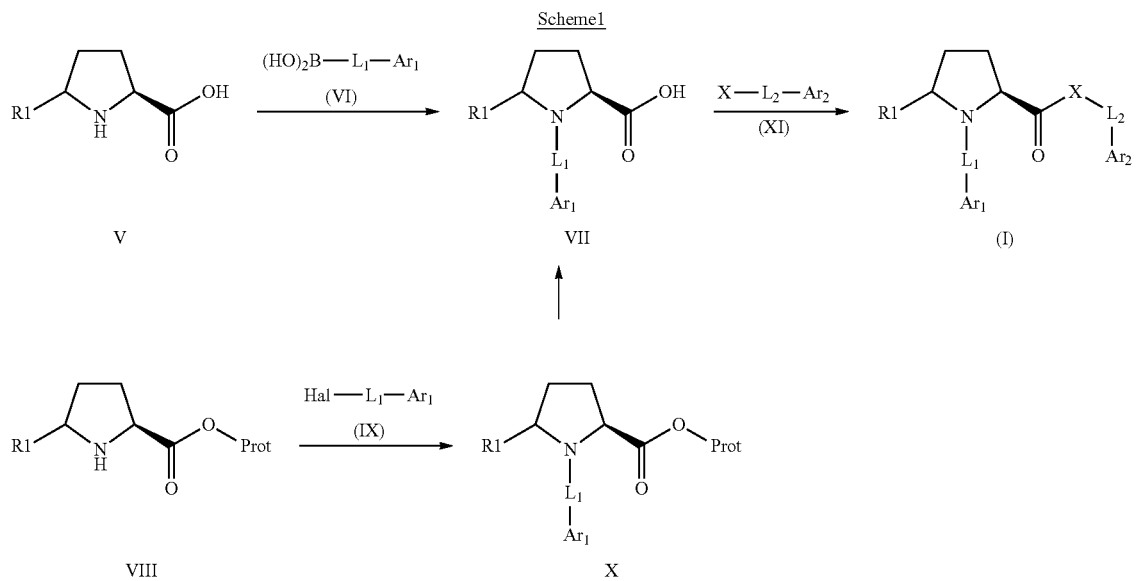

As illustrated in scheme 1, reaction of an appropriately substituted 2-oxoproline (V) with a boronic acid or ester of formula (VI), under standard arylation conditions as described in Step 1 of Example 16, provides an acid of formula (VII). Alternately, the intermediate of formula (VII) can be prepared via standard SNAr chemistry, as described in Step 1 of Example 20, by reacting a compound of formula (VIII) with a suitable halide Hal-L$_1$-Ar$_1$ (IX), wherein Hal=F, Cl, Br or I, in a suitable solvent, to afford ester of formula (X). Prot=acid protecting group, such as tert-butyl ester. Hyrolysis of the compound of formula (X) under standard conditions, such as in the presence of trifluoroacetic acid, provides an acid of formula (VII). Reaction of acid (VII) with an amine of formula (XII), wherein X=NH or NH$_2$, under standard coupling conditions as described in coupling methods A-J of example 1, provides a compound of Formula (I).

Compounds of Formula (III) may also be prepared by scheme 1 by using the appropriately substituted oxo-proline starting material (V).

Compounds of Formula (II and IV) may be synthesized by methods outlined in schemes 2 and 3.

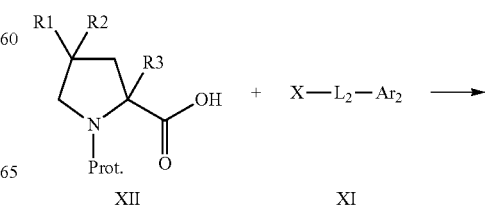

Scheme 2

201
-continued

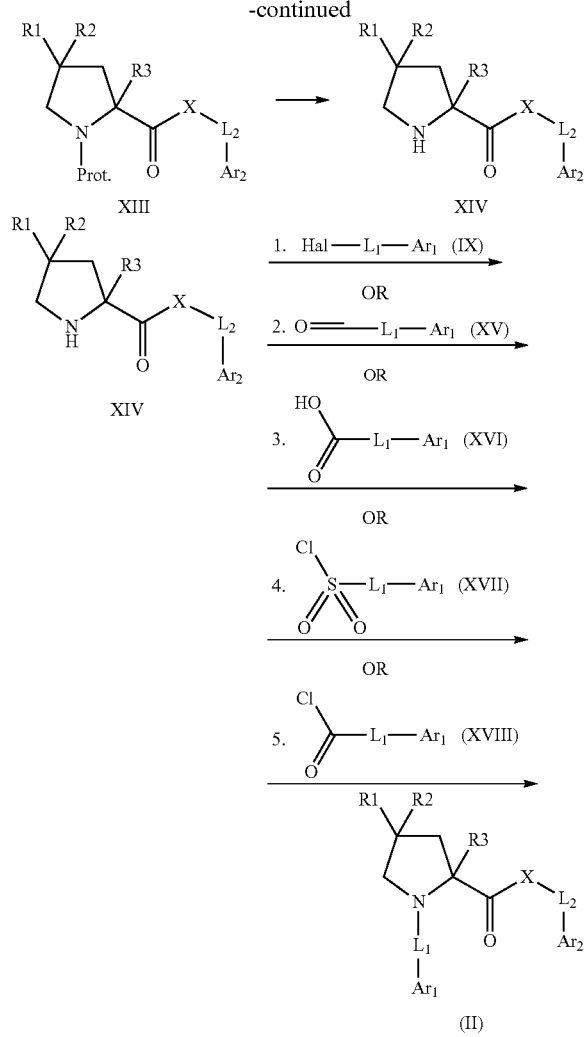

202

Compounds of Formula (II and IV) may be prepared according to scheme 3.

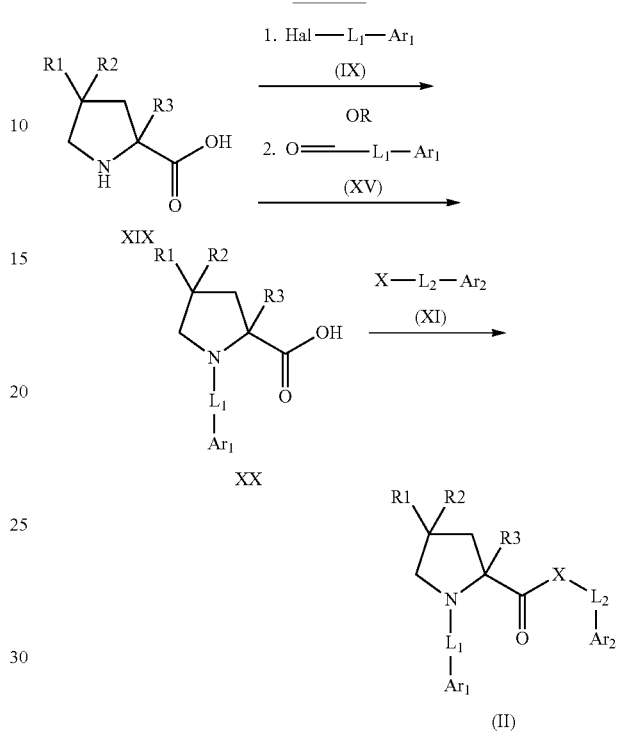

As illustrated in scheme 2, reaction of an appropriately substituted proline (XII) with an amine of formula (XI), wherein X=NH or NH$_2$, under standard coupling conditions and as described in coupling methods A-J of example 1, provides an amide of formula (XIII). Prot.=amine protecting group, such as BOC. Reaction of the intermediate (XIII) with an acid such as hydrochloric acid, in a suitable solvent, provides the deprotected amine intermediate (XIV). Reaction of the intermediate (XIV) with a suitable halide Hal-L$_1$-Ar$_1$ (IX), wherein Hal=F, Cl, Br or I, in a suitable solvent, provides a compound of Formula (II). Intermediate (XIV) may also be reacted with a carbonyl compound of formula (XV) under reductive amination conditions, to provide a compound of Formula (II). Reaction of the intermediate (XIV) with an acid of formula (XVI) under standard coupling conditions, provides a compound of Formula (II). Reaction of intermediate (XIV) with a sulfonyl chloride compound of formula (XVII) under standard sulfonylation conditions provides a compound of Formula (II). Alternately, reaction of the intermediate (XIV) with a carbonyl chloride of formula (XVIII) under standard acylation conditions, provides a compound of formula (II).

Compounds of Formula (IV) may also be prepared by scheme 2 by using the appropriately substituted proline starting material (XII).

As outlined in scheme 3, reaction of the proline starting material of formula (XIX) with a suitable halide Hal-L$_1$-Ar$_1$ (IX), wherein Hal=F, Cl, Br or I, in a suitable solvent, provides a compound of formula (XX). Compound of formula (XIX) may also be reacted with a carbonyl compound of formula (XV) under reductive amination conditions, to provide an intermediate compound of formula (XX).

Reaction of intermediate (XX) with an amine of formula (XI), wherein X=NH or NH$_2$, under standard coupling conditions and as described in coupling methods A-J of example 1, provides a compound of Formula (II).

Compounds of Formula (IV) may also be prepared by scheme 3 by using the appropriately substituted proline starting material (XIX).

Further modification of the initial product of Formula (I), (II), (III) and, (IV) by methods known to one skilled in the art and illustrated in the examples below, provides additional compounds of this invention.

EXAMPLE 1

Synthesis of 1-(3-chloro-5-trifluoromethyl-pyridin-2-yl)-pyrrolidine-2-carboxylic acid (5-tert-butyl-isoxazol-3-yl)-amide

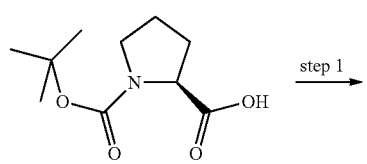

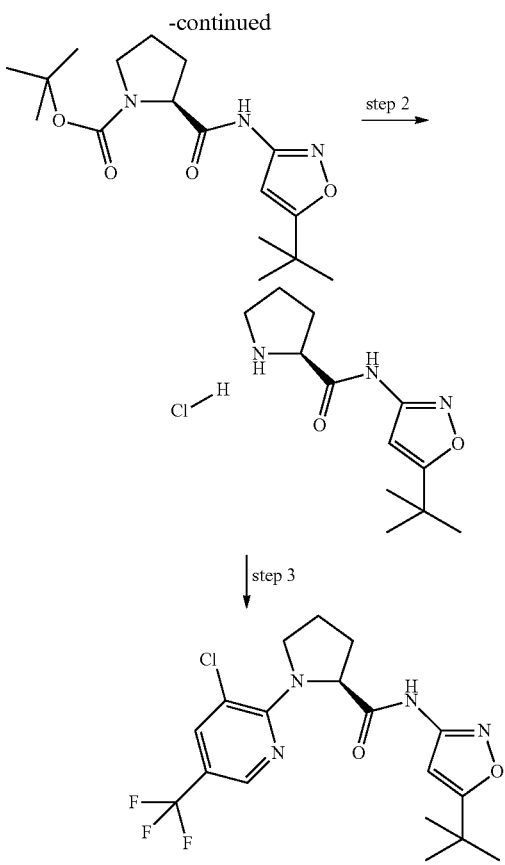

Step 1: Synthesis of (S)-2-(5-tert-butyl-isoxazol-3-ylcarbamoyl)-pyrrolidine-1-carboxylic acid tert-butyl ester Coupling Method A:

To a slurry of N-(tert-butoxycarbonyl)-L-proline (0.5 g; 2.323 mmol) and 3-amino-5-tert-butylisoxazole (0.228 g; 1.626 mmol) in pyridine (9.3 mL; 2.323 mmol) at 0° C. is added phosphorous oxychloride (0.213 mL; 2.323 mmol). The mixture is stirred at 0° C. for 30 minutes and then diluted with water and extracted with ethyl acetate several times. The organics are combined and washed with water and brine, dried (Na$_2$SO$_4$), filtered and concentrated in vacuo to provide the title compound. ESI m/z 338 [M+H]+

While this represents one method of amide bond coupling, several others were used. The following are general coupling methods used to make intermediates.

Coupling Method B:

To a solution of acid (0.5 g; 2.323 mmol) in acetonitrile (2 mL) is added amine (0.377 g, 2.323 mmol), and N,N-diisopropyethylamine (0.809 mL; 4.646 mmol). O-(7-azabenzotriazol-1-yl)-N,N,N',N'-tetramethyluronium hexafluorophosphate (0.516 g; 2.788 mmol) is added and the mixture is heated at 150° C. for 45 minutes in a microwave reactor. The mixture is concentrated followed by dilution with ethyl acetate and subsequent washings with aqueous saturated sodium bicarbonate solution, 1N hydrochloric acid, and brine. The crude material is purified using flash chromatography and a methanol:dichloromethane gradient of 0-20% over 16 column volumes. Product fractions were combined and concentrated to afford intermediate. ESI m/z 360 [M+H]+

Coupling Method C:

Acid (0.5 g; 2.323 mmol) is dissolved in tetrahydrofuran (2 mL) and cooled to −10° C. 4-Methyl morpholine (0.306 mL; 2.788 mmol) is added followed by isobutylchloroformate (0.452 mL; 3.485 mmol). The mixture is stirred for 30 minutes at low temperature after which amine (0.427 g; 2.788 mmol) is added and the mixture is stirred overnight at room temperature. After this time, the mixture is diluted with ethyl acetate and washed with 1N hydrochloric acid, aqueous saturated sodium bicarbonate, and brine. The organic layer is then dried (Na$_2$SO$_4$), filtered and concentrated in vacuo to afford crude material which is purified by flash chromatography to afford intermediate. ESI m/z 351 [M+H]+

Coupling Method D:

A solution containing amine (0.726 g; 4.646 mmol) and acid (1 g; 4.646 mmol) in dichloromethane (10 mL) and N,N-diisopropylamine (2.428 mL; 13.938 mmol) is cooled to 0° C. and chlorotripyrrolidinophosphonijum hexafluorophosphate (1.959 g; 4.646 mmol) is added. The reaction mixture is slowly warmed to room temperature and stirred overnight. After this time, the mixture is concentrated and purified by flash chromatography. Product fractions are pooled and concentrated in vacuo to afford intermediate. ESI m/z 354 [M+H]+

Coupling Method E:

To a stirred solution of acid in 1,2-dichlorethane at ambient temperature N,N-diisopropylethylamine, 2-chloro-1-methylpyridinium iodide, and amine is added. The reaction mixture is heated at 80° C. in an oil bath for 90 minutes. After this time, the reaction mixture is cooled and diluted with dichloromethane. The solution is washed with aqueous sodium bicarbonate solution, 1N sulfuric acid and brine solution. The extracts are combined, dried (Na$_2$SO$_4$), filtered and concentrated in vacuo to afford intermediate. ESI m/z 339 [M+H]+

Coupling Method F:

2-Ethoxy-1-ethoxycarbonyl-1,2-dihydroquinoline (1.604 g; 6.486 mmol) is added to a solution of amine (0.606 g; 4.324 mmol) and acid (1 g; 4.324 mmol) in toluene (20 mL) at room temperature and the mixture is stirred 48 hours. After this time, the mixture is concentrated in vacuo and purified by flash chromatography using an ethyl acetate:hexanes gradient. Product fractions were pooled and concentrated in vacuo to afford intermediate. ESI m/z 354 [M=H]+

Coupling Method G:

Same as coupling method D except bromotripyrrolidinophosphonium hexafluorophosphate is used as a coupling reagent.

Coupling Method H:

A round bottomed flask is equipped with a stir bar and charged with acid (0.5 g; 2.162 mmol) and a chip of dimethylaminopyridine. The flask is placed under an inert atmosphere of argon. Methylene chloride (6 mL) and pyridine (0.367 mL; 4.54 mmol) are added to the flask followed by dropwise addition of chlorotrimethylsilane (0.576 mL; 4.54 mmol). The reaction is stirred for 3 hours at room temperature after which time it is cooled to 0° C. and 2-3 drops of dimethylformamide are added followed by oxalyl chloride (0.189 mL; 2.162 mmol). The reaction is stirred for an hour at 0° C., warmed to room temperature for 30 minutes and cooled to 0° C. before added in aniline (0.333 g; 2.378 mmol) in pyridine (0.577 mL; 7.135 mmol). The mixture is stirred overnight at ambient temperature. After this time, citric acid (0.457 g; 2.378 mmoL) in methanol (4.3 mL) is added and the mixture is stirred 2 hours, diluted with ethyl acetate and washed with 1N hydrochloric acid. The aqueous layer is extracted with ethyl acetate and organics are combined. The combined organics are washed with aqueous saturated sodium bicarbonate solution and brine, dried (Na$_2$SO$_4$), filtered and concentrated. The crude material is purified by flash chromatography, eluting with ethyl acetate to obtain final compound as intermediate. ESI m/z 354 [M+H]+

Coupling Method I:

To a solution of the amine (0.30 mmol) and acid (45.1 mg, 0.20 mmol) in dichloromethane (200 μL) at room temperature is added diisopropylethylamine (139 μL, 0.80 mmol) and a 0.75 M solution of bromotripyrrolidinophosphonium hexafluororphosphate in dichloromethane (400 μL, 0.30 mmol). The reaction is shaken for 16 h. To the reaction solution at room temperature is added diisopropylethylamine (52 μL, 0.30 mmol) and a 0.75 M solution of bromotripyrrolidinophosphonium hexafluororphosphate in dichloromethane (400 μL, 0.30 mmol). The reaction is shaken for 16 h. The reaction is concentrated under reduced pressure. Purification by preparative HPLC provides the desired compound.

Coupling Method J:

To a solution of acid (200 mg, 0.862 mmol) and 1-hydroxybenzotriazole hydrate (176 mg, 1.3 mmol) in N,N-dimethylformamide (2 mL) at room temperature is added 1-(3-dimethylaminopropyl)-3-ethylcarbodiimide hydrochloride (249 mg, 1.3 mmol). The reaction mixture is stirred at room temperature for 20 minutes before adding amine (0.11 mL, 0.865 mmol) and 4-dimethylaminopyridine (4.2 mg, 0.035 mmol). The reaction is stirred for 30 minutes and diluted with water and ethyl acetate. The organic layer is washed with saturated sodium bicarbonate aqueous solution, saturated ammonium chloride aqueous solution and brine, dried (Na$_2$SO$_4$), filtered and concentrated to yield intermediate.

Amide intermediates and the coupling method to synthesize them are found in Table 1.

TABLE 1

| Structure | Name | ESI m/z (+) | Coupling Method |
|---|---|---|---|
| 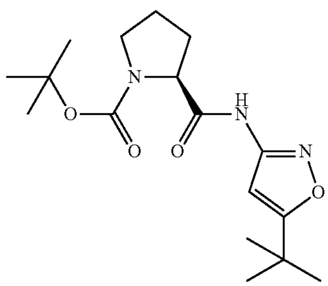 [SMILES: CC(C)(C)OC(=O)N1CCC[C@H]1C(=O)Nc1cc(C(C)(C)C)on1] | (S)-2-(5-tert-Butyl-isoxazol-3-ylcarbamoyl)-pyrrolidine-1-carboxylic acid tert-butyl ester | 338 | A and E |
| 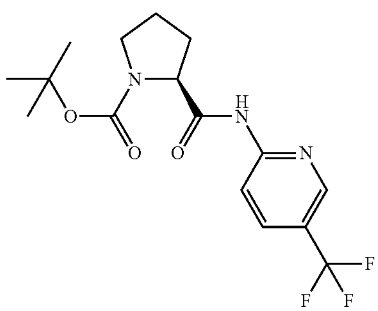 [SMILES: CC(C)(C)OC(=O)N1CCC[C@H]1C(=O)Nc1ccc(C(F)(F)F)cn1] | (S)-2-(5-Trifluoromethyl-pyridin-2-ylcarbamoyl)-pyrrolidine-1-carboxylic acid tert-butyl ester | 360 | B |
| 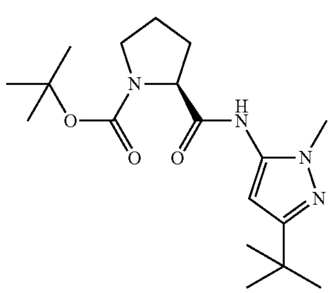 [SMILES: Cn1nc(C(C)(C)C)cc1NC(=O)[C@@H]1CCCN1C(=O)OC(C)(C)C] | (S)-2-(5-tert-Butyl-2-methyl-2H-pyrazol-3-ylcarbamoyl)-pyrrolidine-1-carboxylic acid tert-butyl ester | | C |

TABLE 1-continued

| Structure | Name | ESI m/z (+) | Coupling Method |
|---|---|---|---|
| 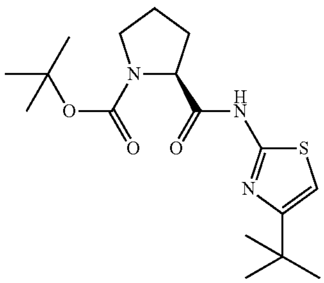 [SMILES: CC(C)(C)OC(=O)N1CCC[C@H]1C(=O)Nc1nc(C(C)(C)C)cs1] | (S)-2-(4-tert-Butyl-thiazol-2-ylcarbamoyl)-pyrrolidine-1-carboxylic acid tert-butyl ester | 354 | D |
| 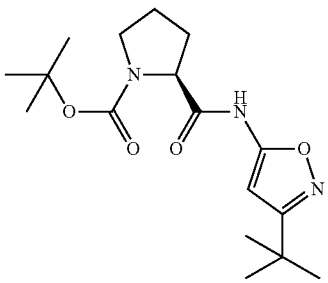 [SMILES: CC(C)(C)OC(=O)N1CCC[C@H]1C(=O)Nc1cc(C(C)(C)C)no1] | (S)-2-(3-tert-Butyl-isoxazol-5-ylcarbamoyl)-pyrrolidine-1-carboxylic acid tert-butyl ester | 338 | D |
| 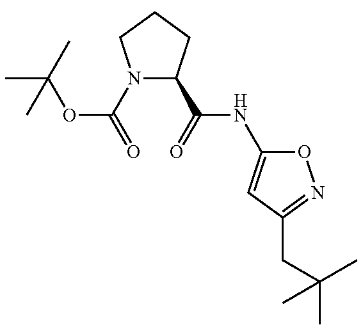 [SMILES: CC(C)(C)Cc1cc(NC(=O)[C@@H]2CCCN2C(=O)OC(C)(C)C)on1] | (S)-2-[3-(2,2-Dimethyl-propyl)-isoxazol-5-ylcarbamoyl]-pyrrolidine-1-carboxylic acid tert-butyl ester | 352 | D |
| 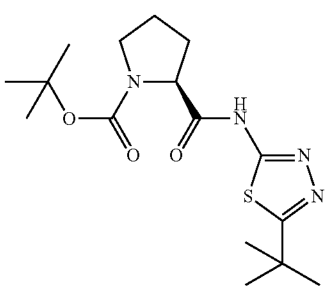 [SMILES: CC(C)(C)OC(=O)N1CCC[C@H]1C(=O)Nc1nnc(C(C)(C)C)s1] | (S)-2-(5-tert-Butyl-1,3,4-thiadiazol-2-ylcarbamoyl)-pyrrolidine-1-carboxylic acid tert-butyl ester | 355 | D |
| 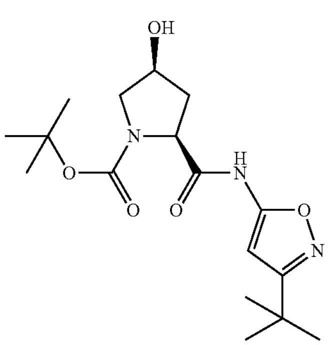 [SMILES: CC(C)(C)OC(=O)N1C[C@@H](O)C[C@H]1C(=O)Nc1cc(C(C)(C)C)no1] | (2S,4S)-2-(3-tert-Butyl-isoxazol-5-ylcarbamoyl)-4-hydroxy-pyrrolidine-1-carboxylic acid tert-butyl ester | 354 | F and H |

TABLE 1-continued

| Structure | Name | ESI m/z (+) | Coupling Method |
|---|---|---|---|
| 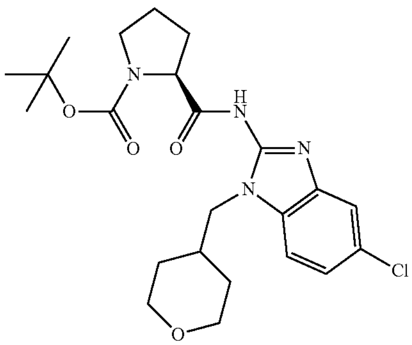 [SMILES: CC(C)(C)OC(=O)N1CCC[C@H]1C(=O)Nc1nc2cc(Cl)ccc2n1CC1CCOCC1] | (S)-2-[5-Chloro-1-(tetrahydro-pyran-4-ylmethyl)-1H-benzimidazol-2-ylcarbamoyl]-pyrrolidine-1-carboxylic acid tert-butyl ester | 463 | G |
| 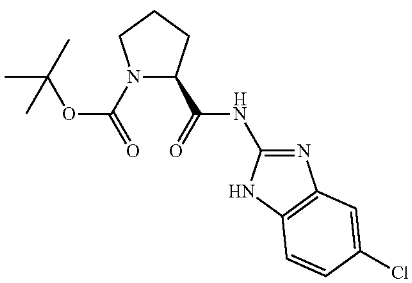 [SMILES: CC(C)(C)OC(=O)N1CCC[C@H]1C(=O)Nc1nc2cc(Cl)ccc2[nH]1] | (S)-2-(5-Chloro-1H-benzimidazol-2-ylcarbamoyl)-pyrrolidine-1-carboxylic acid tert-butyl ester | 365 | D |
| 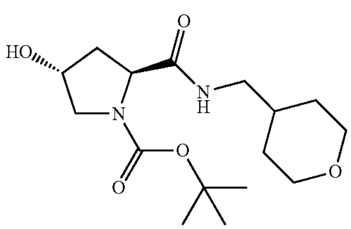 [SMILES: CC(C)(C)OC(=O)N1C[C@H](O)C[C@H]1C(=O)NCC1CCCCC1] | (2S,4R)-4-Hydroxy-2-[(tetrahydro-pyran-4-ylmethyl)-carbamoyl]-pyrrolidine-1-carboxylic acid tert-butyl ester | 329 | J |
| 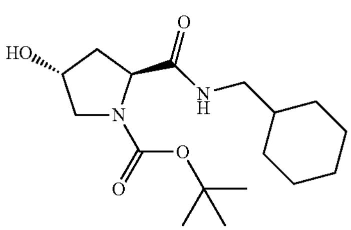 | (2S,4R)-2-(Cyclohexylmethyl-carbamoyl)-4-hydroxy-pyrrolidine-1-carboxylic acid tert-butyl ester | 327 | J |
| 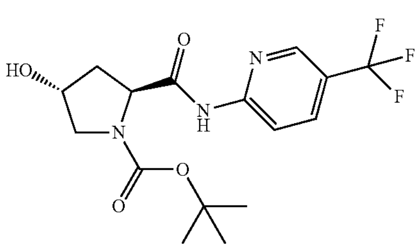 [SMILES: CC(C)(C)OC(=O)N1C[C@H](O)C[C@H]1C(=O)Nc1ccc(C(F)(F)F)cn1] | (2S,4R)-4-Hydroxy-2-(5-trifluoromethyl-pyridin-2-ylcarbamoyl)-pyrrolidine-1-carboxylic acid tert-butyl ester | 376 | F |

TABLE 1-continued

| Structure | Name | ESI m/z (+) | Coupling Method |
|---|---|---|---|
| 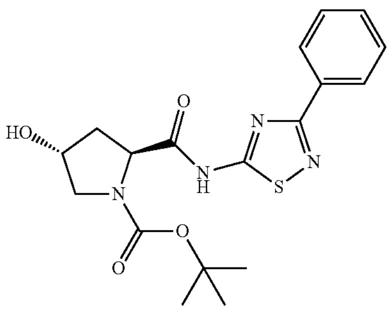 [SMILES: CC(C)(C)OC(=O)N1C[C@H](O)C[C@H]1C(=O)Nc1nc(-c2ccccc2)ns1] | (2S,4R)-4-Hydroxy-2-(3-phenyl-1,2,4-thiadiazol-5-ylcarbamoyl)-pyrrolidine-1-carboxylic acid tert-butyl ester | 391 | F |
| 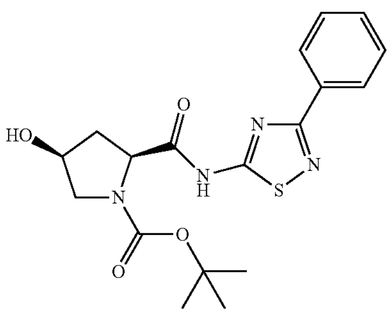 [SMILES: CC(C)(C)OC(=O)N1C[C@@H](O)C[C@H]1C(=O)Nc1nc(-c2ccccc2)ns1] | (2S,4S)-4-Hydroxy-2-(3-phenyl-1,2,4-thiadiazol-5-ylcarbamoyl)-pyrrolidine-1-carboxylic acid tert-butyl ester | 391 | F |
| 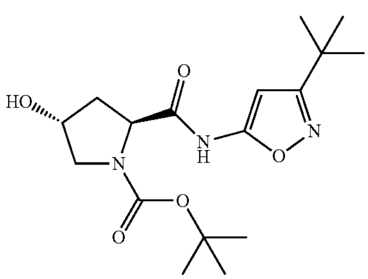 [SMILES: CC(C)(C)OC(=O)N1C[C@H](O)C[C@H]1C(=O)Nc1cc(C(C)(C)C)no1] | (2S,4R)-2-(3-tert-Butyl-isoxazol-5-ylcarbamoyl)-4-hydroxy-pyrrolidine-1-carboxylic acid tert-butyl ester | 354 | F |
| 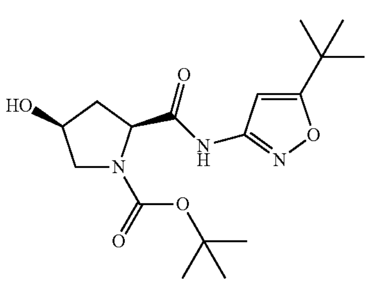 [SMILES: CC(C)(C)OC(=O)N1C[C@@H](O)C[C@H]1C(=O)Nc1cc(C(C)(C)C)on1] | (2S,4S)-2-(5-tert-Butyl-isoxazol-3-ylcarbamoyl)-4-hydroxy-pyrrolidine-1-carboxylic acid tert-butyl ester | 354 | F |

TABLE 1-continued

| Structure | Name | ESI m/z (+) | Coupling Method |
|---|---|---|---|
| 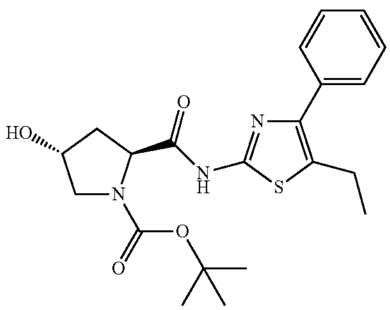 [SMILES: CCc1sc(NC(=O)[C@@H]2C[C@@H](O)CN2C(=O)OC(C)(C)C)nc1-c1ccccc1] | (2S,4R)-2-(5-Ethyl-4-phenyl-thiazol-2-ylcarbamoyl)-4-hydroxy-pyrrolidine-1-carboxylic acid tert-butyl ester | 418 | F |
| 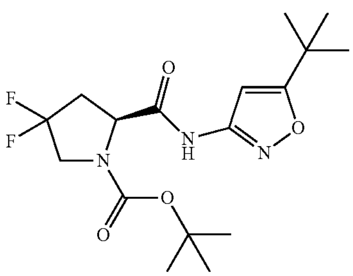 [SMILES: CC(C)(C)OC(=O)N1CC(F)(F)C[C@H]1C(=O)Nc1cc(C(C)(C)C)on1] | (S)-2-(5-tert-Butyl-isoxazol-3-ylcarbamoyl)-4,4-difluoro-pyrrolidine-1-carboxylic acid tert-butyl ester | 374 | F |
| 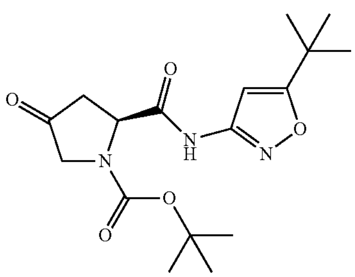 [SMILES: CC(C)(C)OC(=O)N1CC(=O)C[C@H]1C(=O)Nc1cc(C(C)(C)C)on1] | (S)-2-(5-tert-Butyl-isoxazol-3-ylcarbamoyl)-4-oxo-pyrrolidine-1-carboxylic acid tert-butyl ester | 352 | F |
| 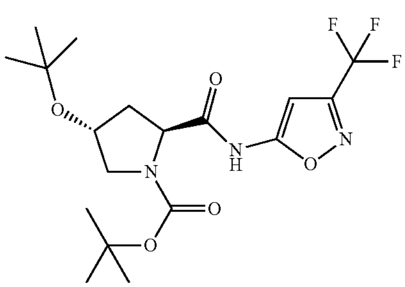 [SMILES: CC(C)(C)OC(=O)N1C[C@H](OC(C)(C)C)C[C@H]1C(=O)Nc1cc(C(F)(F)F)no1] | (2S,4R)-4-tert-Butoxy-2-(3-trifluoromethyl-isoxazol-5-ylcarbamoyl)-pyrrolidine-1-carboxylic acid tert-butyl ester | 322 [M − 100]H+ | A |
| 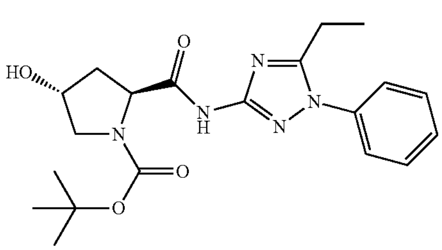 [SMILES: CCc1nc(NC(=O)[C@@H]2C[C@@H](O)CN2C(=O)OC(C)(C)C)nn1-c1ccccc1] | (2S,4R)-4-tert-Butoxy-2-(5-ethyl-1-phenyl-1H-1,2,4-triazol-3-ylcarbamoyl)-pyrrolidine-1-carboxylic acid tert-butyl ester | 458 | A |

TABLE 1-continued

| Structure | Name | ESI m/z (+) | Coupling Method |
|---|---|---|---|
| 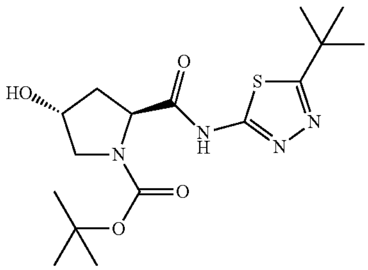 [SMILES: CC(C)(C)OC(=O)N1C[C@H](O)C[C@H]1C(=O)Nc1nnc(C(C)(C)C)s1] | (2S,4R)-4-tert-Butoxy-2-(5-tert-butyl-1,3,4-thiadiazol-2-ylcarbamoyl)-pyrrolidine-1-carboxylic acid tert-butyl ester | 427 | A |
| 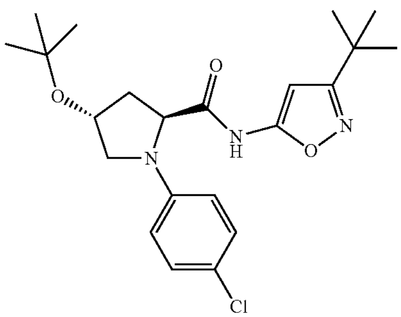 [SMILES: CC(C)(C)O[C@@H]1C[C@@H](C(=O)Nc2cc(C(C)(C)C)no2)N(c2ccc(Cl)cc2)C1] | (2S,4R)-4-tert-Butoxy-1-(4-chloro-phenyl)-pyrrolidine-2-carboxylic acid (3-tert-butyl-isoxazol-5-yl)-amide | 420 | A |
| 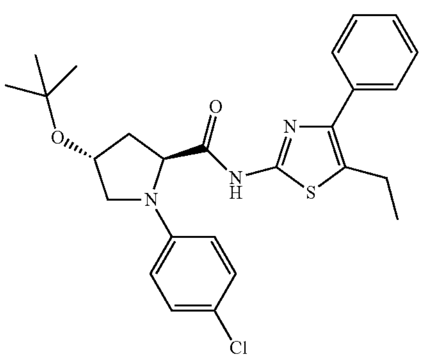 [SMILES: CCc1sc(NC(=O)[C@@H]2C[C@@H](OC(C)(C)C)CN2c2ccc(Cl)cc2)nc1-c1ccccc1] | (2S,4R)-4-tert-Butoxy-1-(4-chloro-phenyl)-pyrrolidine-2-carboxylic acid (5-ethyl-4-phenyl-thiazol-2-yl)-amide | 484 | A |
| 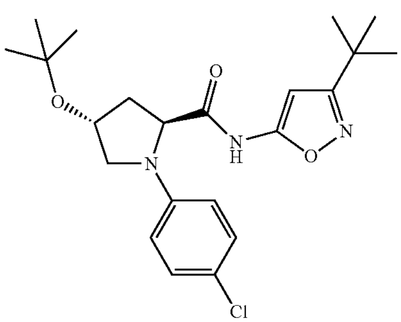 [SMILES: CC(C)(C)O[C@@H]1C[C@@H](C(=O)Nc2cc(C(C)(C)C)no2)N(c2ccc(Cl)cc2)C1] | (2S,4R)-4-tert-Butoxy-1-(4-chloro-phenyl)-pyrrolidine-2-carboxylic acid (5-tert-butyl-isoxazol-3-yl)-amide | 420 | A |

TABLE 1-continued

| Structure | Name | ESI m/z (+) | Coupling Method |
|---|---|---|---|
| 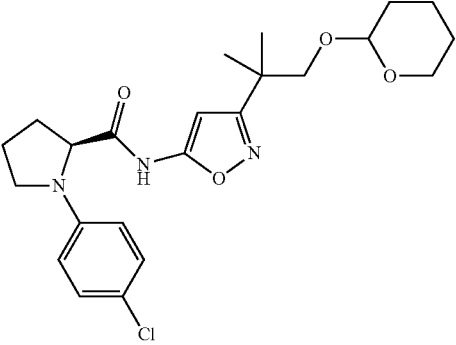 [SMILES: CC(C)(COC1CCCCO1)c1cc(NC(=O)[C@@H]2CCCN2c2ccc(Cl)cc2)on1] | (S)-1-(4-Chloro-phenyl)-pyrrolidine-2-carboxylic acid {3-[1,1-dimethyl-2-(tetrahydro-pyran-2-yloxy)-ethyl]-isoxazol-5-yl}-amide | 448 | A |
| 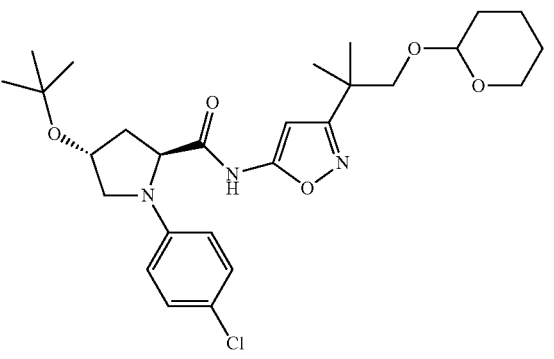 [SMILES: CC(C)(C)O[C@@H]1C[C@@H](C(=O)Nc2cc(C(C)(C)COC3CCCCO3)no2)N(c2ccc(Cl)cc2)C1] | (2S,4R)-4-tert-Butoxy-1-(4-chloro-phenyl)-pyrrolidine-2-carboxylic acid {3-[1,1-dimethyl-2-(tetrahydro-pyran-2-yloxy)-ethyl]-isoxazol-5-yl}-amide | 521 | A |
| 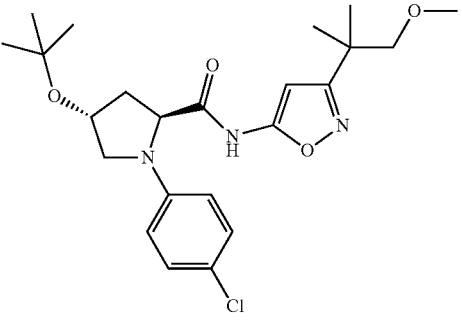 [SMILES: COCC(C)(C)c1cc(NC(=O)[C@@H]2C[C@@H](OC(C)(C)C)CN2c2ccc(Cl)cc2)on1] | (2S,4R)-4-tert-Butoxy-1-(4-chloro-phenyl)-pyrrolidine-2-carboxylic acid [3-(2-methoxy-1,1-dimethyl-ethyl)-isoxazol-5-yl]-amide | 450 | A |
| 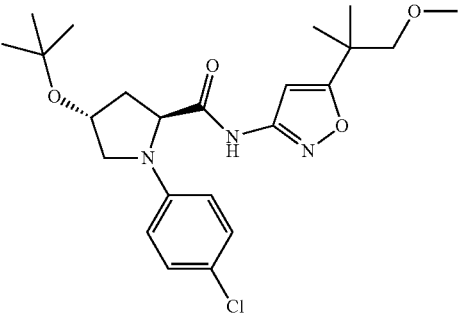 [SMILES: COCC(C)(C)c1cc(NC(=O)[C@@H]2C[C@@H](OC(C)(C)C)CN2c2ccc(Cl)cc2)no1] | (2S,4R)-4-tert-Butoxy-1-(4-chloro-phenyl)-pyrrolidine-2-carboxylic acid [5-(2-methoxy-1,1-dimethyl-ethyl)-isoxazol-3-yl]-amide | 450 | A |

Step 2: Synthesis of (S)-pyrrolidine-2-carboxylic acid (5-tert-butyl-isoxazol-3-yl)-amide; hydrochloride To a flask containing (S)-2-(5-tert-butyl-isoxazol-3-ylcarbamoyl)-pyrrolidine-1-carboxylic acid tert-butyl ester (1.626 mmol) is added 4N hydrochloride in dioxanes (8 mL; 32 mmol). The solution is stirred at room temperature for 4 h and concentrated in vacuo to afford title compound. ESI m/z 238 [M+H]+

Intermediates in Table 2 were also made in similar manner.

TABLE 2

| Structure | Name | ESI m/z (+) | ESI m/z (−) |
|---|---|---|---|
| 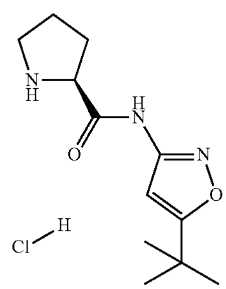 [SMILES: CC(C)(C)c1cc(NC(=O)[C@@H]2CCCN2)no1 ; Cl] | (S)-Pyrrolidine-2-carboxylic acid (5-tert-butyl-isoxazol-3-yl)-amide; hydrochloride |  |  |
| 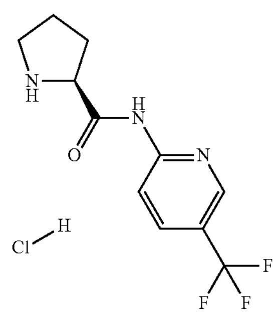 [SMILES: O=C(Nc1ccc(C(F)(F)F)cn1)[C@@H]1CCCN1 ; Cl] | (S)-Pyrrolidine-2-carboxylic acid (5-trifluoromethyl-pyridin-2-yl)-amide; hydrochloride |  |  |
| 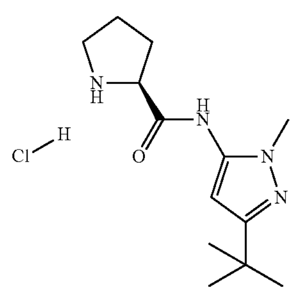 [SMILES: Cl ; Cn1nc(C(C)(C)C)cc1NC(=O)[C@@H]1CCCN1] | (S)-Pyrrolidine-2-carboxylic acid (5-tert-butyl-2-methyl-2H-pyrazol-3-yl)-amide; hydrochloride | 251 |  |
| 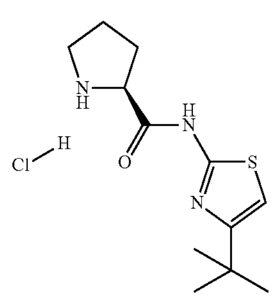 | (S)-Pyrrolidine-2-carboxylic acid (4-tert-butyl-thiazol-2-yl)-amide; hydrochloride | 254 |  |

TABLE 2-continued

| Structure | Name | ESI m/z (+) | ESI m/z (−) |
|---|---|---|---|
| 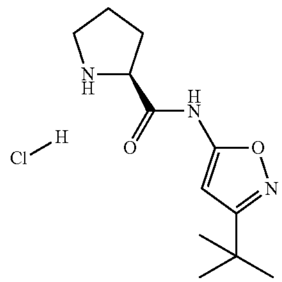 [SMILES: Cl ; CC(C)(C)c1cc(NC(=O)[C@@H]2CCCN2)on1] | (S)-Pyrrolidine-2-carboxylic acid (3-tert-butyl-isoxazol-5-yl)-amide; hydrochloride | 238 |  |
| 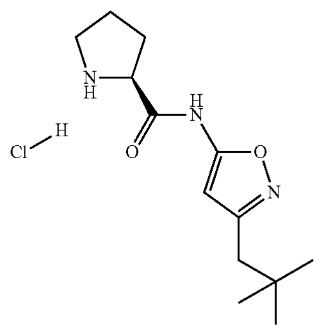 | (S)-Pyrrolidine-2-carboxylic acid [3-(2,2-dimethyl-propyl)-isoxazol-5-yl]-amide; hydrochloride | 252 |  |
| 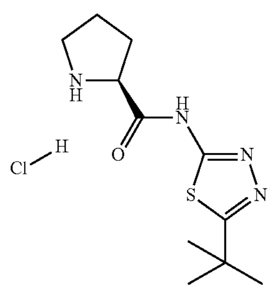 | (S)-Pyrrolidine-2-carboxylic acid (5-tert-butyl-1,3,4-thiadiazol-2-yl)-amide; hydrochloride | 255 |  |
| 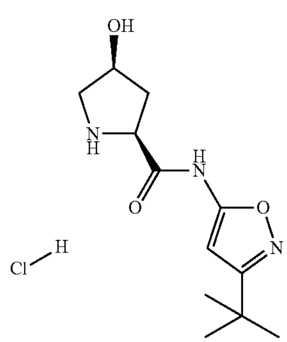 [SMILES: Cl ; CC(C)(C)c1cc(NC(=O)[C@@H]2C[C@H](O)CN2)on1] | (2S,4S)-4-Hydroxy-pyrrolidine-2-carboxylic acid (3-tert-butyl-isoxazol-5-yl)-amide; hydrochloride | 254 |  |

TABLE 2-continued

| Structure | Name | ESI m/z (+) | ESI m/z (−) |
|---|---|---|---|
| 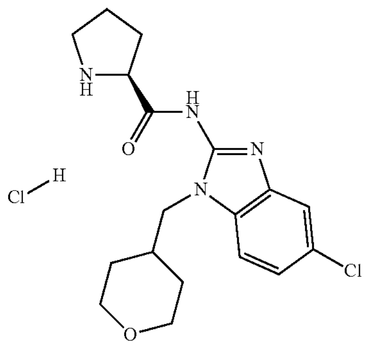 [SMILES: Cl ; O=C(Nc1nc2cc(Cl)ccc2n1CC1CCOCC1)[C@@H]1CCCN1] | (S)-Pyrrolidine-2-carboxylic acid [5-chloro-1-(tetrahydro-pyran-4-ylmethyl)-1H-benzimidazol-2-yl]-amide; hydrochloride | 363 | 361 |
| 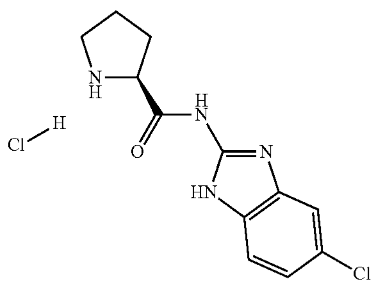 | (S)-Pyrrolidine-2-carboxylic acid (5-chloro-1H-benzimidazol-2-yl)-amide; hydrochloride | 265 | |
| 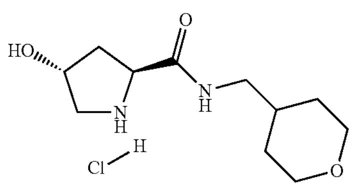 | (2S,4R)-4-Hydroxy-pyrrolidine-2-carboxylic acid (tetrahydro-pyran-4-ylmethyl)-amide; hydrochloride | 229 | |
| 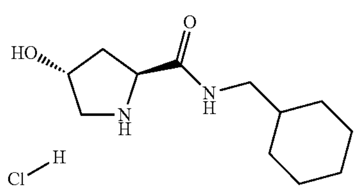 | (2S,4R)-4-Hydroxy-pyrrolidine-2-carboxylic acid cyclohexylmethyl-amide; hydrochloride | 227 | |
| 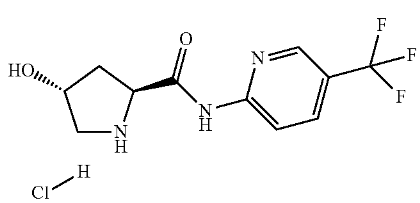 | (2S,4R)-4-Hydroxy-pyrrolidine-2-carboxylic acid (5-trifluoromethyl-pyridin-2-yl)-amide; hydrochloride | 376 | |
| 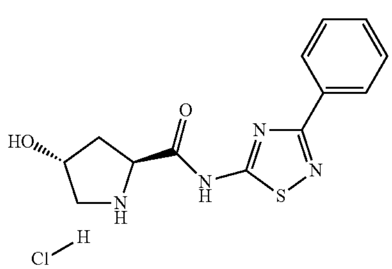 | (2S,4R)-4-Hydroxy-pyrrolidine-2-carboxylic acid (3-phenyl-1,2,4-thiadiazol-5-yl)-amide; hydrochloride | 391 | |

TABLE 2-continued

| Structure | Name | ESI m/z (+) | ESI m/z (−) |
|---|---|---|---|
| 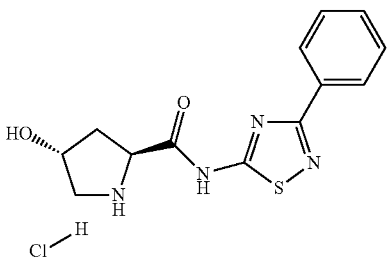 | (2S,4S)-4-Hydroxy-pyrrolidine-2-carboxylic acid (3-phenyl-1,2,4-thiadiazol-5-yl)-amide; hydrochloride | 391 | |
| 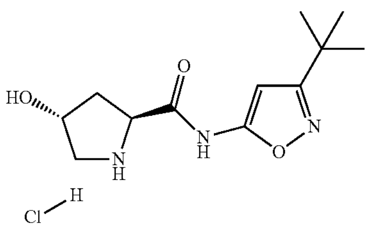 | (2S,4R)-4-Hydroxy-pyrrolidine-2-carboxylic acid (3-tert-butyl-isoxazol-5-yl)-amide; hydrochloride | 354 | |
| 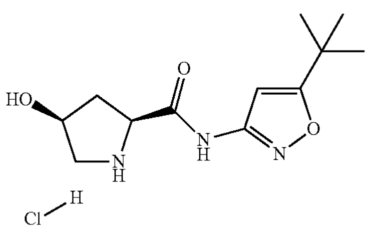 | (2S,4S)-4-Hydroxy-pyrrolidine-2-carboxylic acid (5-tert-butyl-isoxazol-3-yl)-amide; hydrochloride | 354 | |
| 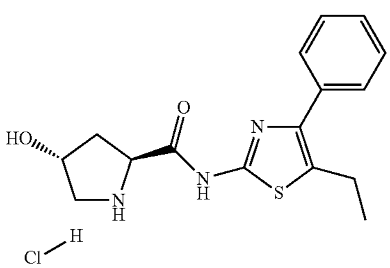 | (2S,4R)-4-Hydroxy-pyrrolidine-2-carboxylic acid (5-ethyl-4-phenyl-thiazol-2-yl)-amide; hydrochloride | 418 | |
| 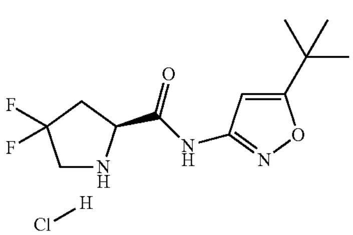 | (S)-4,4-Difluoro-pyrrolidine-2-carboxylic acid (5-tert-butyl-isoxazol-3-yl)-amide; hydrochloride | 374 | |
| 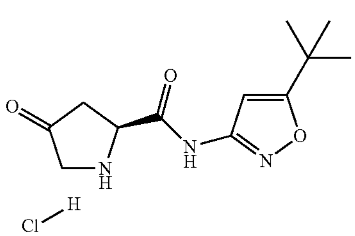 | (S)-4-Oxo-pyrrolidine-2-carboxylic acid (5-tert-butyl-isoxazol-3-yl)-amide; hydrochloride | 352 | |

TABLE 2-continued

| Structure | Name | ESI m/z (+) | ESI m/z (−) |
|---|---|---|---|
| 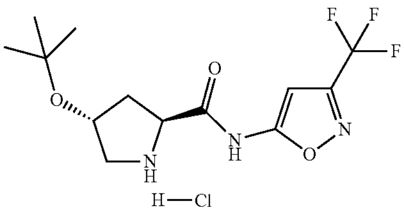 | (2S,4R)-4-tert-Butoxy-pyrrolidine-2-carboxylic acid (3-trifluoromethyl-isoxazol-5-yl)-amide; hydrochloride | 322 | |
| 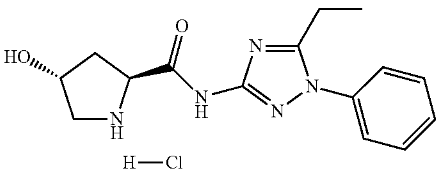 | (2S,4R)-4-Hydroxy-pyrrolidine-2-carboxylic acid (5-ethyl-1-phenyl-1H-1,2,4-triazol-3-yl)-amide; hydrochloride | 302 | |
| 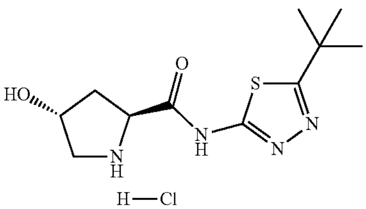 | (2S,4R)-4-Hydroxy-pyrrolidine-2-carboxylic acid (5-tert-butyl-1,3,4-thiadiazol-2-yl)-amide; hydrochloride | 271 | |

Step 3: Synthesis of 1-(3-chloro-5-trifluoromethyl-pyridin-2-yl)-pyrrolidine-2-carboxylic acid (5-tert-butyl-isoxazol-3-yl)-amide A microwave reaction vessel is charged with (S)-pyrrolidine-2-carboxylic acid (5-tert-butyl-isoxazol-3-yl)-amide; hydrochloride, 3-chloro-2-fluoro-5-trifluoromethylpyridine, triethylamine and ethanol. The mixture is heated in a microwave reactor at 175° C. for 1 h, maintaining the watts at 60 to keep the reactor from shutting down. The reaction is cooled to room temperature and concentrated in vacuo to afford an oil which is purified by reverse phase preparative HPLC. Product fractions are combined and concentrated in vacuo to afford title compound (64.4 mg). ESI m/z 417 [M+H]+.

Compounds in Table III Method 1 are prepared in a similar manner.

EXAMPLE 2

Synthesis of 1-isopropyl-pyrrolidine-2-carboxylic acid (5-tert-butyl-isoxazol-3-yl)-amide

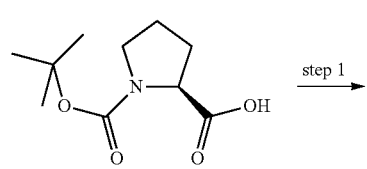

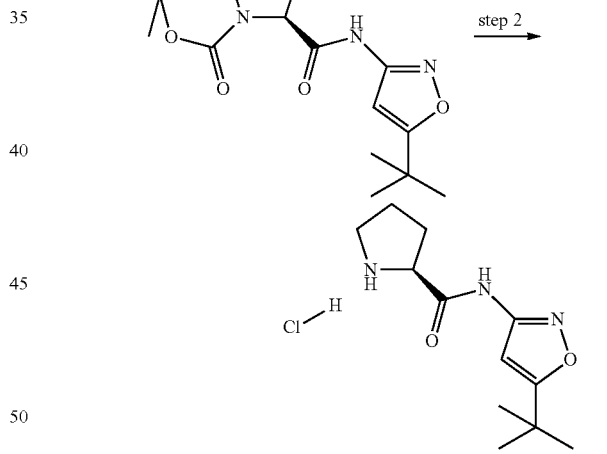

Step 1 and 2 are the same as Example 1 using coupling method A.

Step 3: Synthesis of 1-isopropyl-pyrrolidine-2-carboxylic acid (5-tert-butyl-isoxazol-3-yl)-amide A solution of acetone and (S)-pyrrolidine-2-carboxylic acid (5-tert-butyl-isoxazol-3-yl)-amide; hydrochloride (0.2 g; 0.843 mmol) in dichloroethane (3 mL) with several drops of acetic acid and approximately 10 equivalents of sodium bisulfate is stirred for 30 minutes followed by the addition of sodium cyanoborohydride (0.079 g; 1.265 mmol). The mixture is stirred overnight at room temperature. After this time, the mixture is diluted with ethyl acetate and washed with aqueous sodium bicarbonate solution and brine. The organics are dried ($Na_2SO_4$), filtered and concentrated in vacuo to afford crude material. Excess starting material is removed using polystryrene bound-isocyante resin (500 mg: 1.51 mmol/g) in dichloromethane (5 mL) for several hours. Crude product is eluted from resin using methylene chloride and tetrahydrofuran. The filtrate is concentrated and final purification done using reverse phase preparative HPLC to afford title compound. ESI m/z 280 [M+H]+

Compounds in Table III Method 2 are prepared in a similar manner.

EXAMPLE 3

Synthesis of (S)-1-(4-trifluoromethyl-phenyl)-pyrrolidine-2-carboxylic acid (5-trifluoromethyl-pyridin-2-yl)-amide

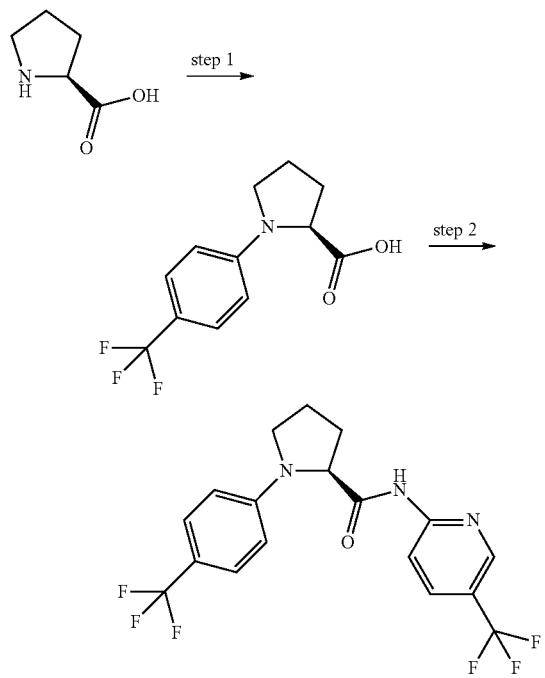

Step 1: Synthesis of (S)-1-(4-trifluoromethyl-phenyl)-pyrrolidine-2-carboxylic acid A reaction vessel containing L-proline, 4-trifluoromethyl-benzenebromide, potassium carbonate and copper iodide is evacuated and purged with argon several times. Dimethylformamide is added and the solution is heated at 90° C. for 4 days in a sealed vessel. After this time, the mixture is cooled to room temperature and diluted with ethyl acetate and water. The two layers are separated and the aqueous is acidified to pH3 using concentrated hydrochloric acid and extracted with ethyl acetate. The combined organics are washed with brine, dried ($Na_2SO_4$), filtered and concentrated in vacuo to afford title compound as intermediate which is used crude in subsequent reactions. ESI m/z 260 [M+H]+

Intermediates in Table 3 are made in a similar fashion.

TABLE 3

| Structure | Name | ESI m/z (+) |
|---|---|---|
| 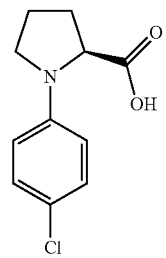 [SMILES: O=C(O)[C@@H]1CCCN1c1ccc(Cl)cc1] | (S)-1-(4-Chloro-phenyl)-pyrrolidine-2-carboxylic acid | 226 |
| 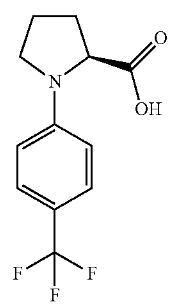 [SMILES: O=C(O)[C@@H]1CCCN1c1ccc(C(F)(F)F)cc1] | (S)-1-(4-Trifluoromethyl-phenyl)-pyrrolidine-2-carboxylic acid | 260 |
| 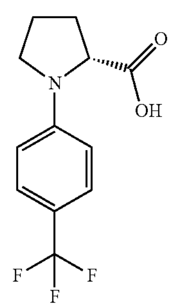 [SMILES: O=C(O)[C@H]1CCCN1c1ccc(C(F)(F)F)cc1] | (R)-1-(4-Trifluoromethyl-phenyl)-pyrrolidine-2-carboxylic acid | 260 |
| 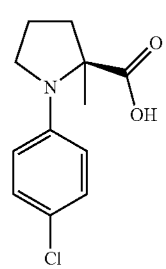 [SMILES: C[C@@]1(C(=O)O)CCCN1c1ccc(Cl)cc1] | (S)-1-(4-Chloro-phenyl)-2-methyl-pyrrolidine-2-carboxylic acid | 240 |

TABLE 3-continued

| Structure | Name | ESI m/z (+) |
|---|---|---|
| 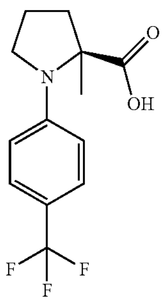 [SMILES: C[C@@]1(C(=O)O)CCCN1c1ccc(C(F)(F)F)cc1] | (S)-2-Methyl-1-(4-trifluoromethyl-phenyl)-pyrrolidine-2-carboxylic acid | 274 |
| 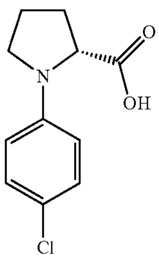 [SMILES: O=C(O)[C@H]1CCCN1c1ccc(Cl)cc1] | (R)-1-(4-Chloro-phenyl)-pyrrolidine-2-carboxylic acid | 226 |
| 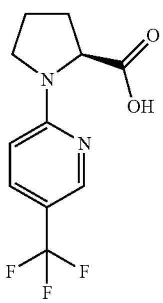 [SMILES: O=C(O)[C@@H]1CCCN1c1ccc(C(F)(F)F)cn1] | (S)-1-(5-Trifluoromethyl-pyridin-2-yl)-pyrrolidine-2-carboxylic acid | 261 |
| 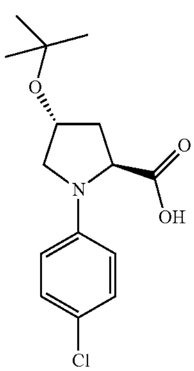 [SMILES: CC(C)(C)O[C@@H]1C[C@@H](C(=O)O)N(c2ccc(Cl)cc2)C1] | (2S,4R)-4-tert-Butoxy-1-(4-chloro-phenyl)-pyrrolidine-2-carboxylic acid | 298 |

Step 2: Synthesis of (S)-1-(4-trifluoromethyl-phenyl)-pyrrolidine-2-carboxylic acid (5-trifluoromethyl-pyridin-2-yl)-amide Amide bond coupling method described in Example 1 coupling method B is used to synthesize the title compound. ESI m/z 404 [M+H]+

Compounds in Table III Method 3 are prepared in a similar manner.

Compounds found in Table III Method 5 are prepared in a similar manner to Example 3 using coupling method D.

Compounds found in Table III Method 6 are prepared in a similar manner to Example 3 using coupling method G.

Compounds found in Table III Method 7 are prepared in a similar manner to Example 3 using coupling method A.

Compounds found in Table III Method 8 are prepared in a similar manner to Example 3 using coupling method A.

EXAMPLE 4

Synthesis of (S)-1-(4-chloro-phenyl)-2-methyl-pyrrolidine-2-carboxylic acid (5-tert-butyl-isoxazol-3-yl)-amide

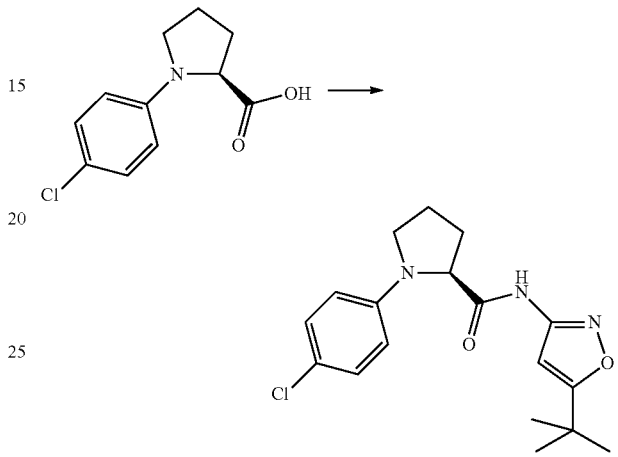

A round bottomed flask is charged with (S)-1-(4-chloro-phenyl)-2-methyl-pyrrolidine-2-carboxylic acid (0.260 g; 1.085 mmol), triethylamine (0.529 mL; 3.798 mmol), and tetrahydrofuran (3 mL). Propylphosphoric anhydride (50% in ethyl acetate) (0.678 mL; 1.139 mmol) is added dropwise and stirred for 30 minutes. 3-Amino-5-tertbutylisoxazole (0.152 g; 1.085 mmol) is added and the reaction is heated at 80° C. for 40 minutes in a microwave reactor. After this time, the reaction mixture is cooled to room temperature, diluted with ethyl acetate and washed with aqueous sodium bicarbonate solution. The aqueous is back extracted with ethyl acetate and the organics are combined and washed with brine, dried ($Na_2SO_4$), filtered and concentrated. Purification by preparative HPLC affords title compound. ESI m/z 362 [M+H]+

Compounds found in Table III Method 4 are prepared in a similar manner.

EXAMPLE 5

Synthesis of (S)-1-(tetrahydro-pyran-4-ylmethyl)-pyrrolidine-2-carboxylic acid (4-tert-butyl-thiazol-2-yl)-amide

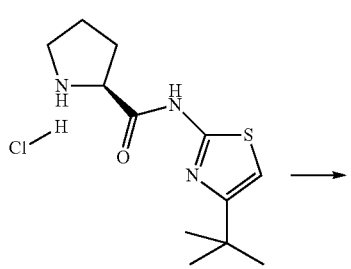

-continued

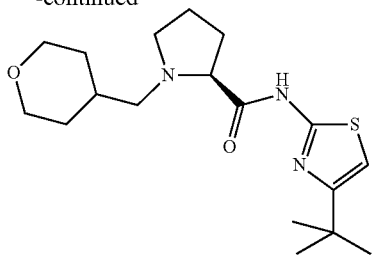

To a solution of (S)-pyrrolidine-2-carboxylic acid (4-tert-butyl-thiazol-2-yl)-amide; hydrochloride (0.310 g; 1.070 mmol) in 1,2-dichloroethane (2 mL) was added tetrahydropyran-4-carbaldehyde (0.244 g; 2.140 mmol), acetic acid (0.2 mL; 3.497 mmol), and sodium sulfate(5-10 equivalents). The mixture is stirred for 30-45 minutes before adding sodium triacetoxyborohydride (0.454 g; 2.140 mmol) and stirring overnight at room temperature. After this time, the mixture is filtered through a plug of silica/Celite® and concentrated in vacuo. Crude material is purified by preparative HPLC. Product fractions are pooled and concentrated in vacuo to afford title compound as an oil. ESI m/z 352 [M+H]+

Compounds in Table III Method 9 are made in a similar manner.

EXAMPLE 6

Synthesis of (S)-1-(3-chloro-5-trifluoromethyl-pyridin-2-yl)-pyrrolidine-2-carboxylic acid (4-tert-butyl-thiazol-2-yl)-amide

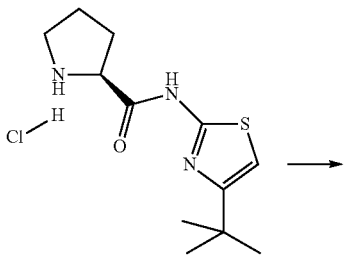

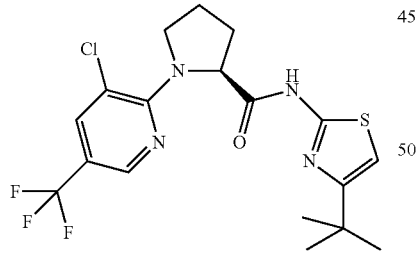

To a vial containing (S)-pyrrolidine-2-carboxylic acid (4-tert-butyl-thiazol-2-yl)-amide; hydrochloride (0.212 g; 0.731 mmol) in dimethylsulfoxide (2 mL) is added N,N-diisopropylethylamine (0.127 mL; 0.731 mmol) and 3-chloro-2-fluoro-5-trifluoromethylpyridine (0.096 mL; 0.731 mmol). The mixture is heated at 100° C. for 1 hour in an oil bath and then cooled to room temperature. The crude mixture is filtered and purified by preparative HPLC chromatography. Product fractions are pooled and concentrated in vacuo to afford title compound. ESI m/z 433 [M+H]+

Compounds in Table III Method 10 are made in a similar manner.

EXAMPLE 7

Synthesis of (S)-1-(4,4-difluoro-cyclohexanecarbonyl)-pyrrolidine-2-carboxylic acid (5-tert-butyl-isoxazol-3-yl)-amide

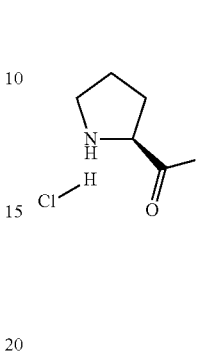

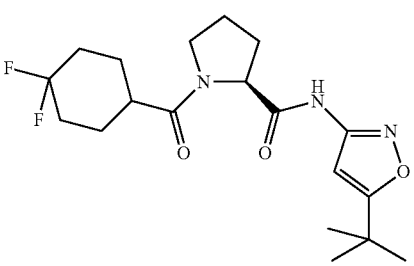

Final compound was achieved via amide bond coupling in a similar manner to Example 1 coupling method A.

Compounds in Table III Method 11 are prepared in a similar manner.

EXAMPLE 8

Synthesis of (S)-1-(1,1-dioxo-1λ⁶-thiomorpholine-4-carbonyl)-pyrrolidine-2-carboxylic acid (5-tert-butyl-isoxazol-3-yl)-amide

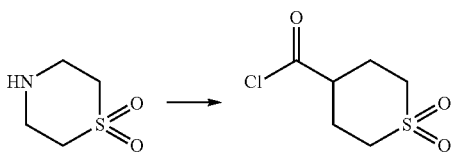

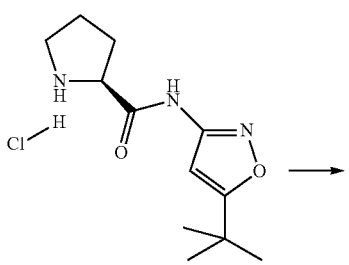

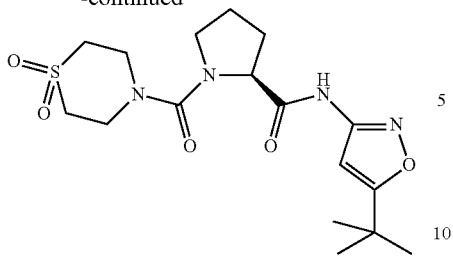
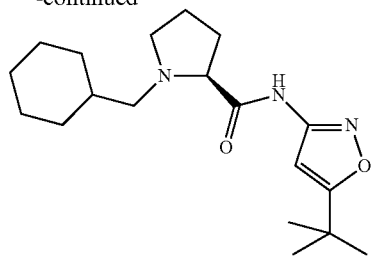

Step 1: Synthesis of 1,1-dioxo-1λ⁶-thiomorpholine-4-carbonyl chloride

Thiomorpholine 1,1-dioxide (1 g; 7.397 mmol) is dispersed in tetrahydrofuran (50 mL) followed by the addition of triethylamine (1.238 mL; 8.88 mmol) and 20% phosgene in toluene (11.743 mL; 22.2 mmol). The reaction mixture is stirred at room temperature overnight. After this time, the mixture is diluted with ether and filtered through Celite®. The Celite® is washed with ether several times and the combined filtrates are concentrated in vacuo to afford title compound as a white solid. ¹H NMR (400 MHz, CHLOROFORM-d) ppm 3.15 (4H, m), 4.13 (2H, s), 4.24 (2H, s).

Step 2: Synthesis of (S)-1-(1,1-dioxo-1λ⁶-thiomorpholine-4-carbonyl)-pyrrolidine-2-carboxylic acid (5-tert-butyl-isoxazol-3-yl)-amide To a solution of (S)-pyrrolidine-2-carboxylic acid (5-tert-butyl-isoxazol-3-yl)-amide; hydrochloride (0.092 g; 0.337 mmol) in tetrahydrofuran (2.5 mL) is added 1,1-dioxo-1λ⁶-thiomorpholine-4-carbonyl chloride (0.067 g; 0.337 mmol) and N,N-diisopropylethylamine (0.123 mL; 0.708 mmol). The mixture is stirred at room temperature for 3 hours before diluting with ethyl acetate and washing with 1N hydrochloric acid and brine. The organics are concentrated in vacuo and purified by preparatory HPLC. The product fractions are pooled and concentrated in vacuo to afford title compound. ESI m/z 399 [M+H]+/397 [M−H]−

Compounds in Table III Method 12 are prepared in a similar manner.

EXAMPLE 9

Synthesis of (S)-1-cyclohexylmethyl-pyrrolidine-2-carboxylic acid (3-tert-butyl-isoxazol-5-yl)-amide

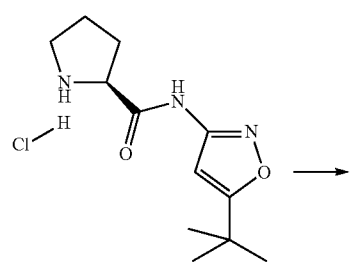

To a solution of (S)-pyrrolidine-2-carboxylic acid (3-tert-butyl-isoxazol-5-yl)-amide; hydrochloride (0.2 g; 0.731 mmol) in N,N-dimethylformamide (4 mL) is added bromomethyl-cyclohexane (0.153 mL; 1.097 mmol), potassium iodide (0.032 mg, 0.197 mmoL), and potassium carbonate (0.505 g; 3.655 mmol). The mixture heated at 60° C. for 7 days. After this time, the mixture is cooled to room temperature, diluted with water and extracted with ethyl acetate. The combined organics are washed with water, 1N hydrochloric acid and brine, dried (Na₂SO₄), filtered and concentrated in vacuo. The crude material is purified by preparative reverse phase HPLC to afford title compound. ESI m/z 334 [M+H]+

Compounds in Table III Method 13 are prepared in a similar manner.

EXAMPLE 10

Synthesis of 3-[(S)-2-(3-tert-butyl-isoxazol-5-ylcarbamoyl)-pyrrolidin-1-yl]-propionic acid tert-butyl ester

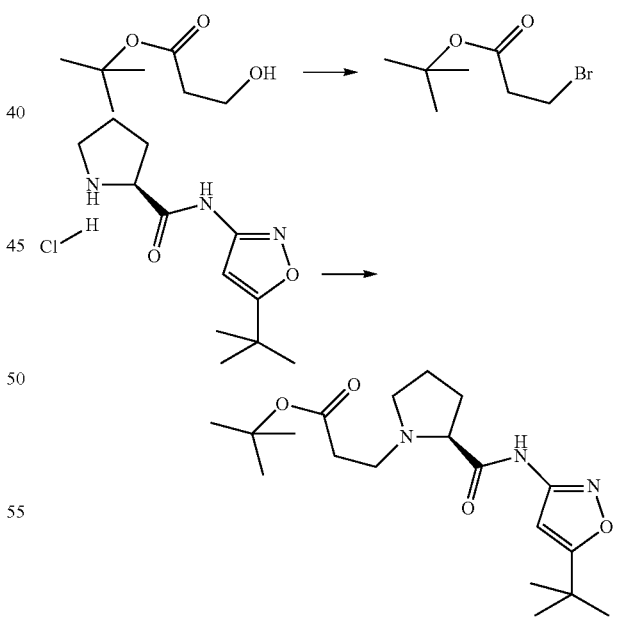

Step 1: Synthesis of 3-bromo-propionic acid tert-butyl ester

3-Hydroxy-propionic acid tert-butyl ester is dissolved in acetonitrile and carbon tetrabromide and triphenylphosphine is added. The mixture is stirred at room temperature overnight. After this time the mixture is concentrated in vacuo. The gummy solid is triturated with hexanes and the liquid decanted, passed through pad of silica to remove any triphenylphosphine oxide, and concentrated in vacuo. $^1$H NMR (400 MHz, CHLOROFORM-d) ppm 1.3 (9H, s), 2.06-2.27 (2H, m), 4.07-4.25 (2H, m).

Step 2: Synthesis of 3-[(S)-2-(3-tert-butyl-isoxazol-5-ylcarbamoyl)-pyrrolidin-1-yl]-propionic acid tert-butyl ester Synthesis is similar to Example 9. ESI m/z 366 [M+H]+/364 [M−H]−

Compounds in Table III Method 13 are prepared in a similar manner.

EXAMPLE 11

Synthesis of (S)-1-cyclopropyl-pyrrolidine-2-carboxylic acid (3-tert-butyl-isoxazol-5-yl)-amide

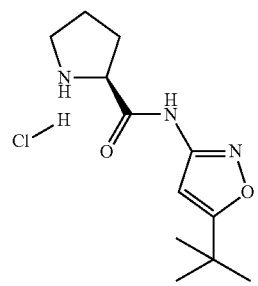

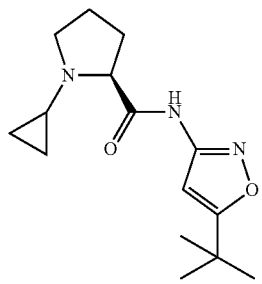

Reference: Tetrahedron Letters 36 (41), 7399-7402, 1995.

(S)-Pyrrolidine-2-carboxylic acid (5-tert-butyl-isoxazol-3-yl)-amide; hydrochloride (0.2 g; 0.731 mmol) is dissolved in methanol and (1-ethoxy-cyclopropoxy)-trimethyl-silane (0.585 mL; 2.924 mmol) and sodium sulfate are added followed by acetic acid (0.419 mL; 7.310 mmol) and sodium cyanoborohydride (0.138 g; 2.193 mmol). The mixture was heated at reflux overnight. After this time, the mixture is cooled, filtered and concentrated in vacuo. The residue is taken up in ethyl acetate and washed with 2M sodium hydroxide solution and brine, dried (Na$_2$SO$_4$), filtered and concentrated in vacuo. The crude material is purified by preparative HPLC to afford title compound. ESI m/z 278 [M+H]+/276 [M−H]−

Compounds in Table III Method 14 are prepared in a similar manner.

EXAMPLE 12

Synthesis of (S)-1-(morpholine-4-carbonyl)-pyrrolidine-2-carboxylic acid (3-tert-butyl-isoxazol-5-yl)-amide

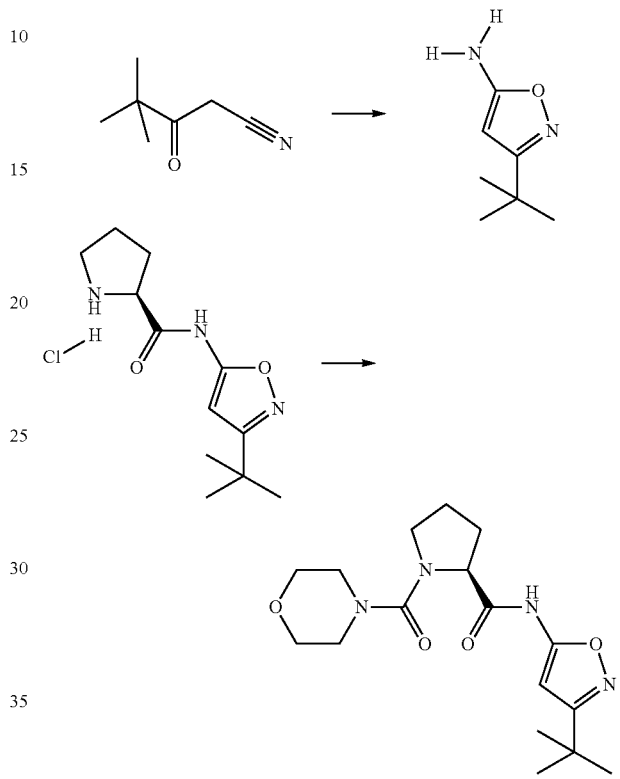

Step 1: Synthesis of 3-tert-butyl-isoxazol-5-ylamine

Hydroxylamine sulfate (27.575 g, 0.168 mol) is added to a stirred solution of 4,4-dimethyl-3-oxopentanenitrile (20 g; 0.160 mol) and sodium hydroxide (26.24 g; 0.656 mol) in water (160 mL). The mixture is heated at reflux for 2 hours, then allowed to cool to room temperature and extracted with methylene chloride. The combined organics are washed with water, dried (Na$_2$SO$_4$), filtered and concentrated in vacuo to afford title compound as a white solid. ESI m/z 141 [M+H]+

Step 2: Synthesis of (S)-pyrrolidine-2-carboxylic acid (3-tert-butyl-isoxazol-5-yl)-amide; hydrochloride Title compound is made as indicated in Table 2 of Example 1.

Step 3: Synthesis of (S)-1-(morpholine-4-carbonyl)-pyrrolidine-2-carboxylic acid (3-tert-butyl-isoxazol-5-yl)-amide To a solution of (S)-pyrrolidine-2-carboxylic acid (3-tert-butyl-isoxazol-5-yl)-amide; hydrochloride (0.2 g; 0.731 mmol) in N,N-dimethylformamide (2 mL) is added morpholine carbonylchloride (0.084 mL; 0.731 mmol) and N,N-diisopropylethylamine (0.267 mL; 1.535 mmol) and the reaction mixture stirred overnight at room temperature. After this time, the mixture is diluted with water and extracted with ethyl acetate. The combined organics are washed with 1N hydrochloric acid and brine, dried (Na$_2$SO$_4$), filtered and concentrated in vacuo. The crude material is purified by preparative HPLC to afford title compound. ESI m/z 351 [M+H]+/349 [M−H]−

Compounds in Table III Method 15 are prepared in a similar manner.

EXAMPLE 13

Synthesis of [(S)-2-(3-tert-butyl-isoxazol-5-ylcarbamoyl)-pyrrolidin-1-yl]-acetic acid A solution of 20% trifluoroacetic acid in methylene chloride (20 mL) is added to [(S)-2-(3-tert-butyl-isoxazol-5-ylcarbamoyl)-pyrrolidin-1-yl]-acetic acid tert-butyl ester (0.23 g; 0.654 mmol) and the reaction mixture is stirred at room temperature overnight. After this time, the mixture is concentrated in vacuo and purified by preparative HPLC to afford title compound. ESI m/z 296 [M+H]+/294 [M−H]−

Compounds in Table III Method 16 are prepared in a similar manner.

EXAMPLE 14

Synthesis of (S)-1-(4-chloro-phenyl)-pyrrolidine-2-carboxylic acid [5-chloro-1-(tetrahydro-pyran-4-ylmethyl)-1H-benzimidazol-2-yl]-amide

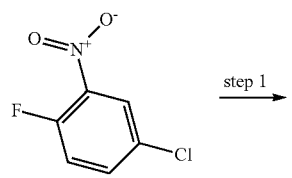

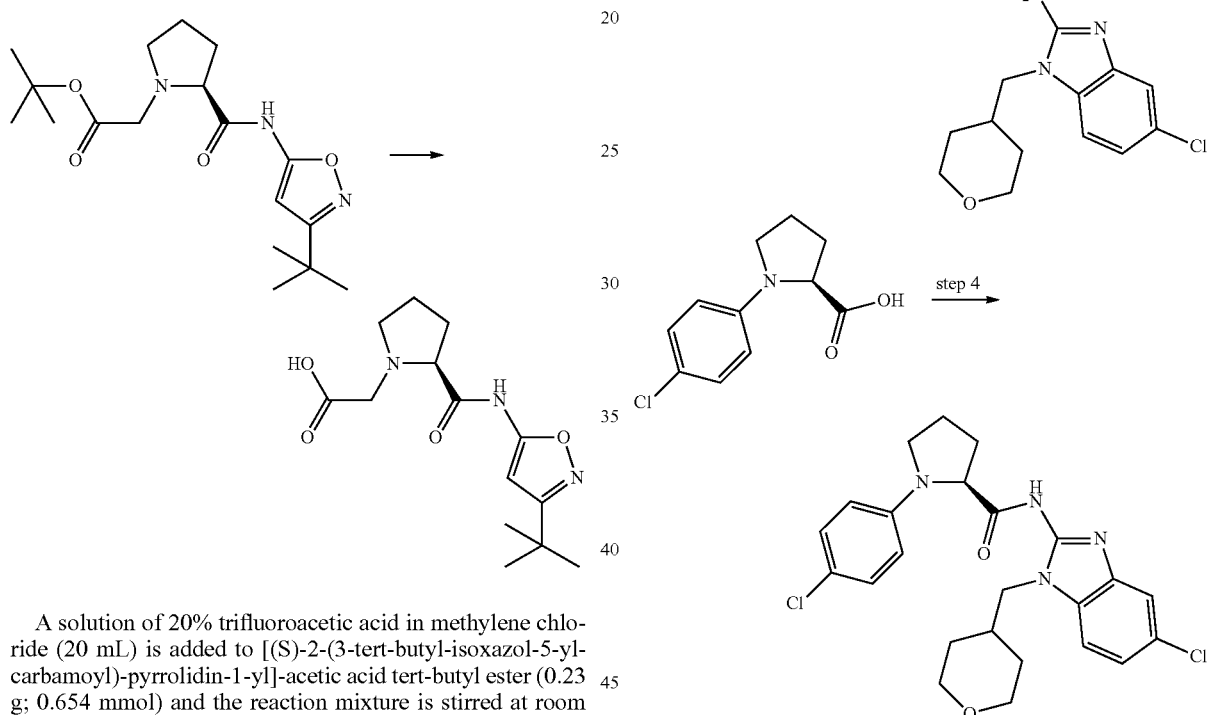

Step 1: Synthesis of (4-chloro-2-nitro-phenyl)-(tetrahydro-pyran-4-ylmethyl)-amine 2-Fluoro-5-chloronitrobenzene (0.762 g; 4.341 mmol), tetrahydropyran methyl amine (0.5 g; 4.341 mmol), N,N-diisopropylethylamine (0.756 mL; 4.341 mmol) and dimethylsulfoxide (2 mL) are heated at 80° C. in an oil bath for 4 days. After this time the reaction is cooled to room temperature, diluted with water and extracted with ethyl acetate. The combined organics are washed with water and brine and concentrated in vacuo to afford title compound as an orange oil which solidified upon standing and was used crude in subsequent reactions. ESI m/z 271 [M+H]+

Step 2: Synthesis of 4-chloro-N$^1$-(tetrahydro-pyran-4-ylmethyl)-benzene-1,2-diamine To a solution of (4-chloro-2-nitro-phenyl)-(tetrahydro-pyran-4-ylmethyl)-amine (1.28 g; 4.729 mmol) in tetrahydrofuran (25 mL) was added tin metal (1.740 g; 14.660 mmol) and 1N hydrochloric acid (32.157 mL; 32.157 mmol) and the reaction is stirred at room temperature overnight. After this time, the mixture is diluted with 1N sodium hydroxide solution (1.6 g NaOH/40 mL water; 40 mmol) and filtered through Celite®, washing with ethyl acetate. The filtrate is extracted with ethyl acetate and the combined organics are washed with water and brine, dried (Na$_2$SO$_4$), filtered and concentrated in vacuo to afford title compound which was used without further purification. ESI m/z 241 [M+H]+

Step 3: Synthesis of 5-chloro-1-(tetrahydro-pyran-4-ylmethyl)-1H-benzimidazol-2-ylamine 4-Chloro-N$^1$-(tetrahydro-pyran-4-ylmethyl)-benzene-1,2-diamine (1.026 g; 4.261 mmol) is dissolved in ethanol (65 mL) and cyanogen bromide (0.903 g; 8.522 mmol) is added. The reaction is stirred at room temperature overnight. After this time the mixture is concentrated in vacuo to afford title compound as a tan solid which was used without further purification. ESI m/z 266 [M+H]+/264 [M−H]−

Step 4: Synthesis of (S)-1-(4-chloro-phenyl)-pyrrolidine-2-carboxylic acid [5-chloro-1-(tetrahydro-pyran-4-ylmethyl)-1H-benzimidazol-2-yl]-amide Title compound is prepared in a similar procedure described by D. ESI m/z 473 [M+H]+/471 [M−H]−

Compounds in Table III Method 5 are prepared in a similar manner.

EXAMPLE 15

Synthesis of (S)-1-(tetrahydro-pyran-4-ylmethyl)-pyrrolidine-2-carboxylic acid (3-phenyl-1,2,4-thiadiazol-5-yl)-amide

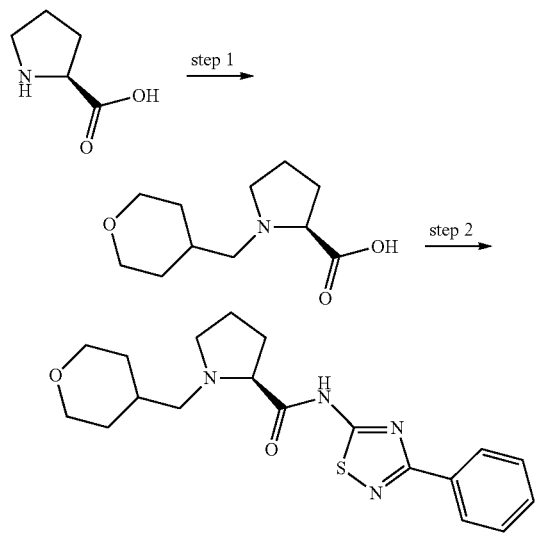

Step 1: Synthesis of (S)-1-(tetrahydro-pyran-4-ylmethyl)-pyrrolidine-2-carboxylic acid To a solution of L-proline (1 g; 8.686 mmol) in 1,2-dichloroethane (10 mL)/acetic acid (1.98 mL; 33.007 mmol)) is added tetrahydro-pyran-4-carbaldehyde (0.991 g; 8.686 mmol) and sodium sulfate (~10 equivalents). After 45 minutes of agitation on an orbital shaker, MP-triacetoxyborohydride resin (4.272 g; 10.423 mmol) is added. The mixture is agitated at room temperature overnight and filtered, washing resin with methylene chloride. The combined filtrate is washed with aqueous saturated sodium bicarbonate solution and brine, dried (Na$_2$SO$_4$), filtered and concentrated in vacuo. Excess acetic acid is removed by successive azeotropic distillation with toluene on the rotary evaporator. Title compound is afforded by this method. ESI m/z 214 [M+H]+

Compounds in Table 4 are made in a similar fashion.

TABLE 4

| Structure | Name | ESI m/z (+) |
| --- | --- | --- |
| 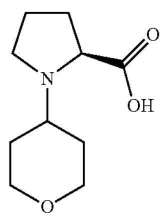 [SMILES: O=C(O)[C@@H]1CCCN1C1CCOCC1] | (S)-1-(Tetrahydro-pyran-4-yl)-pyrrolidine-2-carboxylic acid | 200 |
| 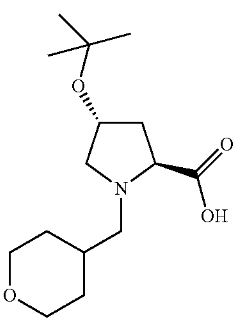 [SMILES: CC(C)(C)O[C@@H]1C[C@@H](C(=O)O)N(CC2CCOCC2)C1] | (2S,4R)-4-tert-Butoxy-1-(tetrahydro-pyran-4-ylmethyl)-pyrrolidine-2-carboxylic acid | 286 |

Step 2: Synthesis of (S)-1-(tetrahydro-pyran-4-ylmethyl)-pyrrolidine-2-carboxylic acid (3-phenyl-1,2,4-thiadiazol-5-yl)-amide Title compound was made using a similar procedure to coupling method G. ESI m/z 373 [M+H]+/371 [M−H]−

Compounds in Table III Method 6 are prepared using a similar procedure.

EXAMPLE 16

Synthesis of (S)-1-(4-chloro-phenyl)-5-oxo-pyrrolidine-2-carboxylic acid (5-tert-butyl-isoxazol-3-yl)-amide

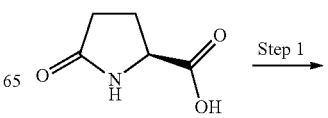

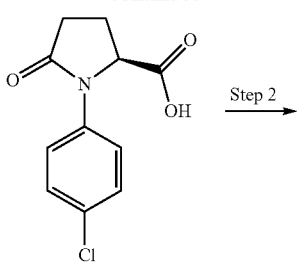

Step 2 →

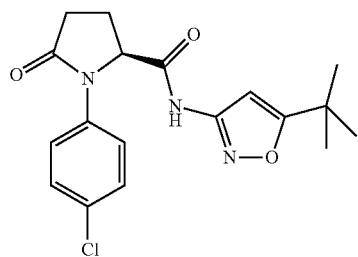

Step 1: Synthesis of (S)-1-(4-chloro-phenyl)-5-oxo-pyrrolidine-2-carboxylic acid To a stirred suspension of (S)-5-oxo-pyrrolidine-2-carboxylic acid (775 mg, 6 mmol) in acetonitrile (10 mL) 1,8-diazabicyclo[5,4,0]undec-7-ene (DBU) (1.8 mL, 12 mmol) is added at room temperature. After 10 min di-μ-hydroxy-bis [N,N,N',N'-tetramethylenediamine)-copper (II) chloride (Cu-TMEDA) (300 mg, 0.65 mmol) is added to the clear solution. The bluish green colored mixture is stirred for 10 min and 4-chlorophenylboronic acid (1 g, 6.4 mmol) is added. After 20 h acetonitrile is evaporated in vacuo, the concentrate taken up in ammonium chloride (150 mL) and the aqueous layer is washed with ethyl acetate (3×100 mL). The aqueous layer is cooled in an ice-bath, treated with 1 N sulfuric acid to pH 2 and extracted with ethyl acetate (3×100 mL). Combined organic extracts washed with brine (2×50 mL), dried over anhydrous Na$_2$SO$_4$ and solvent removed in vacuo to give the title compound as an off-white solid. ESI m/z 240 [M+H]+.

Using a similar procedure, the 5-oxo-pyrrolidine-2-carboxylic acids listed in Table 5 are synthesized. (S)-1-[4-(tert-Butoxycarbonyl-methyl-amino)-phenyl]-5-oxo-pyrrolidine-2-carboxylic acid is prepared by utilizing methyl-[4-(4,4,5,5-tetramethyl-1,3,2-dioxaborolan-2-yl)-phenyl]-carbamic acid tert-butyl ester instead of the corresponding boronic acid.

TABLE 5

| Structure | Name | ESI m/z (+) | ESI m/z (−) |
|---|---|---|---|
|  | (S)-5-oxo-1-phenyl-pyrrolidine-2-carboxylic acid | 206 |  |
| 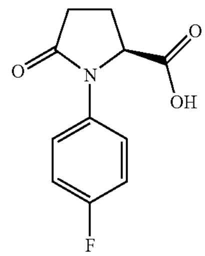 [SMILES: O=C(O)[C@@H]1CCC(=O)N1c1ccc(F)cc1] | (S)-1-(4-fluoro-phenyl)-5-oxo-pyrrolidine-2-carboxylic acid | 224 |  |
| 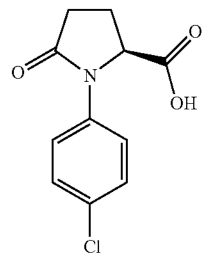 [SMILES: O=C(O)[C@@H]1CCC(=O)N1c1ccc(Cl)cc1] | (S)-1-(4-chloro-phenyl)-5-oxo-pyrrolidine-2-carboxylic acid | 240 |  |
| 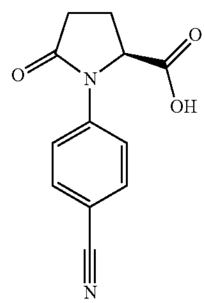 [SMILES: N#Cc1ccc(N2C(=O)CC[C@H]2C(=O)O)cc1] | (S)-1-(4-cyano-phenyl)-5-oxo-pyrrolidine-2-carboxylic acid | 231 |  |
| 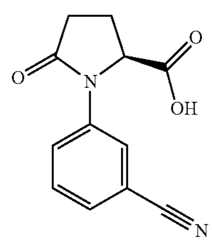 [SMILES: N#Cc1cccc(N2C(=O)CC[C@H]2C(=O)O)c1] | (S)-1-(3-cyano-phenyl)-5-oxo-pyrrolidine-2-carboxylic acid | 231 |  |
| 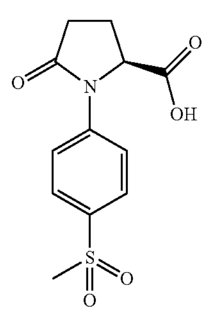 [SMILES: CS(=O)(=O)c1ccc(N2C(=O)CC[C@H]2C(=O)O)cc1] | (S)-1-(4-methane-sulfonyl-phenyl)-5-oxo-pyrrolidine-2-carboxylic acid | 284 |  |

TABLE 5-continued

| Structure | Name | ESI m/z (+) | ESI m/z (−) |
|---|---|---|---|
| 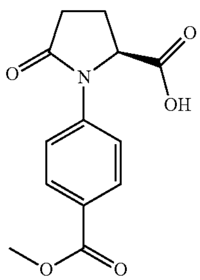 [SMILES: COC(=O)c1ccc(N2C(=O)CC[C@H]2C(=O)O)cc1] | (S)-1-(4-methoxy-carbonyl-phenyl)-5-oxo-pyrrolidine-2-carboxylic acid | 264 | |
| 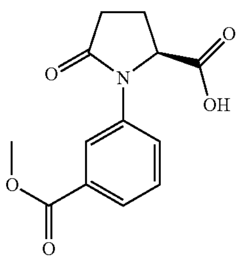 [SMILES: COC(=O)c1cccc(N2C(=O)CC[C@H]2C(=O)O)c1] | (S)-1-(3-methoxy-carbonyl-phenyl)-5-oxo-pyrrolidine-2-carboxylic acid | 264 | |
| 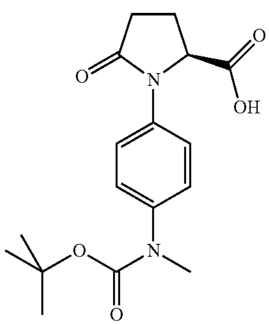 [SMILES: CN(C(=O)OC(C)(C)C)c1ccc(N2C(=O)CC[C@H]2C(=O)O)cc1] | (S)-1-[4-(tert-butoxycarbonyl-methyl-amino)-phenyl]-5-oxo-pyrrolidine-2-carboxylic acid | 335 | |
| 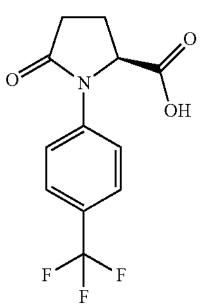 [SMILES: O=C(O)[C@@H]1CCC(=O)N1c1ccc(C(F)(F)F)cc1] | (S)-5-Oxo-1-(4-trifluoromethyl-phenyl)-pyrrolidine-2-carboxylic acid | 274 | |
| 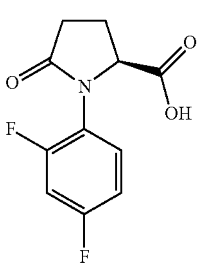 [SMILES: O=C(O)[C@@H]1CCC(=O)N1c1ccc(F)cc1F] | (S)-1-(2,4-Difluoro-phenyl)-5-oxo-pyrrolidine-2-carboxylic acid | 242 | |
| | (S)-1-(5-Chloro-thiophen-2-yl)-5-oxo-pyrrolidine-2-carboxylic acid | 246 | |
| | (S)-1-(4-Chloro-2-fluoro-phenyl)-5-oxo-pyrrolidine-2-carboxylic acid | 258 | |
| | (S)-5-Oxo-1-p-tolyl-pyrrolidine-2-carboxylic acid | 220 | 218 |
| | (S)-1-(4-Ethyl-phenyl)-5-oxo-pyrrolidine-2-carboxylic acid | 234 | 232 |
| | (S)-1-(4-Isopropyl-phenyl)-5-oxo-pyrrolidine-2-carboxylic acid | 248 | 246 |

TABLE 5-continued

| Structure | Name | ESI m/z (+) | ESI m/z (−) |
|---|---|---|---|
| 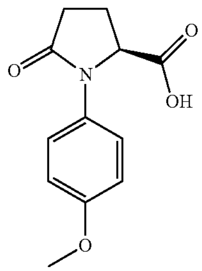 [SMILES: COc1ccc(N2C(=O)CC[C@H]2C(=O)O)cc1] | (S)-1-(4-Methoxy-phenyl)-5-oxo-pyrrolidine-2-carboxylic acid | 236 | 234 |
| 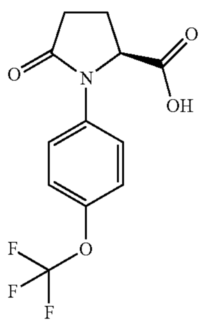 [SMILES: O=C(O)[C@@H]1CCC(=O)N1c1ccc(OC(F)(F)F)cc1] | (S)-5-Oxo-1-(4-trifluoromethoxy-phenyl)-pyrrolidine-2-carboxylic acid | 290 | 288 |
| 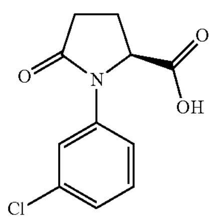 [SMILES: O=C(O)[C@@H]1CCC(=O)N1c1cccc(Cl)c1] | (S)-1-(3-Chloro-phenyl)-5-oxo-pyrrolidine-2-carboxylic acid | 240 | |
| 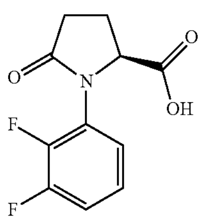 [SMILES: O=C(O)[C@@H]1CCC(=O)N1c1cccc(F)c1F] | (S)-1-(2,3-Difluoro-phenyl)-5-oxo-pyrrolidine-2-carboxylic acid | 242 | |
| 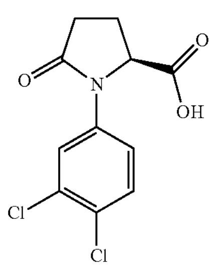 [SMILES: O=C(O)[C@@H]1CCC(=O)N1c1ccc(Cl)c(Cl)c1] | (S)-1-(3,4-Dichloro-phenyl)-5-oxo-pyrrolidine-2-carboxylic acid | 274 | |
| 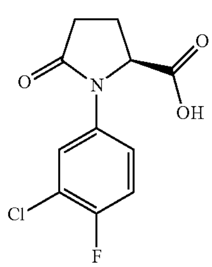 [SMILES: O=C(O)[C@@H]1CCC(=O)N1c1ccc(F)c(Cl)c1] | (S)-1-(3-Chloro-4-fluoro-phenyl)-5-oxo-pyrrolidine-2-carboxylic acid | 258 | |
| | (S)-1-(3,5-Difluoro-phenyl)-5-oxo-pyrrolidine-2-carboxylic acid | 242 | |
| | (S)-1-(3-Fluoro-4-methyl-phenyl)-5-oxo-pyrrolidine-2-carboxylic acid | 238 | |
| | (S)-1-(3-Fluoro-phenyl)-5-oxo-pyrrolidine-2-carboxylic acid | 224 | |
| | (S)-5-Oxo-1-(4-vinyl-phenyl)-pyrrolidine-2-carboxylic acid | 232 | |
| | (S)-1-(4-Chloro-3-fluoro-phenyl)-5-oxo-pyrrolidine-2-carboxylic acid | 258 | |
| | (S)-1-(4-Chloro-3-methyl-phenyl)-5-oxo-pyrrolidine-2-carboxylic acid | 254 | |

TABLE 5-continued

| Structure | Name | ESI m/z (+) | ESI m/z (−) |
|---|---|---|---|
| | (S)-1-(3-Fluoro-4-methoxy-phenyl)-5-oxo-pyrrolidine-2-carboxylic acid | 254 | |
| | (S)-1-(4-Cyano-3-fluoro-phenyl)-5-oxo-pyrrolidine-2-carboxylic acid | 249 | |
| | (S)-1-(3-Chloro-4-methyl-phenyl)-5-oxo-pyrrolidine-2-carboxylic acid | 254 | |
| | (S)-1-(4-Difluoromethyl-phenyl)-5-oxo-pyrrolidine-2-carboxylic acid | n/a | |
| | (S)-1-(3,4-Difluoro-phenyl)-5-oxo-pyrrolidine-2-carboxylic acid | 242 | |
| | (S)-1-(4-Fluoro-3-methyl-phenyl)-5-oxo-pyrrolidine-2-carboxylic acid | 238 | |
| | (S)-5-Oxo-1-(3,4,5-trifluoro-phenyl)-pyrrolidine-2-carboxylic acid | 260 | |
| | (S)-1-(4-Methoxy-methyl-phenyl)-5-oxo-pyrrolidine-2-carboxylic acid | 250 | |
| | (S)-1-(4-Fluoro-methyl-phenyl)-5-oxo-pyrrolidine-2-carboxylic acid | 238 | |

Step 2: Synthesis of (S)-1-(4-chloro-phenyl)-5-oxo-pyrrolidine-2-carboxylic acid (5-tert-butyl-isoxazol-3-yl)-amide Title compound is prepared using a similar procedure to Example 1 coupling method D. ESI m/z 362 [M+H]+

Compounds in Table III Method 5 are prepared in a similar manner.

Compounds in Table III Method 6 are prepared in a similar manner using coupling method G.

Compounds in Table III Method 7 are prepared in a similar manner using coupling method A.

Compounds in Table III Method 17 are prepared in a similar manner using coupling method I.

EXAMPLE 17

Synthesis of (S)-1-(4-nitro-phenyl)-5-oxo-pyrrolidine-2-carboxylic acid (5-tert-butyl-isoxazol-3-yl)-amide

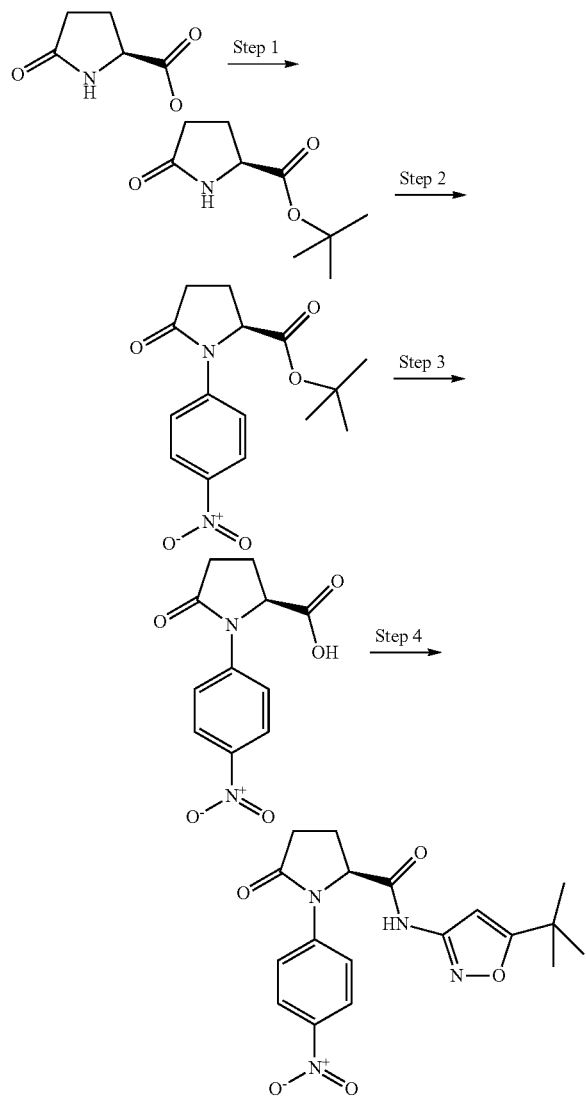

Step 1: Synthesis of (S)-5-oxo-pyrrolidine-2-carboxylic acid tert-butyl ester A pressure flask is charged with (S)-(−)-2-pyrrolidone-5-carboxylic acid (25 g, 193.6 mmol) and dichloromethane (100 mL) and the stirred suspension is cooled in a dry ice acetone bath. Liquid 2-methylpropene (150 mL) is added followed by concentrated sulfuric acid (0.5 mL). The pressure flask is sealed and the reaction mixture is stirred at room temperature for 48 h. The pressure flask is cooled in a dry acetone bath and the reaction mixture is diluted with dichloromethane (500 mL) and treated with a saturated solution of sodium bicarbonate until the effervescence is ceased. The organic layer is separated, washed with saturated solution of sodium bicarbonate (300 mL), brine (300 mL), dried over anhydrous Na$_2$SO$_4$ and solvent removed in vacuo to give the title compound as a white crystalline solid. The crude material is used without purification.

Step 2: Synthesis of (S)-1-(4-nitro-phenyl)-5-oxo-pyrrolidine-2-carboxylic acid tert-butyl ester To a stirred solution of (S)-5-oxo-pyrrolidine-2-carboxylic acid tert-butyl ester (1.85 g, 10 mmol) in dimethylsulfoxide (10 mL) at room temperature, sodium hydride (440 mg of 60% dispersion in mineral oil, 11 mmol) is added in portions over a period of 20 min. After 30 min, 4-fluoronitrobenzene (1.06 mL, 10 mmol) is added and the mixture is heated by placing in an oil-bath maintained at 80° C. for 4 h. The reaction mixture is allowed to cool to room temperature, treated with saturated ammonium chloride solution (150 mL) and extracted with ethyl acetate (250 mL). Organic extracts are combined, washed with brine (100 mL), dried over anhydrous Na$_2$SO$_4$ and solvent removed in vacuo. The crude is purified chromatography over silica gel eluting with hexanes/ethyl acetate and the title compound is obtained as a light yellow solid, ESI m/z 307 [M+H]+.

Using a similar procedure, the 5-oxo-pyrrolidine-2-carboxylic acid tert-butyl esters listed in Table 6 are synthesized.

TABLE 6

| Structure | Name | ESI m/z (+) |
|---|---|---|
| 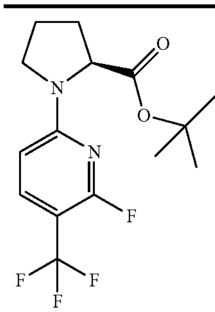 | (S)-1-(6-Fluoro-5-trifluoromethyl-pyridin-2-yl)-pyrrolidine-2-carboxylic acid tert-butyl ester | n/a |
| 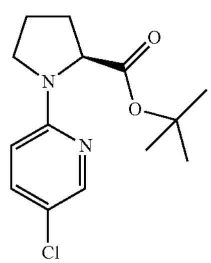 [SMILES: CC(C)(C)OC(=O)[C@@H]1CCCN1c1ccc(Cl)cn1] | (S)-1-(5-Chloro-pyridin-2-yl)-pyrrolidine-2-carboxylic acid tert-butyl ester | 297 |

Step 3: Synthesis of (S)-1-(4-nitro-phenyl)-5-oxo-pyrrolidine-2-carboxylic acid (S)-1-(4-nitro-phenyl)-5-oxo-pyrrolidine-2-carboxylic acid tert-butyl ester (800 mg, 2.6 mmol) is treated with trifluoroacetic acid (5 mL) at room temperature. After 1 h trifluoroacetic acid is evaporated in vacuo and the concentrate treated with ice/water. Precipitated light brownish solid is filtered washed with water and dried to give the title compound, ESI m/z 251 [M+H]+.

Step 4: Synthesis of (S)-1-(4-nitro-phenyl)-5-oxo-pyrrolidine-2-carboxylic acid (5-tert-butyl-isoxazol-3-yl)-amide The title compound, ESI m/z 373 [M+H]+ is prepared utilizing a procedure similar to the one described in Example 16, step 2.

Compounds found in Table III Method 18 are made using a similar procedure.

EXAMPLE 18

Synthesis of (S)-1-(3-methylcarbamoyl-phenyl)-5-oxo-pyrrolidine-2-carboxylic acid (5-tert-butyl-isoxazol-3-yl)-amide

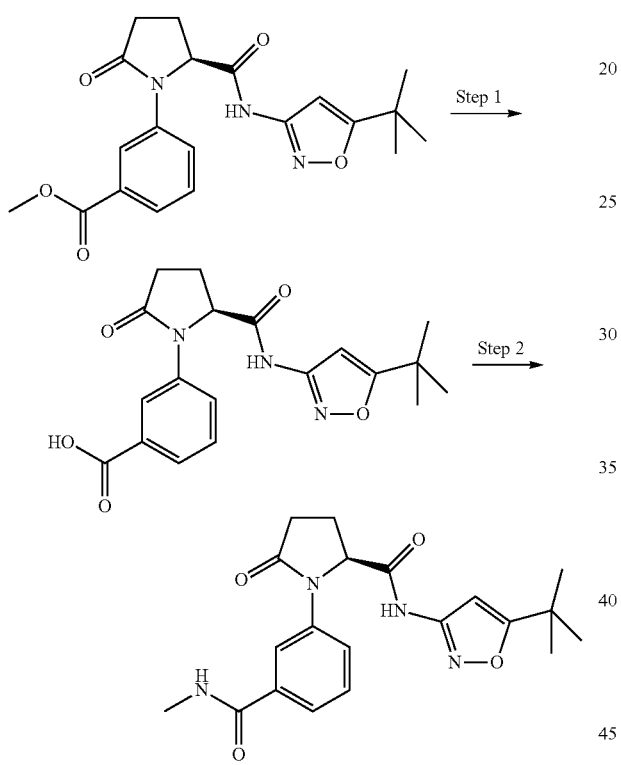

Step 1: Synthesis of 3-[(S)-2-(5-tert-butyl-isoxazol-3-ylcarbamoyl)-5-oxo-pyrrolidin-1-yl]-benzoic acid To a solution of 3-[(S)-2-(5-tert-butyl-isoxazol-3-ylcarbamoyl)-5-oxo-pyrrolidin-1-yl]-benzoic acid methyl ester (870 mg, 2.23 mmol) in methanol (30 mL) a 2 M solution of sodium hydroxide in water (5 mL, 10 mmol) is added at room temperature. After 18 h solvent is evaporated in vacuo, the concentrate is cooled in an ice-bath and acidified to pH 2 using 1 N sulfuric acid. Precipitated white solid is filtered, washed with water and dried to give the title compound, ESI m/z 372 [M+H]+.

Step 2: Synthesis of (S)-1-(3-methylcarbamoyl-phenyl)-5-oxo-pyrrolidine-2-carboxylic acid (5-tert-butyl-isoxazol-3-yl)-amide To a stirred solution of 3-[(S)-2-(5-tert-butyl-isoxazol-3-ylcarbamoyl)-5-oxo-pyrrolidin-1-yl]-benzoic acid (75 mg, 0.2 mmol) in dichloromethane (1 mL) 1-ethyl-3-(3-dimethylaminopropyl)carbodiimide hydrochloride (EDC hydrochloride) (42 mg, 0.22 mmol) is added at room temperature. After 5 minutes methylamine (0.5 mL of 2 M solution in tetrahydrofuran, 1 mmol) is added. After 2 h solvent is removed in vacuo and the crude is purified by chromatography over silica gel eluting with methanol/dichloromethane to give the title compound as a white solid, ESI m/z 385 [M+H]+.

Examples listed in Table III Method 19 are prepared according to a similar procedure.

EXAMPLE 19

Synthesis of (S)-1-(3-methylcarbamoyl-phenyl)-5-oxo-pyrrolidine-2-carboxylic acid (5-tert-butyl-isoxazol-3-yl)-amide

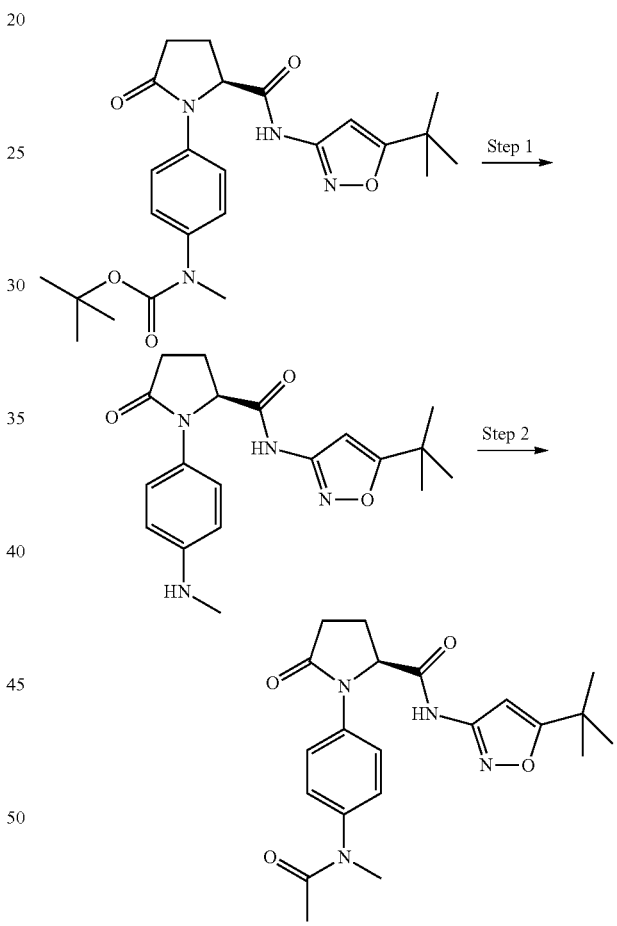

Step 1: Synthesis of (S)-1-(4-methylamino-phenyl)-5-oxo-pyrrolidine-2-carboxylic acid (5-tert-butyl-isoxazol-3-yl)-amide A solution of {4-[(S)-2-(5-tert-butyl-isoxazol-3-ylcarbamoyl)-5-oxo-pyrrolidin-1-yl]-phenyl}-methyl-carbamic acid tert-butyl ester (550 mg, 1.21 mmol) in dichloromethane (5 mL) is cooled in an ice bath. A pre-cooled trifluoroacetic acid (15 mL) is added and the mixture is kept in ice-bath for 30 minutes. Trifluoroacetic acid is evaporated in vacuo, and the residue is treated with ice and sodium bicarbonate solution. Extracted with ethyl acetate (1×150 mL) and the combined extracts washed with brine (50 mL) dried over anhydrous Na₂SO₄ and solvent removed in vacuo to give the title compound, ESI m/z 357 [M+H]+.

Step 2: Synthesis of (S)-1-(3-methylcarbamoyl-phenyl)-5-oxo-pyrrolidine-2-carboxylic acid (5-tert-butyl-isoxazol-3-yl)-amide A stirred solution of (S)-1-(4-methylamino-phenyl)-5-oxo-pyrrolidine-2-carboxylic acid (5-tert-butyl-isoxazol-3-yl)-amide (53 mg, 0.15 mmol) and pyridine (30 μL, 0.37 mmol) in dichloromethane (1 mL) is cooled in an ice-bath. Acetyl chloride (20 μL, 0.28 mmol) is added and ice-bath is removed after 30 minutes and the mixture is allowed to stand at room temperature for 2 h. The reaction mixture is diluted with dichloromethane (100 mL), washed with 1 N hydrochloric acid (30 mL), brine (30 mL) and solvent is evaporated in vacuo. The crude is purified by chromatography over silica gel eluting with methanol/dichloromethane to give the title compound, ESI m/z 399 [M+H]+.

Examples listed in Table III Method 20 are prepared according to a similar procedure.

EXAMPLE 20

Synthesis of S)-1-(3-chloro-5-trifluoromethyl-pyridin-2-yl)-5-oxo-pyrrolidine-2-carboxylic acid (5-tert-butyl-isoxazol-3-yl)-amide

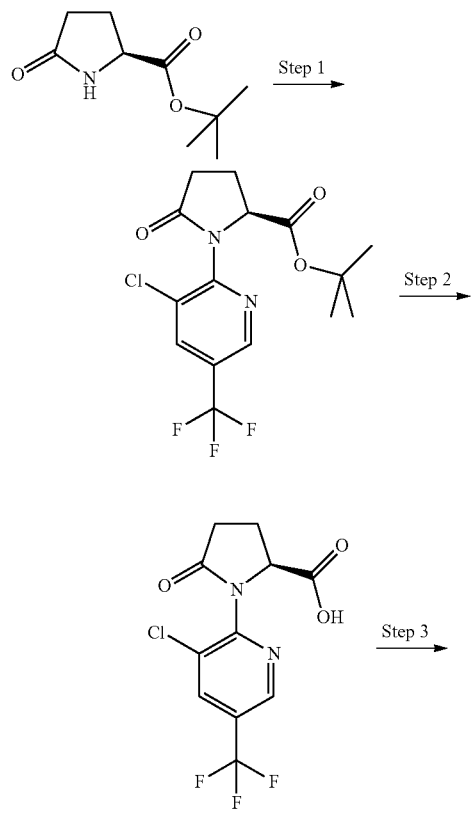

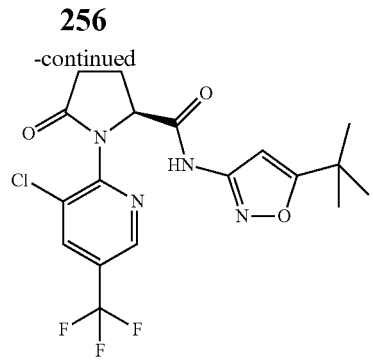

Step 1: Synthesis of (S)-1-(3-chloro-5-trifluoromethyl-pyridin-2-yl)-5-oxo-pyrrolidine-2-carboxylic acid tert-butyl ester To a stirred solution of (S)-5-oxo-pyrrolidine-2-carboxylic acid tert-butyl ester (740 mg, 4 mmol) in N,N-dimethylformamide (5 mL) sodium hydride (180 mg of 60% dispersion in mineral oil, 4.5 mmol) is added at room temperature. After 10 minutes, 3-chloro-2-fluoro-5-trifluoromethylpyridine (1 mL, 8 mmol) is added and the suspension stirred at room temperature. After 3 h the reaction mixture is treated with saturated ammonium chloride solution (150 mL), extracted with dichloromethane (2×100 mL). Combined extracts washed with brine (2×50 mL), water, dried over anhydrous Na₂SO₄ and solvent removed in vacuo. The crude is purified by chromatography over silica gel eluting with hexanes/ethyl acetate to give the title compound, ESI m/z 365 [M+H]+.

Step 2: Synthesis of (S)-1-(3-chloro-5-trifluoromethyl-pyridin-2-yl)-5-oxo-pyrrolidine-2-carboxylic acid (S)-1-(3-Chloro-5-trifluoromethyl-pyridin-2-yl)-5-oxo-pyrrolidine-2-carboxylic acid tert-butyl ester (760 mg, 2.1 mmol) is treated with pre-cooled trifluoroacetic acid (5 mL). The clear solution is kept at room temperature for 1 h. Trifluoroacetic acid is evaporated in vacuo and the concentrate is treated with ice/water. Precipitated white solid is filtered, washed with water to give the title compound, ESI m/z 309 [M+H]+.

Step 3: Synthesis of (S)-1-(3-chloro-5-trifluoromethyl-pyridin-2-yl)-5-oxo-pyrrolidine-2-carboxylic acid (5-tert-butyl-isoxazol-3-yl)-amide The title compound, ESI m/z 431 [M+H]+ is prepared utilizing a procedure similar to the one described in Example 16, step 2.

Examples listed in Table III Method 21 are prepared according to a similar procedure.

EXAMPLE 21

Synthesis of (S)-1-(4-chloro-benzenesulfonyl)-pyrrolidine-2-carboxylic acid (5-tert-butyl-isoxazol-3-yl)-amide

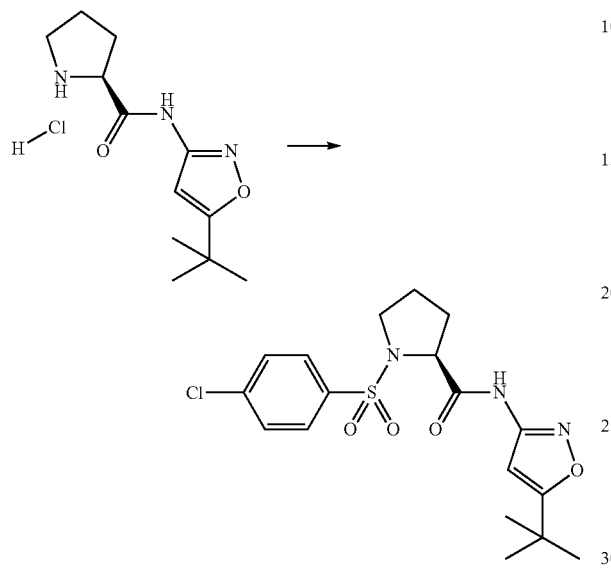

To a solution of (S)-pyrrolidine-2-carboxylic acid (5-tert-butyl-isoxazol-3-yl)-amide; hydrochloride (0.150 g; 0.580 mmol) in N,N-dimethylformamide (2 mL) is added 4-chlorophenylsulfonyl chloride (0.122 g; 0.580 mmol) and triethylamine (0.243 mL; 1.740 mmol). The mixture is stirred at room temperature overnight. After this time, the mixture is diluted with water and extracted with ethyl acetate. The combined organics are washed with aqueous saturated sodium bicarbonate solution, 1N hydrochloric acid, and brine, dried (Na$_2$SO$_4$), filtered and concentrated in vacuo. The crude material is purified by preparative HPLC to afford title compound. ESI m/z 412 [M+NH$_4$]+

Compounds found in Table III Method 22 are made in a similar manner.

EXAMPLE 22

Synthesis of (2S,4R)-4-hydroxy-1-(tetrahydro-pyran-4-ylmethyl)-pyrrolidine-2-carboxylic acid [4-(4-chloro-phenyl)-thiazol-2-yl]-amide

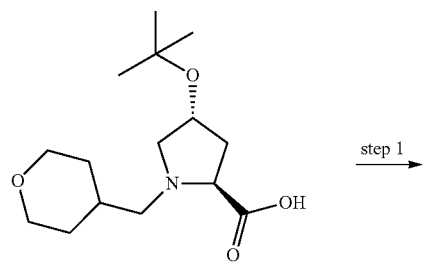

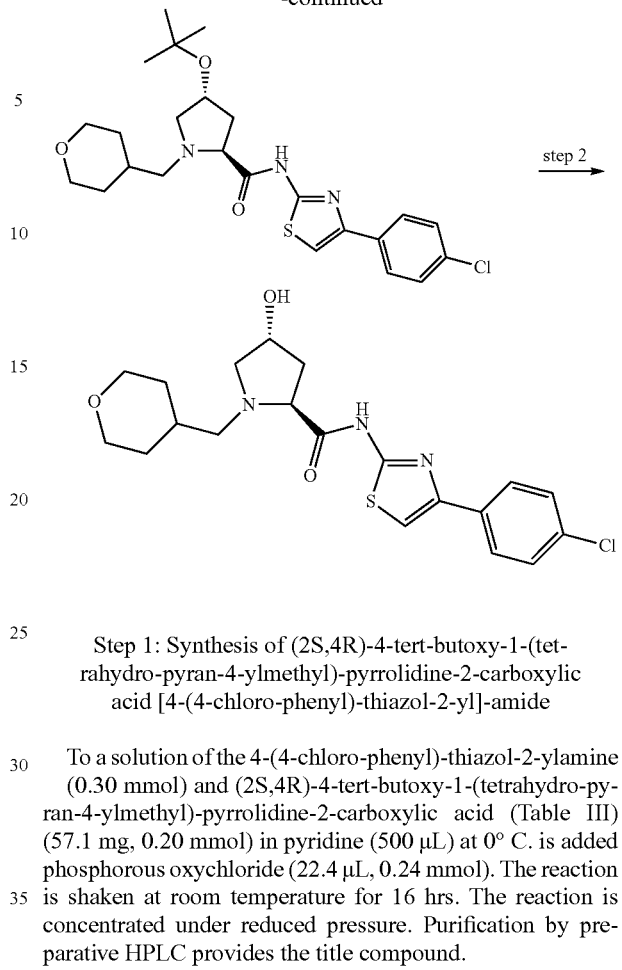

Step 1: Synthesis of (2S,4R)-4-tert-butoxy-1-(tetrahydro-pyran-4-ylmethyl)-pyrrolidine-2-carboxylic acid [4-(4-chloro-phenyl)-thiazol-2-yl]-amide To a solution of the 4-(4-chloro-phenyl)-thiazol-2-ylamine (0.30 mmol) and (2S,4R)-4-tert-butoxy-1-(tetrahydro-pyran-4-ylmethyl)-pyrrolidine-2-carboxylic acid (Table III) (57.1 mg, 0.20 mmol) in pyridine (500 μL) at 0° C. is added phosphorous oxychloride (22.4 μL, 0.24 mmol). The reaction is shaken at room temperature for 16 hrs. The reaction is concentrated under reduced pressure. Purification by preparative HPLC provides the title compound.

Step 2: Synthesis of (2S,4R)-4-hydroxy-1-(tetrahydro-pyran-4-ylmethyl)-pyrrolidine-2-carboxylic acid [4-(4-chloro-phenyl)-thiazol-2-yl]-amide To the product obtained from the HPLC is added trifluoroacetic acid (500 μL). The reaction is shaken at room temperature for 2 hrs then it is concentrated under reduced pressure. Purification by preparative HPLC provides title compound. ESI m/z 422 [M+H]+; 420 [M−H]−

Compounds in Table III Method 23 were made in a similar manner.

EXAMPLE 23

Synthesis of (2S,4S)-4-hydroxy-1-(tetrahydro-pyran-4-ylmethyl)-pyrrolidine-2-carboxylic acid (3-fluoro-4-trifluoromethyl-phenyl)-amide

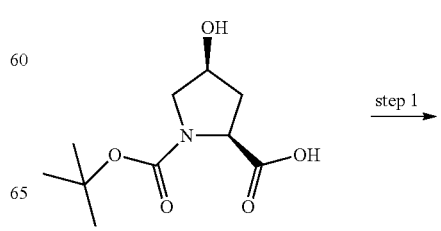

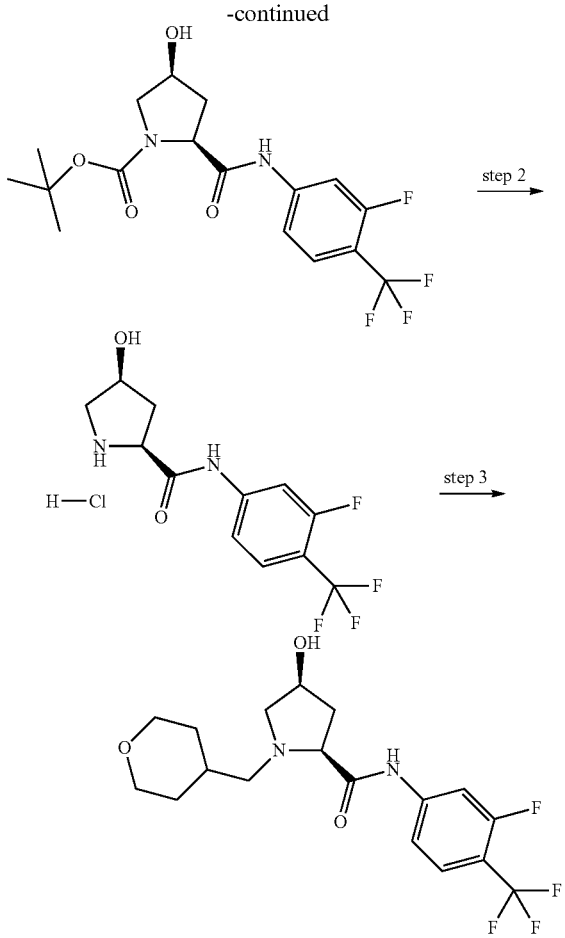

Step 1: Synthesis of (2S,4S)-2-(3-fluoro-4-trifluoromethyl-phenylcarbamoyl)-4-hydroxy-pyrrolidine-1-carboxylic acid tert-butyl ester To a solution of the 3-fluoro-4-trifluoromethyl-phenylamine (0.30 mmol) and (2S,4S)-4-hydroxy-pyrrolidine-1,2-dicarboxylic acid 1-tert-butyl ester (69.4 mg, 0.30 mmol) in toluene (600 μL) at 0° C. is added a 1.13 M solution of 2-ethoxy-1-ethoxycarbonyl-1,2-dihydroquinoline (400 g/L, 0.45 mmol). The reaction is shaken at room temperature for 16 hrs. The reaction is concentrated under reduced pressure. Purification by preparative HPLC provides title compound.

Step 2: Synthesis of (2S,4S)-4-hydroxy-pyrrolidine-2-carboxylic acid (3-fluoro-4-trifluoromethyl-phenyl)-amide; hydrochloride To a solution of (2S,4S)-2-(3-fluoro-4-trifluoromethyl-phenylcarbamoyl)-4-hydroxy-pyrrolidine-1-carboxylic acid tert-butyl ester obtained from the HPLC in dichloromethane (1.0 mL) is added 4.0 M hydrogen chloride in dixoane (500 μL). The reaction is shaken at room temperature for 16 hrs then it is concentrated under reduced pressure to afford title compound.

Step 3: Synthesis of (2S,4S)-4-hydroxy-1-(tetrahydro-pyran-4-ylmethyl)-pyrrolidine-2-carboxylic acid (3-fluoro-4-trifluoromethyl-phenyl)-amide Dimethyl formamide is added to the (2S,4S)-4-hydroxy-pyrrolidine-2-carboxylic acid (3-fluoro-4-trifluoromethyl-phenyl)-amide; hydrochloride to give ~0.1 M solution. To the solution are added acetic acid (53 μL) and a 0.5 M solution of the tetrahydropyranyl-4-carboxaldehyde in dimethyl formamide (2.0 equiv.). The reaction was shaken for 4 hrs. To the reaction is added a 0.75 M solution of sodium cyanoborohydride (3.0 equiv.). The reaction is shaken for 16 hrs. Water (100 μL) is added and the reaction is concentrated under reduced pressure. Purification by preparative HPLC provides the title compound. ESI m/z 391 [M+H]+; 389 [M−H]−.

Compounds in Table III Method 24 are made in a similar manner.

EXAMPLE 24

Synthesis of (2S,4R)-4-hydroxy-1-(5-trifluoromethyl-pyridin-2-yl)-pyrrolidine-2-carboxylic acid cyclohexylmethyl-amide

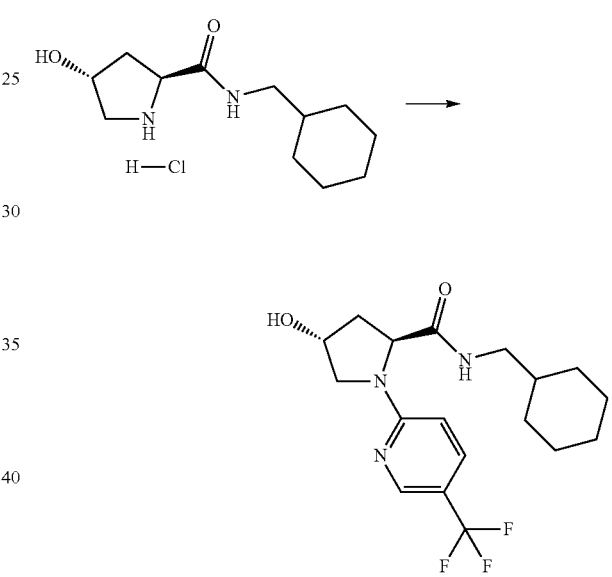

A mixture of (2S,4R)-4-hydroxy-pyrrolidine-2-carboxylic acid cyclohexylmethyl-amide; hydrochloride (75 mg, 0.285 mmol), dichlorobis(tri-o-tolylphosphine) palladium (II) (11 mg, 0.014 mmol), copper iodide (2.7 mg, 0.014 mmol), potassium carbonate (78.8 mg, 0.57 mmol), tetraethylammonium bromide (10.2 mg, 0.048 mmol) and 2-bromo-5-trifluoromethylpyridine (64.4 mg, 0.285 mmol) is evacuated and filled with Argon three cycles. Triethylamine (0.16 mL, 1.14 mmol), N,N-dimethylformamide (1 mL) and water (0.1 mL) are added and the reaction mixture is heated to 100° C. under Argon atmosphere for 22 h. The reaction is diluted with ethyl acetate and concentrated. The residue is purified by flash chromatography on silica eluting with methanol/dichloromethane which provides the title compound, m/z 372 [M+H+].

Compounds in Table III Method 25 are prepared in a similar manner.

EXAMPLE 25

Synthesis of (2S,4R)-1-(4,4-difluoro-cyclohexanecarbonyl)-4-hydroxy-pyrrolidine-2-carboxylic acid (tetrahydro-pyran-4-ylmethyl)-amide

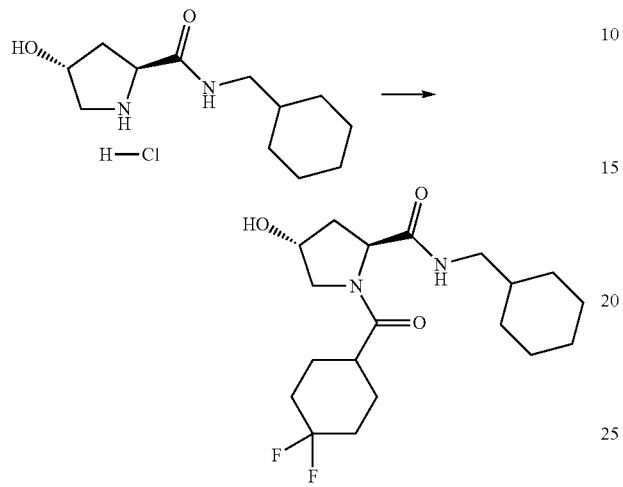

Amide bond coupling method described in Example 1, coupling method J is used to synthesize the title compound. ESI m/z 373 [M+H$^+$].

Compounds in Table III Method 26 are prepared in a similar manner.

EXAMPLE 26

Synthesis of (2S,4R)-4-hydroxy-1-(tetrahydro-pyran-4-ylmethyl)-pyrrolidine-2-carboxylic acid (5-tert-butyl-isoxazol-3-yl)-amide To a solution of (2S,4R)-4-hydroxy-pyrrolidine-2-carboxylic acid (5-tert-butyl-isoxazol-3-yl)-amide; hydrochloride (100 mg, 0.338 mmol) in N,N-dimethylformamide (2 mL) is added tetrahydro-pyran-4-carbaldehyde (77 mg, 0.676 mmol) and acetic acid (0.073 mL, 1.28 mmol). The reaction is stirred at room temperature for 45 minutes before adding sodium cyanoborohydride (42.5 mg, 0.676 mmol). The reaction is stirred at room temperature overnight. The reaction is quenched with saturated sodium bicarbonate aqueous solution and extracted with ethyl acetate twice. The organics are combined and washed with brine, dried over Na$_2$SO$_4$, filtered and concentrated under reduced pressure. Purification by chromatography on silica eluting with methanol/dichloromethane provides the title compound with low purity and further purification by pre-HPLC yields pure title compound, m/z 352 [M+H$^+$].

Compounds in Table III Method 27 are prepared in a similar manner.

EXAMPLE 27

Synthesis of (S)-1-(4,4-difluoro-cyclohexanecarbonyl)-4,4-difluoro-pyrrolidine-2-carboxylic acid (5-tert-butyl-isoxazol-3-yl)-amide

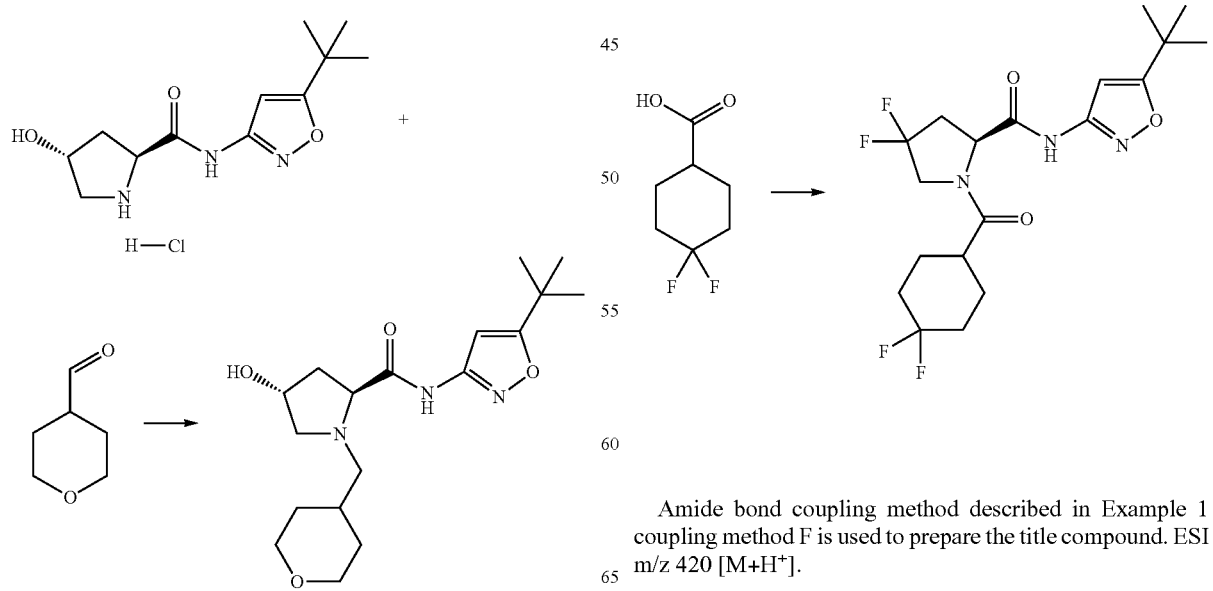

Amide bond coupling method described in Example 1 coupling method F is used to prepare the title compound. ESI m/z 420 [M+H$^+$].

Compounds in Table III Method 28 are prepared in a similar manner.

EXAMPLE 28

Synthesis of (S)-1-(3-chloro-5-trifluoromethyl-pyridin-2-yl)-4-oxo-pyrrolidine-2-carboxylic acid (5-tert-butyl-isoxazol-3-yl)-amide

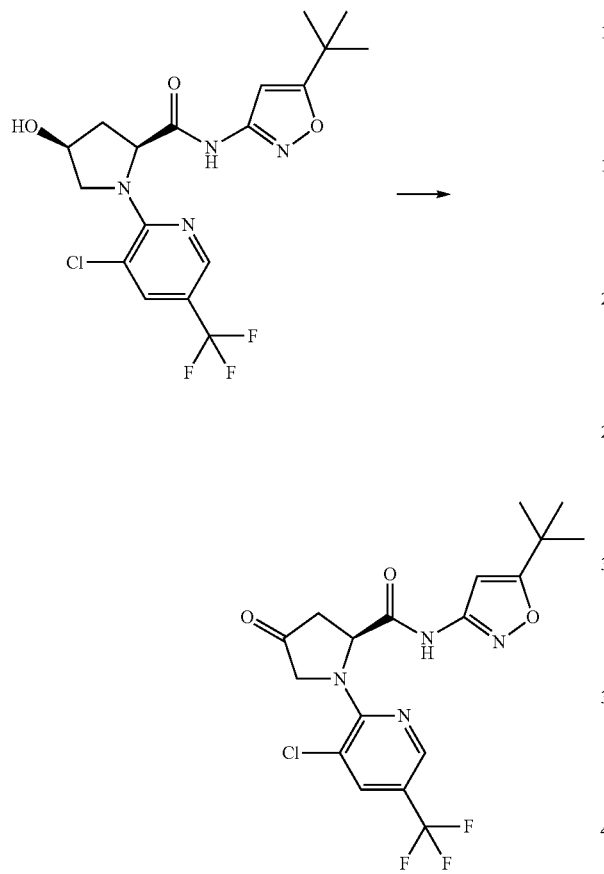

To a solution of (2S,4S)-1-(3-chloro-5-trifluoromethyl-pyridin-2-yl)-4-hydroxy-pyrrolidine-2-carboxylic acid (5-tert-butyl-isoxazol-3-yl)-amide (183 mg, 0.423 mmol) in dimethyl sulfoxide (5 mL) is added triethylamine (0.118 mL, 0.846 mmol) and sulfur trioxide pyridine complex (115 mg, 0.72 mmol). The reaction is stirred at room temperature for 4 hours. More triethylamine (0.18 mL, 1.27 mmol) and sulfur trioxide pyridine complex (155 mg, 0.97 mmol) are added to the reaction mixture and the stirring is continued for another 2 hours. The reaction is quenched with 1N hydrochloric acid aqueous solution and the solid precipitated out of the solution is filtered and dissolved in dichloromethane and washed with saturated sodium bicarbonate aqueous solution and brine, dried over $Na_2SO_4$, filtered and concentrated under reduced pressure. Purification by chromatography on silica eluting with ethyl acetate/hexanes and further purification using pre LC-MS provides the title compound, ESI m/z 431 [M+H$^+$].

Compounds in Table III Method 29 are prepared in a similar manner.

EXAMPLE 29

Synthesis of (2S,4R)-1-(4-chloro-phenyl)-4-hydroxy-pyrrolidine-2-carboxylic acid (5-tert-butyl-isoxazol-3-yl)-amide

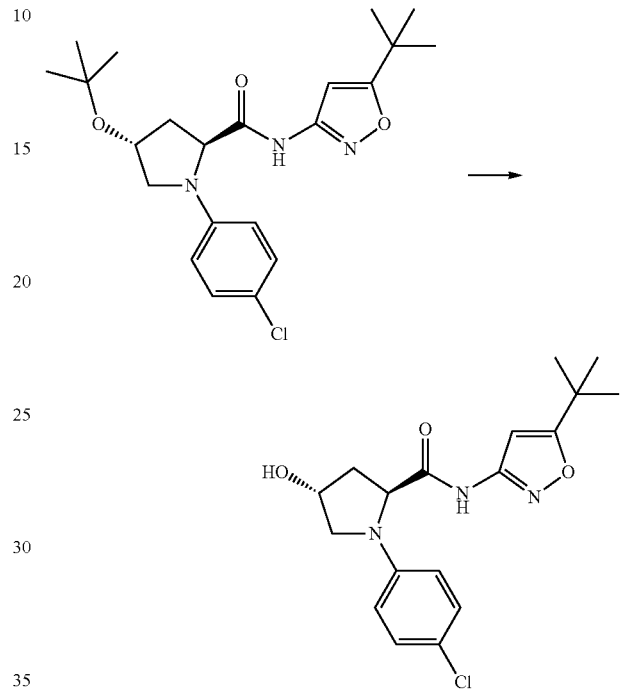

(2S,4R)-4-tert-Butoxy-1-(4-chloro-phenyl)-pyrrolidine-2-carboxylic acid (5-tert-butyl-isoxazol-3-yl)-amide (45 mg, 0.107 mmol) is dissolved in trifluoroacetic acid (0.5 mL, 6.49 mmol) at room temperature and the reaction is stirred at room temperature for 1 hour. The reaction is concentrated under reduced pressure and purification by chromatography on silica eluting with ethyl acetate/hexanes provides the title compound. ESI m/z 364 [M+H$^+$].

Compounds in Table III Method 30 are prepared in a similar manner.

EXAMPLE 30

Synthesis of (2S,4R)-4-hydroxy-1-(2-morpholin-4-yl-pyrimidin-4-yl)-pyrrolidine-2-carboxylic acid (5-tert-butyl-isoxazol-3-yl)-amide

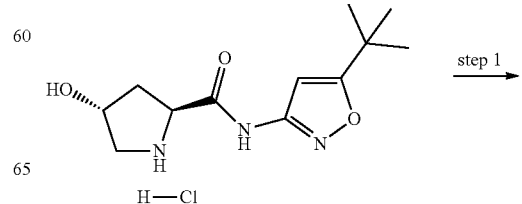
step 1

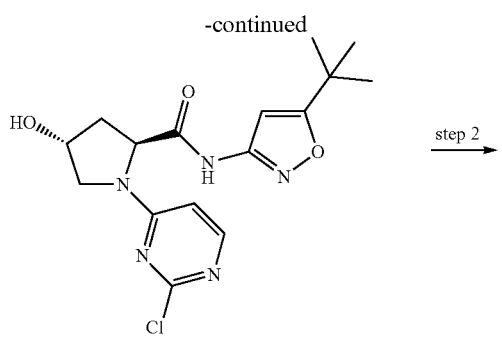

chromatography on silica eluting with methanol/dichloromethane provides the title compound. ESI m/z 417 [M+H⁺].

Compounds in Table III Method 31 are prepared in a similar manner.

EXAMPLE 31

Synthesis of (2S,4R)-4-hydroxy-1-pyrimidin-4-yl-pyrrolidine-2-carboxylic acid (5-tert-butyl-isoxazol-3-yl)-amide

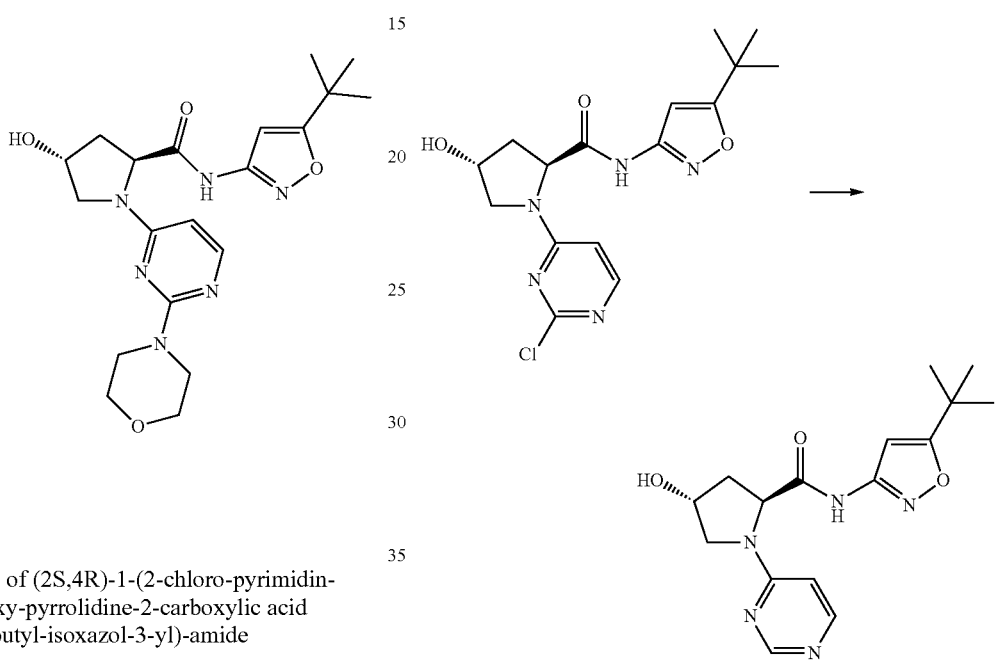

Step 1: Synthesis of (2S,4R)-1-(2-chloro-pyrimidin-4-yl)-4-hydroxy-pyrrolidine-2-carboxylic acid (5-tert-butyl-isoxazol-3-yl)-amide 2,4-Dichloropyrimidine (33.2 mg, 0.223 mmol) is added to the solution of (2S,4R)-4-Hydroxy-pyrrolidine-2-carboxylic acid (5-tert-butyl-isoxazol-3-yl)-amide; hydrochloride (66 mg, 0.223 mmol) and diisopropylethylamine (0.078 mL, 0.446 mmol) in ethanol (2 mL). The reaction is stirred at room temperature overnight. The reaction is quenched with saturated sodium bicarbonate aqueous solution and extracted with ethyl acetate twice. The organics are combined and washed with brine, dried over Na₂SO₄, filtered and concentrated under reduced pressure. Purification by chromatography on silica eluting with methanol/dichloromethane provides the title compound. ESI m/z 366 [M+H⁺].

Step 2: Synthesis of (2S,4R)-4-hydroxy-1-(2-morpholin-4-yl-pyrimidin-4-yl)-pyrrolidine-2-carboxylic acid (5-tert-butyl-isoxazol-3-yl)-amide Morpholine (0.01 mL, 0.115 mmol) is added to a solution of (2S,4R)-1-(2-chloro-pyrimidin-4-yl)-4-hydroxy-pyrrolidine-2-carboxylic acid (5-tert-butyl-isoxazol-3-yl)-amide (42 mg, 0.115 mmol) and diisopropylethylamine (0.02 mL, 0.115 mol). The reaction is stirred at 60° C. overnight. More morpholine (0.01 mL, 0.115 mmol) is added and the reaction is stirred at 80° C. for 3.5 hours. The reaction is diluted with water and extracted with ethyl acetate twice. The organics are combined and washed with brine, dried over Na₂SO₄, filtered and concentrated under reduced pressure. Purification by 10% Pd/C (40 mg) is added to a solution of (2S,4R)-1-(2-chloro-pyrimidin-4-yl)-4-hydroxy-pyrrolidine-2-carboxylic acid (5-tert-butyl-isoxazol-3-yl)-amide (100 mg, 0.273 mmol) in ethanol (2 mL). The reaction is stirred under hydrogen atmosphere overnight at room temperature. The reaction is filtered through Celite® and the filtrate is concentrated. Purification by pre-HPLC eluting with 4-45% acetonitrile/water provides the title compound. ESI m/z 332 [M+H⁺].

Compounds found in Table III Method 32 are prepared in a similar manner.

EXAMPLE 32

Synthesis of (2R,4R)-4-hydroxy-1-(5-trifluoromethyl-pyridin-2-yl)-pyrrolidine-2-carboxylic acid (5-trifluoromethyl-pyridin-2-yl)-amide

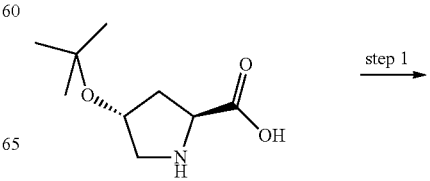

-continued

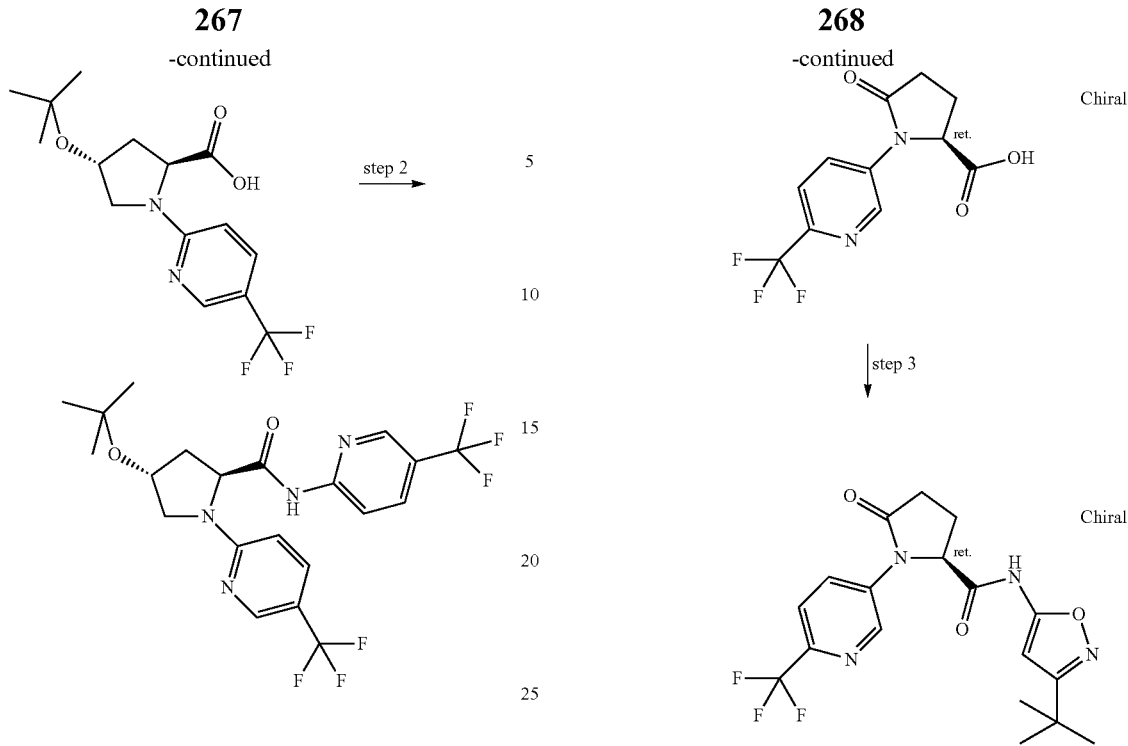

Synthesis of (2S,4R)-4-tert-butoxy-1-(5-trifluoromethyl-pyridin-2-yl)-pyrrolidine-2-carboxylic acid Title compound is prepared using procedure described in Example 26. ESI m/z 323 [M+H]+

Step 2: Synthesis of (2R,4R)-4-hydroxy-1-(5-trifluoromethyl-pyridin-2-yl)-pyrrolidine-2-carboxylic acid (5-trifluoromethyl-pyridin-2-yl)-amide Title compound is prepared using coupling method E described in Example 1. ESI m/z 421 [M+H]+

Compounds found in Table III Method 33 are prepared in this manner.

EXAMPLE 33

Synthesis of 5-oxo-1-(6-trifluoromethyl-pyridin-3-yl)-pyrrolidine-2-carboxylic acid (3-tert-butyl-isoxazol-5-yl)-amide

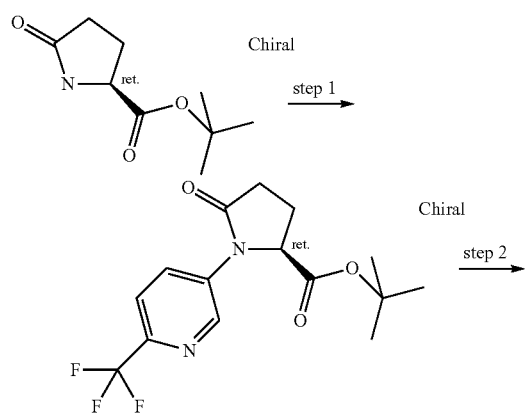

-continued

Step 1: Synthesis of (S)-5-Oxo-1-(6-trifluoromethyl-pyridin-3-yl)-pyrrolidine-2-carboxylic acid tert-butyl ester A solution of cesium carbonate (1.539 g; 4.725 mmol), copper bromide (0.032 g; 0.225 mmol) and ethyl-2-oxocyclohexanecarboxylate (0.072; 0.45 mmol) in anhydrous dimethyl sulfoxide (1.25 mL) is degassed with argon and stirred 30 minutes. To this solution is added (S)-5-oxo-pyrrolidine-2-carboxylic acid tert-butyl ester (0.5 g; 2.699 mmol) and 5-bromo-2-trifluoromethylpyridine (0.508 g; 2.25 mmol) in 1 mL anhydrous dimethyl sulfoxide. The mixture is heated in a sealed tube to 60° C. in an oil bath and stirred overnight. The reaction mixture is cooled to room temperature, filtered through Celite® and washed with ethyl acetate. The combined organics are washed with brine, dried over sodium sulfate and concentrated under reduced pressure. ESI m/z 331 [M+H]+

Step 2: Synthesis of (S)-5-Oxo-1-(6-trifluoromethyl-pyridin-3-yl)-pyrrolidine-2-carboxylic acid Similar to Example 17, Step 2. ESI m/z 275 [M+H]+

Step 3: Synthesis of 5-oxo-1-(6-trifluoromethyl-pyridin-3-yl)-pyrrolidine-2-carboxylic acid (3-tert-butyl-isoxazol-5-yl)-amide Coupling method A is used. ESI m/z 331 [M+H]+

Compounds in Table III Method 36 are made using a similar procedure.

EXAMPLE 34

Synthesis of (S)-1-(6-Fluoro-5-trifluoromethyl-pyridin-2-yl)-5-oxo-pyrrolidine-2-carboxylic acid (3-tert-butyl-isoxazol-5-yl)-amide

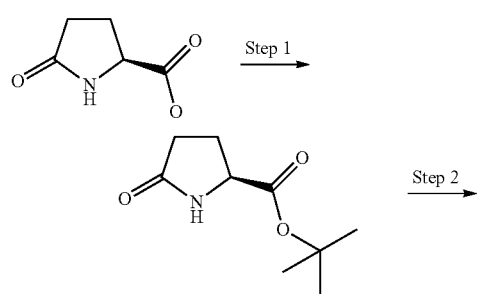

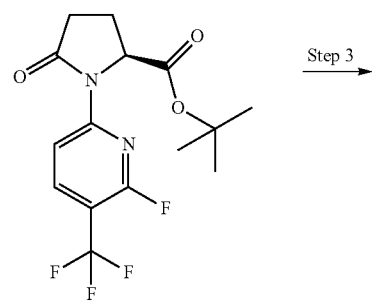

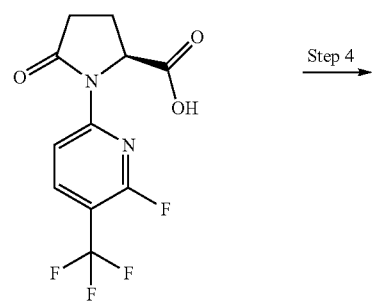

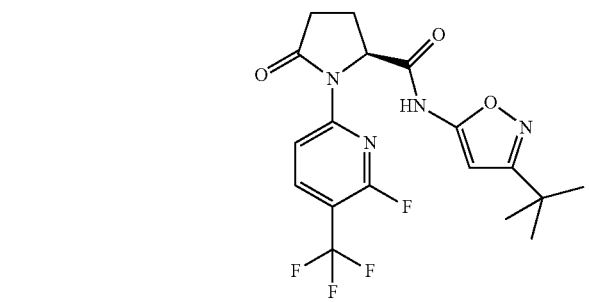

Experimental sequence same as Example 17 except coupling method A is used. ESI m/z 415 [M+H]+

Compounds in Table III Method 37 are made using a similar procedure.

EXAMPLE 35

Synthesis of (S)-5-oxo-1-(4-trifluoromethyl-phenyl)-pyrrolidine-2-carboxylic acid [3-(2-hydroxy-1,1-dimethyl-ethyl)-isoxazol-5-yl]-amide

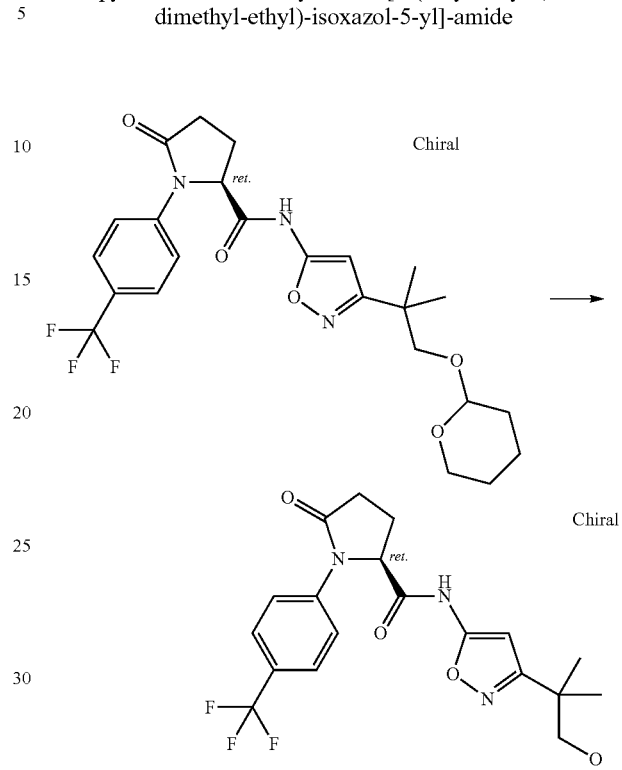

(S)-5-Oxo-1-(4-trifluoromethyl-phenyl)-pyrrolidine-2-carboxylic acid {3-[1,1-dimethyl-2-(tetrahydro-pyran-2-yloxy)-ethyl]-isoxazol-5-yl}-amide is synthesized in a similar manner as Example 16, Method 7. (S)-5-Oxo-1-(4-trifluoromethyl-phenyl)-pyrrolidine-2-carboxylic acid {3-[1,1-dimethyl-2-(tetrahydro-pyran-2-yloxy)-ethyl]-isoxazol-5-yl}-amide (0.546 g; 1.103 mmol) is dissolved in 2 mL ethanol and pyridinium p-toluenesulfonate (0.055 g; 0.221 mmol) is added. The mixture is heated at 55° C. for 4 h and then concentrated and purified by reverse phase HPLC to afford title compound. ESI m/z 412 [M+H]+

Compounds in Table III Method 38 are made using a similar procedure.

EXAMPLE 36

Synthesis of 1-(4-Hydroxymethyl-phenyl)-5-oxo-pyrrolidine-2-carboxylic acid (5-tert-butyl-isoxazol-3-yl)-amide

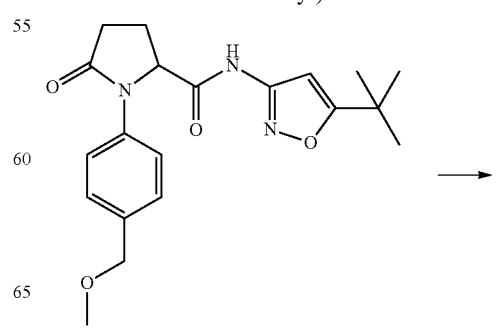

-continued

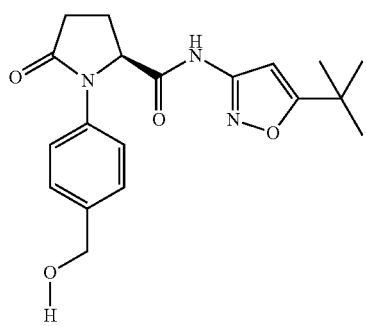

1-(4-Methoxymethyl-phenyl)-5-oxo-pyrrolidine-2-carboxylic acid (5-tert-butyl-isoxazol-3-yl)-amide (0.130 g; 0.350 mmol) is diluted with ethanethiol (1.988 mL; 26.880 mmol) and cooled to 0° C. To this solution is added aluminum trichloride (0.793 g; 5.950 mmol). The solution is stirred for 3 hours, slowly warming to room temperature. The solution is added dropwise to a solution of water containing concentrated hydrochloric acid. The aqueous is extracted with ethyl acetate. The organics are combined and washed with brine, dried over sodium sulfate, filtered and concentrated. Purification by preparative HPLC afforded title compound. ESI m/z 358 [M+H]+

Compounds in Table III Method 39 are made using a similar procedure.

EXAMPLE 37

Synthesis of (S)-5-Oxo-1-(4-trifluoromethyl-phenyl)-pyrrolidine-2-carboxylic acid [5-(2-hydroxy-1,1-dimethyl-ethyl)-isoxazol-3-yl]-amide

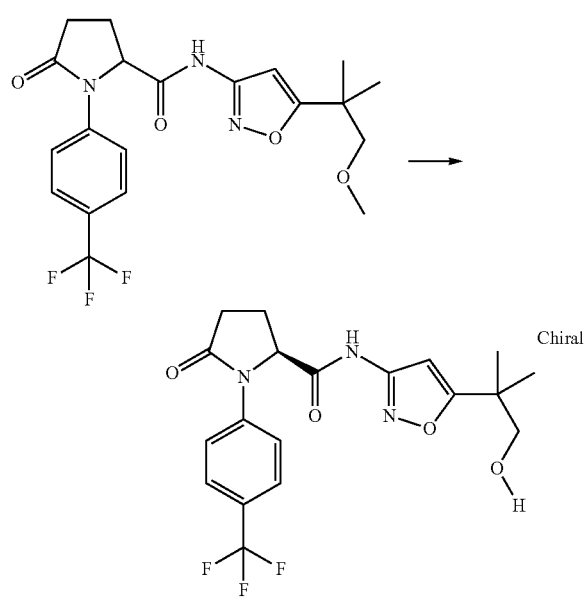

Reference: Chem. Bull. Pharm. 31, (11) 4178-4180.
5-Oxo-1-(4-trifluoromethyl-phenyl)-pyrrolidine-2-carboxylic acid [5-(2-methoxy-1,1-dimethyl-ethyl)-isoxazol-3-yl]-amide (0.025 g; 0.059 mmol) and sodium iodide (0.088 g; 0.590 mmol) are diluted with dichloromethane (1 mL) and acetonitrile (2 mL; 0.059 mmol) and the solution is cooled to 0° C. Aluminum trichloride (0.079 g; 0.590 mmol) is added and the solution stirred for 3 hours, slowly warming to room temperature. The mixture is diluted with water and extracted with dichloromethane. The organics are combined and washed with aqueous sodium thiosulfate. The organics are concentrated and purified by reverse phase HPLC to afford title compound. ESI m/z 412 [M+H]+

Compounds in Table III Method 40 are made using a similar procedure.

EXAMPLE 38

Synthesis of (S)-1-(4-Chloro-phenyl)-pyrrolidine-2-carboxylic acid [3-(2-hydroxy-1,1-dimethyl-ethyl)-isoxazol-5-yl]-amide

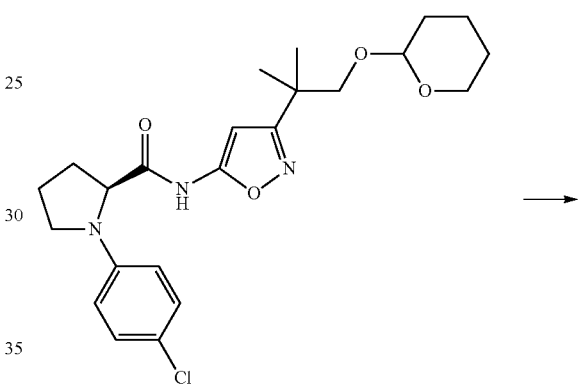

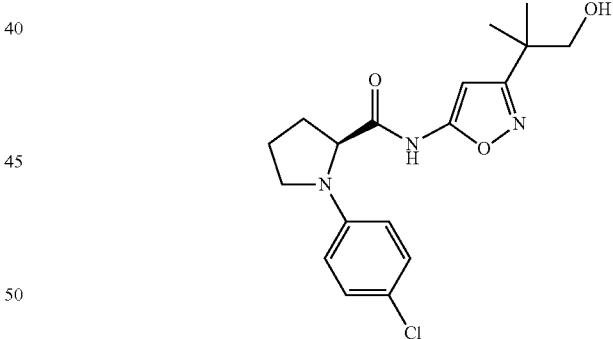

To a suspension of (S)-1-(4-Chloro-phenyl)-pyrrolidine-2-carboxylic acid {3-[1,1-dimethyl-2-(tetrahydro-pyran-2-yloxy)-ethyl]-isoxazol-5-yl}-amide (130 mg, 0.29 mmol) in the mixture of methanol in water (10:1, 3 mL) is added p-toluenesulfonic acid monohydrate (10 mg, 0.053 mmol) and acetonitrile (1 mL). The reaction mixture is stirred at room temperature for 18 hours. After this time, the reaction mixture is concentrated in vacuo. Purification by flash chromatography on silica gel using ethyl acetate/hexanes provides the title compound, ESI m/z 364 [M+H⁺].

Compounds in Table III Method 41 are made using a similar procedure.

EXAMPLE 39

Synthesis of (S)-1-(5-fluoro-pyridin-2-yl)-5-oxo-pyrrolidine-2-carboxylic acid (3-tert-butyl-isoxazol-5-yl)-amide

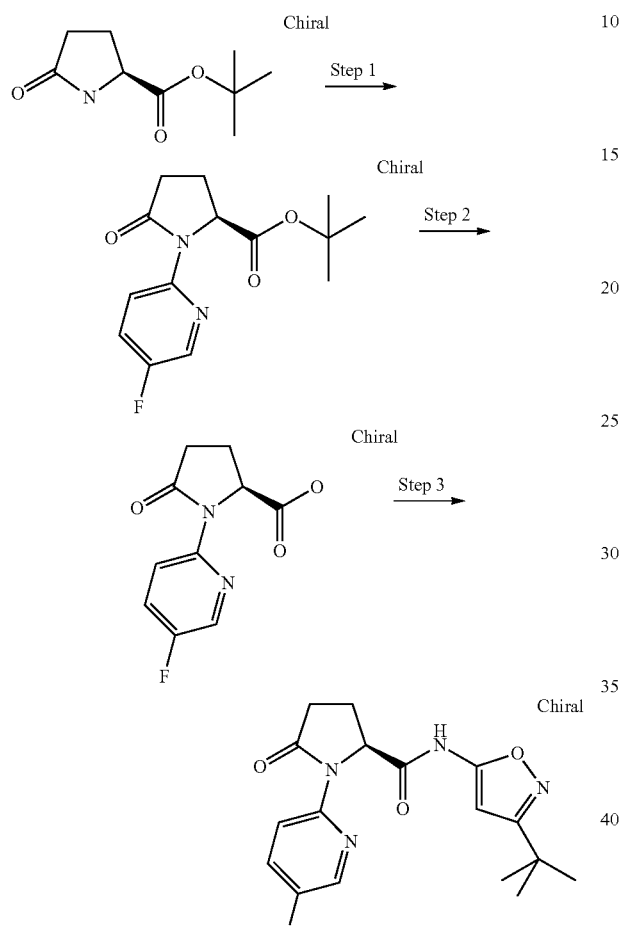

Step 1: Synthesis of (S)-1-(5-fluoro-pyridin-2-yl)-5-oxo-pyrrolidine-2-carboxylic acid tert-butyl ester To a pressure tube containing (S)-5-oxo-pyrrolidine-2-carboxylic acid tert-butyl ester (0.5 g, 2.699 mmol), 2-bromo-5-fluoropyridine (0.57 g, 3.239 mmol), cesium carbonate (1.231 g, 3.779 mmol), Xantphos (0.156 g, 0.27 mmol), and tris (dibenzylideneacetone)palladium (0) (0.247 g, 0.27 mmol) is added 13.5 mL degassed anhydrous 1,4-dioxane. The mixture is heated at 120° C. under an atmosphere of Argon overnight. The solution is cooled to room temperature, filtered through Celite®, and concentrated under reduced pressure. The crude material is purified by flash chromatography eluting product with 305 ethyl acetate/heptanes. The product fractions are pooled and concentrated under reduced pressure to afford 45 mg of title compound. Yield 6%. ESI m/z 225=MH+

Step 2: Synthesis of (S)-1-(5-Fluoro-pyridin-2-yl)-5-oxo-pyrrolidine-2-carboxylic acid Conditions are similar to those used for Example 20 Step 2. ESI m/z 225=MH+

Step 3: Synthesis of (S)-1-(5-fluoro-pyridin-2-yl)-5-oxo-pyrrolidine-2-carboxylic acid (3-tert-butyl-isoxazol-5-yl)-amide Conditions used are similar to those used in Example 1, Coupling method A to afford 2 mg of title compound. Yield 3%. ESI m/z 347=MH+

Compounds in Table III Method 42 are made using a similar procedure.

EXAMPLE 40

Synthesis of (S)-1-(5-chloro-pyrimidin-2-yl)-5-oxo-pyrrolidine-2-carboxylic acid (3-tert-butyl-isoxazol-5-yl)-amide

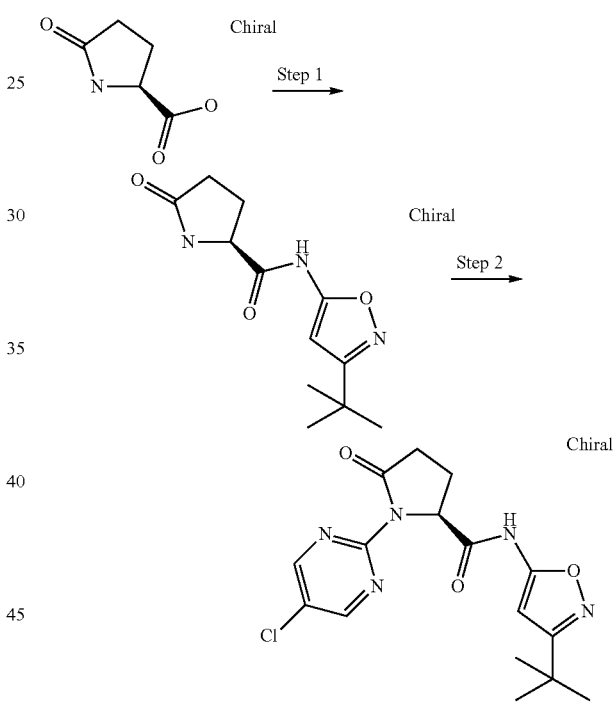

Step 1: Synthesis of (S)-5-oxo-pyrrolidine-2-carboxylic acid (3-tert-butyl-isoxazol-5-yl)-amide To solution of the (S)-5-oxo-pyrrolidine-2-carboxylic acid (6 g, 46.47 mmol) in tetrahydrofuran (50 mL) is added thionyl chloride (6.75 ml, 92.94 mmol) and stirred at room temperature for 2-3 hours. The solvent is removed under reduced pressure and the residue is dissolved in tetrahydrofuran (20 mL) and added dropwise to a solution of 3-tert-butyl-isoxazol-5-ylamine (6.514 g, 46.47 mmol) and diisopropylamine (24.28 ml, 139.41 mmol) in tetrahydrofuran (50 mL) at room temperature. The reaction is stirred overnight at room temperature then diluted with dichloromethane and washed sequentially with water and saturated brine solution. The organics are dried over sodium sulfate, filtered and solvents removed under vacuum. The crude residue is purified by flash column chromatography eluting with 5-10% methanol/dichloromethane. The product rich fractions are pooled and evaporated to afford 3.02 g title compound, 32.7% yield. ESI m/z 252=MH+.

Step 2: Synthesis of (S)-1-(5-chloro-pyrimidin-2-yl)-5-oxo-pyrrolidine-2-carboxylic acid (3-tert-butyl-isoxazol-5-yl)-amide Conditions used are similar to Example 39, Step 1. Yield 8%. ESI m/z 364=MH+

Compounds in Table III Method 43 are made using a similar procedure.

EXAMPLE 41

Synthesis of (2S,4R)-4-tert-Butoxy-1-(4-chloro-phenyl)-pyrrolidine-2-carboxylic acid [3-(2-hydroxy-1,1-dimethyl-ethyl)-isoxazol-5-yl]-amide

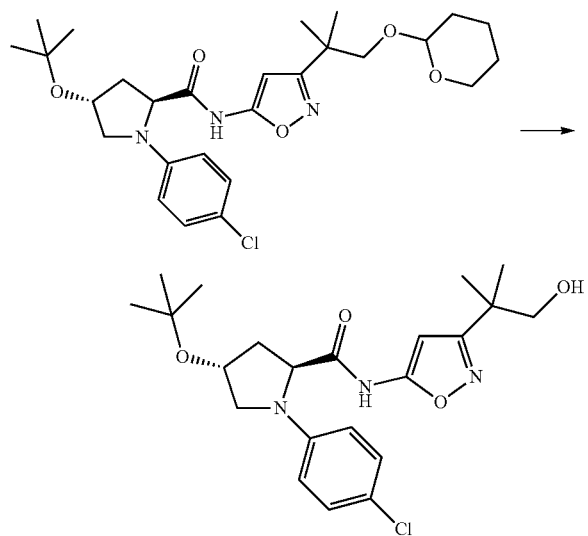

A solution of (2S,4R)-4-tert-Butoxy-1-(4-chloro-phenyl)-pyrrolidine-2-carboxylic acid {3-[1,1-dimethyl-2-(tetrahydro-pyran-2-yloxy)-ethyl]-isoxazol-5-yl}-amide (123 mg, 0.237 mmol) and pyridinium p-toluenesulfonate (20 mg, 0.047 mmol) in ethanol (2 mL) is heated at 55° C. for 42 hours. After this time, the reaction mixture is concentrated in vacuo. Purification by flash chromatography on silica gel using ethyl acetate/hexanes provides the title compound, m/z 436 [M+H⁺].

EXAMPLE 42

Synthesis of (S)-1-(5-Fluoro-6-methyl-pyridin-2-yl)-5-oxo-pyrrolidine-2-carboxylic acid (3-tert-butyl-isoxazol-5-yl)amide

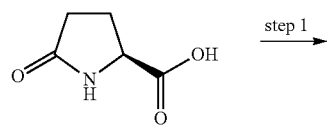

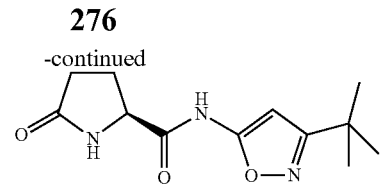

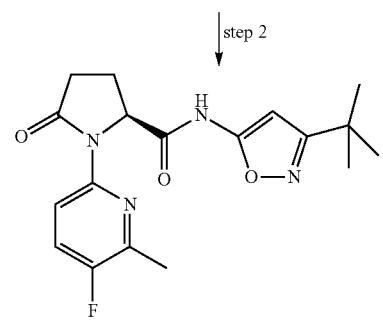

Step 1: Synthesis of (S)-5-oxo-pyrrolidine-2-carboxylic acid (3-tert-butyl-isoxazol-5-yl)-amide Conditions used are similar to Example 40, Step 1.

Step 2 Synthesis of (S)-1-(5-fluoro-6-methyl-pyridin-2-yl)-5-oxo-pyrrolidine-2-carboxylic acid (3-tert-butyl-isoxazol-5-yl)amide (S)-5-Oxo-pyrrolidine-2-carboxylic acid (3-tert-butyl-isoxazol-5-yl)-amide (300 mg, 1.19 mmol), tris(dibenzylideneacteone)dipalladium (0) (32.80 mg, 0.036 mmol), Xantphos ® (62.20 mg, 0.011 mmol), caesium carbonate (654.16 mg, 2.01 mmol) and 6-bromo-3-fluoro-2-methylpyridine (226.90, 1.20 mmol) are charged to a vessel, diluted with dioxane (anhydrous, 3 ml) and heated to 100° C. overnight. On completion, the reaction is diluted with ethyl acetate and partitioned between water. The organic phase is separated, dried over sodium sulphate and the solvents removed under vacuum. The crude residue is purified by flash column chromatography eluting with a gradient solution of heptane/ethyl acetate 0-50% to isolate 117 mg of title compound as a white solid, yield 27%. ESI m/z 361=MH+

Compounds found in Table III Method 44 are prepared in this manner.

EXAMPLE 43

Synthesis of (S)-1-(tetrahydro-pyran-4-yl)-pyrrolidine-2-carboxylic acid [3-(2-hydroxy-1,1-dimethyl-ethyl)-isoxazol-5-yl]-amide

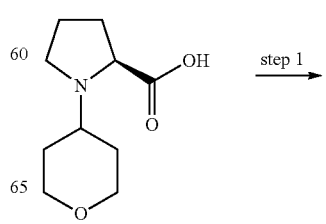

-continued

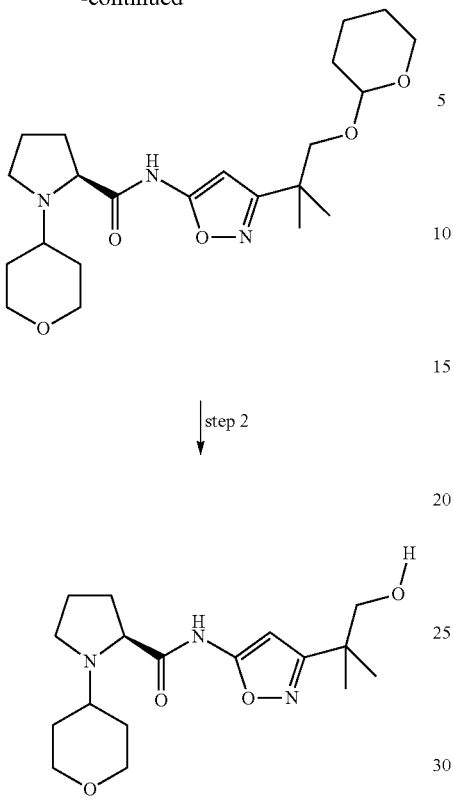

Step 1: Synthesis of (S)-1-(tetrahydro-pyran-4-yl)-pyrrolidine-2-carboxylic acid {3-[1,1-dimethyl-2-(tetrahydro-pyran-2-yloxy)-ethyl]-isoxazol-5-yl}-amide (S)-1-(Tetrahydro-pyran-4-yl)-pyrrolidine-2-carboxylic acid (0.2 g; 1.004 mmol) is dissolved in 5 mL of dimethyl formamide and O-(7-azabenzotriazol-1-yl)-N,N,N',N'-tetramethyluronium PF6 (0.573 g, 1.506 mmol) and diethylisopropyl amine (0.626 mL, 3.514 mmol) are added. The mixture is stirred at room temperature for 30 minutes. 3-[1,1-dimethyl-2-(tetrahydro-pyran-2-yloxy)-ethyl]isoxazole-5-yl amine (0.241 g, 1.004 mmol) is dissolved in 5 mL of dimethylformamide and sodium hydride (60% in mineral oil, 0.1 g, 2.510 mmol) is added at 0° C. The above solution is added and the mixture warmed to room temperature and stirred for 1 h. The reaction is quenched with water and methanol and concentrated under reduced pressure. The crude mixture is purified by flash chromatraphy (SiO2) to afford 0.075 g of title compound as an oil. 18% yield, ESI m/z 422=MH+.

Step 2 Synthesis of (S)-1-(tetrahydro-pyran-4-yl)-pyrrolidine-2-carboxylic acid [3-(2-hydroxy-1,1-dimethyl-ethyl)-isoxazol-5-yl]-amide Conditions used are similar to Example 35, except the mixture is heated at 75° C. Yield 33%, ESI m/z 338=MH+.

Compounds found in Table III Method 45 are prepared in this manner.

The following methods are used to prepare starting materials described:

Synthesis of (S)-4,4-difluoro-pyrrolidine-1,2-dicarboxylic acid 1-tert-butyl ester

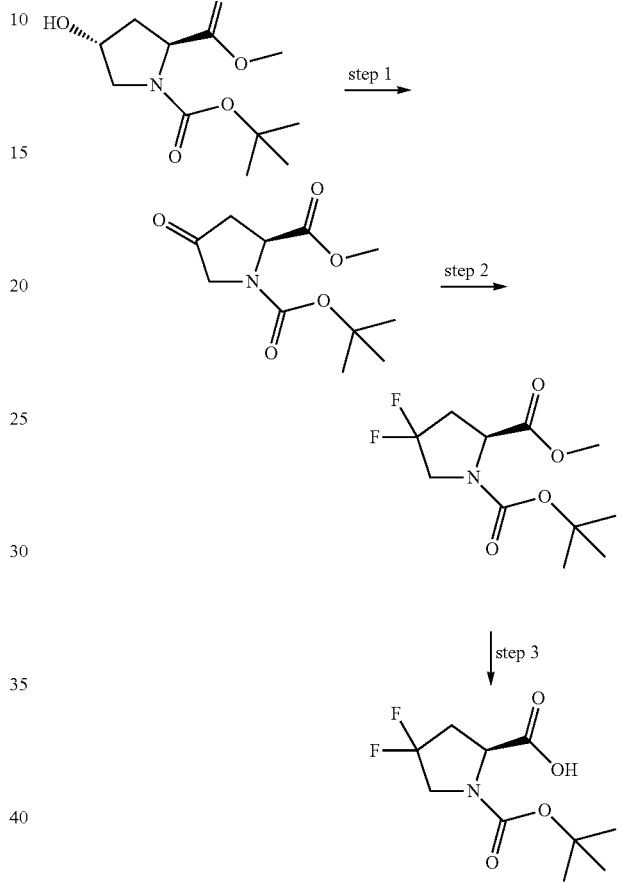

Step 1: Synthesis of (S)-4-oxo-pyrrolidine-1,2-dicarboxylic acid 1-tert-butyl ester 2-methyl ester Jones' reagent (11 mL, 88.5 mmol) is added dropwise over a period of 5 minutes to a solution of Boc-HYP-OMe (3 g, 12.2 mmol) in acetone (150 mL). The stirring is continued for an additional 30 minutes. The reaction is quenched with methanol (3 mL) and stirred at room temperature overnight. The reaction mixture is filtered through Celite® and the filtrate is concentrated under reduced pressure. It was diluted with water and extracted with dichloromethane 3 times. The organics are combined and washed with brine, dried over $Na_2SO_4$, filtered and concentrated under reduced pressure to yield the title compound. ESI m/z 144 [M+H+-100].

General preparation of Jones' reagent can be found in *J. Chem. Soc.* 1953, 2548.

Step 2: Synthesis of (S)-4,4-difluoro-pyrrolidine-1,2-dicarboxylic acid 1-tert-butyl ester 2-methyl ester (Diethylamino)sulfur trifluoride (2.2 mL, 16.8 mmol) is added to a solution of (S)-4-oxo-pyrrolidine-1,2-dicarboxylic acid 1-tert-butyl ester 2-methyl ester (1.36 g, 5.599 mmol) in dichloromethane (6 mL) at −78° C. The reaction is slowly warmed up to room temperature and stirred overnight. The reaction mixture is diluted with dichloromethane and cooled to 0° C. and carefully quenched with saturated sodium bicarbonate aqueous solution. The aqueous layer is extracted with dichloromethane twice. The organics are combined and washed with brine, dried over $Na_2SO_4$, filtered and concentrated under reduced pressure to provide the title compound. ESI m/z 166 [M+H$^+$−100].

Step 3: (S)-4,4-difluoro-pyrrolidine-1,2-dicarboxylic acid 1-tert-butyl ester

Lithium hydroxide monohydrate (469 mg, 11.2 mmol) is added to a solution of (S)-4,4-difluoro-pyrrolidine-1,2-dicarboxylic acid 1-tert-butyl ester 2-methyl ester (1.48 g, 5.59 mmol) in 3:1 acetonitrile in water (20 mL). The reaction is stirred at room temperature for 2 hours. The reaction mixture is concentrated under reduced pressure and diluted with water and extracted with ether. The aqueous layer is acidified to PH~1 and extracted with ethyl acetate 3 times. The organics are combined and washed with brine, dried over $Na_2SO_4$, filtered and concentrated under reduced pressure to yield the title compound. ESI m/z 152 [M+H$^+$−100].

Synthesis of (2S,4R)-4-tert-butoxy-pyrrolidine-1,2-dicarboxylic acid 1-tert-butyl ester

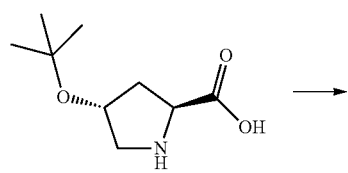

To a suspension of H-HYP (tBu)-OH (850 mg, 4.54 mmol) in 2:1 tetrahydrofuran/dichloromethane (15 mL) are added triethylamine (1.36 mL, 9.76 mmol) and di-t-butyldicarbonate (1.49 g, 6.81 mmol). The reaction is stirred at room temperature overnight. The reaction is concentrated under reduced pressure and dissolved in diethyl ether and washed with 1N sodium hydroxide aqueous solution. The aqueous layer is acidified to PH~1 by adding concentrated hydrochloric acid aqueous solution and extracted with ethyl acetate twice. The organics are combines and washed with brine, filtered and concentrated under reduce pressure to provide the title compound. ESI m/z 188 [M+H$^+$−100].

Synthesis of (S)-4-oxo-pyrrolidine-1,2-dicarboxylic acid 1-tert-butyl ester

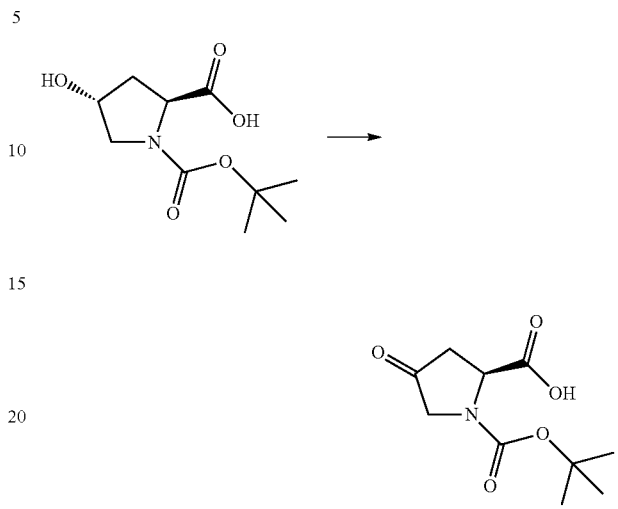

Jones' reagent (3.9 mL, 31.3 mmol) is added dropwise over a period of 5 mins to a solution of Boc-L-hydroxyproline (1 g, 4.3 mmol) in acetone (55 mL). The stirring is continued for an additional 30 minutes. The reaction is quenched with methanol (1 mL) and stirred at room temperature for 10 minutes. The reaction mixture is filtered through Celite® and the filtrate is concentrated under reduced pressure. It was diluted with water and extracted with dichloromethane 3 times. The organics are combined and washed with brine, dried over $Na_2SO_4$, filtered and concentrated under reduced pressure to yield the title compound. ESI m/z 130 [M+H$^+$−100].

Synthesis of 3-[1,1-dimethyl-2-(tetrahydro-pyran-2-yloxy)-ethyl]-isoxazol-5-ylamine

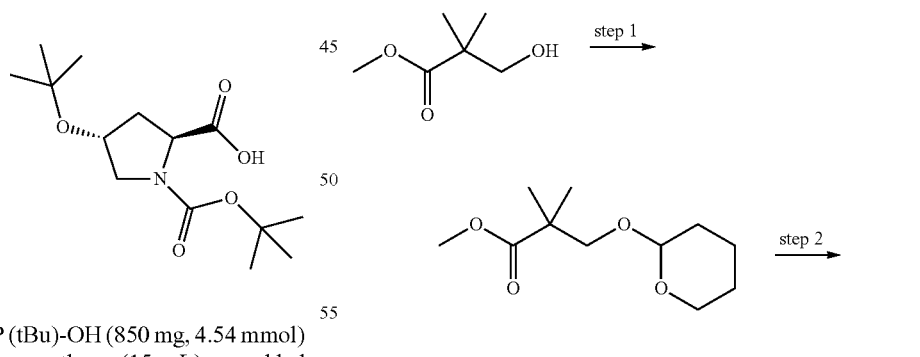

-continued

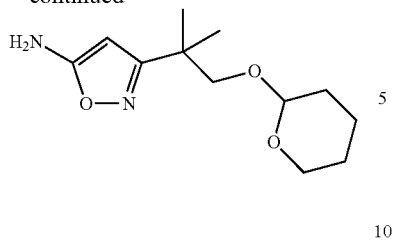

Step 1: Synthesis of 2,2-dimethyl-3-(tetrahydro-pyran-2-yloxy)-propionic acid methyl ester To a solution of hydroxypivalic acid methyl ester (4 mL, 31.36 mmol) in dichloromethane (20 mL) is added 3,4-dihydro-2H-pyran (5.84 mL, 63.99 mmol). The reaction mixture is cooled to 0° C. and sulfuric acid on silica gel (125 mg, 0.2 mL sulfuric acid/10 g silica gel) is added and the reaction mixture is stirred at room temperature for 25 minutes. After this time, the reaction mixture is filtered through a glass funnel and concentrated under reduced pressure to yield the title compound. It is used without purification.

Step 2: Synthesis of 4,4-dimethyl-3-oxo-5-(tetrahydro-pyran-2-yloxy)-pentanenitrile A solution of 2,2-dimethyl-3-(tetrahydro-pyran-2-yloxy)-propionic acid methyl ester (7.67 g, 35.46 mmol) and acetonitrile (2.6 mL, 49.65 mmol) in toluene (20 mL) is added dropwise to the refluxing suspension of 60% sodium hydride in mineral oil (1.99 g, 49.65 mmol) in toluene (40 mL). After the addition, the reaction mixture is stirred at reflux for 3 hours. After this time, the reaction mixture is cooled to room temperature and the aqueous layer is neutralized to PH~6-7 by adding 1N hydrochloric acid aqueous solution. The layers are combined and the aqueous layer is extracted with ethyl acetate. The organic layers are combined and washed with brine, dried (Na2SO4), filtered and concentrated under reduced pressure to yield the title compound. It is used without purification.

Step 3: Synthesis of 3-[1,1-dimethyl-2-(tetrahydro-pyran-2-yloxy)-ethyl]-isoxazol-5-ylamine Hydroxyamine sulfate (0.729 g, 4.439 mmol) is added to a stirred solution of 4,4-dimethyl-3-oxo-5-(tetrahydro-pyran-2-yloxy)-pentanenitrile (2 g, 8.878 mmol) and sodium hydroxide (0.764 g, 19.1 mmol) in water (20 mL). The reaction mixture is stirred at reflux for 18 hours. After this time, the reaction mixture is cooled to room temperature and extracted with ethyl acetate. The organic layers are combined and washed with brine, dried (Na2SO4), filtered and concentrated to yield the title compound, m/z 157 [M+H$^+$–84]. 1H NMR (400 MHz, DMSO-d) δ ppm 1.17 (6H, d), 1.45 (4H, br), 1.58 (1H, br), 1.68 (1H, br), 3.26 (1H, d), 3.4 (1H, br), 3.59 (1H, d), 3.68 (1H, br), 4.5 (1H, br), 4.88 (1H, s), 6.43 (2H, s).

Synthesis of 5-(2-methoxy-1,1-dimethyl-ethyl)-isoxazol-3-ylamine

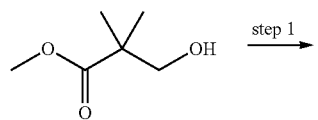

-continued

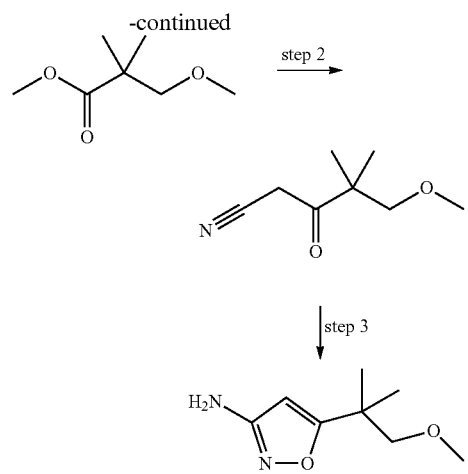

Step 1: Synthesis of 3-methoxy-2,2-dimethyl-propionic acid methyl ester

Powdered potassium hydroxide (3.519 g, 62.712 mmol) is stirred in DMSO (30 mL) for 5 minutes before adding hydroxypivalic acid methyl eater (2 mL, 15.678 mmol) and methyl iodide (3.904 mL, 62.712 mmol). The reaction mixture is stirred at room temperature for 30 minutes. The mixture is quenched with water and extracted with dichloromethane 3 times. The organics are combined and washed with water twice then brine, dried over Na2SO4, filtered and concentrated in vacuo to provide the title compound.

Step 2: Synthesis of 5-methoxy-4,4-dimethyl-3-oxo-pentanenitrile

60% sodium hydride in mineral oil (667.2 mg, 16.68 mmol) in toluene (15 mL) is heated to reflux. A solution of 3-methoxy-2,2-dimethyl-propionic acid methyl ester (1.742 g, 11.916 mmol) and acetonitrile (0.878 mL, 16.68 mmol) in toluene (5 mL) is added dropwise through an additional funnel into the NaH suspension in toluene. After the addition, the reaction is stirred at reflux for 3 hours. After cooling, the reaction mixture is neutralized to PH~7 by adding 1N HCl aqueous solution. The mixture is extracted with ethyl acetate 3 times. The organics are combined and washed with brine, dried over Na2SO4, filtered and concentrated in vacuo to afford the title compound.

Step 3: Synthesis of 5-(2-methoxy-1,1-dimethyl-ethyl)-isoxazol-3-ylamine

A solution of hydroxylamine sulfate (976 mg, 5.947 mmol) in water (4 mL) is added to a stirred solution of 5-methoxy-4,4-dimethyl-3-oxo-pentanenitrile (1.678 g, 10.812 mmol) and sodium hydroxide (490.3 mg, 11.89 mmol) in water (13 mL). The reaction mixture is heated to reflux over 30 minutes and kept at reflux for 1 hour. After cooling, 37% HCl aqueous solution (0.8 mL, 9.73 mmol) is added and the mixture is heated to reflux for 20 minutes. After cooling, the mixture's pH is adjusted to ~12 by adding 40% sodium hydroxide aqueous solution. The mixture is extracted with methylene chloride 3 times. The organics are combined and washed with brine, dried over Na2SO4, filtered and concentrated in vacuo.

Purification by flash chromatography on silica gel using methanol/methylene chloride provides the title compound, m/z 171 [M+H$^+$].

Synthesis of 3-(2-methoxy-1,1-dimethyl-ethyl)-isoxazol-5-ylamine

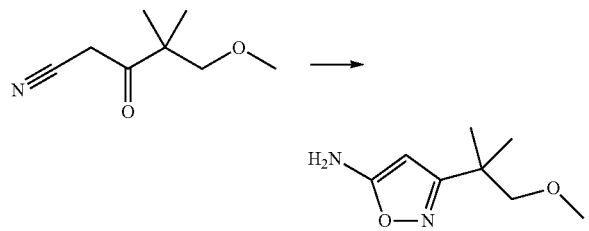

Hydroxyamine sulfate (1.56 g, 9.504 mmol) is added to a stirred solution of 5-methoxy-4,4-dimethyl-3-oxo-pentanenitrile (2.95 g, 19.008 mmol) and sodium hydroxide (1.635 g, 40.865 mmol) in water (40 mL). The reaction mixture is heated in 100° C. oil bath for 6 hours. After this time, the reaction mixture is diluted with water and extracted with ethyl acetate 3 times. The organics are combined and washed with brine, dried over Na2SO4, filtered and concentrated in vacuo. Purification by flash chromatography on silica gel using methanol/methylene chloride provides the title compound, m/z 171 [M+H$^+$].

Synthesis of 3-(4-methoxy-phenyl)-1,2,4-thiadiazol-5-ylamine

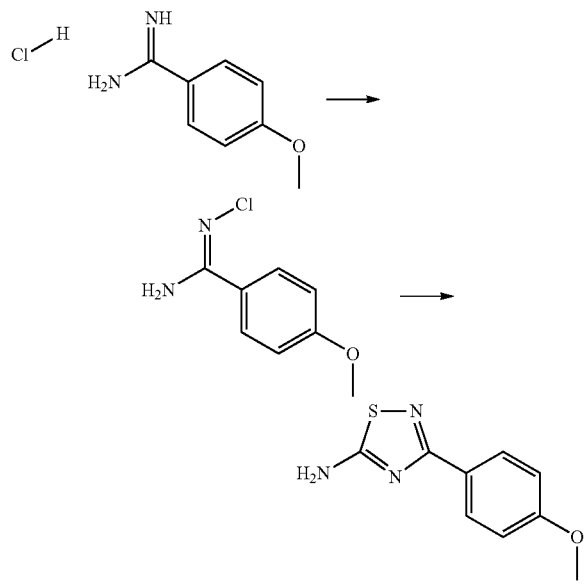

Reference: BOMC 2001, 9, 3231-3241.

Step 1: Synthesis of 4-methoxy-benzchloroamidine

Sodium hypochlorite (45 mL, 0.705M, 48.2 mmol) is added to a solution of 4-methoxy-benzamidine hydrochloride (9 g, 48.2 mmol) in 90 mL of water at 0° C. The mixture is stirred for 2 h at 0° C. then extracted with methylene chloride. The combined organics are dried over sodium sulfate, filtered and concentrated under reduced pressure to afford 5.5 g of title compound. ESI m/z 185=MH+

Step 2: Synthesis of 3-(4-methoxy-phenyl)-1,2,4-thiadiazol-5-ylamine

4-Methoxy-benzchloroamidine (5.5 g, 29.7 mmol) is dissolved in 100 mL of methanol and cooled to 0° C. Potassium thiocyanate (5.7 g, 59.5 mmol) is added portion wise and the mixture allowed to warm to room temperature and stir overnight. The mixture is concentrated under reduced pressure, dissolved with water and extracted with ethyl acetate. The combined organics are dried over sodium sulfate, filtered and concentrated to afford 4.3 g of title compound. 70% yield, ESI m/z 208=MH+.

Synthesis of 3-tert-Butyl-isothiazol-5-ylamine

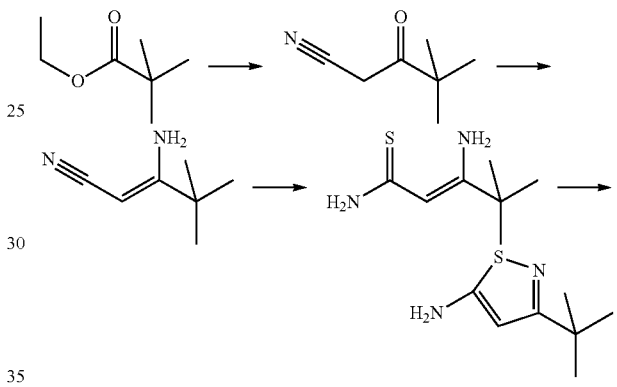

Step 1: Synthesis of 4,4-dimethyl-3-oxo-pentanenitrile

To a refluxed solution of sodium hydride (33.18 g, 553.03 mmol) in 275 mL of cyclohexane is added a mixture of 2,2-dimethyl-propionic acid ethyl ester (30 g, 230.43 mmol) in 79 mL acetonitrile (553.03 mmol) in 25 mL of cyclohexane. The mixture is maintained at 80° C. overnight. The mixture is cooled to room temperature, diluted with water and extracted with ethyl acetate. The combined organics are washed with water, dried over sodium sulfate, filtered and concentrated to afford title compound which was used crude in subsequent reaction. ESI m/z 124=MH–

Step 2: Synthesis of (Z)-3-amino-4,4-dimethyl-pent-2-enenitrile

To a solution of 4,4-dimethyl-3-oxo-pentanenitrile (22 g, 175.76 mmol) in 250 mL of ethanol is added ammonium nitrate (21 g; 263.64 mmol). The mixture is stirred under reflux overnight while ammonia gas is bubbled through the solution. The mixture is cooled to room temperature and diluted with 100 mL of water. The mixture is concentrated under reduced pressure to remove most of the ethanol. Aqueous sodium hydroxide (140 mL, 0.3N) is added and the mixture is extracted with ether (2×200 mL). The combined organic layers are washed with 50 mL of water, dried over sodium sulfate, filtered and concentrated under reduced pressure to afford title compound. Assumed quantitative yield and used crude in subsequent reaction. ESI m/z 125=MH+

Step 3: Synthesis of (Z)-3-amino-4,4-dimethyl-pent-2-enethioic acid amide (Z)-3-amino-4,4-dimethyl-pent-2-enenitrile (26 g, 209.35 mmol), sodium sulfide decahydrate (5.71 g, 73.27 mmol) and tetrabutyl ammonium chloride (9.31 g, 33.49 mmol) in benzene and water (215 mL, 2.5:1, v/v) is stirred at 75° C. under hydrogen sulfide gas for three days. 200 mL of ethyl acetate is added and the layers separated. The organic layer is washed with water, dried over sodium sulfate, filtered and concentrated under reduced pressure to afford the title compound. Yield 23% over three steps. ESI m/z 159=MH+

Step 4: Synthesis of 3-tert-Butyl-isothiazol-5-ylamine

To a stirred solution of (Z)-3-amino-4,4-dimethyl-pent-2-enethioic acid amide (8.3 g, 525 mmol) and potassium carbonate (14.4 g, 105 mmol) in 140 mL of diethyl ether is added a solution of iodine (13.2 g, 52.5 mmol) in 20 mL of diethyl ether at reflux. The mixture is refluxed for 2 h and cooled. Water is added and the layers separated. The organic layer is washed with water, dried over sodium sulfate, filtered and concentrated under reduced pressure. The crude mixture is purified by flash chromatography to afford title compound in 53% yield. ESI m/z 157=MH+

Synthesis of 2,5-dichloro-pyrimidine

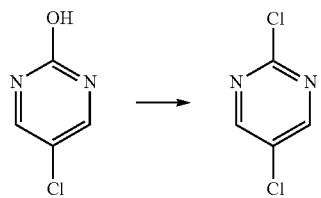 [SMILES: Oc1ncc(Cl)cn1 ; Clc1cnc(Cl)nc1]

Phosphorous oxychloride (7.013 mL, 76.610 mmol) is added to 2-hydroxy-5-chloropyrimidine (2 g, 15.322 mmol) and the mixture is heated at reflux for 30 minutes. The crude mixture is concentrated under reduced pressure to afford 1.120 g of title compound. ESI m/z 149=MH+

Synthesis of 2-(4-fluoromethyl-phenyl)-4,4,5,5-tetramethyl-1,3,2-dioxaborolane

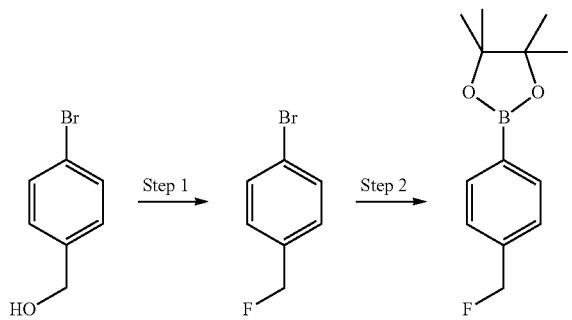

Step 1: Synthesis of 1-bromo-4-fluoromethyl-benzene

To a solution of (4-bromo-phenyl)-methanol (1 g, 5.347 mmol) in 2 mL of dichloromethane is added [bis(2-methoxyethyl)amino]sulfurtrifluoride (1.084 mL, 5.882 mmol) at 0° C. The reaction is slowly warmed to room temperature over 3 hours after which it is quenched with aqueous saturated sodium bicarbonate solution. The organic phase is separated from aqueous and dried over sodium sulfate, filtered and concentrated under reduced pressure to afford 990 mg of yellow oil which is used without characterization or purification.

Step 2: Synthesis of 2-(4-fluoromethyl-phenyl)-4,4,5,5-tetramethyl-1,3,2-dioxaborolane A flask is charged with 1-bromo-4-fluoromethyl-benzene (0.280 g, 1.481 mmol), bis(pinacolato)diboron (0.752 g, 2.962 mmol), potassium acetate (0.436 g, 4.443 mmol), 1,1'-bis(diphenylphosphino)ferrocene palladium (II) chloride complex with dichloromethane (0.121 g, 0.148 mmol) and 15 mL of degassed anhydrous 1.4-dioxane is added. The mixture is stirred under an atmosphere of Argon at 90° C. for 18 hours. The mixture is cooled to room temperature, filtered and partitioned between ethyl acetate and 5% aqueous sodium chloride solution. The aqueous phase is extracted with ethyl acetate and the combined organics washed with brine, dried over magnesium sulfate, filtered and concentrated under reduced pressure. The crude material is purified by flash chromatography eluting with ethyl acetate/heptanes to afford 270 mg of title compound. $^1$H NMR (400 MHz, CHLOROFORM-d) δ ppm 1.23 (12H, s), 5.34 (1H, s), 5.45 (1H, s), 7.21 (2H, d, J=7.43 Hz), 7.71 (2H, d, J=8.78 Hz)

Synthesis of 2-(4,4-difluoromethyl-phenyl)-4,4,5,5-tetramethyl-1,3,2-dioxaborolane

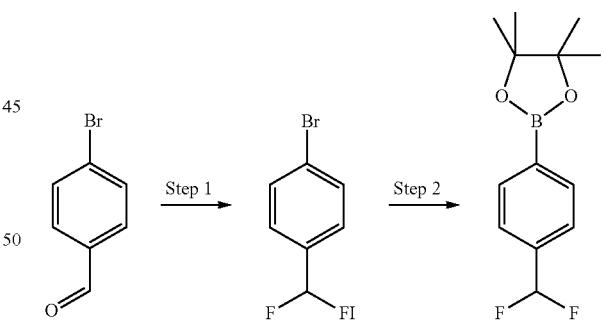

Step 1: Synthesis of 1-bromo-4,4-difluoromethyl-benzene

Following a procedure adapted from Synthesis, 1973, 787, a mixture of 4-bromobenzaldehyde (0.4 g, 2.162 mmol) and diethylaminosulfure trifluoride (0.283 mL, 2.162 mmol) is heated carefully until incipient exothermic reactions and then at 60° C. for 15 minutes. The mixture is dissolved in dichloromethane and poured into ice water. The product is extracted using dichloroethane, dried over sodium sulfate, filtered and concentrated under reduced pressure to afford 0.380 g of title compound product, 85% yield. $^1$H NMR (400 MHz, CHLO- ROFORM-d) δ ppm 6.61 (1H, t, J=56.7 Hz), 7.38 (2H, d, J=8.1 Hz), 7.6 (2H, d, J=9.4 Hz).

Step 2: Synthesis of 2-(4,4-difluoromethyl-phenyl)-4,4,5,5-tetramethyl-1,3,2-dioxaborolane Compound is prepared in a similar manner to 2-(4-fluoromethyl-phenyl)-4,4,5,5-tetramethyl-1,3,2-dioxaborolane above to afford 0.44 g of title compound, 94% yield. ESI m/z 255=MH+

Assessment of Biological Properties

The biological properties of the compounds of the invention were assessed using the assays described below.

A. Human CB1 and CB2 Receptor Binding:

Experimental Method:

CB2 membranes were purchased and made from HEK293 EBNA cells stably transfected with human CB2 receptor cDNA (Perkin Elmer Life and Analytical Sciences). CB1 membranes were isolated from HEK cells stably co-transfected with human CB1 receptor and Gα16 cDNA's. The membrane preparation was bound to scintillation beads (Ysi-Poly-L-lysine SPA beads, GE Healthcare) for 4 hours at room temperature in assay buffer containing 50 mM Tris, pH 7.5, 2.5 mM EDTA, 5 mM $MgCl_2$, 0.8% fatty acid free Bovine Serum Albumin. Unbound membrane was removed by washing in assay buffer. Membrane-bead mixture was added to 96-well assay plates in the amounts of 15 ug membrane per well (CB2) or 2.5 ug per well (CB1) and 1 mg SPA bead per well. Compounds were added to the membrane-bead mixture in dose-response concentrations ranging from $1 \times 10^{-5}$ M to $1 \times 10^{-10}$ M with 0.25% DMSO, final. The competition reaction was initiated with the addition of $^3$H-CP55940 (Perkin Elmer Life and Analytical Sciences) at a final concentration of 1.5 nM (CB2) or 2.5 nM (CB1). The reaction was incubated at room temperature for 18 hours and read on TopCount NXT plate reader. Total and non-specific binding was determined in the absence and presence of 1.25 uM Win 55212 (Sigma). IC50 values for each compound were calculated as the concentration of compound that inhibits the specific binding of the radioactively labeled ligand to the receptor by 50% using the XLFit 4.1 four parameter logistic model. IC50 values were converted to inhibition constant (Ki) values using Cheng-Prusoff equation.

B. CB2R Mediated Modulation of cAMP Synthesis:

Compounds of the invention were evaluated for their CB2 agonist or inverse agonist activity in accordance with the following experimental method. Compounds which were shown to bind to CB2 by the binding assay described above but which were not shown to exhibit CB2R-mediated modulation of cAMP synthesis by this assay were presumed to be CB2 antagonists.

Experimental Method:

CHO cells expressing human CB2R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

C. CB1R Mediated Modulation of cAMP Synthesis:

Compounds of the invention were evaluated for their CB1 agonist or inverse agonist activity in accordance with the following experimental method. Compounds which were shown to bind to CB1 by the binding assay described above but which were not shown to exhibit CB1R-mediated modulation of cAMP synthesis by this assay were presumed to be CB1 antagonists.

Experimental Method:

CHO cells expressing human CB1R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

Compounds Having Agonist Activity

Through the use of the above described assays compounds were found to exhibit agonistic activity and thus to be particularly well suited for the treatment of pain as well as for the treatment of inflammation. Preferred CB2 agonists will have CB2 CAMP @ EC50 nM of less than 500 nM.

Therapeutic Use

As can be demonstrated by the assays described above, the compounds of the invention are useful in modulating the CB2 receptor function. By virtue of this fact, these compounds have therapeutic use in treating disease-states and conditions mediated by the CB2 receptor function or that would benefit from modulation of the CB2 receptor function.

As the compounds of the invention modulate the CB2 receptor function, they have very useful anti-inflammatory and immune-suppressive activity and they can be used in patients as drugs, particularly in the form of pharmaceutical compositions as set forth below, for the treatment of disease-states and conditions.

As noted before, those compounds which are CB2 agonists can also be employed for the treatment of pain.

The agonist compounds according to the invention can be used in patients as drugs for the treatment of the following disease-states or indications that are accompanied by inflammatory processes:

(i) Lung diseases: e.g. asthma, bronchitis, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis;

(ii) Rheumatic diseases or autoimmune diseases or musculoskeletal diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis; collagenoses of any genesis, e.g., systemic lupus erythematosus, scleroderma, polymyositis, dermatomyositis, Sjögren syndrome, Still disease, Felty syndrome; and osteoporosis and other bone resorption diseases;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vascular diseases: panarteritis nodosa, polyarteritis nodosa, periarteritis nodosa, arteritis temporalis, Wegner granulomatosis, giant cell arthritis, atherosclerosis, reperfusion injury and erythema nodosum;

(v) Dermatological diseases: e.g. dermatitis, psoriasis; sunburn, burns, eczema;

(vi) Renal diseases: e.g. nephrotic syndrome; and all types of nephritis, e.g., glomerulonephritis; pancreatits;

(vii) Hepatic diseases: e.g. acute liver cell disintegration; acute hepatitis of various genesis, e.g., viral, toxic, drug-induced; and chronically aggressive and/or chronically intermittent hepatitis;

(viii) Gastrointestinal diseases: e.g. inflammatory bowel diseases, irritable bowel syndrome, regional enteritis (Crohns disease), colitis ulcerosa; gastritis; aphthous ulcer, celiac disease, regional ileitis, gastroesophageal reflux disease;

(ix) Neuroprotection: e.g. in the treatment of neurodegeneration following stroke; cardiac arrest; pulmonary bypass; traumatic brain injury; spinal cord injury or the like;

(x) Eye diseases: allergic keratitis, uveitis, or iritis; conjunctivitis; blepharitis; neuritis nervi optici; choroiditis; glaucoma and sympathetic ophthalmia;

(xi) Diseases of the ear, nose, and throat (ENT) area: e.g. tinnitus; allergic rhinitis or hay fever; otitis externa; caused by contact eczema, infection, etc.; and otitis media;

(xii) Neurological diseases: e.g. brain edema, particularly tumor-related brain edema; multiple sclerosis; acute encephalomyelitis; meningitis; acute spinal cord injury; trauma; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection); Guillain-Barre syndrome; myasthenia gravis, stroke; and various forms of seizures, e.g., nodding spasms;

(xiii) Blood diseases: acquired hemolytic anemia; aplastic anemia, and idiopathic thrombocytopenia;

(xiv) Tumor diseases: acute lymphatic leukemia; Hodgkin's disease, malignant lymphoma; lymphogranulomatoses; lymphosarcoma; solid malignant tumors; extensive metastases;

(xv) Endocrine diseases: endocrine ophthalmopathy; endocrine orbitopathia; thyrotoxic crisis; Thyroiditis de Quervain; Hashimoto thyroiditis; Morbus Basedow; granulomatous thyroiditis; struma lymphomatosa; and Graves disease; type I diabetes (insulin-dependent diabetes);

(xvi) Organ and tissue transplantations and graft-versus-host diseases;

(xvii) Severe states of shock, e.g., septic shock, anaphylactic shock, and systemic inflammatory response syndrome (SIRS);

(xviii) Acute pain such as dental pain, perioperative, postoperative pain, traumatic pain, muscle pain, pain in burned skin, sun burn, trigeminal neuralgia, sun burn; spasm of the gastrointestinal tract or uterus, colics;

(xix) Visceral pain such as pain associated with chronic pelvic pain, pancreatitis, peptic ulcer, interstitial cystitis, renal colic, angina, dysmenorrhoea, menstruation, gynaecological pain, irritable bowel syndrome (IBS), non-ulcer dyspepsia, non-cardiac chest pain, myocardial ischemia;

(xx) Neuropathic pain such as low back pain, non-herpetic neuralgia, post herpetic neuralgia, diabetic neuropathy, nerve injury, acquired immune deficiency syndrome (AIDS) related neuropathic pain, head trauma, painful traumatic mononeuropathy, toxin and chemotherapy induced pain, phantom limb pain, painful polyneuropathy, thalamic pain syndrome, post-stroke pain, central nervous system injury, post surgical pain, stump pain, repetitive motion pain, pain induced by post mastectomy syndrome, multiple sclerosis, root avulsions, postthoracotomy syndrome, neuropathic pain associated hyperalgesia and allodynia.

(xxi) Inflammatory/nociceptive pain induced by or associated with disorders such as osteoarthritis, rheumatoid arthritis, rheumatic disease, teno-synovitis, gout, vulvodynia, myofascial pain (muscular injury, fibromyalgia), tendonitis, osteoarthritis, juvenile arthritis, spondylitis, gouty arthritis, psoriatic arthritis, muscoskeletal pain, fibromyalgia, sprains and strains, sympathetically maintained pain, myositis, pain associated with migraine, toothache, influenza and other viral infections such as the common cold, rheumatic fever, systemic lupus erythematosus;

(xxii) Cancer pain induced by or associated with tumors such as lymphatic leukemia; Hodgkin's disease, malignant lymphoma; lymphogranulomatoses; lymphosarcoma; solid malignant tumors; extensive metastases;

(xxiii) Headache such as cluster headache, migraine with and without aura, tension type headache, headache with different origins, headache disorders including prophylactic and acute use;

(xxiv) various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, and granulocyte transfusion, sarcoidosis, gingivitis, pyrexia. edema resulting from trauma associated with burns, sprains or fracture, cerebral oedema and angioedema, Diabetes such as diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion).

Other indications include: epilepsy, septic shock e.g. as antihypovolemic and/or antihypotensive agents, cancer, sepsis, osteoporosis, benign prostatic hyperplasia and hyperactive bladder, pruritis, vitiligo, general gastrointestinal disorders, disturbances of visceral motility at respiratory, genitourinary, gastrointestinal or vascular regions, wounds, burns, tissue damage and postoperative fever, syndromes associated with itching.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art.

The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

The invention claimed:

1. A compound of the formula (I)

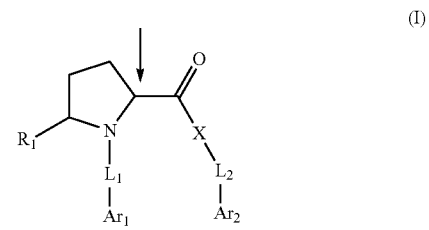

X is NH;
Ar$_1$ is chosen
phenyl, benzoxazolyl, benzothiazolyl, benzimidazolyl, dioxanyl, tetrahydrofuranyl, oxazolyl, isoxazolyl, thiazolyl, pyrazolyl, pyrrolyl, imidazolyl, thienyl, thiadiazolyl, triazolyl, thiomorpholinyl, 1,1-Dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, Dihydro-2H-quinolinyl, isoquinolinyl, quinazolinyl, indazolyl, indolyl, isoindolyl, benzofuranyl, benzopyranyl and benzodioxolyl each optionally substituted by 1-3 C$_{1-6}$ alkyl, C$_{1-6}$ alkoxy, CN, halogen, NO$_2$, —S(O)$_2$—C$_{1-3}$ alkyl, —CO$_2$—C$_{1-4}$ alkyl, C(O)—NH(C$_{1-3}$ alkyl), —C(O)—N(C$_{1-3}$ alkyl)$_2$, —N(C$_{1-3}$ alkyl), —N(C$_{1-3}$ alkyl)—C(O)—C$_{1-4}$ alkyl, —N(C$_{1-3}$ alkyl)—S(O)$_2$—C$_{1-3}$ alkyl, morpholinyl or piperazinyl;
Ar$_2$ is chosen from
benzoxazolyl, benzothiazolyl, benzimidazolyl, oxazolyl, isoxazolyl, thiazolyl, pyrazolyl, pyrrolyl, imidazolyl, thienyl, thiadiazolyl, triazolyl, pyridinyl, pyrimidinyl, pyridazinyl, pyrazinyl, triazinyl, quinolinyl, isoquinolinyl, quinazolinyl, indazolyl, thieno[2,3-d]pyrimidinyl, indolyl, isoindolyl and benzofuranyl, each optionally substituted by 1-3 C$_{1-6}$ alkyl, cyclopropyl, cyclohexyl, phenyl, CN, halogen, pyrimidinyl, acetyl or oxo (=O);
L$_1$ is a bond;
L$_2$ is chosen from a bond, —CH$_2$— and —CH$_2$—CH$_2$—;
wherein L$_2$ where possible is optionally substituted by halogen or C$_{1-3}$ alkyl;
R$_1$ is chosen from oxo (=O );
m is 0, 1 or 2;
wherein each Ar$_1$ and Ar$_2$, or the substituents thereof are optionally partially or fully halogenated;
the stereogenic carbon indicated with an arrow is in the (S) configuration;
or a pharmaceutically acceptable salt thereof.

2. The compound according to claim 1 and wherein:
Ar$_1$ is chosen from phenyl, thienyl, pyridinyl, pyrimidinyl, pyrazine and triazine each optionally substituted by 1-3 C$_{1-6}$ alkyl, C$_{1-6}$ alkoxy, CN, halogen, NO$_2$, —S(O)$_2$—C$_{1-3}$ alkyl, —CO$_2$—C$_{1-4}$alkyl, —NH(C$_{1-3}$alkyl)—

CO$_2$—C$_{1-4}$ alkyl, —C(O)—NH(C$_{1-3}$ alkyl), —C(O)—N(C$_{1-3}$alkyl)$_2$, —NH(C$_{1-3}$ alkyl), —N(C$_{1-3}$ alkyl)—C(O)—C$_{1-4}$ alkyl, —N(C$_{1-3}$alkyl)—S(O)$_2$—C$_{1-3}$ alkyl, morpholinyl or piperazinyl;

Ar$_2$ is oxazolyl, isoxazolyl, thiadiazolyl, pyrazolyl, triazolyl, thiazolyl, pyridinyl, benzimidazolyl, benzothiazolyl and benzoxazolyl, each optionally substituted by 1-3 C$_{1-5}$alkyl, cyclopropyl, cyclohexyl, phenyl, CN, halogen, pyrimidinyl, acetyl or oxo (=O);

L$_2$ is chosen from a bond and —CH$_2$—.

3. The compound according to claim 2 and wherein:

Ar$_1$ is chosen from pyridinyl, phenyl and thienyl each optionally substituted by 1-3 C$_{1-6}$ alkyl, C$_{1-6}$ alkoxy, CN, halogen, NO$_2$, —S(O)$_2$—C$_{1-3}$alkyl,—CO$_2$—C$_{1-4}$alkyl, —NH(C$_{1-3}$ alkyl)—CO$_2$—C$_{1-4}$alkyl, —C(O)—NH(C$_{1-3}$alkyl), —C(O)—N(C$_{1-3}$alkyl)$_2$, —NH(C$_{1-3}$ alkyl), —N(C$_{1-3}$alkyl)—C(O)—C$_{1-4}$alkyl or —N(C$_{1-3}$ alkyl)—S(O)$_2$—C$_{1-3}$ alkyl;

Ar$_2$ is chosen from isoxazolyl optionally substituted by 1-3 C$_{1-5}$alkyl and cyclopropyl.

4. The compound according to claim 3 and wherein:

Ar$_2$ is chosen from

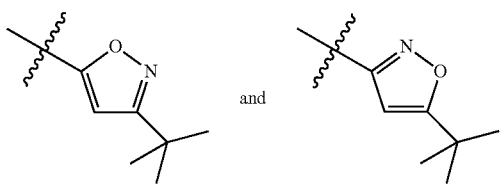

and

5. A compound of the formula (III)

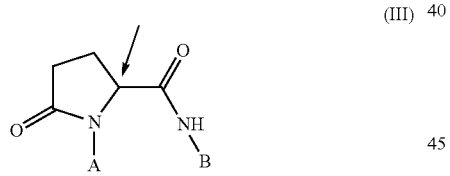 (III)

wherein

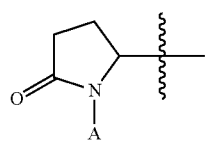

of the formula (III) is chosen from A1 - A56 of Table I, and

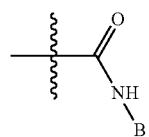

of the formula (III) is chosen from B1 -B25 of Table I,

TABLE I

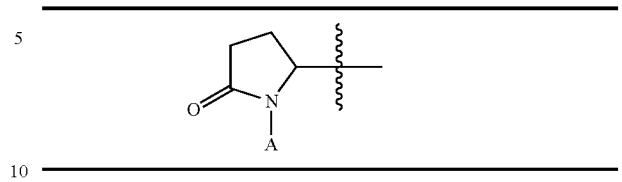

| | |
|---|---|
| 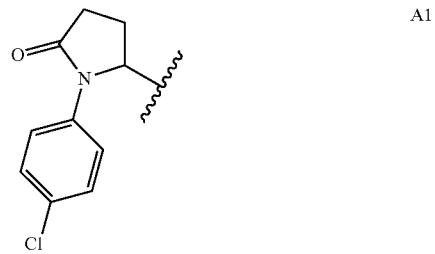 | A1 |
| 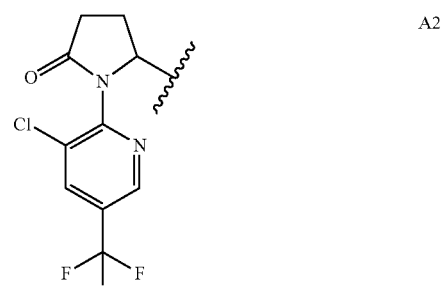 | A2 |
| 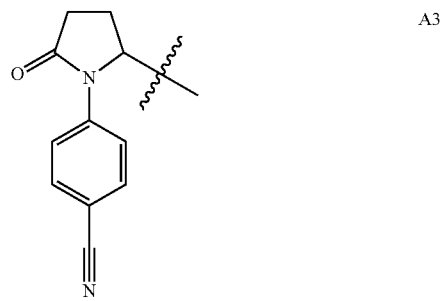 | A3 |
| 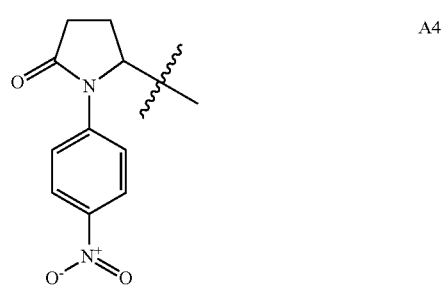 | A4 |
| 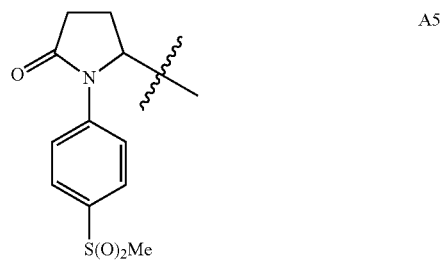 | A5 |

TABLE I-continued
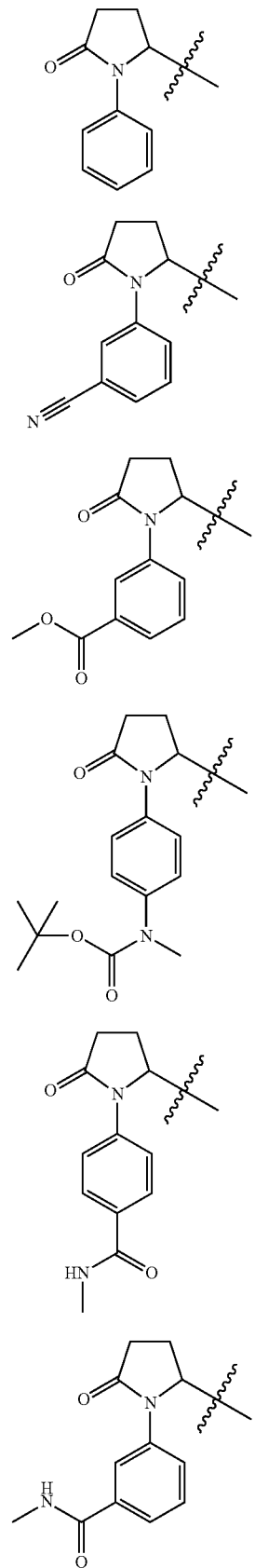
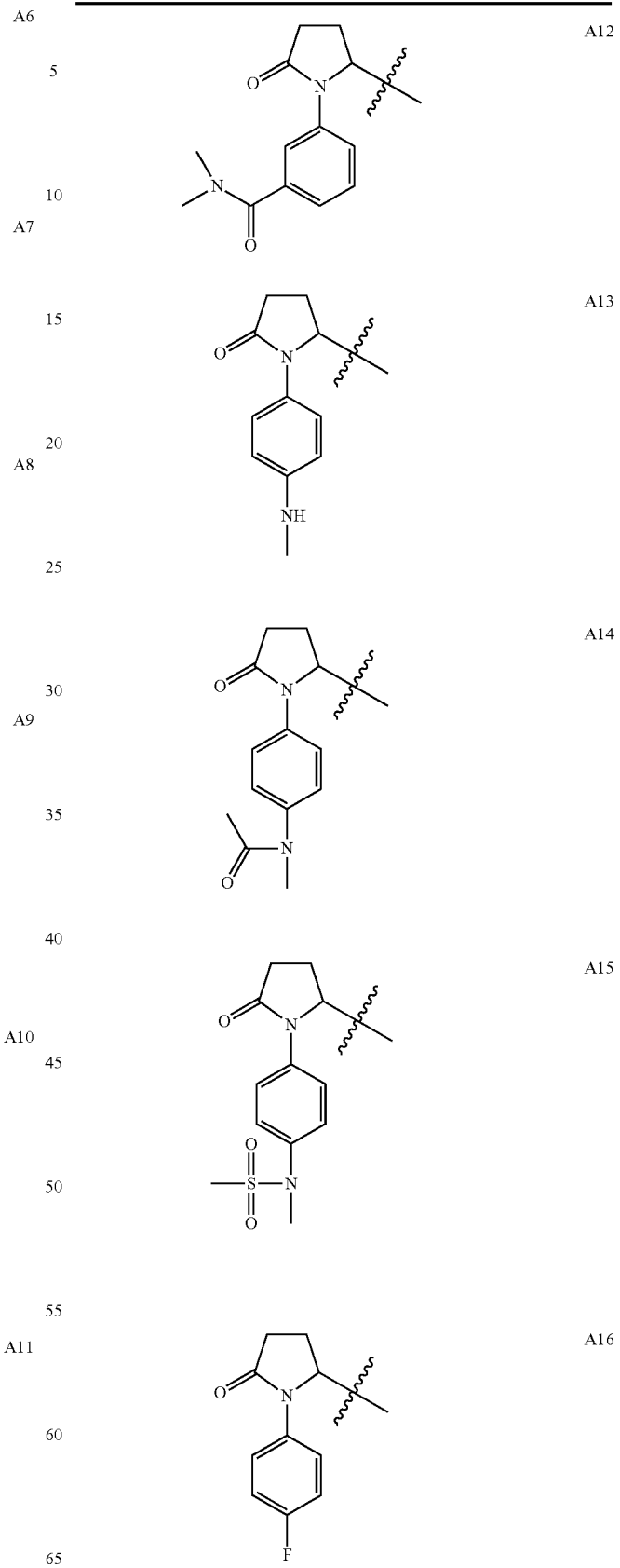

TABLE I-continued
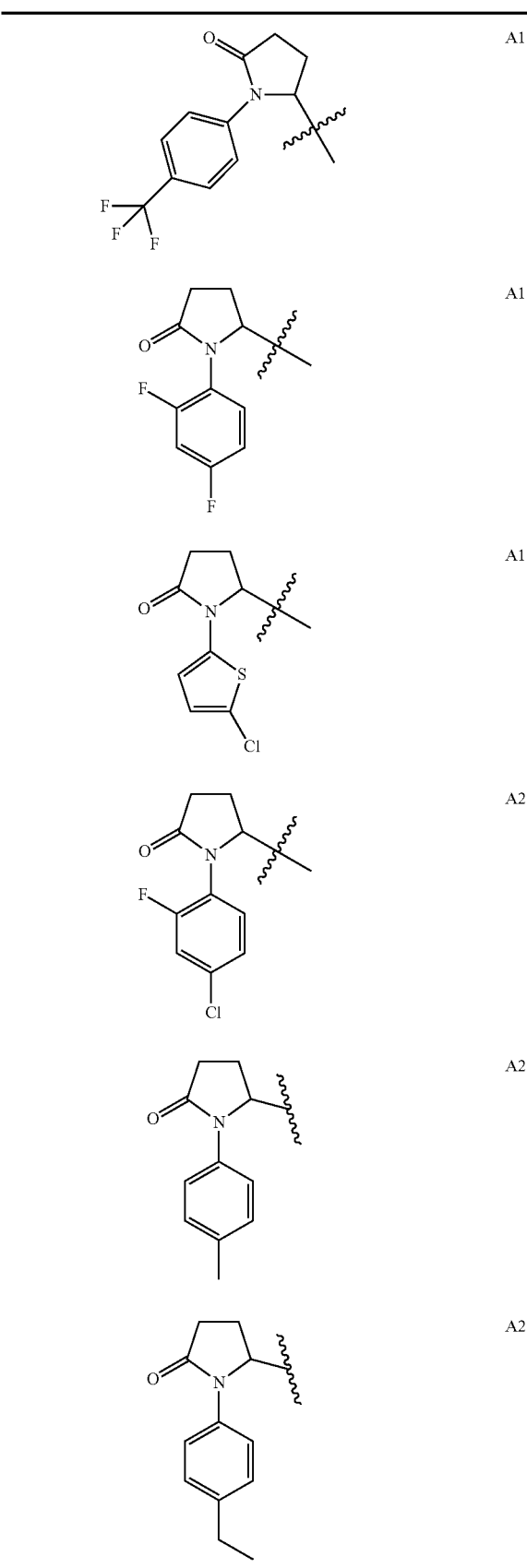
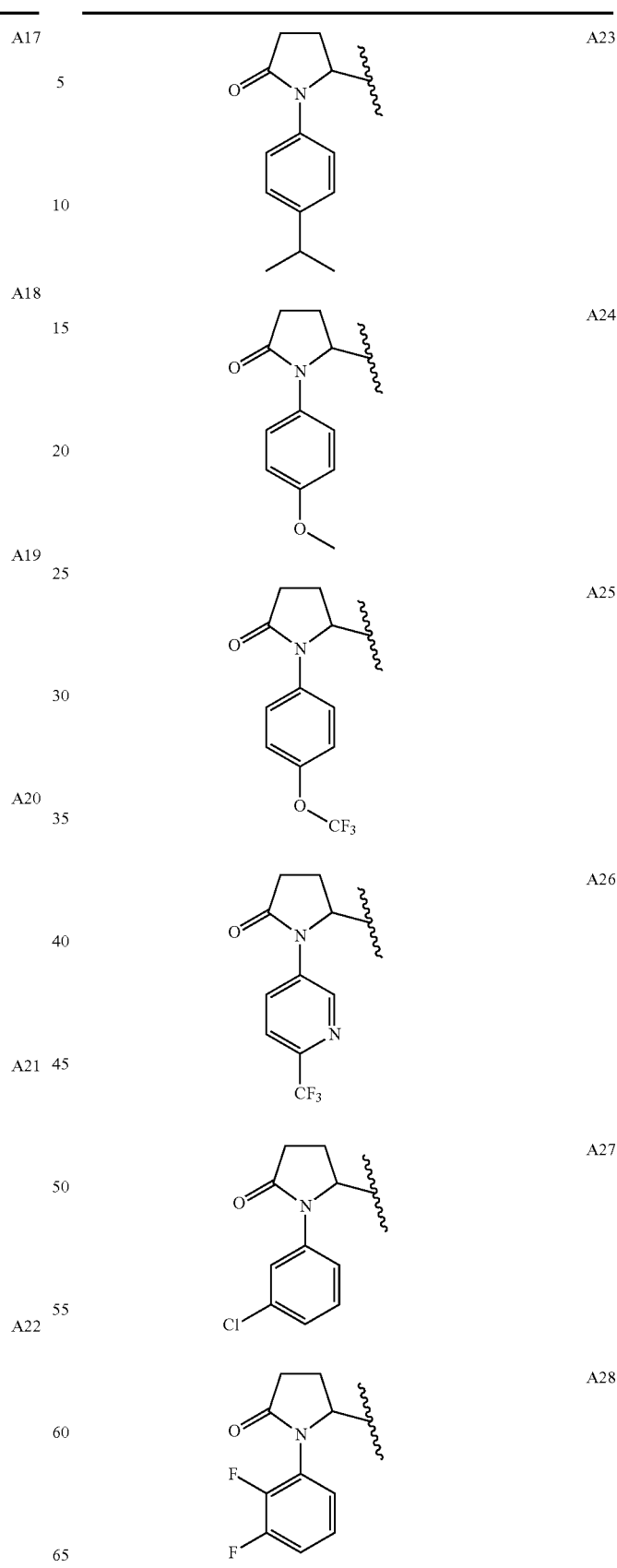

TABLE I-continued
| | |
|---|---|
| 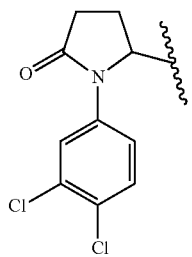 [SMILES: *C1CCC(=O)N1c1ccc(Cl)c(Cl)c1] | A29 |
| 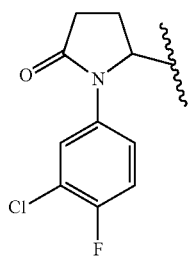 [SMILES: *C1CCC(=O)N1c1ccc(F)c(Cl)c1] | A30 |
| 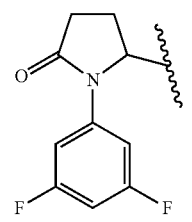 | A31 |
| 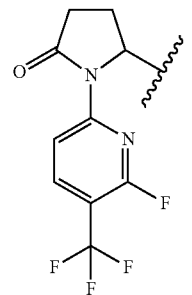 [SMILES: *C1CCC(=O)N1c1ccc(C(F)(F)F)c(F)n1] | A32 |
| 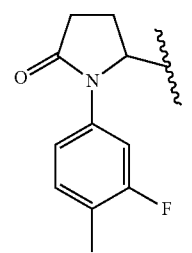 | A33 |
| 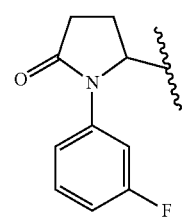 [SMILES: *C1CCC(=O)N1c1cccc(F)c1] | A34 |
TABLE I-continued
| | |
|---|---|
| 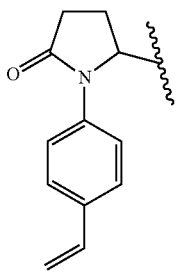 [SMILES: *C1CCC(=O)N1c1ccc(C=C)cc1] | A35 |
| 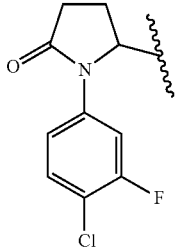 [SMILES: *C1CCC(=O)N1c1ccc(Cl)c(F)c1] | A36 |
| 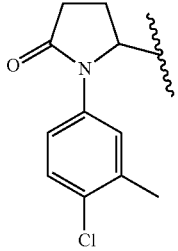 [SMILES: *C1CCC(=O)N1c1ccc(Cl)c(C)c1] | A37 |
| 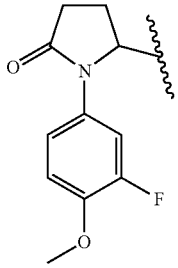 [SMILES: *C1CCC(=O)N1c1ccc(OC)c(F)c1] | A38 |
| 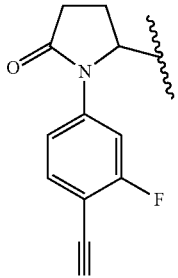 | A39 |
| 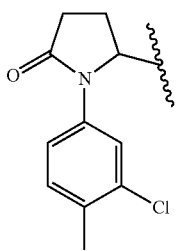 [SMILES: *C1CCC(=O)N1c1ccc(C)c(Cl)c1] | A40 |

TABLE I-continued
| | |
|---|---|
| 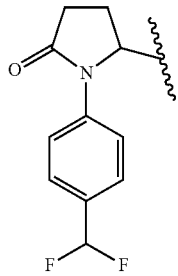 [SMILES: *C1CCC(=O)N1c1ccc(C(F)F)cc1] | A41 |
| 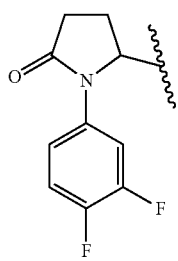 [SMILES: *C1CCC(=O)N1c1ccc(F)c(F)c1] | A42 |
| 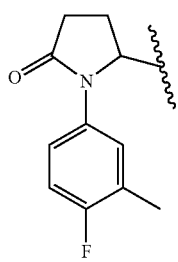 [SMILES: *C1CCC(=O)N1c1ccc(F)c(C)c1] | A43 |
| 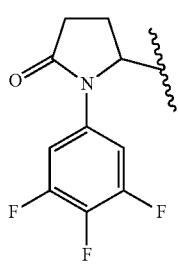 | A44 |
| 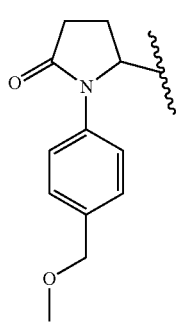 [SMILES: *C1CCC(=O)N1c1ccc(COC)cc1] | A45 |
| 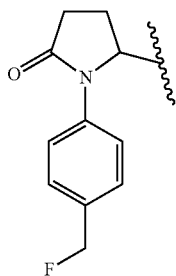 [SMILES: *C1CCC(=O)N1c1ccc(CF)cc1] | A46 |
| 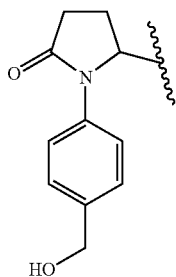 [SMILES: *C1CCC(=O)N1c1ccc(CO)cc1] | A47 |
| 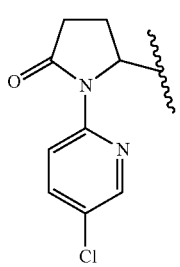 [SMILES: *C1CCC(=O)N1c1ccc(Cl)cn1] | A48 |
| 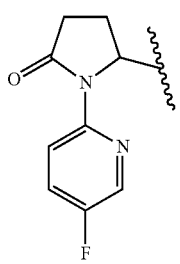 [SMILES: *C1CCC(=O)N1c1ccc(F)cn1] | A49 |
| 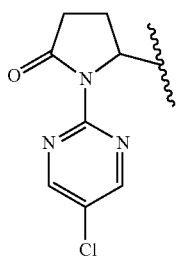 [SMILES: *C1CCC(=O)N1c1ncc(Cl)cn1] | A50 |
| 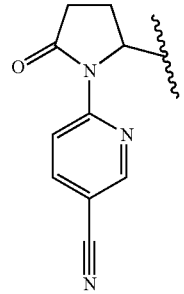 [SMILES: *C1CCC(=O)N1c1ccc(C#N)cn1] | A51 |

TABLE I-continued
| | |
|---|---|
| 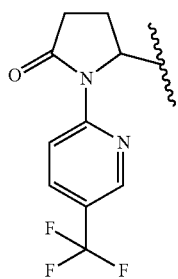 [SMILES: *C1CCC(=O)N1c1ccc(C(F)(F)F)cn1] | A52 |
| 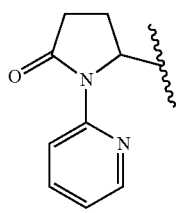 [SMILES: *C1CCC(=O)N1c1ccccn1] | A53 |
| 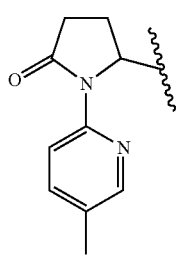 [SMILES: *C1CCC(=O)N1c1ccc(C)cn1] | A54 |
| 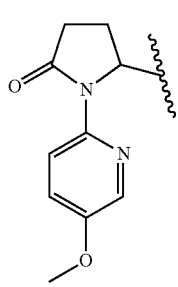 [SMILES: *C1CCC(=O)N1c1ccc(OC)cn1] | A55 |
| 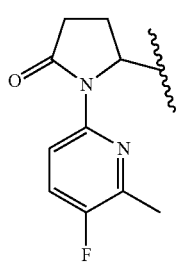 [SMILES: *C1CCC(=O)N1c1ccc(F)c(C)n1] | A56 |
| 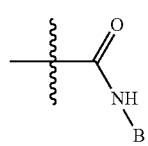 | |
TABLE I-continued
| | |
|---|---|
| 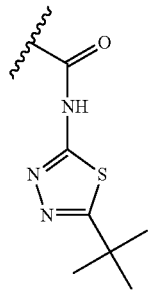 [SMILES: *C(=O)Nc1nnc(C(C)(C)C)s1] | B1 |
| 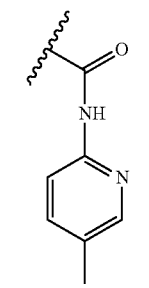 | B2 |
| 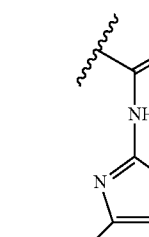 | B3 |
| 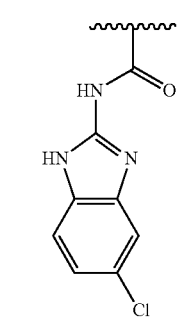 | B4 |
| 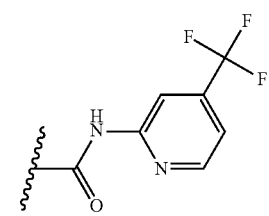 [SMILES: *C(=O)Nc1cc(C(F)(F)F)ccn1] | B5 |
| 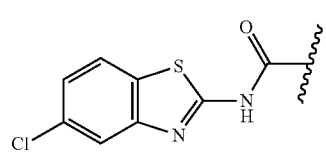 [SMILES: *C(=O)Nc1nc2cc(Cl)ccc2s1] | B6 |

TABLE I-continued
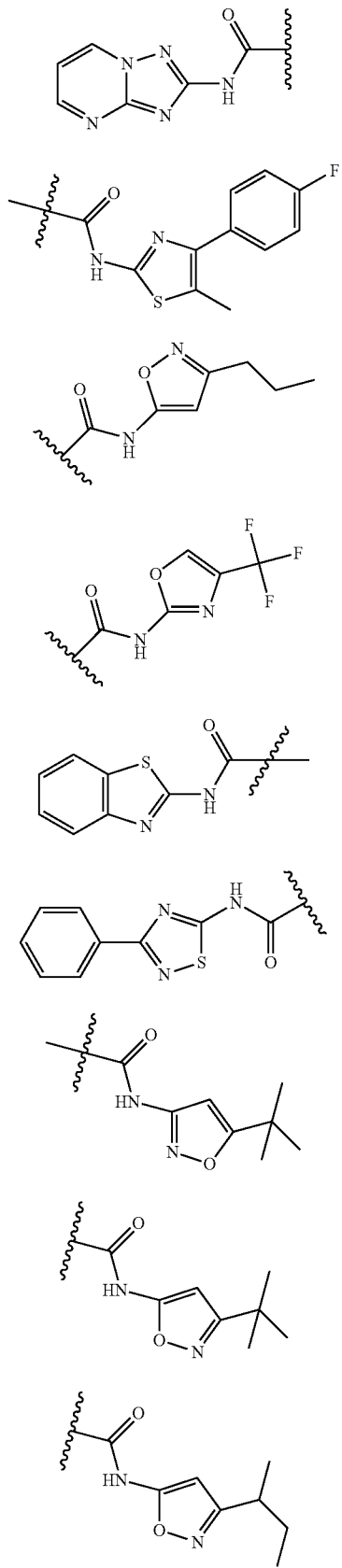
B7
B8
B9
B10
B11
B12
B13
B14
B15
TABLE I-continued
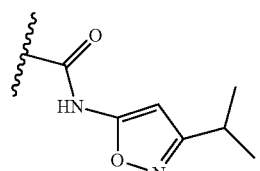
B16
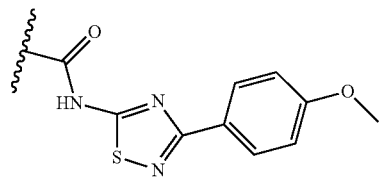 [SMILES: *C(=O)Nc1nc(-c2ccc(OC)cc2)ns1]
B17
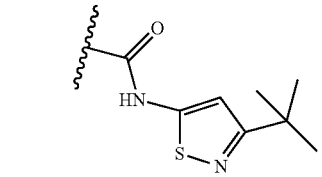 [SMILES: *C(=O)Nc1cc(C(C)(C)C)ns1]
B18
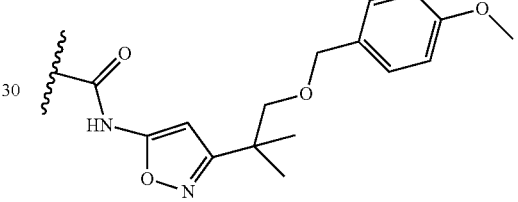
B19
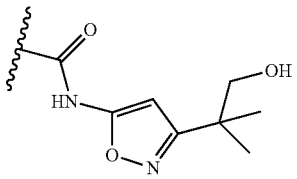 [SMILES: *C(=O)Nc1cc(C(C)(C)CO)no1]
B20
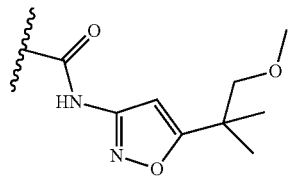 [SMILES: *C(=O)Nc1cc(C(C)(C)COC)on1]
B21
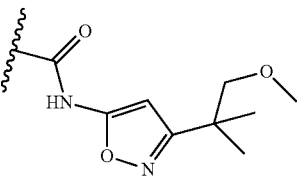 [SMILES: *C(=O)Nc1cc(C(C)(C)COC)no1]
B22
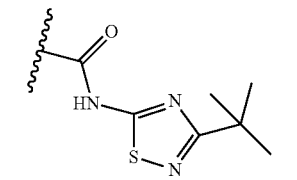 [SMILES: *C(=O)Nc1nc(C(C)(C)C)ns1]
B23

TABLE I-continued
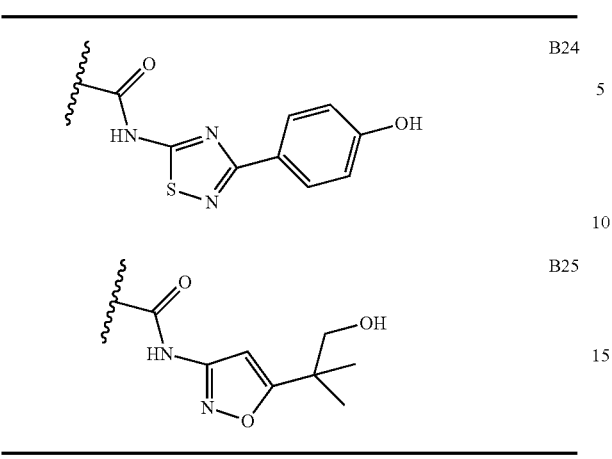
or a pharmaceutically acceptable salt thereof.
6. The compound according to claim 5 wherein the stereogenic carbon indicated with an arrow formula (III) is in the (S) configuration.
7. A compound chosen from
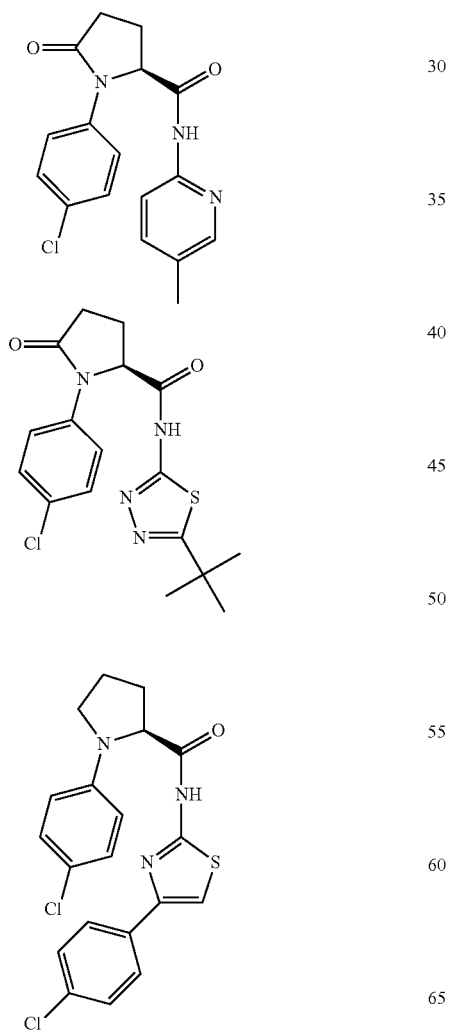
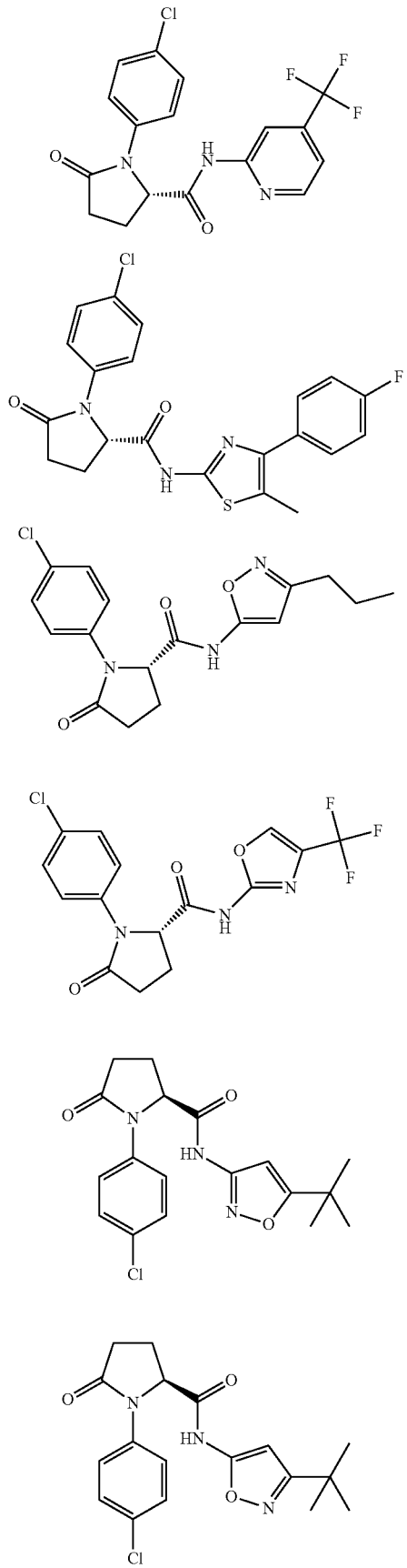

309
-continued
310
-continued
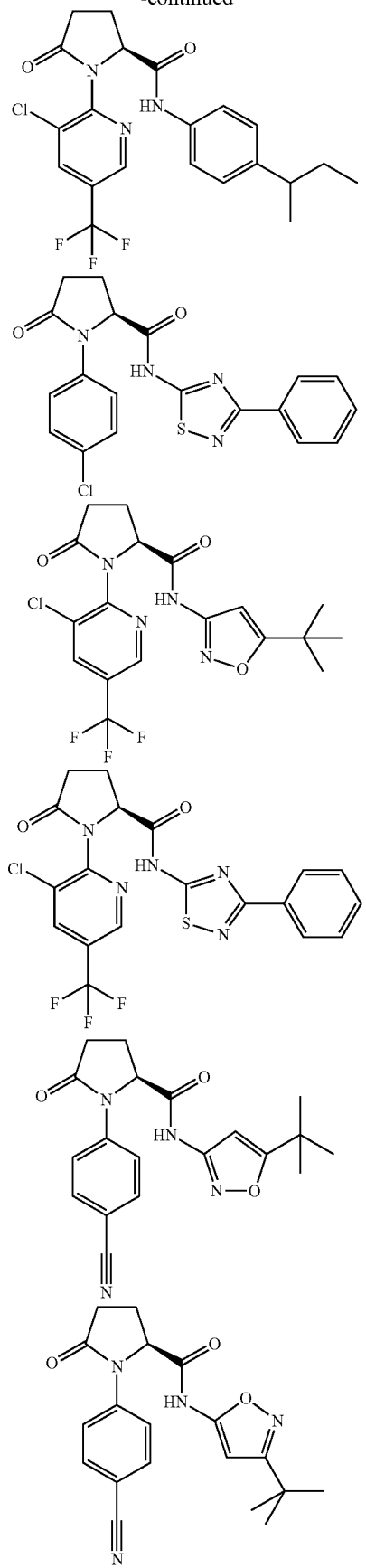
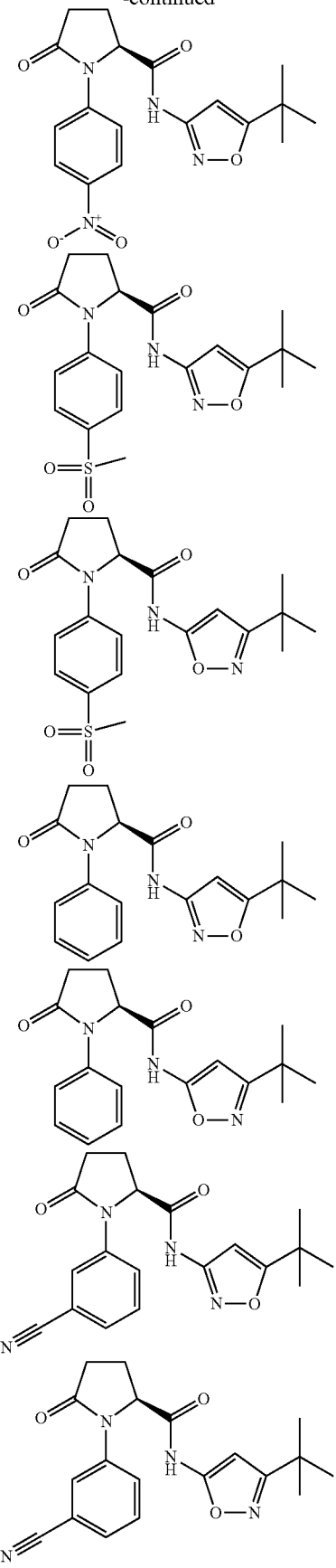

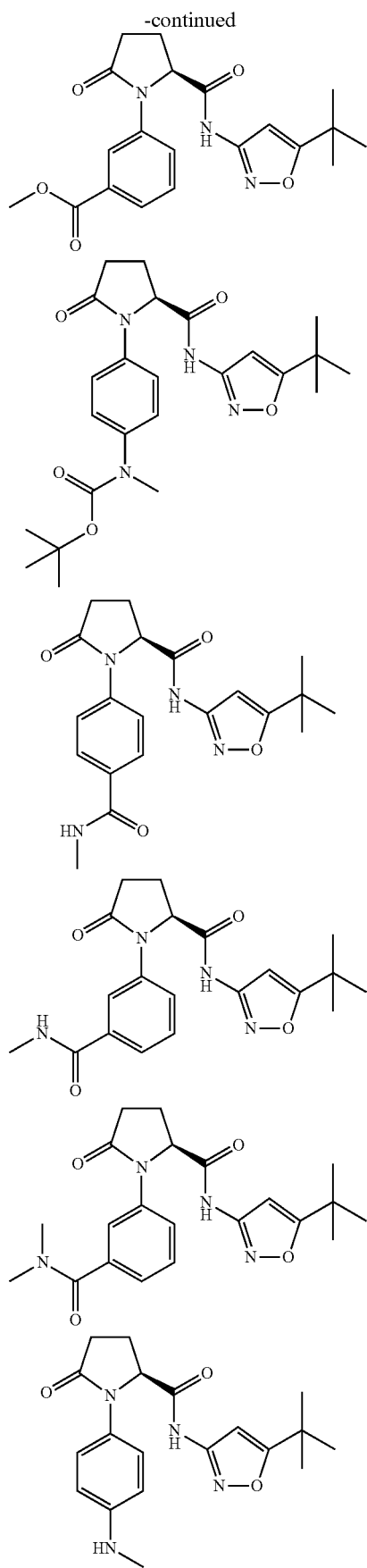
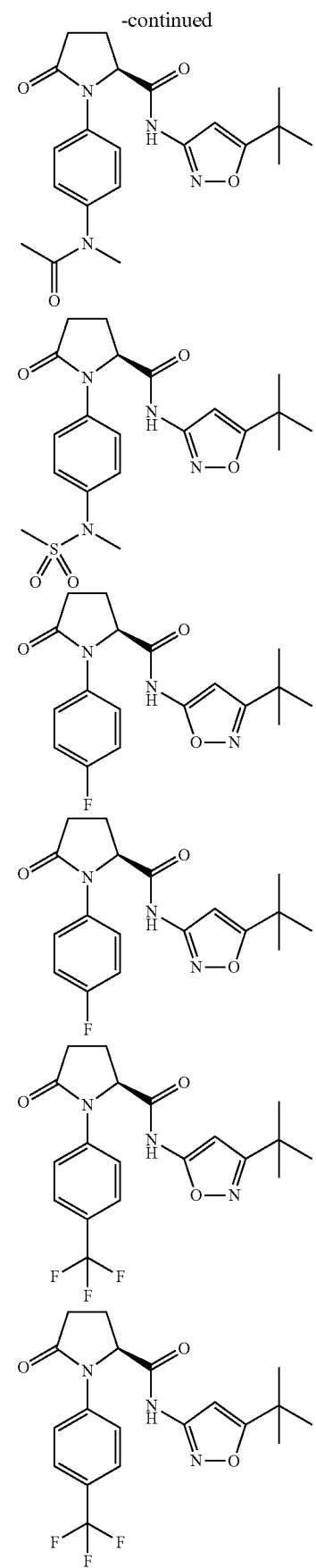

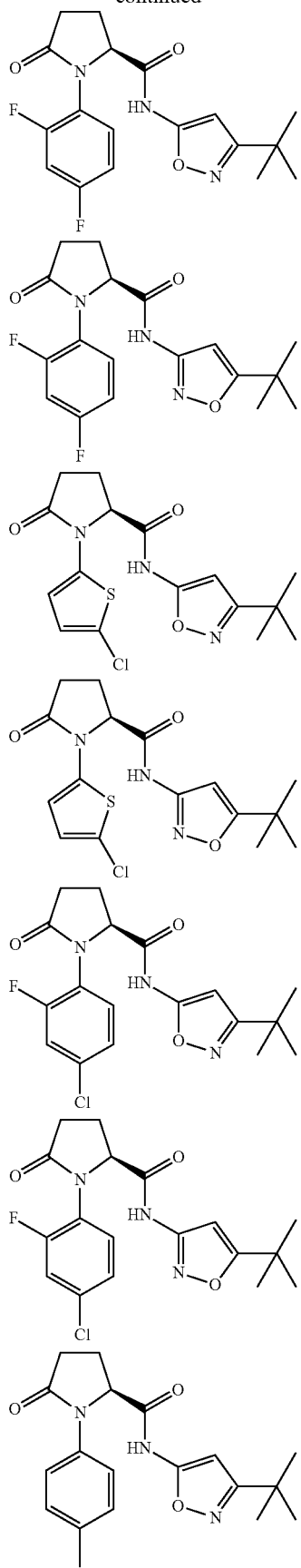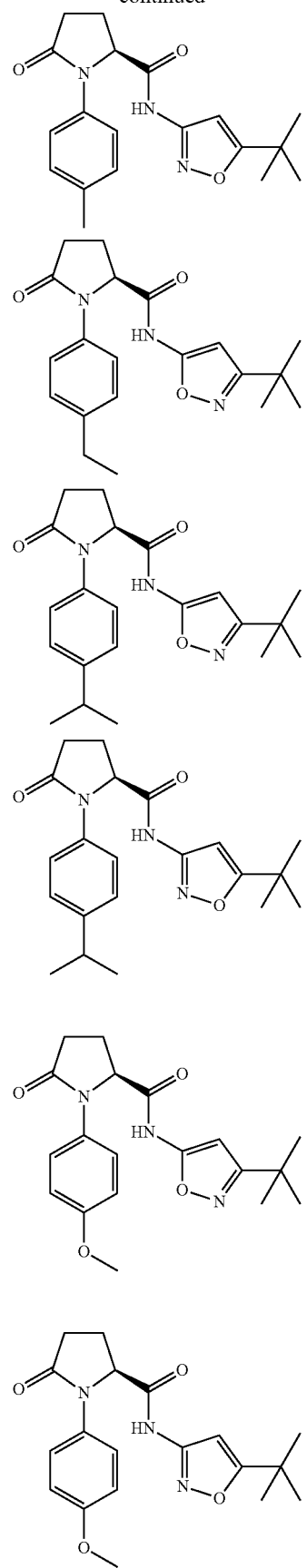

315
-continued
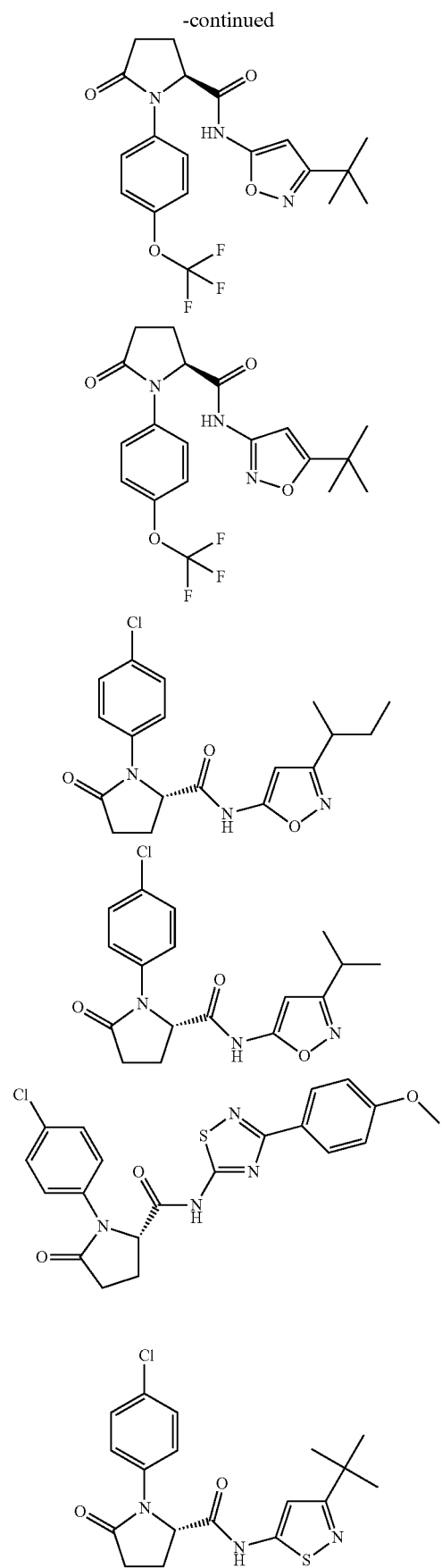
316
-continued
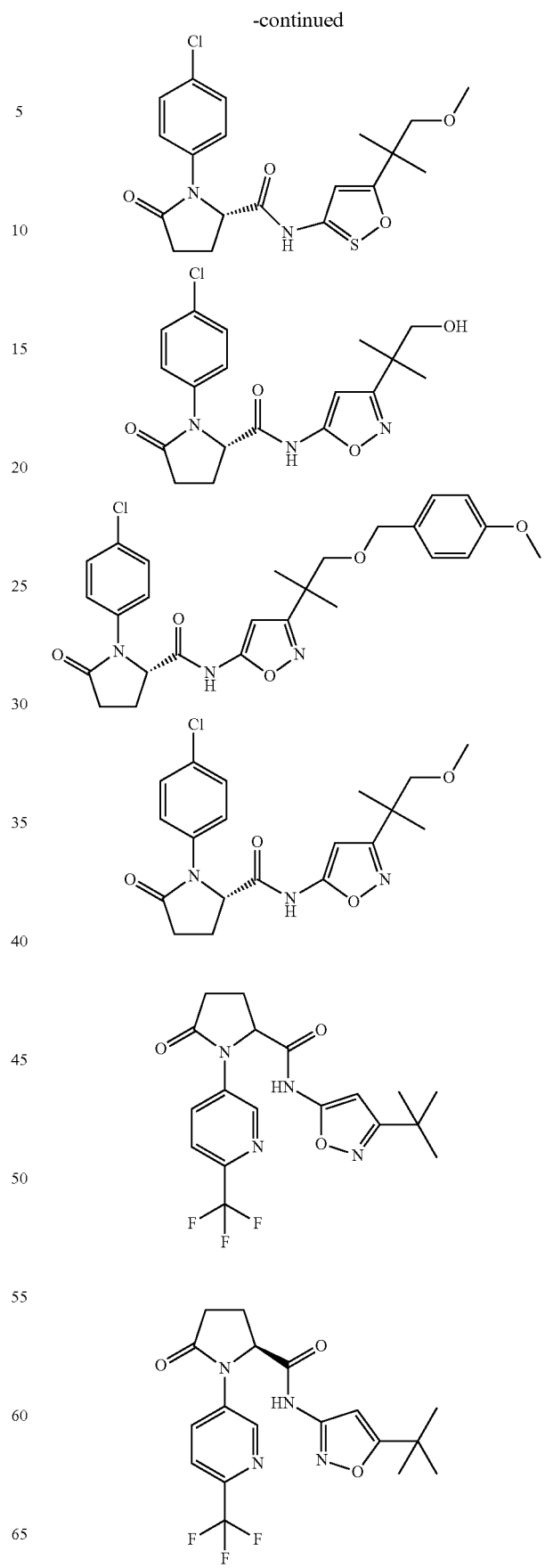

317
-continued
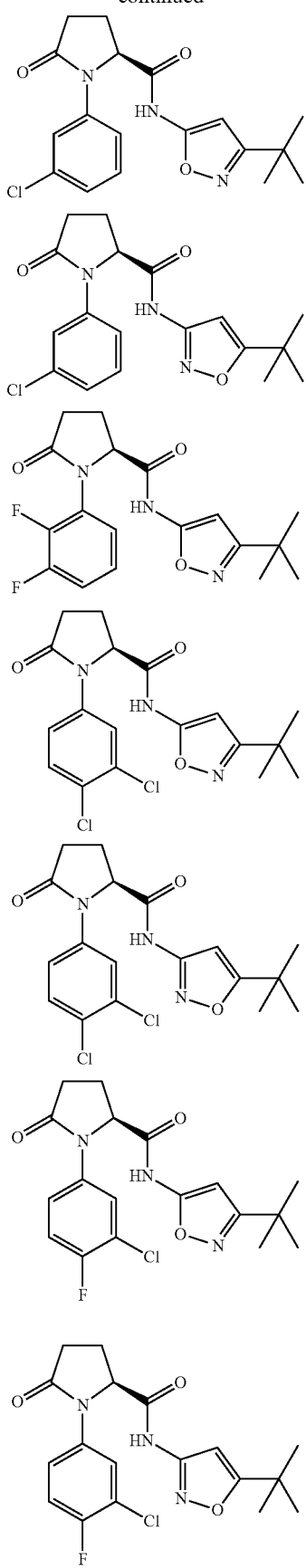
318
-continued
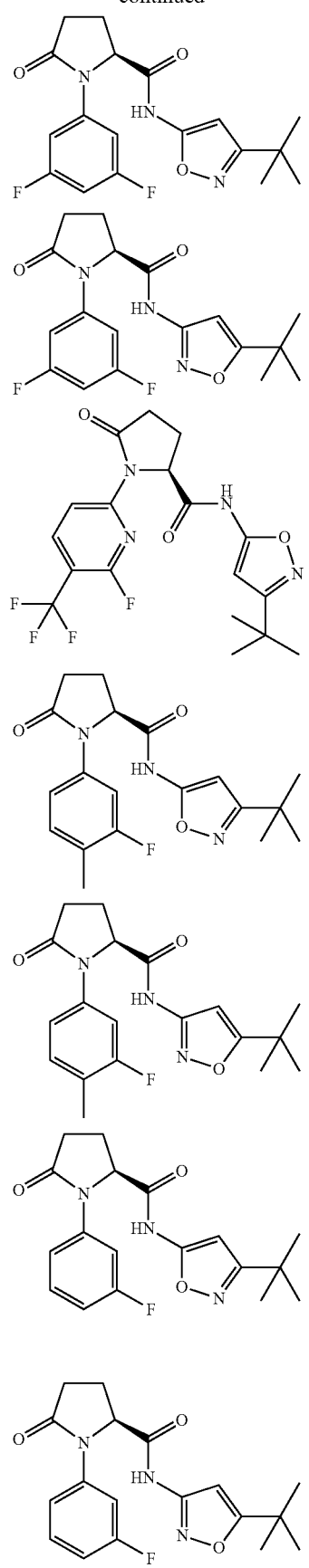

| 319 -continued | 320 -continued |
|---|---|
| 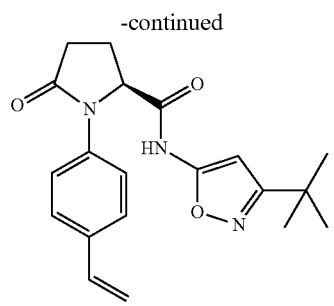 | 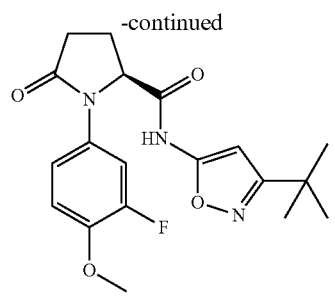 |
| 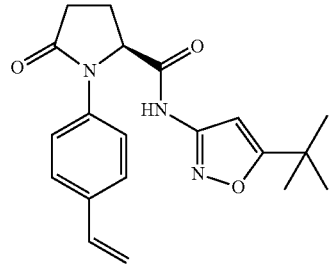 | 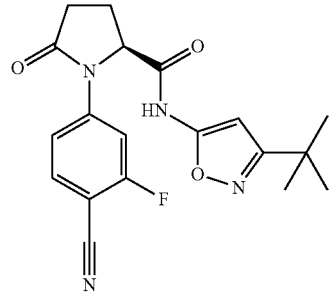 |
| 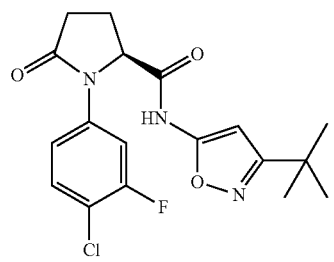 | 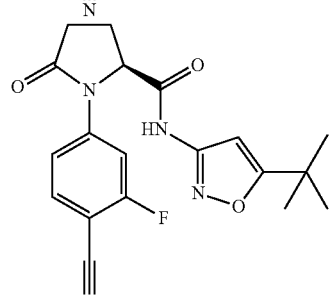 |
| 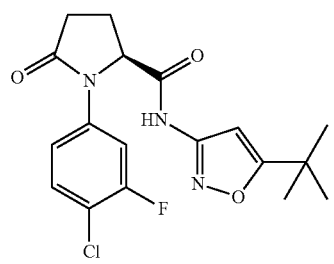 | 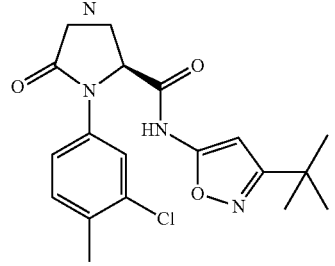 |
| 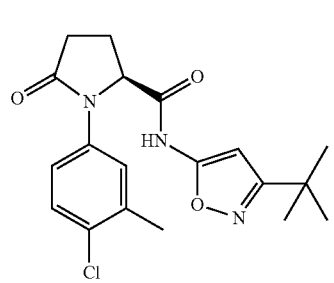 | 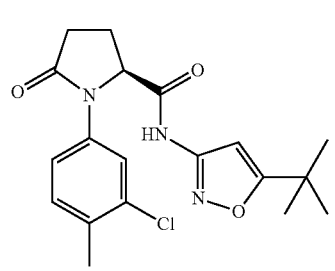 |
| 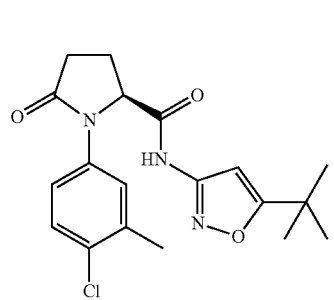 | 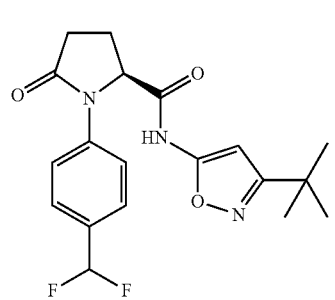 |

321
-continued
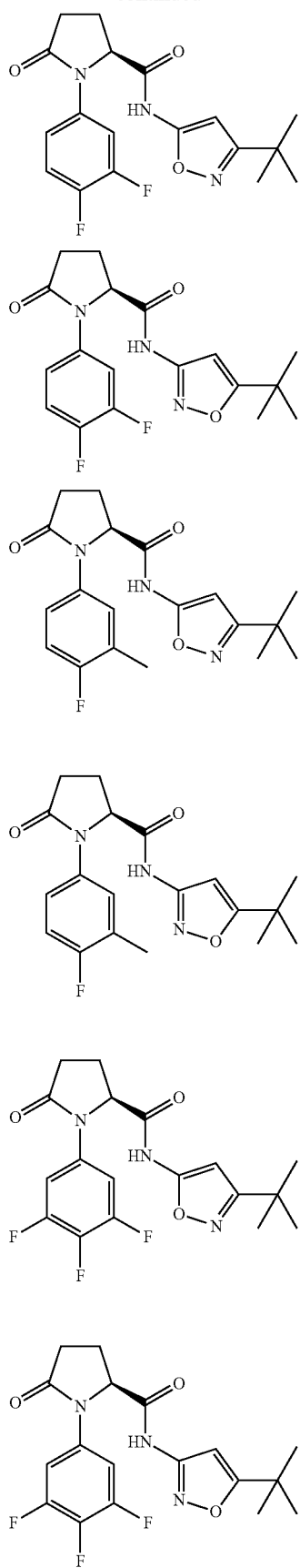
322
-continued
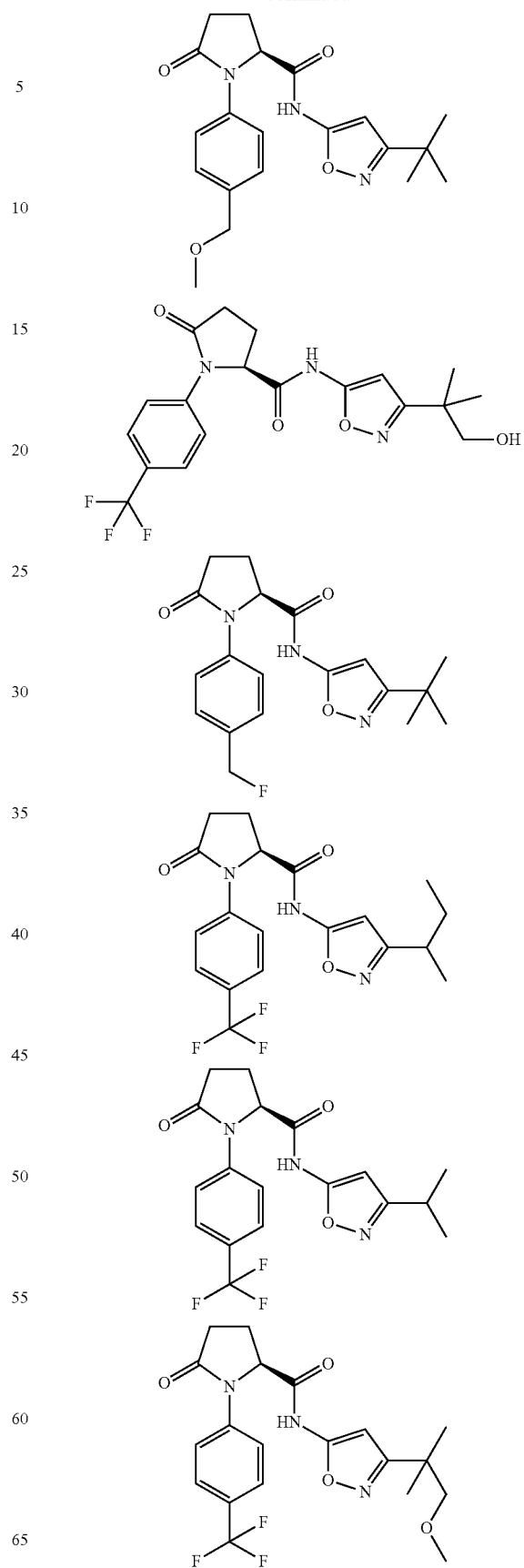

323
-continued
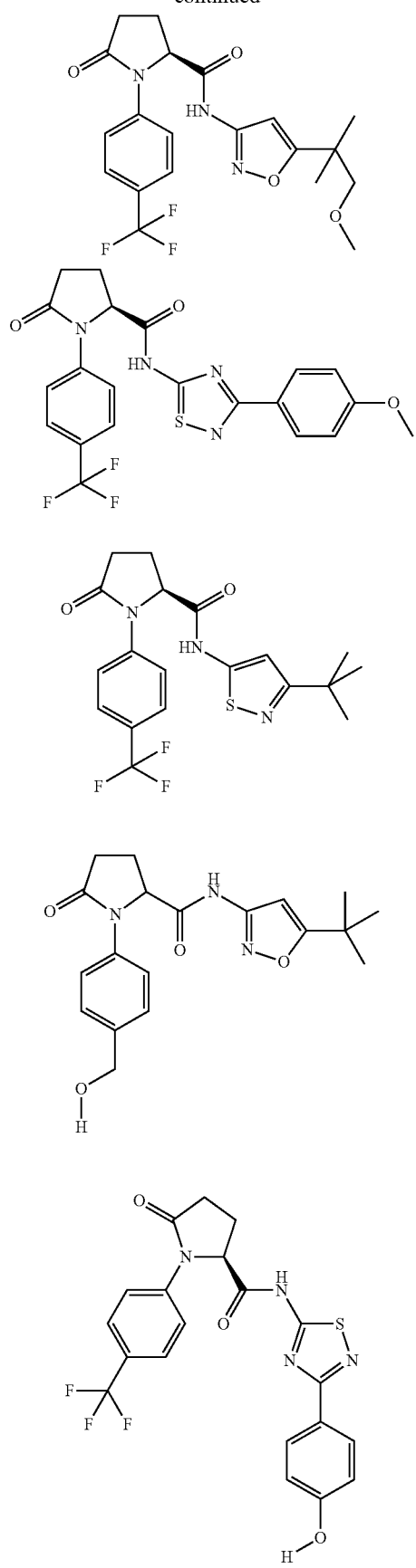
324
-continued
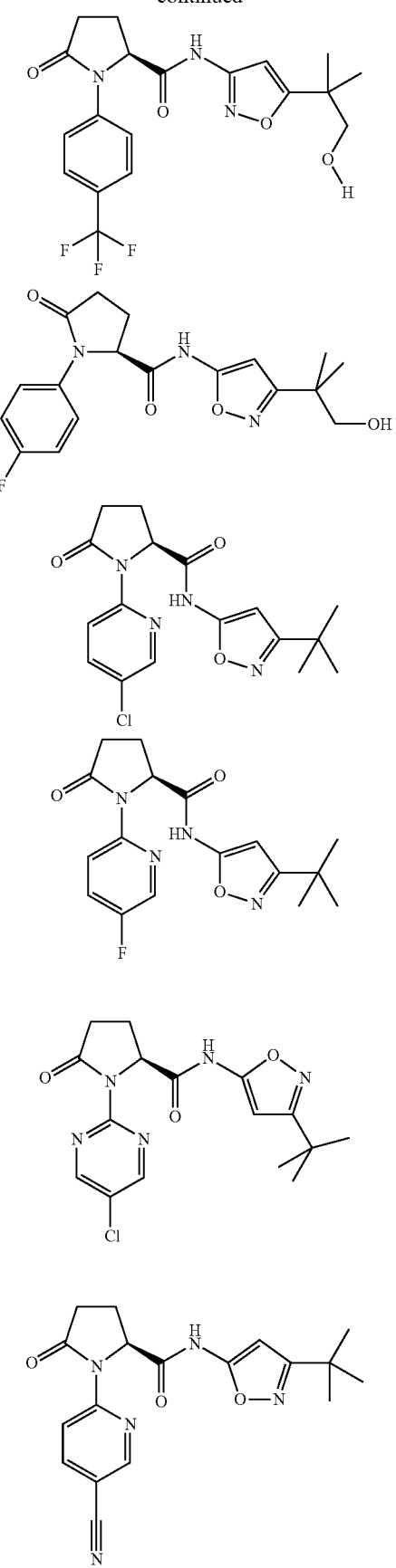

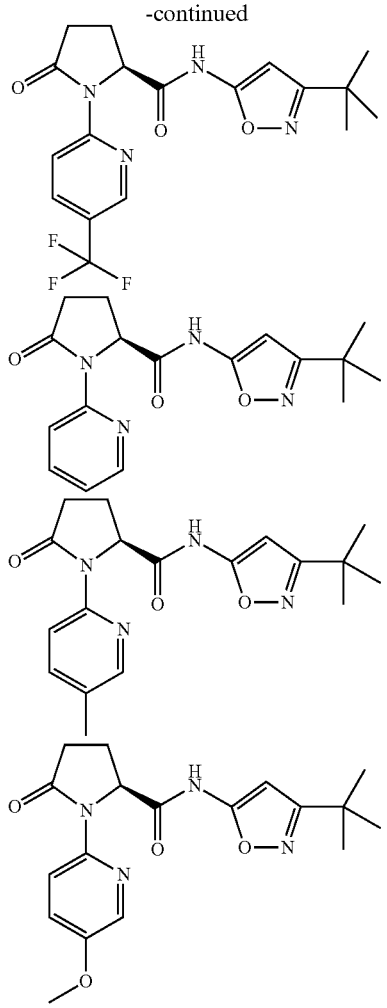

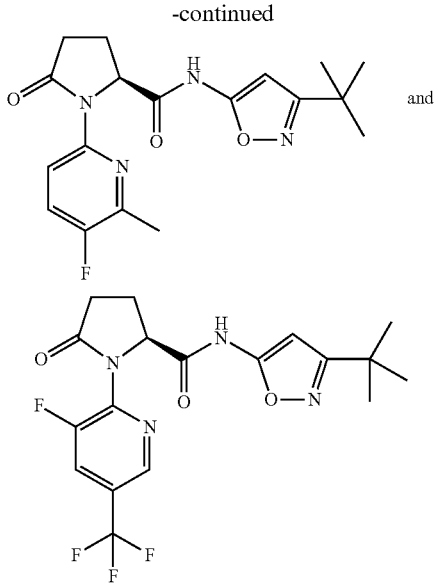 and or a pharmaceutically acceptable salt thereof.

8. A pharmaceutical composition comprising a therapeutically effective amount of a compound according to claim 1 and one or more pharmaceutically acceptable carriers and/or adjuvants.

9. A method of treating pain comprising administering a therapeutically effective amount of a compound according to claim 1.

10. The method according to claim 9 wherein the pain is chosen from acute pain, visceral pain, neuropathic pain, inflammatory and nociceptive pain, cancer pain, and headache.

* * * * *

UNITED STATES PATENT AND TRADEMARK OFFICE
CERTIFICATE OF CORRECTION

PATENT NO. : 8,629,157 B2  Page 1 of 1
APPLICATION NO. : 13/141105
DATED : January 14, 2014
INVENTOR(S) : Berry et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 88 days.

Signed and Sealed this
Twenty-second Day of September, 2015

Michelle K. Lee
*Director of the United States Patent and Trademark Office*